(12) United States Patent
Chen et al.

(10) Patent No.: US 11,787,757 B2
(45) Date of Patent: Oct. 17, 2023

(54) PHENOL DERIVATIVE, AND PREPARATION PROCESS AND USE THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Xiaowei Chen, Beijing (CN); Kecheng Wei, Beijing (CN); Yuxiang Liang, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 151 days.

(21) Appl. No.: 17/309,050

(22) PCT Filed: Oct. 16, 2019

(86) PCT No.: PCT/CN2019/111409
§ 371 (c)(1),
(2) Date: Apr. 16, 2021

(87) PCT Pub. No.: WO2020/078369
PCT Pub. Date: Apr. 23, 2020

(65) Prior Publication Data
US 2022/0041535 A1 Feb. 10, 2022

(30) Foreign Application Priority Data
Oct. 16, 2018 (CN) .......................... 201811201086.9

(51) Int. Cl.
*C07C 39/16* (2006.01)
*C07D 303/14* (2006.01)
(Continued)

(52) U.S. Cl.
CPC ............ *C07C 39/16* (2013.01); *C07D 303/14* (2013.01); *C07D 339/08* (2013.01);
(Continued)

(58) Field of Classification Search
CPC ......... C07C 39/16; C07C 69/30; C07C 69/33; C07C 39/15; C07C 37/72; C07C 67/58;
(Continued)

(56) References Cited

U.S. PATENT DOCUMENTS 2,807,653 A 9/1957 Filbey et al.
2,947,724 A 8/1960 Ambelang
(Continued)

FOREIGN PATENT DOCUMENTS

CN 1611563 A 5/2005
CN 101892111 A 11/2010
(Continued)

OTHER PUBLICATIONS

The Reactions of Lignin during Sulphate Cooking, Acta Chem. Scand. 20, No. 7 (Year: 1966).*
(Continued)

*Primary Examiner* — Taiwo Oladapo
(74) *Attorney, Agent, or Firm* — NKL Law; Allen Xue

(57) ABSTRACT

A phenol derivative of the present invention has a structure as represented by the formula (I):
(Continued)

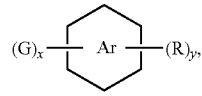

(I)

The functional groups are defined in the description. The phenol derivative can be used as the antioxidant in lubricating oil, lubricating grease, plastic, rubber, or can be used as the base oil of the lubricating oil and the lubricating grease and the antiwear additive of the lubricating oil and the lubricating grease.

3 Claims, 4 Drawing Sheets

(51) Int. Cl.
| | |
|---|---|
| C07D 339/08 | (2006.01) |
| C07D 341/00 | (2006.01) |
| C07D 405/04 | (2006.01) |
| C07D 405/06 | (2006.01) |
| C07D 405/14 | (2006.01) |
| C07D 409/06 | (2006.01) |
| C07D 409/14 | (2006.01) |
| C07D 495/04 | (2006.01) |
| C07D 519/00 | (2006.01) |
| C10M 129/14 | (2006.01) |
| C10M 129/18 | (2006.01) |
| C10M 129/74 | (2006.01) |
| C10M 135/34 | (2006.01) |

(52) U.S. Cl.
CPC ......... *C07D 341/00* (2013.01); *C07D 405/04* (2013.01); *C07D 405/06* (2013.01); *C07D 405/14* (2013.01); *C07D 409/06* (2013.01); *C07D 409/14* (2013.01); *C07D 495/04* (2013.01); *C07D 519/00* (2013.01); *C10M 129/14* (2013.01); *C10M 129/18* (2013.01); *C10M 129/74* (2013.01); *C10M 135/34* (2013.01)

(58) Field of Classification Search
CPC .. C07D 303/14; C07D 339/08; C07D 341/00; C07D 405/04; C07D 405/06; C07D 405/14; C07D 409/06; C07D 409/14; C07D 495/04; C07D 519/00; C07D 303/28; C07D 331/02; C07D 495/08; C07D 333/02; C07D 409/04; C07D 493/04; C10M 129/14; C10M 129/18; C10M 129/74; C10M 135/34; C10M 2207/024; C10M 2207/042; C10M 2207/283; C10M 2219/024; C10M 135/02; C10M 2207/026; C10M 2207/281; C10M 2219/102; C10N 2030/06; C10N 2030/10
See application file for complete search history.

(56) References Cited

U.S. PATENT DOCUMENTS 2,947,789 A  8/1960  Ambelang
4,479,782 A  10/1984  Orlowski et al.

FOREIGN PATENT DOCUMENTS

| CN | 103154206 A | 6/2013 |
|---|---|---|
| CN | 104745280 A | 7/2015 |
| CN | 105175698 A | 12/2015 |
| CN | 105189716 A | 12/2015 |
| CN | 105219458 A | 1/2016 |
| CN | 106118804 A | 11/2016 |
| CN | 107098917 A | 8/2017 |
| CN | 107827795 A | 3/2018 |
| KR | 20180079152 A | 7/2018 |

OTHER PUBLICATIONS

Rasad, Vadakkethonippurathu Sivankutty Nair et al.; "Multifunctional alcohols obtained from cardanol, multifunctional acrylic crosslinker and pendant phosphorous flame retardant derivatives thereof";STN CA Caesar accession No. 1130; XP055920882; Oct. 2, 2009; Database accession No. 2009:1247925; pp. 1-3.
Marg, Rafi; "Multifunctional Alcohols obtained from Cardanol, Multifunctional Acrylic Crosslinker and Pendant Phosphorous Flame Retardant Derivatives Thereof"; Council fo Scientific and Industrial Research; Oct. 2, 2009; XP055920887; pp. 1-19.
Neuse, Eberhard et al.; "Cardanol Derivatives as PVC Plasticizers. Part 1: Synthesis"; South African Journal of Science; vol. 72, No. 8; Aug. 1, 1976; XP000995582; ISSN: 0038-2353; pp. 233-237.
Telvekar, Vikas N. et al.; "Novel Iodine Reagent System for Regioselective Cleavage of Epoxides to Alcohols"; Synthetic Communications; vol. 40, No. 14; Jun. 25, 2010; XP055920953; ISSN: 0039-7911; pp. 2108-2112.
Orlowski Jan A. et al.; "Visible Light-cured orthodontic Adhesive"; Elsevier Life Sciences IP Limited; Oct. 30, 1984; Database Accession No. 15206664; XP055920970.
Afewerki, Samson et al.; "The Chemical Synthesis and Applications of Tropane Alkaloids"; Elsevier Life Sciences IP Limited; Sep. 7, 2018; pp. 151-233; Database accession No. 34386064 Abstract; XP 055920997.
Boisselier, Veronique Le et al.; "Bismuth(III)-Catalyzed Oxidative Cleavage of Aryl Epoxides: Substituent Effects on the Kinetics of the Oxidation Reaction"; Elsevier Life Sciences IP Limited; XP055921003; Database accession No. 7130672 Abstract.
Zheng, Tianyu et al.; "Diverse Ring Opening of Thietanes and Other Cyclic Sulfides: An Electrophilic Aryne Activation Approach"; Elsevier Life Sciences IP Limited; Dec. 7, 2017; Database accession No. 32323584; SP055921033 Abstract.
Gierer, Josef et al.; "The Reactions of Lignin During Sulphate Cooking. Part X. Synthesis and Alkaline Treatment of Model Compounds Representing Intermediary Episulphide Structures"; ACTA Chemica Scandinavica; vol. 20, No. 7; Year: 1966; pp. 1769-1777; XP055921049.
De Almeida, Mayara O. et al.; "Development of Fully Bio-Based Lubricants from Agro-Industrial Residues under Environmentally Friendly Processeds"; European Journal of Lipid Science and Technology.; vol. 122,No. 5; Feb. 14, 2020; pp. 1-11; XP055954089; ISSN: 1438-7697.
CAS. STN Registry; RN 6159-12-0 et al., Mar. 1, 2010, pp. 1-10.
Eberhard W. Neuse et al., Cardanol Derivatives as PVC Plasticizers. II. Plasticizer Evaluation; Journal of Applied Polymer Science, vol. 21, Dec. 31, 1977, pp. 3023-3033.

* cited by examiner

PHENOL DERIVATIVE, AND PREPARATION PROCESS AND USE THEREOF

TECHNICAL FIELD

The present invention relates to a phenol derivative, especially relates to a phenol derivative applicable for the antioxidant, the base oil, and the additive of lubricating oil/lubricating grease. The present invention also relates to the lubricating oil/lubricating grease containing the phenol derivative, and the base oil containing the phenol derivative.

BACKGROUND TECHNOLOGY

With the rapid development of the modern industry and the increasingly prominent environmental problems, the requirements for use performance, operational reliability, service life, biodegradability, low toxicity or non-toxicity of lubricants are becoming higher and higher. The development of lubricants at present and in the future will face many challenges. Among others, renewability, energy-saving, environmental friendliness, low-cost, good versatility, high performance, long lifetime and the like have become the main direction of lubricant research and development. Traditional mineral-based lubricants have been difficult to meet these rigorous requirements. In addition, due to the non-renewability and lower biodegradability of mineral-based lubricants, it faces the dual pressure of resource depletion and environmental pollution. Moreover, as fossil resources are increasingly depleted, people are increasingly concerned about environmental protection and energy conservation, and laws and regulations with high requirements for environmental protection are issued, the cost advantage of traditional petroleum-based mineral oil is being weakened, and its application fields are also limited to some extent.

On the other hand, biomass lubricating oils derived from organisms can be recycled and reused without causing irreversible damage to the environment and have prominent properties. For example, vegetable oils have renewable and biodegradable properties. Compared with the traditional mineral base oil, they have the advantages of low volatility, high flash point, high viscosity index, excellent lubricity and the like. Vegetable oil has become the main resource for high-quality bio-based lubricating oil base oil. Of course, vegetable oils also have the problems of poor oxidation stability and poor low-temperature fluidity. The higher the unsaturated acid content of the vegetable oil, the better its low-temperature fluidity, but at the same time the worse the oxidation stability, which is mainly caused by the C=C double bond present in the vegetable oil.

Therefore, improving the anti-oxidation stability of the vegetable oil is the key to its use as the lubricating oil base oil. For this reason, people have adopted many methods to improve the performance of vegetable oils. CN104745280A discloses a method for producing the vegetable oil-based lubricating oil, wherein high-oleic sunflower seed oil and castor oil are used and mixed to obtain the lubricating oil base oil with the anti-oxidation performance meeting the requirements. CN101892111A discloses a method for obtaining biodegradable and non-toxic lubricating oil base oil that has good lubricating performance and anti-oxidation performance by the hydrogenation and the modification of the soybean oil. CN106118804A discloses a method for obtaining the lubricating oil base oil with good oxidation stability and lubricity through the esterification and the modification of the watermelon seed oil. CN103154206A discloses a method for modifying the vegetable oil through hydrolysis, oligomerization and hydroisomerization to obtain high-performance hydrocarbon lubricating oil base oil. CN105189716A discloses a method for obtaining the high-performance hydrocarbon lubricating oil base oil by polymerizing olefins after removing the carbonyl group of vegetable oil. However, many of the above methods can only obtain lubricating oil base oils with lower kinematic viscosity, and cannot obtain high-viscosity lubricating oil base oils with a kinematic viscosity greater than 20 $mm^2/s$ at 100° C. In addition, CN105175698A discloses a high-viscosity and degradable lubricating oil base oil with good lubricating properties obtained by modifying the castor oil with the polymerization of dicarboxylic acid and dihydric polyol. However, the acid value and the pour point of the base oil obtained by this method are relatively high and easy to emulsify, it cannot be used as other types of lubricating oils such as engine lubricating oil, gear oil, hydraulic oil, compressor oil and the like, except as the metal working fluid.

High-viscosity base oil is an indispensable component for blending high-viscosity lubricating oils. Among mineral oils, only BS bright oil belongs to the high-viscosity base oil. At present, there are scarcely any low cost products that can replace high-viscosity base oil such as BS bright oil.

In addition, antioxidants are indispensable additives for lubricating oil, fuel oil and plastics and rubber processing industries. There are many types of antioxidants, mainly including phenol type, amine type, phenolic ester type, thioester type, phosphite type, and the like. Among others, the phenol-type antioxidants are widely used because of their excellent antioxidation effect.

The hindered phenol antioxidant widely used in the field such as lubricating oil and fuel oil is a symmetric hindered phenol antioxidant, and there are many related patents. For example, CN1611563A provides a symmetric hindered phenol antioxidant, which has the characteristics of low condensation point and strong anti-oxidation performance, but has the disadvantage of strong steric hindrance in the molecule structure that is ubiquitously held by the symmetric hindered phenol antioxidants.

In addition, the friction modifiers are essential additives in the lubricating oil industry, can be used to improve the lubricity of oil products and reduce the friction coefficient of friction surfaces, and mainly include animal and vegetable oils, oleic acid, vulcanized animal and vegetable oils, long-chain fatty amines, amides, and some phosphorus-containing compounds and the like. Among others, vulcanized animal and vegetable oils are used at the soonest, and are widely used because of their excellent lubrication and anti-friction effects.

At present, the friction modifiers widely used in the field of lubricating oils are vulcanized cottonseed oil (T404), vulcanized olefin cottonseed oil (T405), and the like, but their anti-wear and anti-friction properties need to be further improved. There are also many related patents. For example, CN107098917A discloses a sulfurized erucic acid anti-wear anti-friction agent, which has the characteristics of light color and good oil solubility in the hydrogenated base oil, and has excellent antiwear, antifriction properties, but its chemical structure contains carboxyl groups, leading to higher acid value of oil products and adversely affecting the corrosion stability of oil products. CN107827795A discloses a vulcanized glycerol trioleate anti-wear and anti-friction agent, which has good lubricity and extreme pressure property, but its anti-wear and anti-friction properties are not superior to traditional friction modifiers T404 and T405.

Cardanol is a main component of cashew nut shell oil, is a natural phenolic compound, is an important agricultural by-product in cashew nut production, and is wide in source and huge in reserve. Therefore, using this kind of abundant and low-cost natural compounds as raw materials to synthesize asymmetric hindered phenol antioxidants conforms to the requirements of green chemistry and the requirements of the national sustainable development strategy.

SUMMARY OF THE INVENTION

The inventors of the present invention have conducted in-depth research and found that the phenol derivatives with specific structures exhibit excellent anti-oxidation performance, excellent friction improvement performance, and low acid value, without causing metal corrosion. In addition, the phenol derivative with the specific structure, as a high-viscosity lubricating oil base oil, exhibits excellent properties such as low pour point, high kinematic viscosity, and high viscosity index. Hence, it is possible to provide the antioxidant, the friction modifier, and the base oil of the lubricating oil that have better performance than those of the prior art. In addition, the inventors of the present invention have found that the phenol derivative of the specific structure of the present invention can be synthesized by using cardanol as starting material, thereby the effective utilization of cardanol as an agricultural by-product can be achieved.

The present invention provides a phenol derivative, a preparation process thereof, and use thereof; the present invention also provides a lubricating oil/lubricating grease containing the phenol derivative, and a base oil containing the phenol derivative.

Specifically, the present invention provides a phenol derivative, which has a structure as represented by the formula (I):

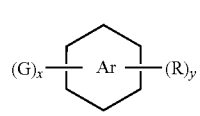

(I)

In the formula (I), x groups G are bonded to the ring group Ar, y groups R are bonded to the ring group Ar;
  x groups G are, identical to or different from each other, each independently selected from —OH,

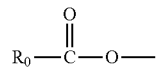

and —OR$_0$, wherein groups R$_0$ are each independently selected from C$_{1-50}$ hydrocarbyl optionally substituted by one or more substituent groups, C$_{6-20}$ aryl substituted by one or more substituent groups and C$_{3-50}$ hetero hydrocarbyl optionally substituted by one or more substituent groups (preferably selected from C$_{1-50}$ linear or branched alkyl and linear or branched C$_{3-50}$ heteroalkyl); x is selected from an integral number of 1-10 (preferably an integral number of 1-5);
  y groups R are, identical to or different from each other, each independently selected from hydrogen, C$_{1-50}$ hydrocarbyl optionally substituted by one or more substituent groups, C$_{6-20}$ aryl substituted by one or more substituent groups, C$_{3-50}$ hetero hydrocarbyl optionally substituted by one or more substituent groups, C$_{1-50}$ alkoxyl optionally substituted by one or more substituent groups and a group represented by the formula (II) (preferably selected from hydrogen, C$_{1-50}$ linear or branched alkyl, C$_{1-50}$ linear or branched alkenyl, linear or branched C$_{3-50}$ heteroalkyl, C$_{1-50}$ linear or branched alkyloxy and a group represented by the formula (II)), wherein at least one group R is selected from a group represented by the formula (II);

(II)

Groups L in y groups R are each independently selected from single bond, (m+1)-valent C$_{1-50}$ hydrocarbyl optionally substituted by one or more substituent groups and (m+1)-valent C$_{3-50}$ hetero hydrocarbyl optionally substituted by one or more substituent groups (preferably selected from single bond, (m+1)-valent C$_{1-50}$ linear or branched alkyl and (m+1)-valent linear or branched C$_{3-50}$ heteroalkyl); y is selected from an integral number of 1-10 (preferably an integral number of 1-5);

m groups A in formula (II) are each independently selected from a group represented by the formula (III), a group represented by the formula (IV), a group represented by the formula (V), a group represented by the formula (VI), a group represented by the formula (VII) and a group represented by the formula (VIII); the numbers m in formula (II) are each independently selected from an integral number of 1-10 (preferably an integral number of 1-5);

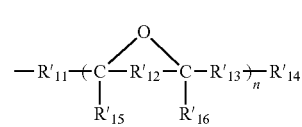

(III)

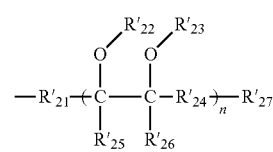

(IV)

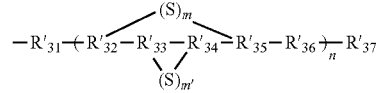

(V)

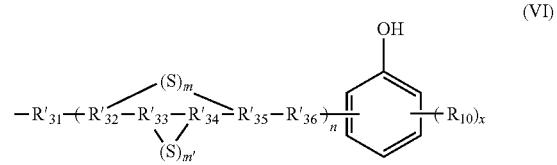

(VI)

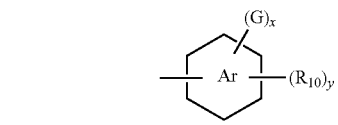

(VII)

-continued

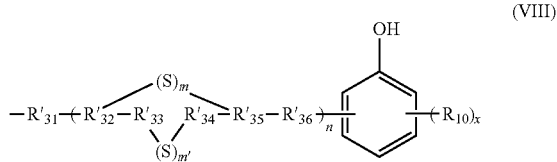

(VIII)

In the formula (III), $R_{11}'$ is selected from single bond and $C_{1-20}$ linear or branched alkylene (preferably selected from single bond and $C_{1-4}$ linear or branched alkylene); groups $R_{12}'$ in n repeating units are, identical to or different from each other, each independently selected from single bond and $C_{1-20}$ linear or branched alkylene (preferably each independently selected from single bond and $C_{1-4}$ linear or branched alkylene); groups $R_{13}'$ in n repeating units are, identical to or different from each other, each independently selected from single bond and $C_{1-20}$ linear or branched alkylene (preferably each independently selected from single bond and $C_{1-4}$ linear or branched alkylene); $R_{14}'$ is selected from hydrogen and $C_{1-20}$ linear or branched alkyl (preferably selected from hydrogen and $C_{1-4}$ linear or branched alkyl); groups $R_{15}'$ in n repeating units are, identical to or different from each other, each independently selected from hydrogen and $C_{1-20}$ linear or branched alkyl (preferably each independently selected from hydrogen and $C_{1-4}$ linear or branched alkyl); groups $R_{16}'$ in n repeating units are, identical to or different from each other, each independently selected from hydrogen and $C_{1-20}$ linear or branched alkyl (preferably each independently selected from hydrogen and $C_{1-4}$ linear or branched alkyl); n is an integral number of 1-10 (preferably an integral number of 1-3);

In the formula (IV), group $R_{21}'$ is selected from single bond and $C_{1-20}$ linear or branched hydrocarbylene (preferably selected from single bond and $C_{1-4}$ linear or branched alkylene); groups $R_{22}'$ and $R_{23}'$ in n repeating units are, identical to or different from each other, each independently selected from

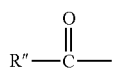

and hydrogen (preferably each independently

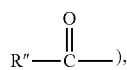

wherein R" is $C_{1-30}$ linear or branched alkyl (preferably selected from $C_{1-20}$ linear or branched alkyl); in each repeating unit, at least one group of groups $R_{22}'$ and $R_{23}'$ is

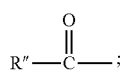

groups $R_{24}'$ in n repeating units are, identical to or different from each other, each independently selected from single bond and $C_{1-20}$ linear or branched hydrocarbylene (preferably each independently selected from single bond and $C_{1-4}$ linear or branched alkylene); groups $R_{25}'$ and $R_{26}'$ in n repeating units are, identical to or different from each other, each independently selected from hydrogen and $C_{1-20}$ linear or branched alkyl (preferably each independently selected from hydrogen and $C_{1-4}$ linear or branched alkyl); group $R_{27}'$ is selected from hydrogen and $C_{1-20}$ linear or branched hydrocarbyl (preferably selected from hydrogen and $C_{1-10}$ linear or branched alkyl); n is a positive integer (preferably a positive integral number of 1-30, more preferably a positive integral number of 1-5);

In the formula (V) and the formula (VI), group $R_{31}'$ is each independently selected from single bond and $C_{1-20}$ linear or branched alkylene (preferably selected from single bond and $C_{1-4}$ linear or branched alkylene); groups $R_{32}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{33}'$ in n repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{34}'$ in n repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{35}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched branched alkyl); in each alkyl); groups $R_{36}'$ in n repeating units are, identical to or different from each other, each independently selected from single bond and $C_{1-20}$ linear or branched alkylene (preferably each independently selected from single bond, $C_{1-4}$ linear or branched alkylene); group $R_{37}'$ is selected from hydrogen and $C_{1-20}$ linear or branched alkyl (preferably selected from hydrogen and $C_{1-4}$ linear or branched alkyl); n is an integral number of 1-10 (preferably an integral number of 1-3); the numbers m in n repeating units are, identical to or different from each other, each independently selected from an integral number of 0-10 (preferably an integral number of 0-5); the numbers m' in n repeating units are, identical to or different from each other, each independently selected from an integral number of 0-10 (preferably an integral number of 0-5); in each repeating unit of the formulae (V) and (VI), when m is greater than 0, the linking group formed by m sulfur atoms is bonded to groups $R_{32}'$ and $R_{35}'$; when m' is greater than 0, the linking group formed by m' sulfur atoms is bonded to groups $R_{33}'$ and $R_{34}'$; in each repeating unit of the formulae (V) and (VI), when group $R_{33}'$ is single bond, one end connected to group $R_{33}'$ of the linking group formed by m' sulfur atoms is bonded to group $R_{32}'$, when group $R_{34}'$ is single bond, one end connected to group $R_{34}'$ of the linking group formed by m' sulfur atoms is bonded to group $R_{35}'$; in the formula (VI), x groups $R_{10}$ are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups and $C_{1-50}$ alkoxyl optionally substituted by one or more substituent groups (preferably selected from hydrogen, $C_{1-50}$ linear or branched alkyl, $C_{1-50}$ linear or branched alkenyl, linear or branched $C_{3-50}$ heteroalkyl and $C_{1-50}$ linear or branched alkyloxy), x is selected from an integral number of 1-10 (preferably an integral number of 1-5);

In the formula (VII), x groups G are, identical to or different from each other, each independently selected from —OH,

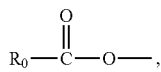

—OR$_0$, wherein groups R$_0$ are each independently selected from C$_{1-50}$ hydrocarbyl optionally substituted by one or more substituent groups, C$_{6-20}$ aryl substituted by one or more substituent groups and C$_{3-50}$ hetero hydrocarbyl optionally substituted by one or more substituent groups (preferably selected from C$_{1-50}$ linear or branched alkyl and linear or branched C$_{3-50}$ heteroalkyl); x is selected from an integral number of 1-10 (preferably an integral number of 1-5); y is selected from an integral number of 1-10 (preferably an integral number of 1-5); in the formula (VII), y groups R$_{10}$ are, identical to or different from each other, each independently selected from hydrogen, C$_{1-50}$ hydrocarbyl optionally substituted by one or more substituent groups, C$_{6-20}$ aryl substituted by one or more substituent groups, C$_{3-50}$ hetero hydrocarbyl optionally substituted by one or more substituent groups and C$_{1-50}$ alkoxyl optionally substituted by one or more substituent groups (preferably selected from hydrogen, C$_{1-50}$ linear or branched alkyl, Ci-50 linear or branched alkenyl, linear or branched C$_{3-50}$ heteroalkyl and C$_{1-50}$ linear or branched alkyloxy), x is selected from an integral number of 1-10 (preferably an integral number of 1-5), y is selected from an integral number of 1-10 (preferably an integral number of 1-5);

In the formula (VIII), group R$_{31}$' is each independently selected from single bond and C$_{1-20}$ linear or branched alkylene (preferably selected from single bond and C$_{1-4}$ linear or branched alkylene); groups R$_{32}$' in n repeating units are, identical to or different from each other, each independently selected from divalent, trivalent or tetravalent C$_{1-20}$ linear or branched alkyl (preferably each independently selected from divalent, trivalent or tetravalent C$_{1-4}$ linear or branched alkyl); groups R$_{33}$' in n repeating units are, identical to or different from each other, each independently selected from H and divalent C$_{1-20}$ linear or branched alkyl (preferably each independently selected from H and divalent C$_{1-4}$ linear or branched alkyl); groups R$_{34}$' in n repeating units are, identical to or different from each other, each independently selected from H and divalent C$_{1-20}$ linear or branched alkyl (preferably each independently selected from H and divalent C$_{1-4}$ linear or branched alkyl); groups R$_{35}$' in n repeating units are, identical to or different from each other, each independently selected from divalent, trivalent or tetravalent C$_{1-20}$ linear or branched alkyl (preferably each independently selected from divalent, trivalent or tetravalent C$_{1-4}$ linear or branched alkyl); groups R$_{36}$' in n repeating units are, identical to or different from each other, each independently selected from single bond and C$_{1-20}$ linear or branched alkylene (preferably each independently selected from single bond, C$_{1-4}$ linear or branched alkylene); the numbers m in n repeating units are, identical to or different from each other, each independently selected from an integral number of 0-10 (preferably an integral number of 0-5); the numbers m' in n repeating units are, identical to or different from each other, each independently selected from an integral number of 0-10 (preferably an integral number of 0-5), m+m'>0; in each repeating unit of the formula (VIII), when m is greater than 0, the linking group formed by m sulfur atoms is bonded to groups R$_{32}$' and R$_{35}$'; when m' is greater than 0, the linking group formed by m' sulfur atoms is bonded to groups R$_{33}$' and R$_{34}$'; in each repeating unit of the formula (VIII), when group R$_{33}$' is H, one end connected to group R$_{33}$' of the linking group formed by m' sulfur atoms is bonded to group R$_{32}$'; when group R$_{34}$' is H, one end connected to group R$_{34}$' of the linking group formed by m' sulfur atoms is bonded to group R$_{35}$'; in the formula (VIII), x groups R$_{10}$ are, identical to or different from each other, each independently selected from hydrogen, C$_{1-50}$ hydrocarbyl optionally substituted by one or more substituent groups, C$_{6-20}$ aryl substituted by one or more substituent groups, C$_{3-50}$ hetero hydrocarbyl optionally substituted by one or more substituent groups and C$_{1-50}$ alkoxyl optionally substituted by one or more substituent groups (preferably selected from hydrogen, C$_{1-50}$ linear or branched alkyl, C$_{1-50}$ linear or branched alkenyl, linear or branched C$_{3-50}$ heteroalkyl and C$_{1-50}$ linear or branched alkyloxy), x is selected from an integral number of 1-10 (preferably an integral number of 1-5); in each repeating unit of the formula (VIII), groups R$_{31}$' and R$_{36}$' can be each independently substituted by a group represented by the formula (VIII-1); in each repeating unit of the formula (VIII), groups R$_{32}$', R$_{33}$', R$_{34}$' and R$_{35}$' can be each independently substituted by a group represented by the formula (V),

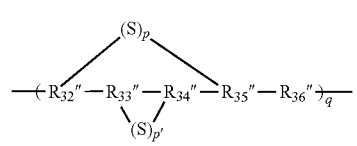

(VIII-1)

In the formula (VIII-1), groups R$_{32}$" in q repeating units are, identical to or different from each other, each independently selected from divalent, trivalent or tetravalent C$_{1-20}$ linear or branched alkyl (preferably each independently selected from divalent, trivalent or tetravalent C$_{1-4}$ linear or branched alkyl); groups R$_{33}$" in q repeating units are, identical to or different from each other, each independently selected from single bond and divalent or trivalent C$_{1-20}$ linear or branched alkyl (preferably each independently selected from single bond, divalent or trivalent C$_{1-4}$ linear or branched alkyl); groups R$_{34}$" in q repeating units are, identical to or different from each other, each independently selected from single bond and divalent or trivalent C$_{1-20}$ linear or branched alkyl (preferably each independently selected from single bond, divalent or trivalent C$_{1-4}$ linear or branched alkyl); groups R$_{35}$" in q repeating units are, identical to or different from each other, each independently selected from divalent, trivalent or tetravalent C$_{1-20}$ linear or branched alkyl (preferably each independently selected from divalent, trivalent or tetravalent C$_{1-4}$ linear or branched alkyl); groups R$_{36}$" in q repeating units are, identical to or different from each other, each independently selected from single bond and C$_{1-20}$ linear or branched alkylene (preferably each independently selected from single bond, C$_{1-4}$ linear or branched alkylene); q is an integral number of 1-10 (preferably an integral number of 1-3); the numbers p in q repeating units are, identical to or different from each other, each independently selected from an integral number of 0-10 (preferably an integral number of 0-5); the numbers p' in q repeating units are, identical to or different from each other, each independently selected from an integral number of 0-10

(preferably an integral number of 0-5); in each repeating unit of the formula (VIII-1), when p is greater than 0, the linking group formed by p sulfur atoms is bonded to groups $R_{32}''$ and $R_{35}''$; when p' is greater than 0, the linking group formed by p' sulfur atoms is bonded to groups $R_{33}''$ and $R_{34}''$; in each repeating unit of the formula (VIII-1), when group $R_{33}''$ is single bond, one end connected to group $R_{33}''$ of the linking group formed by p' sulfur atoms is bonded to group $R_{32}''$, when group $R_{34}''$ is single bond, one end connected to group $R_{34}''$ of the linking group formed by p' sulfur atoms is bonded to group $R_{35}''$;

The ring group

in the formula (I) is each independently selected from (x+y)-valent $C_{3-20}$ cycloalkyl (preferably $C_{3-6}$ cycloalkyl, more preferably cyclopentyl, cyclohexyl) and (x+y)-valent $C_{6-20}$ aryl (preferably $C_{6-14}$ aryl, more preferably phenyl, biphenylyl, naphthyl, anthryl, phenanthryl);

The ring group

in the formula (VII) is each independently selected from (x+y+1)-valent $C_{3-20}$ cycloalkyl (preferably $C_{3-6}$ cycloalkyl, more preferably cyclopentyl, cyclohexyl), (x+y+1)-valent $C_{6-20}$ aryl (preferably $C_{6-14}$ aryl, more preferably phenyl, biphenylyl, naphthyl, anthryl, phenanthryl);

The above-mentioned "substituent group" is selected from $C_{1-20}$ alkyl, $C_{1-20}$ alkoxyl, $C_{6-10}$ aryl, hydroxy, amino, mercapto and halogen atom.

The phenol derivative according to any of the aforesaid aspects, wherein, the ring groups

in the formula (I) and the formula (VII) are each independently selected from $C_{3-6}$ cycloalkane group and $C_{6-14}$ aryl group, and preferably each independently selected from cyclohexane group and benzene ring group.

The phenol derivative according to any of the aforesaid aspects, wherein, in the formula (I), x is 1, y is 1, group G and group R are located at the meta-position in relation to one another. In other words, based on group G, group R is located at the meta-position.

The phenol derivative according to any of the aforesaid aspects, wherein, in the formula (I), x is 1, y is 2, group G is located at the ortho-position of one group R and at the meta-position of another group R. In other words, based on group G, one group R is located at the ortho-position, and one group R is located at the meta-position. Preferably, two groups R are located at the para position (each located at the para-position in relation to one another).

The phenol derivative according to any of the aforesaid aspects, which is selected from the following specific compounds or a mixture thereof in any proportion:

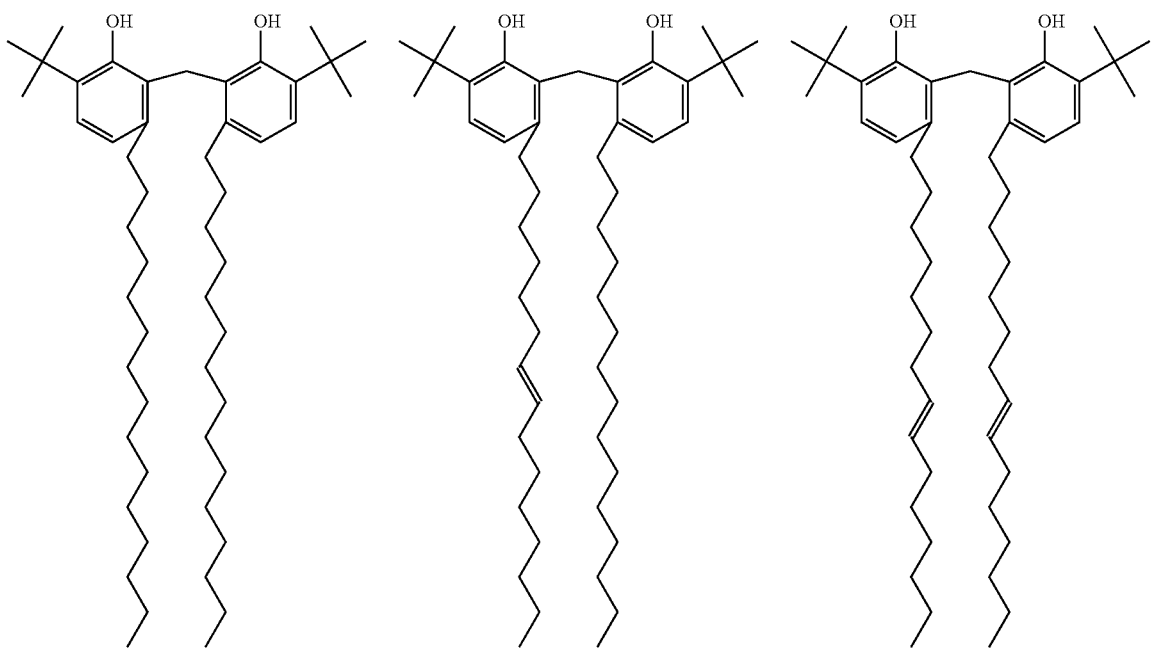

11
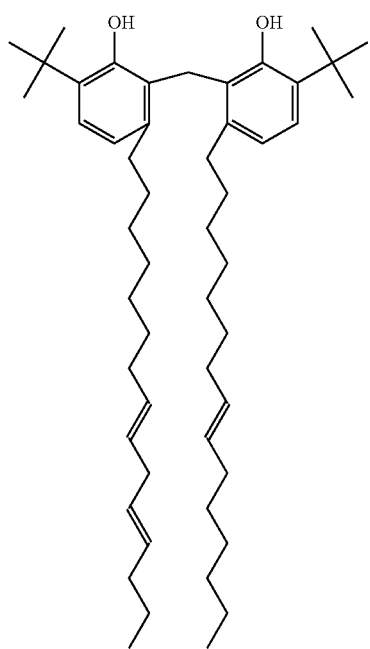
-continued
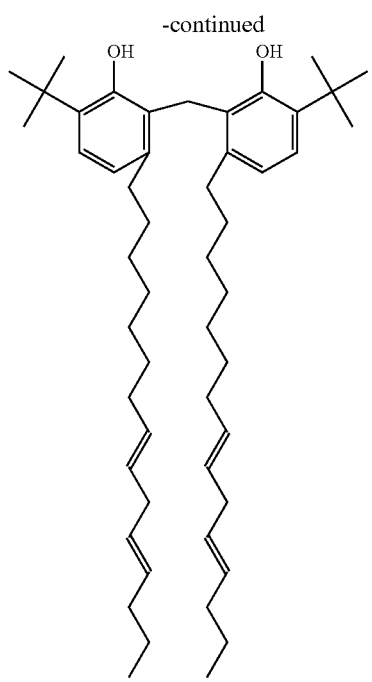
12
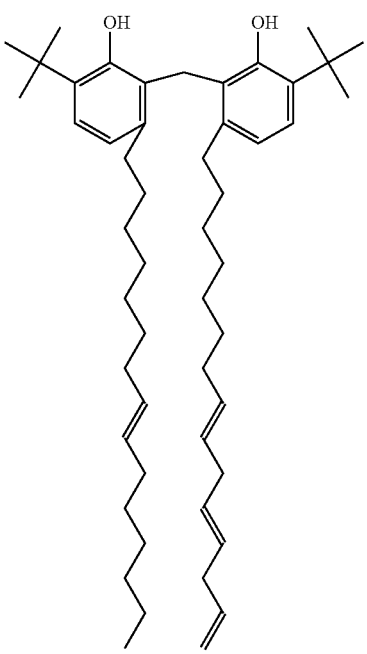
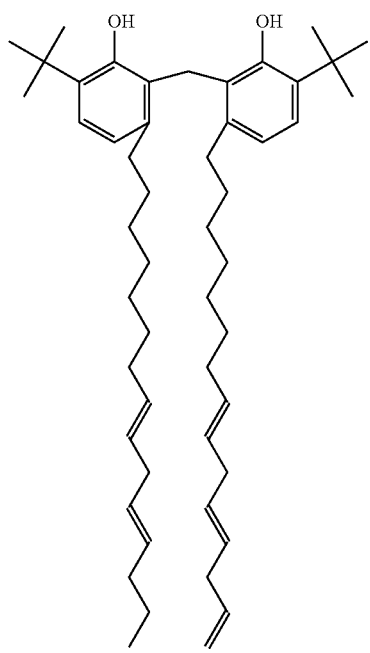
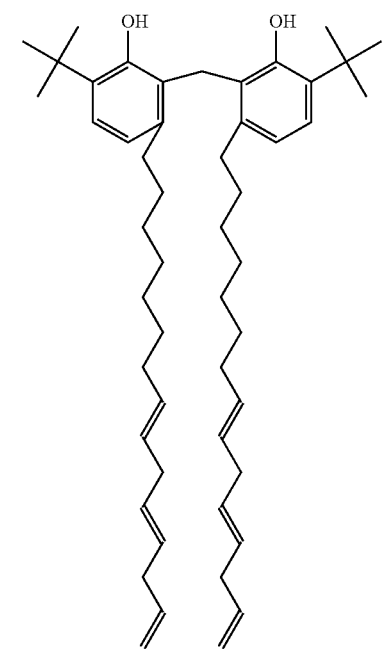

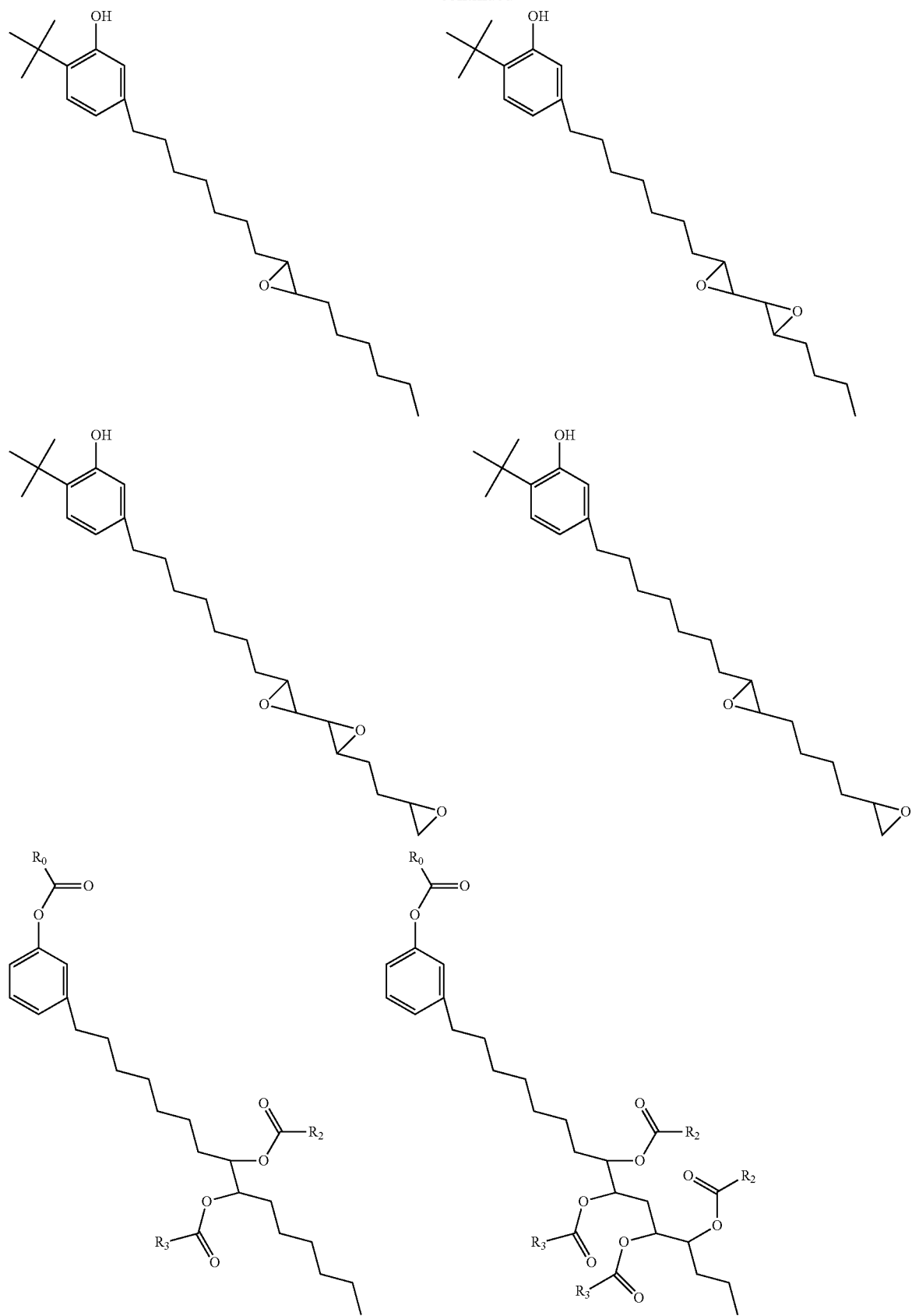

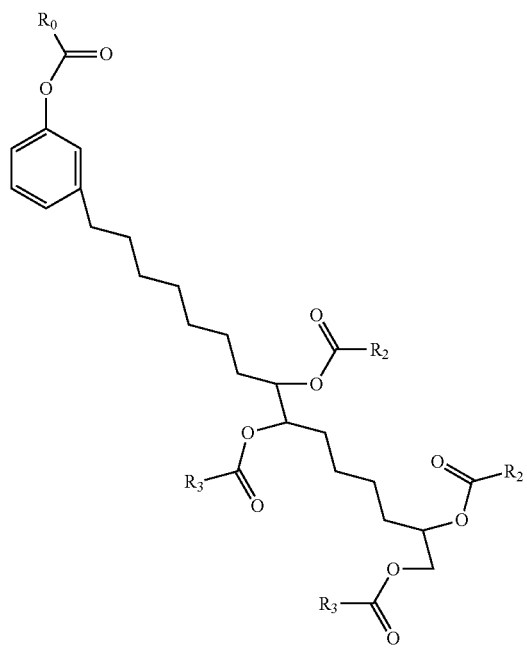
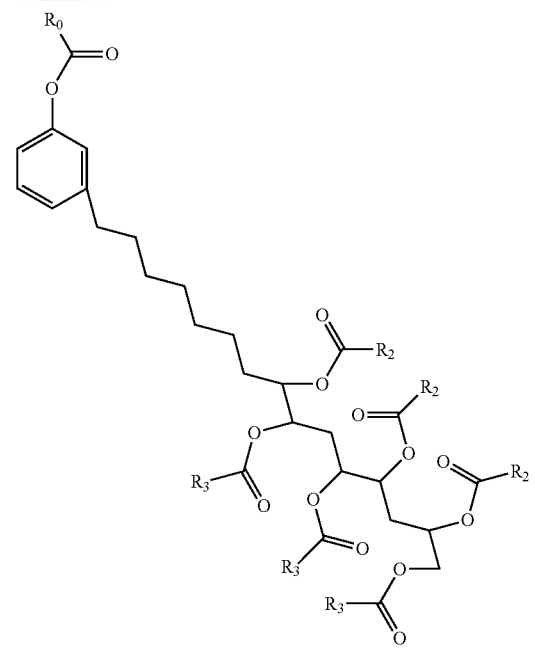
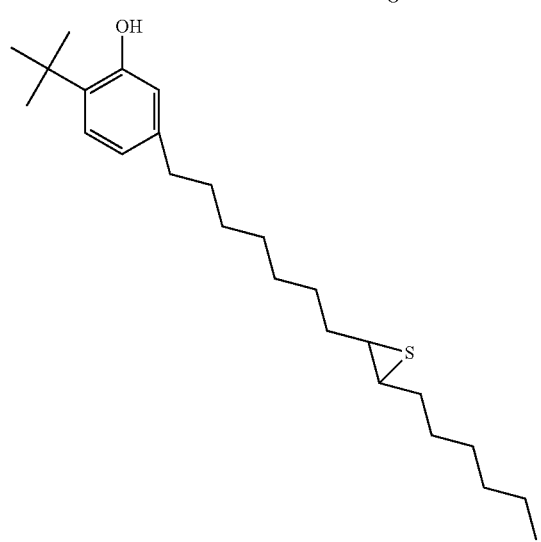
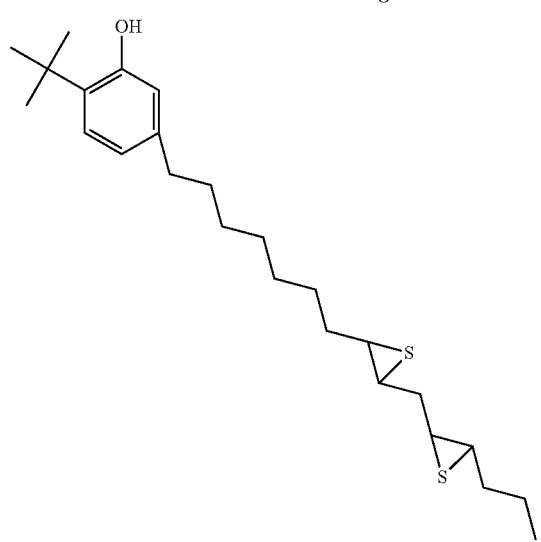
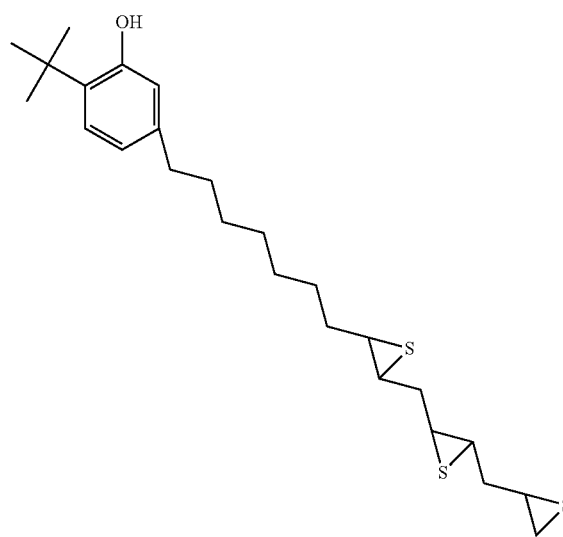
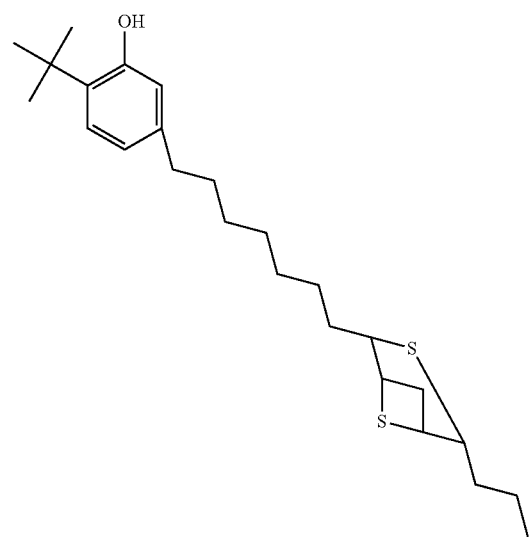

-continued
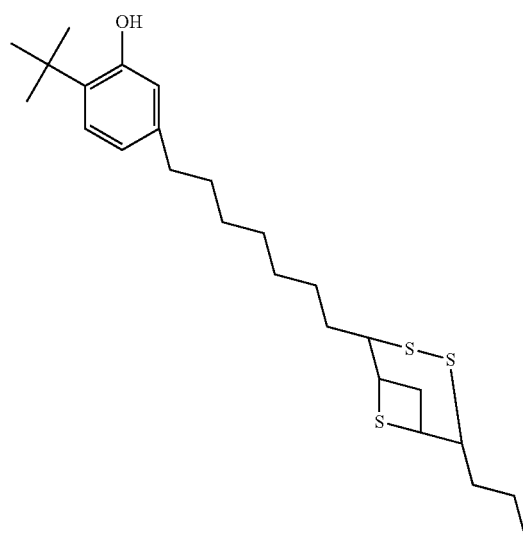
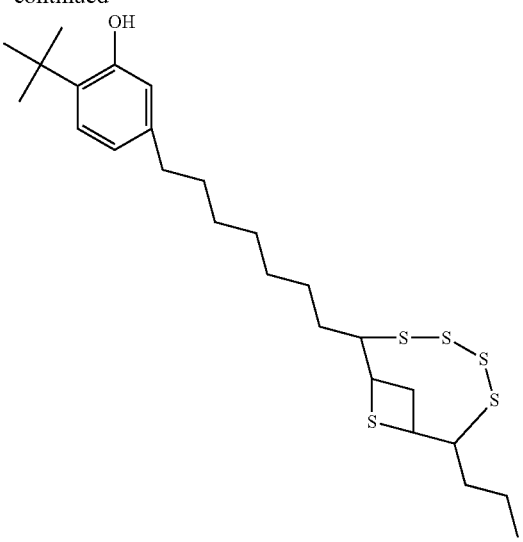
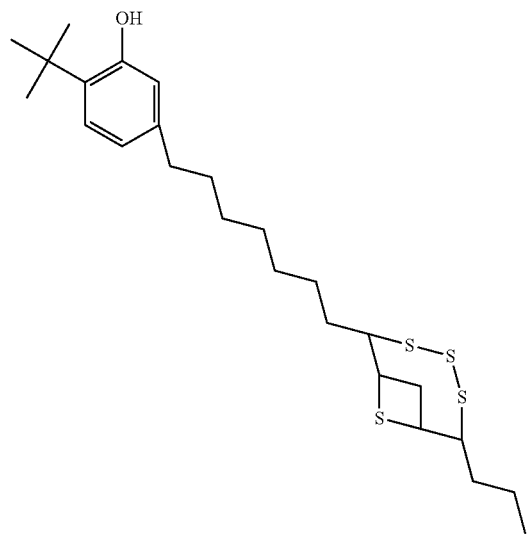
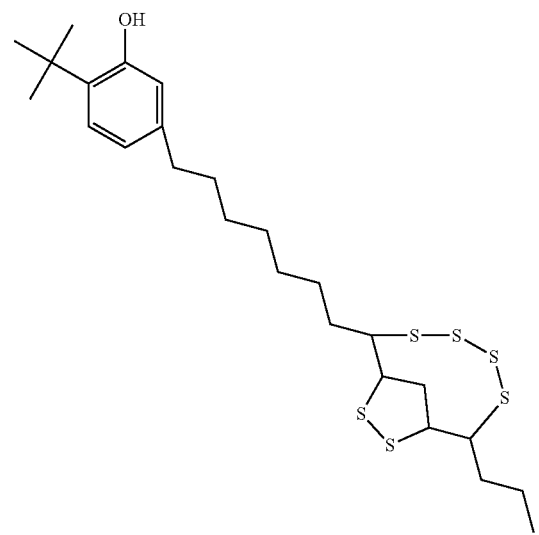
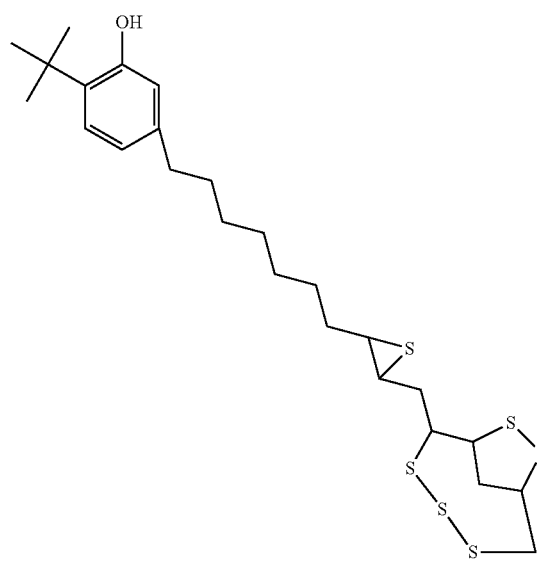
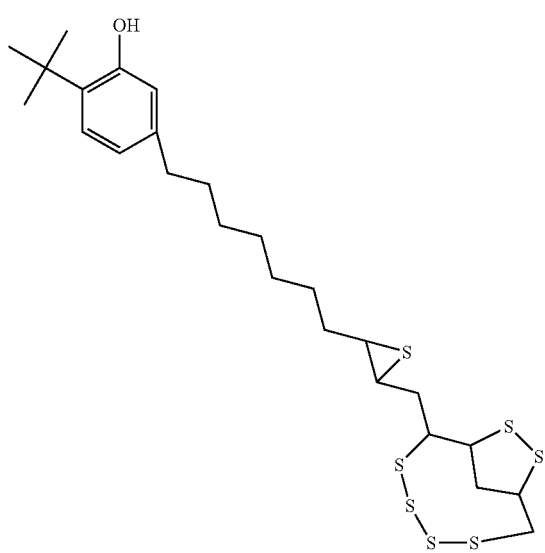

-continued
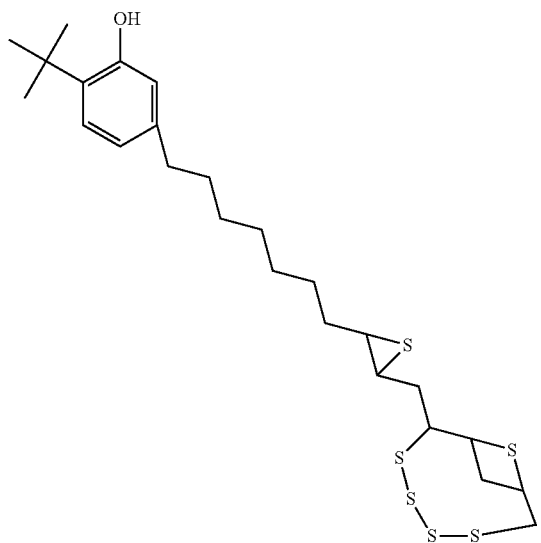
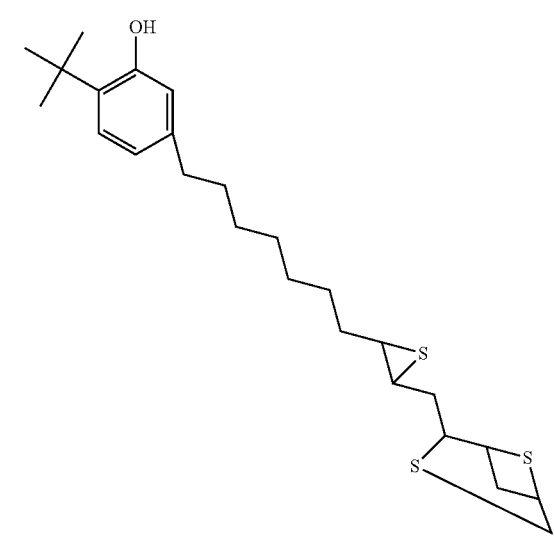
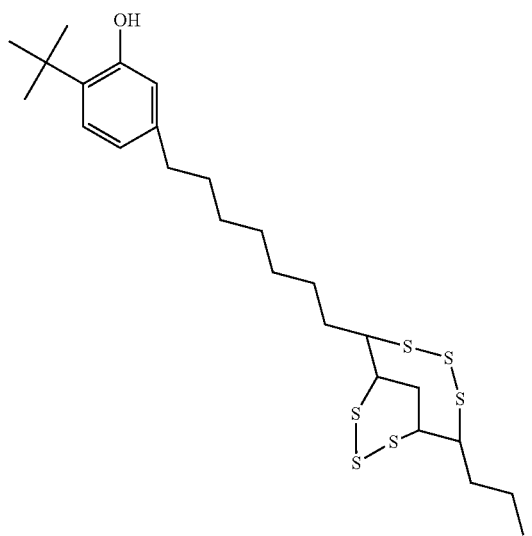
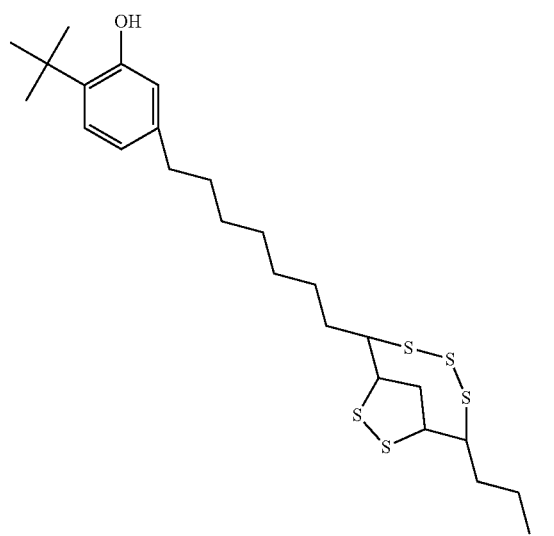
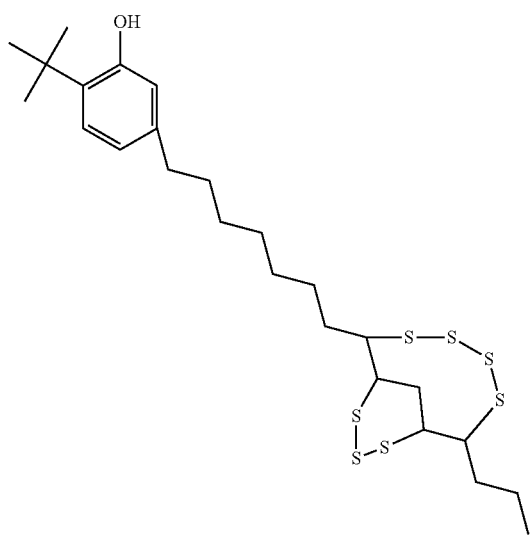
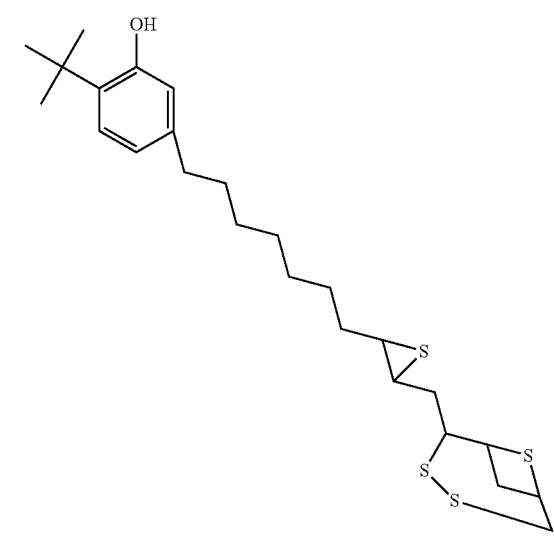

21
22
-continued
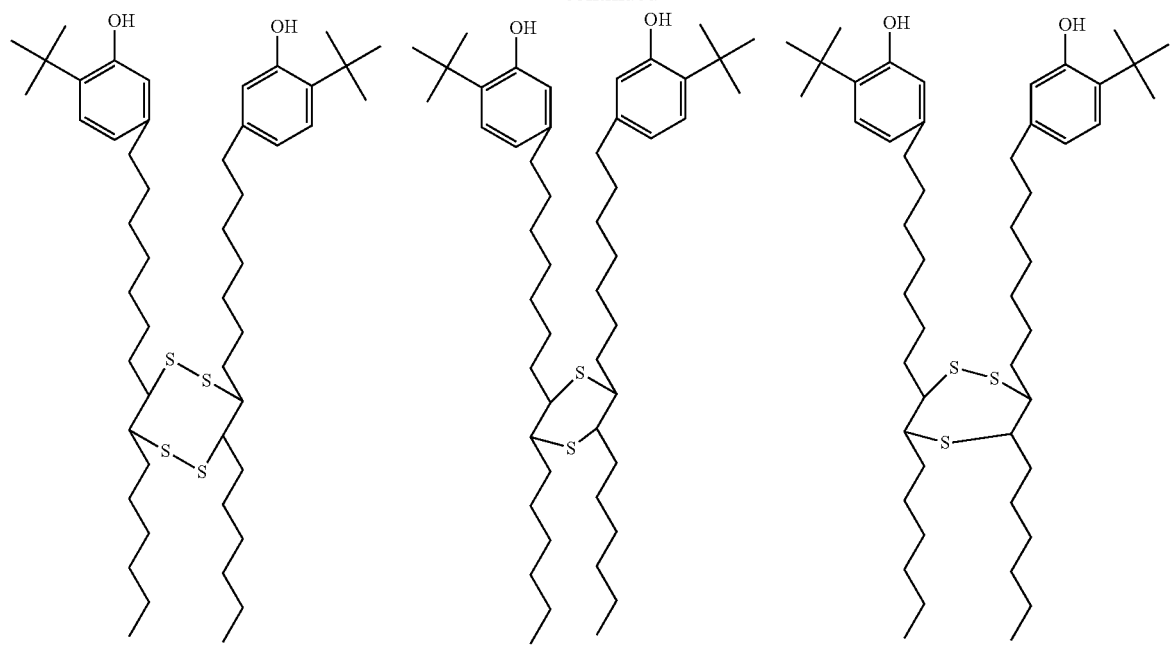
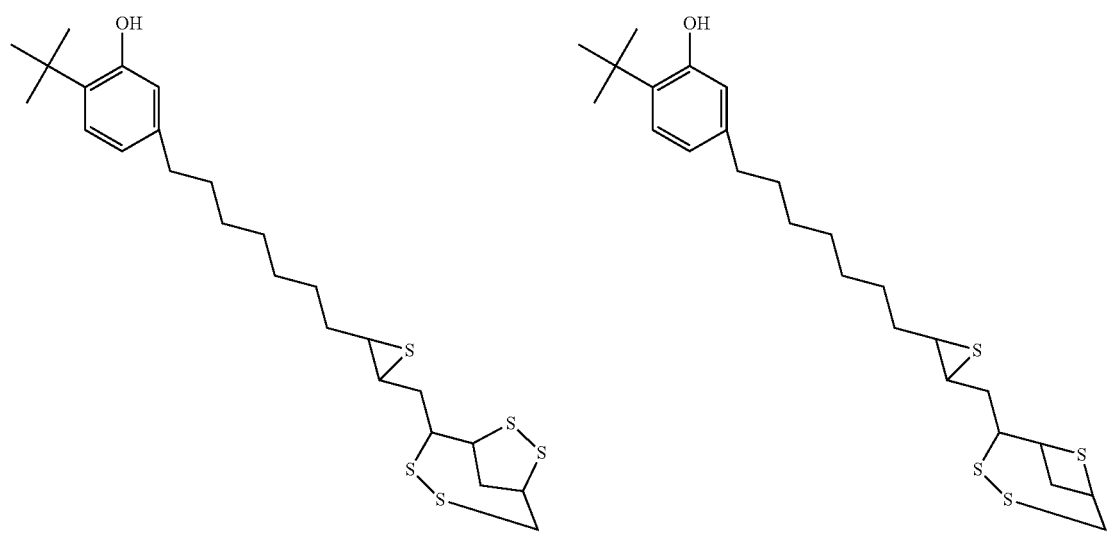

-continued
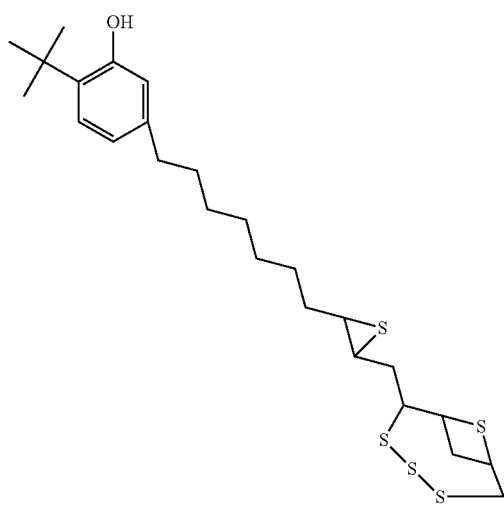
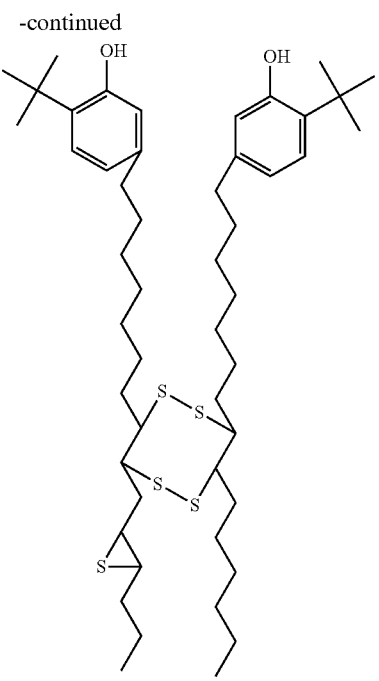
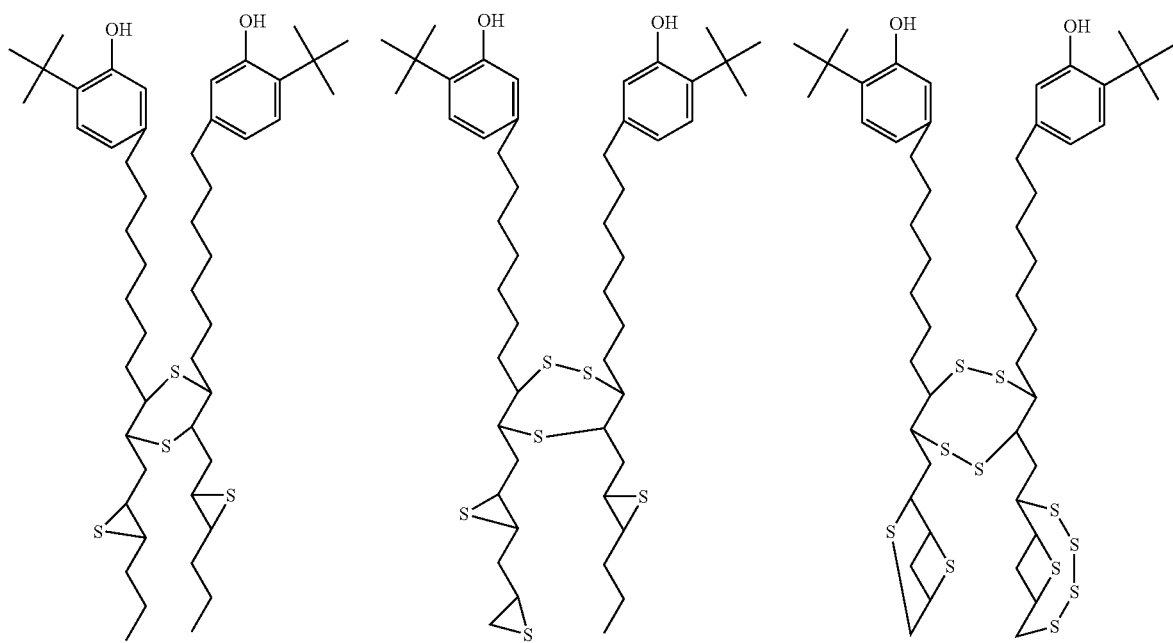

25
26
-continued
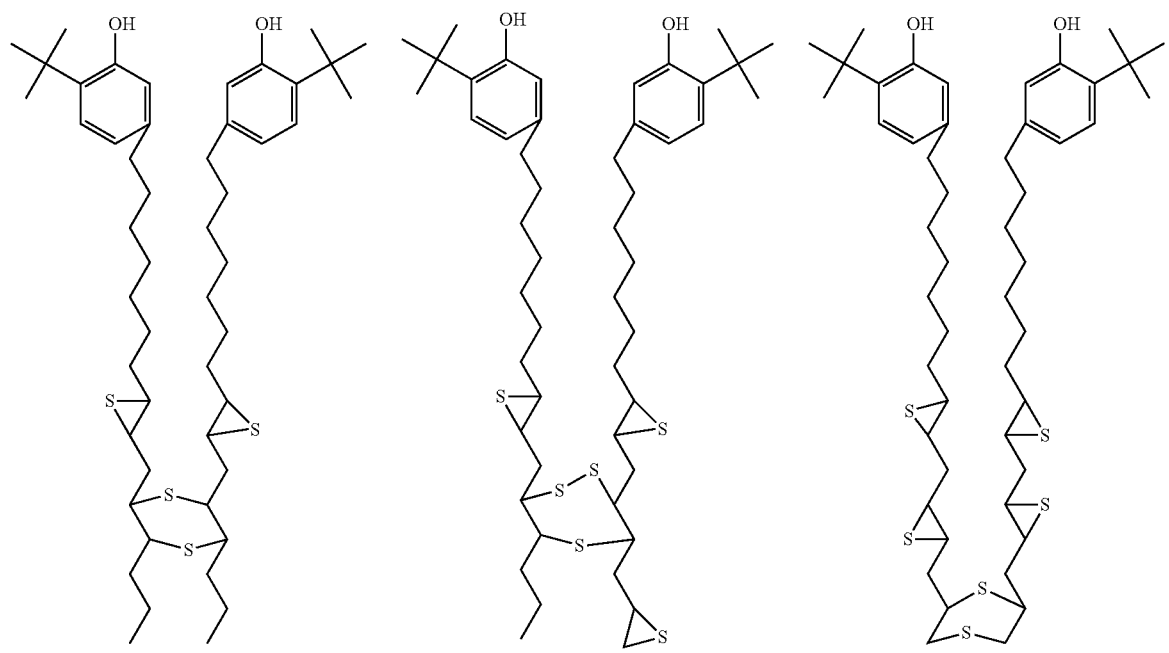
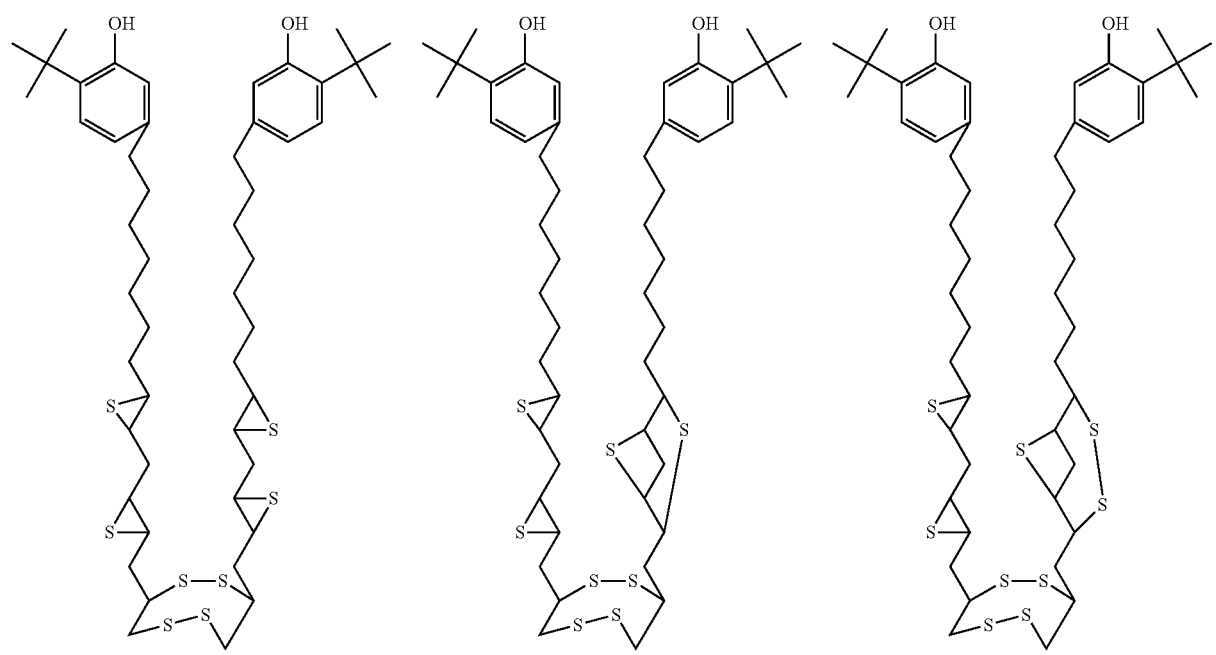

-continued
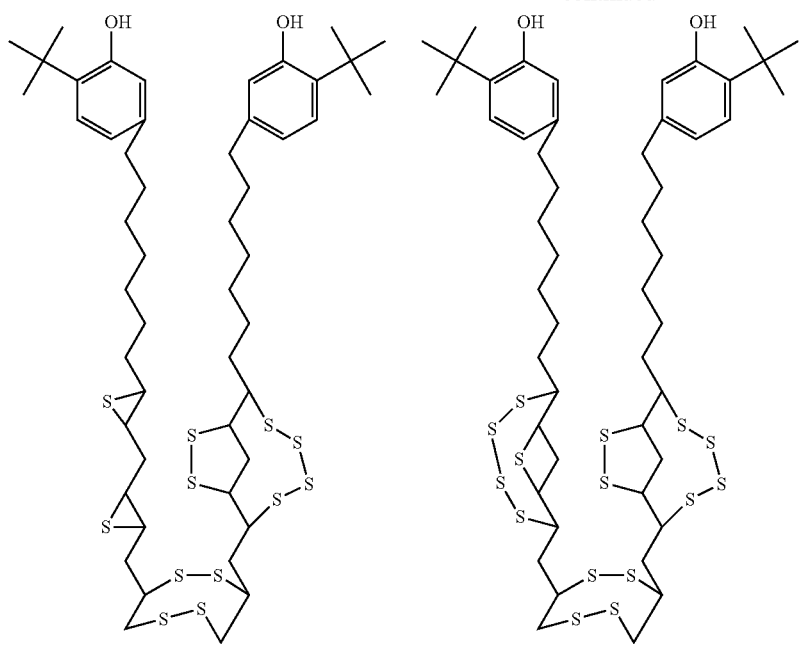
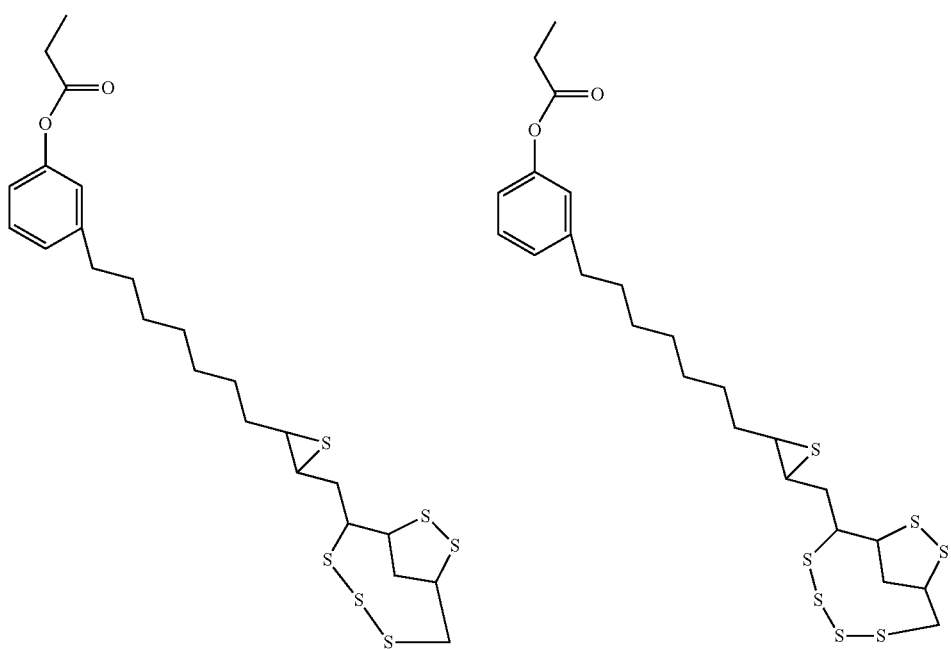

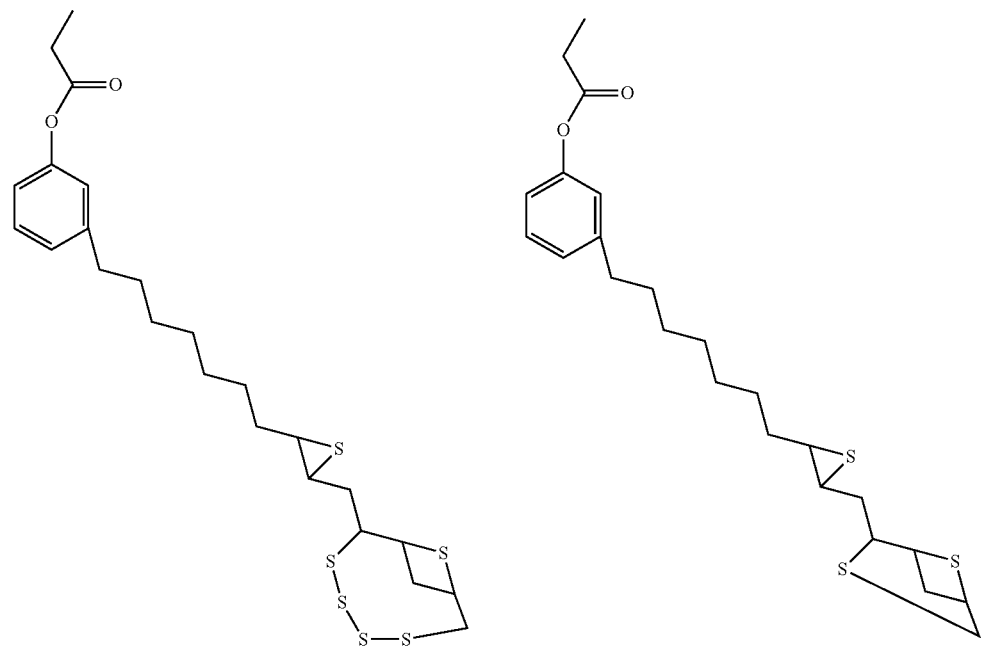 [SMILES: CCC(=O)Oc1cccc(CCCCCCCC2SC2CC2SSSSCC3CC2S3)c1 ; CCC(=O)Oc1cccc(CCCCCCCC2SC2CC2SCC3CC2S3)c1]
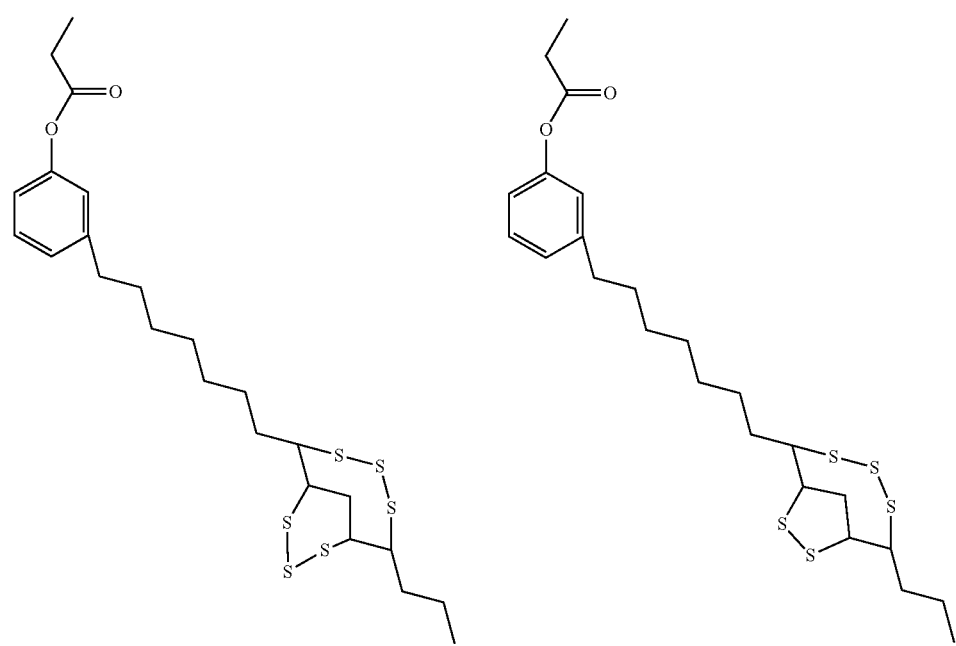

-continued
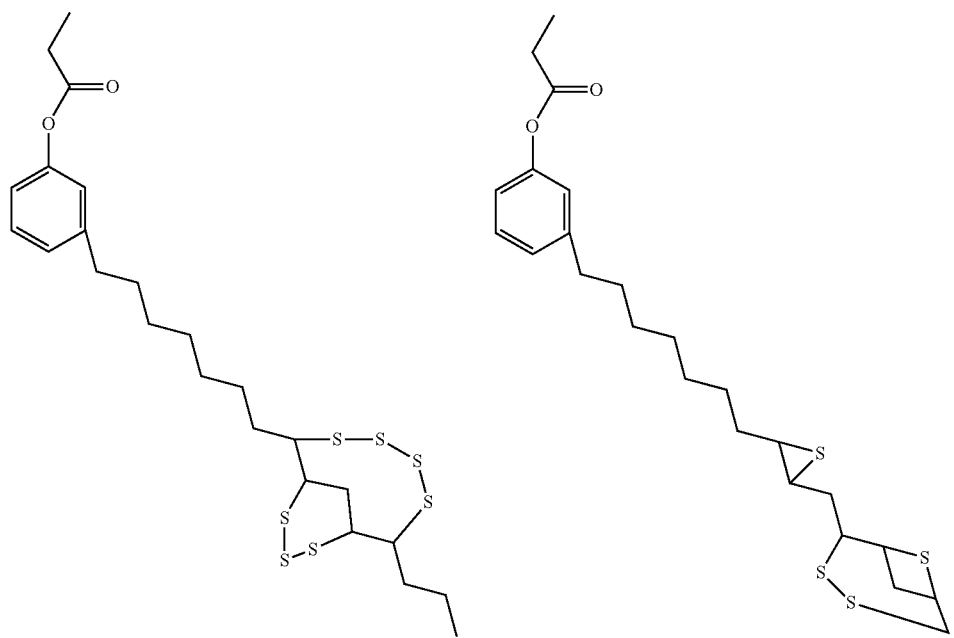
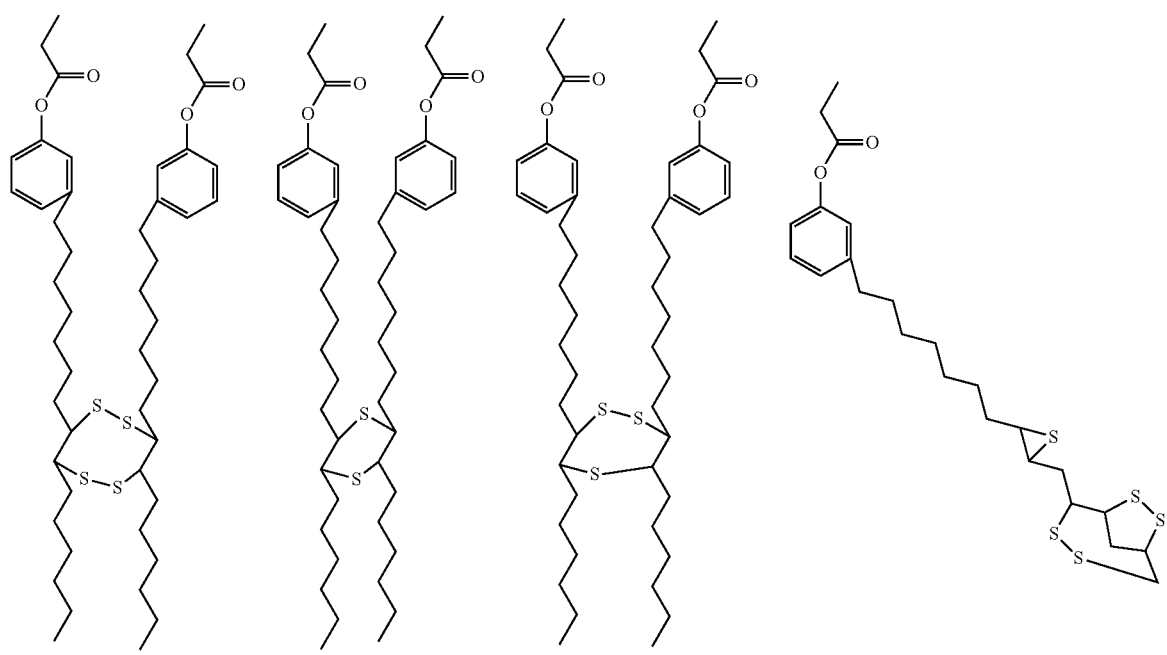

33
34
-continued
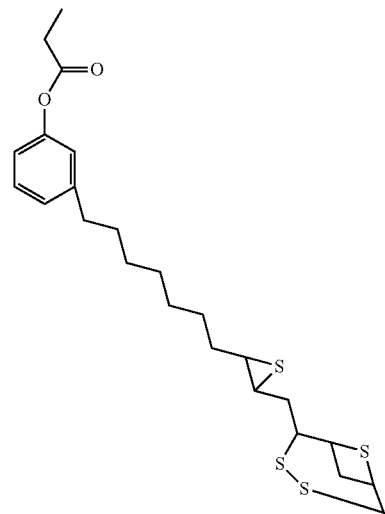
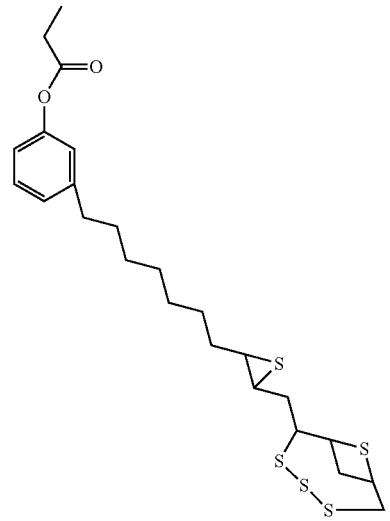
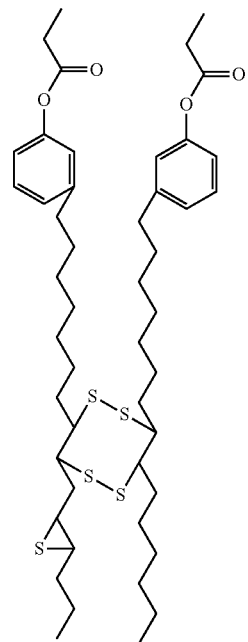
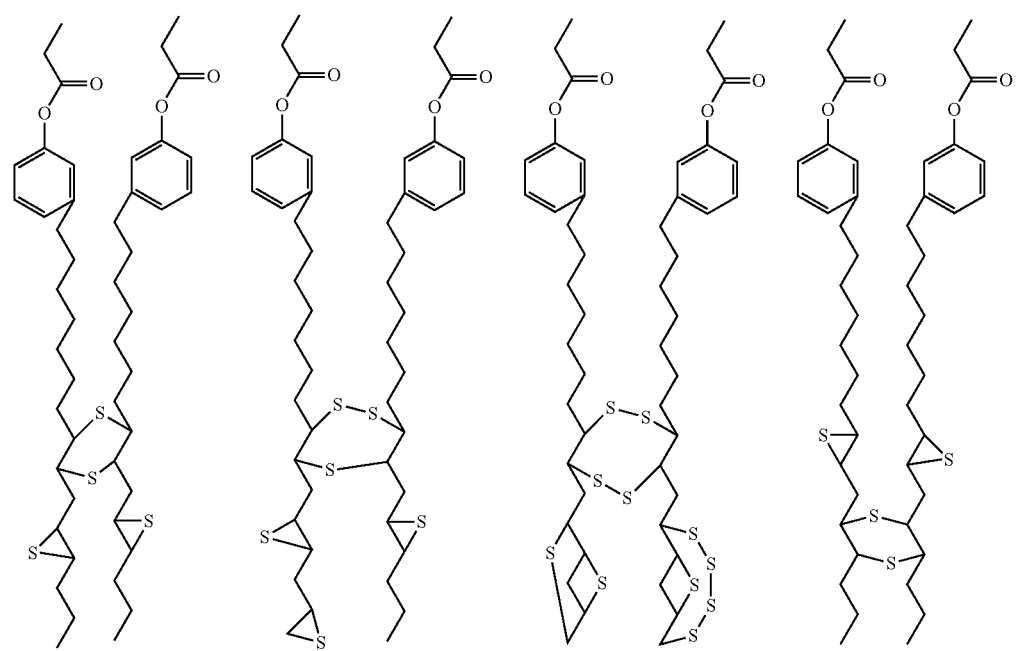

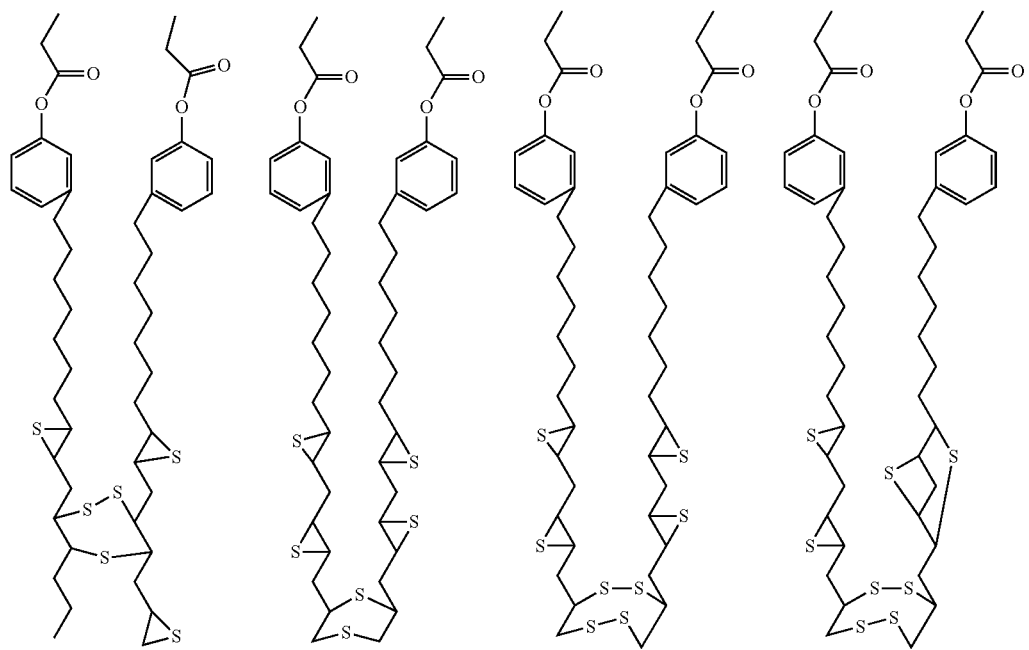
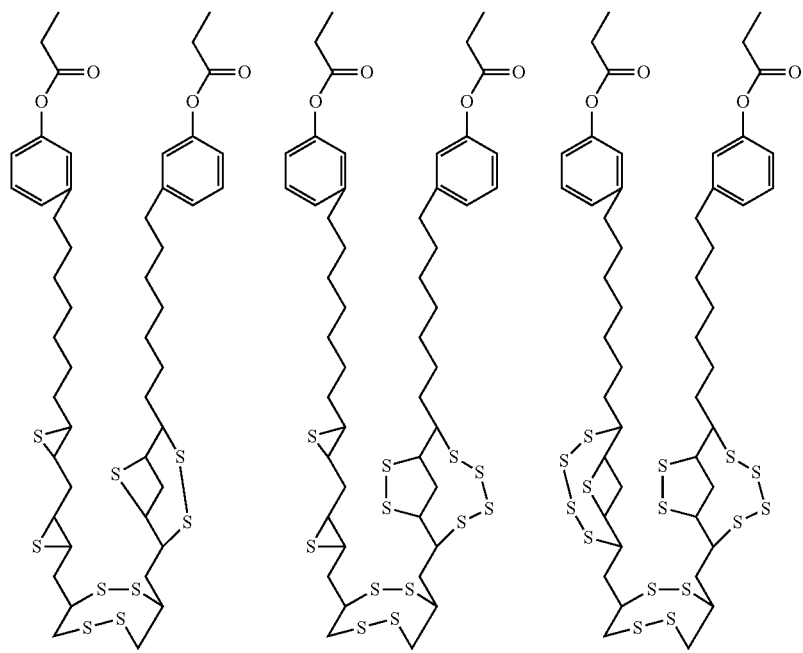 [SMILES: CCC(=O)Oc1cccc(CCCCCCCC2SSC(CC3CSSCC(CC4SC4CC4SC4CCCCCCCc4cccc(OC(=O)CC)c4)SS3)C3CC2S3)c1 ; CCC(=O)Oc1cccc(CCCCCCCC2SSSSC(CC3CSSCC(CC4SC4CC4SC4CCCCCCCc4cccc(OC(=O)CC)c4)SS3)C3CC2SS3)c1 ; CCC(=O)Oc1cccc(CCCCCCCC2SSSSC(CC3CSSCC(CC4SSSSC(CCCCCCCc5cccc(OC(=O)CC)c5)C5CC4S5)SS3)C3CC2SS3)c1]

-continued

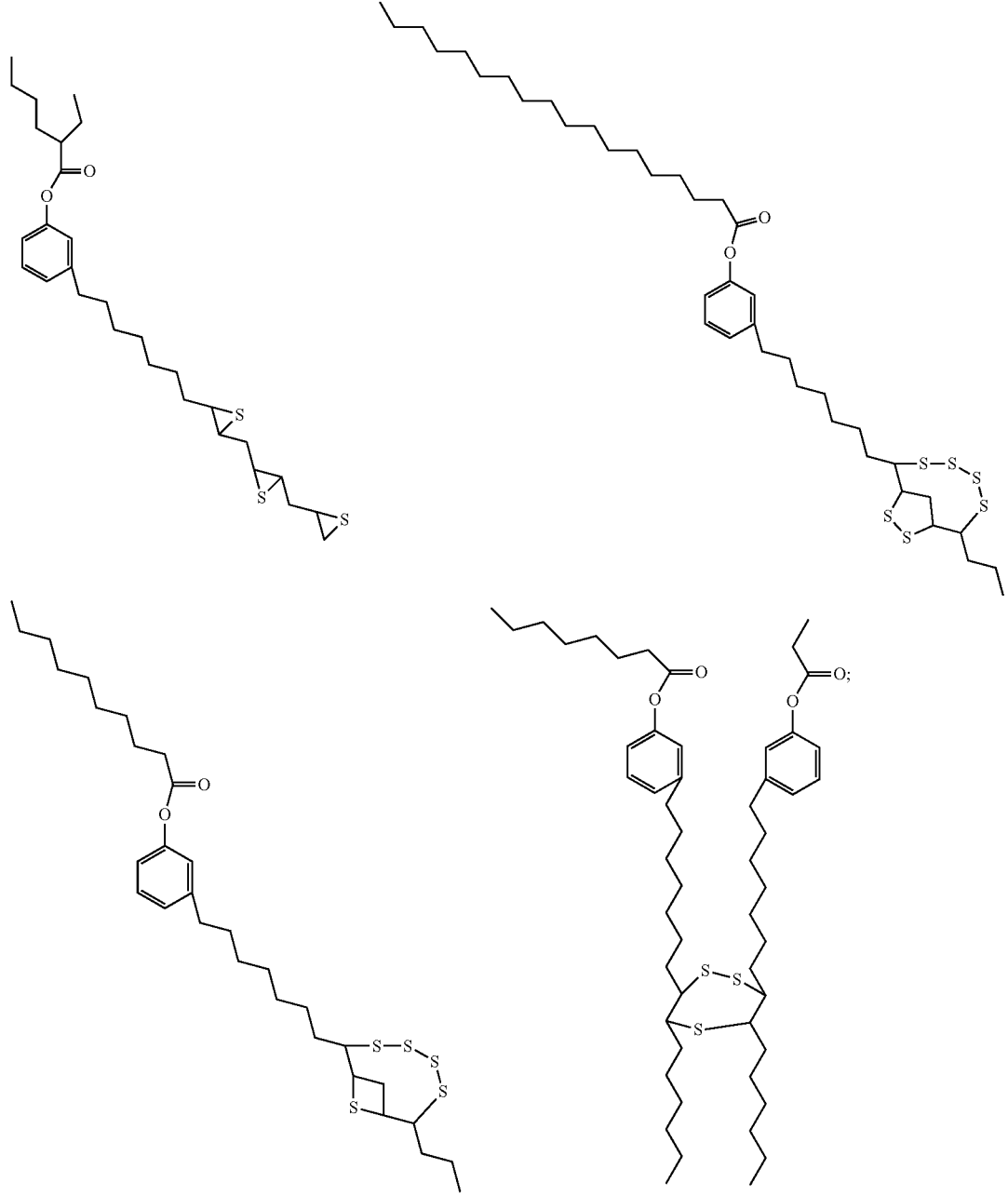

Wherein, $R_0$, $R_2$ and $R_3$ are defined as above (preferably, groups $R_0$ are ethyl, groups $R_2$ are each independently selected from $C_2$-$C_{18}$ alkyl, groups $R_3$ are each independently selected from $C_2$-$C_{18}$ alkyl).

The present invention provides a process of preparing a phenol derivative, which comprises a first step of subjecting the compound represented by the general formula (I') to at least one reaction of an epoxidation reaction, a sulfurization reaction and a coupling reaction, and a second step of subjecting to one or more reactions of an optional esterification reaction, an optional alkylation reaction and an optional hydrogenation reaction;

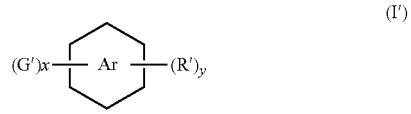

In the formula (I'), x groups G' are bonded to the ring group Ar, y groups R' are bonded to the ring group Ar;

x groups G' are, identical to or different from each other, each independently selected from —OH and H, wherein at least one group G' is -OH; x is selected from an integral number of 1-10 (preferably an integral number of 1-5);

y groups R' are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups, $C_{1-50}$ alkyloxy optionally substituted by one or more substituent groups and a group represented by the formula (II') (preferably selected from hydrogen, $C_{1-50}$ linear or branched alkyl, linear or branched $C_{3-50}$ heteroalkyl, $C_{1-50}$ linear or branched alkyloxy and a group represented by the formula (II')), wherein at least one group R' is selected from a group represented by the formula (II');

(II')

Groups L in y groups R' are each independently selected from single bond, (m+1)-valent $C_{1-50}$ hydrocarbyl optionally substituted by one or more substituent groups and (m+1)-valent $C_{3-50}$ hetero hydrocarbyl optionally substituted by one or more substituent groups (preferably selected from single bond, (m+1)-valent $C_{1-50}$ linear or branched alkyl and (m+1)-valent linear or branched $C_{3-50}$ heteroalkyl); y is selected from an integral number of 1-10 (preferably an integral number of 1-5); m groups A' in the formula (II') are each independently selected from a group represented by the formula (III'); the numbers m in the formula (II') are each independently selected from an integral number of 1-10 (preferably an integral number of 1-5);

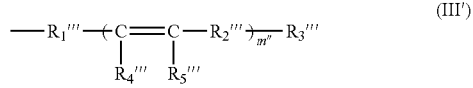

(III')

Wherein group $R_1'''$ is selected from single bond and $C_{1-20}$ linear or branched alkylene (preferably selected from single bond and $C_{1-4}$ linear or branched alkylene); groups $R_2'''$ in m" repeating units are, identical to or different from each other, each independently selected from single bond and $C_{1-20}$ linear or branched alkylene (preferably each independently selected from single bond and $C_{1-4}$ linear or branched alkylene); group $R_3'''$ is selected from hydrogen and $C_{1-20}$ linear or branched alkyl (preferably selected from hydrogen and $C_{1-4}$ linear or branched alkyl); groups $R_4'''$ in m" repeating units are, identical to or different from each other, each independently selected from hydrogen and $C_{1-20}$ linear or branched alkyl (preferably each independently selected from hydrogen and $C_{1-4}$ linear or branched alkyl); groups $R_5'''$ in m" repeating units are, identical to or different from each other, each independently selected from hydrogen and $C_{1-20}$ linear or branched alkyl (preferably each independently selected from hydrogen and $C_{1-4}$ linear or branched alkyl); m" is an integral number of 1-10 (preferably an integral number of 1-5, more preferably an integral number of 1-3);

The ring group

is selected from (x+y)-valent $C_{3-20}$ cycloalkyl (preferably $C_{3-6}$ cycloalkyl, more preferably cyclopentyl, cyclohexyl) and (x+y)-valent $C_{6-20}$ aryl (preferably $C_{6-14}$ aryl, more preferably phenyl, biphenylyl, naphthyl, anthryl, phenanthryl);

The above-mentioned "substituent group" is selected from $C_{1-20}$ alkyl, $C_{1-20}$ alkoxyl, $C_{6-10}$ aryl, hydroxy, amino, mercapto and halogen atom.

In the process of preparing the phenol derivative according to any of the aforesaid aspects, a hydrolyzing reaction is also included after the epoxidation reaction in the first step. In the process of preparing the phenol derivative according to any of the aforesaid aspects, the esterification reaction in the second step is performed after the hydrolyzing reaction step.

The process of preparing the phenol derivative according to any of the aforesaid aspects can also comprise a third step of subjecting to at least one reaction selected from an epoxidation reaction, a sulfurization reaction and a coupling reaction and different from the reactions in the first step.

The phenol compound represented by the general formula (X) of the present invention is preferably derived from cardanol in the cashew nut shell liquid as the natural plant product, which has a structure of:

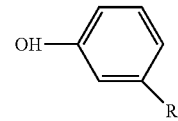

Wherein, R is $C_{15}H_{31+x}$, x is 0, −2, −4 or −6.

According to the process of preparing the phenol derivative of the present invention, in case that one or more reactions of an optional esterification reaction, an optional alkylation reaction and an optional hydrogenation reaction in the second step is performed, either the compound represented by the general formula (I') can be subjected to at least one reaction of an epoxidation reaction, a sulfurization reaction and a coupling reaction in the first step, followed by one or more reactions of an optional esterification reaction, an optional alkylation reaction and an optional hydrogenation reaction in the second step, or the compound represented by the general formula (I') can be subjected to one or more reactions of an optional esterification reaction, an optional alkylation reaction and an optional hydrogenation reaction in the second step, followed by at least one reaction of an epoxidation reaction, a sulfurization reaction and a coupling reaction in the first step. Namely, in the process of preparing the phenol derivative of the present invention, the order between one or more steps of the optional esterification reaction step, the optional alkylation reaction step, and the optional hydrogenation reaction step (the first step) and at least one step selected from the coupling reaction step, the epoxidation reaction step, and the sulfurization reaction step (the second step) is not limited, and can be arbitrarily adjusted according to the requirement. Moreover, in the first step, if the multistep reaction is performed, the order among the optional esterification reaction step, the optional alkylation reaction step, and the optional hydrogenation reaction step is also not limited, and can be arbitrarily adjusted according to the requirement. Moreover, in the second step, if the multistep reaction is performed, the order among the coupling reaction step, the epoxidation reaction step, and the sulfurization reaction step is also not limited, and can be arbitrarily adjusted according to the requirement. It will be appreciated by those skilled in the art that, in the case that the side reaction is reduced as much as possible, the order of the above-mentioned reaction steps can be adjusted.

In addition, the process of preparing the phenol derivative of the present invention can also comprise, a third step of subjecting to at least one reaction selected from an epoxidation reaction, a sulfurization reaction and a coupling reaction and different from the reactions in the first step. The third step can be performed after the first step and before the second step, and can also be performed after the first step and the second step.

The lubricating oil provided by the present invention comprises a base oil and the above phenol derivative of the present invention.

The lubricating grease provided by the present invention comprises a base oil and the above phenol derivative of the present invention.

The base oil of the present invention comprises the above phenol derivative of the present invention. The present invention provides a composition, which contains the above phenol derivative of the present invention.

Invention Effect

The process of preparing the phenol derivative of the present invention is simple and easy to be operated, and has high product yield with high purity. In addition, cardanol can be used as raw material in the present invention, and it is a green raw material and easy to be obtained.

Moreover, the phenol derivative of the present invention is excellent in antioxidation performance and can be used as an excellent antioxidant. The phenol derivative of the present invention is excellent in lubrication performance, antiwear performance and antifriction performance and can provide excellent lubricating oil additives. Moreover, the phenol derivative of the present invention is excellent in viscosity-temperature performance and low temperature performance, and can be used as a high viscosity base oil.

DETAILED DESCRIPTION

Figure 1:
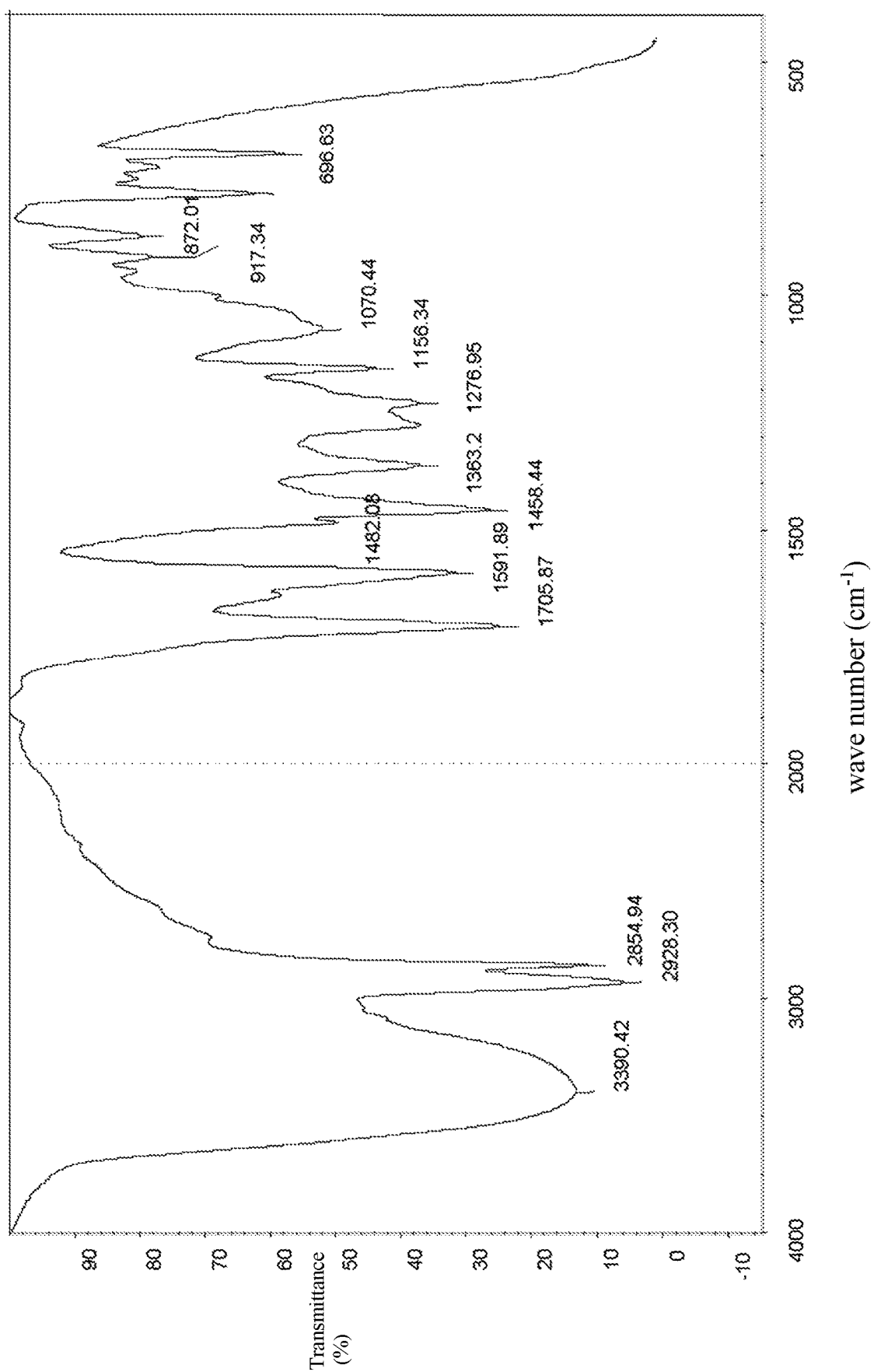
FIG. 1 is the infrared spectrum of the product of Example 1-3.

Reference will now be made in detail to the present embodiments of the present invention, but it should be understood that the scope of the invention is not limited by the embodiments, but is defined by the appended claims.

All publications, patent applications, patents, and other references mentioned in this specification are herein incorporated by reference in their entirety. Unless defined otherwise, all technical and scientific terms used herein have the same meanings as commonly understood by those skilled in the art to which this invention belongs. In case of conflict, the present specification, including definitions, will control.

When the specification derives a material, a substance, a process, a step, a device, an element and the like with the expression such as "known to those skilled in the art", "prior art", or a synonym thereof, it is intended that the objects derived by such a prefix encompasses those having been conventionally used in the art at the time of filing this application, but also includes those which may not be so commonly used at the present time, but will become known in the art as being suitable for a similar purpose.

In the context of this specification, except for what is explicitly stated, any item or matter not mentioned is directly applicable to those known in the art without any changes. Moreover, any of the embodiments described herein can be freely combined with one or more other embodiments described herein, and the resulting technical solutions or technical ideas are regarded as part of the original disclosure or the original record of the present invention, and should not be regarded as new content that has not been disclosed or anticipated in this specification, unless those skilled in the art believe that the combination is obviously unreasonable.

In practicing or testing the present invention, methods and materials similar or equivalent to those described herein can be used, but applicable methods and materials have been described herein.

In the absence of an explicit indication, all percentages, parts, ratios and the like mentioned in this specification are based on the weight, unless the basis on the weight is not consistent with the conventional knowledge of those skilled in the art.

In the context of the present invention, the expression "halo" refers to fluorine, chlorine, bromine or iodine.

In the context of the present invention, the term "hydrocarbyl" has the meaning conventionally known in the art, comprising linear or branched alkyl, linear or branched alkenyl, linear or branched alkynyl, cycloalkyl, cycloalkenyl, cycloalkynyl, aryl or combination groups thereof, preferably linear or branched alkyl, linear or branched alkenyl, cycloalkyl, cycloalkenyl, aryl or combination groups thereof. As the hydrocarbyl group of the present invention, for example, $C_{1-50}$ hydrocarbyl, $C_{1-30}$ hydrocarbyl, $C_{1-20}$ hydrocarbyl, $C_{1-10}$ hydrocarbyl, $C_{1-6}$ hydrocarbyl, $C_{1-4}$ hydrocarbyl can be specifically enumerated, and it includes $C_{1-50}$ linear or branched alkyl, $C_{1-40}$ linear or branched alkyl, $C_{1-30}$ linear or branched alkyl, $C_{1-20}$ linear or branched alkyl, $C_{1-10}$ linear or branched alkyl, $C_{1-6}$ linear or branched alkyl, $C_{1-4}$ linear or branched alkyl; $C_{2-50}$ linear or branched alkenyl, $C_{2-40}$ linear or branched alkenyl, $C_{2-30}$ linear or branched alkenyl, $C_{2-20}$ linear or branched alkenyl, $C_{2-10}$ linear or branched alkenyl, $C_{2-6}$ linear or branched alkenyl, $C_{2-4}$ linear or branched alkenyl, $C_{2-50}$ linear or branched alkynyl, $C_{2-40}$ linear or branched alkynyl, $C_{2-30}$ linear or branched alkynyl, $C_{2-20}$ linear or branched alkynyl, $C_{2-10}$ linear or branched alkynyl, $C_{2-6}$ linear or branched alkynyl, $C_{2-4}$ linear or branched alkynyl, $C_{3-50}$ cycloalkyl, $C_{3-40}$ cycloalkyl, $C_{3-30}$ cycloalkyl, $C_{3-20}$ cycloalkyl, $C_{3-10}$ cycloalkyl, $C_{3-8}$ cycloalkyl, $C_{3-6}$ cycloalkyl, $C_{3-50}$ cycloalkenyl, $C_{3-40}$ cycloalkenyl, $C_{3-30}$ cycloalkenyl, $C_{3-20}$ cycloalkenyl, $C_{3-10}$ cycloalkenyl, $C_{3-8}$ cycloalkenyl, $C_{3-6}$ cycloalkenyl, $C_{3-50}$ cycloalkynyl, $C_{3-40}$ cycloalkynyl, $C_{3-30}$ cycloalkynyl, $C_{3-20}$ cycloalkynyl, $C_{3-10}$ cycloalkynyl, $C_{3-8}$ cycloalkynyl, $C_{3-6}$ cycloalkynyl, $C_{6-50}$ aryl, $C_{6-40}$ aryl, $C_{6-30}$ aryl, $C_{6-20}$ aryl, $C_{6-10}$ aryl or combination groups thereof, wherein preferably $C_{1-50}$ linear or branched alkyl, $C_{2-50}$ linear or branched alkenyl, $C_{3-50}$ cycloalkyl, $C_{3-50}$ cycloalkenyl, $C_{6-50}$ aryl or combination groups thereof. The combination group includes a group obtained by bonding or substituting of one or more groups selected from linear or branched alkyl, linear or branched alkenyl, linear or branched alkynyl, cycloalkyl, cycloalkenyl, cycloalkynyl and aryl, as mentioned above. Said bonding refers to that one group and other one or more groups form chemical bond(s) (preferably covalent bond(s)). Said substituting refers to one group as substituent group replaces the hydrogen atom in the other group. As said combination group, for example, a group obtained by bonding or substituting of one or more $C_{1-50}$ linear or branched alkyl groups (preferably one or more $C_{1-20}$ linear or branched alkyl groups) and one or more $C_{6-50}$ aryl groups (preferably one or more phenyl or naphthyl groups), a group obtained by bonding or substituting of one or more $C_{1-50}$ linear or branched alkenyl groups (preferably one or more $C_{1-20}$ linear or branched alkenyl groups) and one or more $C_{6-50}$ aryl groups (preferably one or more phenyl or naphthyl groups), a group obtained by bonding or substituting of one or more $C_{1-50}$ linear or branched alkyl groups (preferably one or more $C_{1-20}$ linear or branched alkyl groups) and one or more $C_{3-50}$ cycloalkyl groups (preferably one or more cyclobutyl, cyclopentyl or cyclohexyl groups), a group obtained by bonding or substituting of one or more $C_{1-50}$ linear or branched alkenyl groups (preferably one or more $C_{1-20}$ linear or branched alkenyl groups) and one or more $C_{3-50}$ cycloalkyl groups (preferably one or more cyclobutyl, cyclopentyl or cyclohexyl groups), a group obtained by bonding or substituting of one or more $C_{1-50}$ linear or branched alkyl groups (preferably one or more $C_{1-20}$ linear or branched alkyl groups) and one or more $C_{3-50}$ cycloalkenyl groups (preferably one or more cyclobutenyl, cyclobutadienyl, cyclopentenyl, cyclopentadienyl, cyclohexenyl or cyclohexadienyl groups), a group obtained by bonding or substituting of one or more $C_{1-50}$ linear or branched alkenyl groups (preferably one or more $C_{1-20}$ linear or branched alkenyl groups) and one or more $C_{3-50}$ cycloalkenyl groups (preferably one or more cyclobutenyl, cyclobutadienyl, cyclopentenyl, cyclopentadienyl, cyclohexenyl or cyclohexadienyl groups) can be enumerated, but not limited thereto. As the combination group, for example one or more $C_{1-50}$ linear or branched alkyl phenyl groups, one or more phenyl $C_{1-50}$ linear or branched alkyl groups or one or more groups of $C_{1-50}$ linear or branched alkyl phenyl bonded to $C_{1-50}$ linear or branched alkyl and the like can be further enumerated, among others $C_{1-50}$ linear or branched alkyl phenyl (for example tert-butyl phenyl), phenyl $C_{1-50}$ linear or branched alkyl (for example benzyl) or $C_{1-50}$ linear or branched alkyl phenyl bonded to $C_{1-50}$ linear or branched alkyl (for example tert-butyl benzyl) can also be enumerated.

In the context of the present invention, the term "hetero hydrocarbyl" refers to a group obtained by directly substituting one or more (such as 1-4, 1-3, 1-2 or 1) —$CH_2$— groups within the hydrocarbyl molecule structure (excluding the ends of the main chain or any side chains in the hydrocarbyl molecule structure) for a substituent group selected from —O—, —S—, —N=N— and —NR— (where R' is H or $C_{1-4}$ linear or branched alkyl) or by directly substituting one or more (for example 1-4, 1-3, 1-2 or 1) —CH= groups within the hydrocarbyl molecule structure (excluding the ends of the main chain or any side chains in the hydrocarbyl molecule structure) for a substituent group —N=. Obviously, from the viewpoint of structure stability, when a plurality of substituent groups are present, the substituent groups are not directly bonded to each other; and only when a plurality of —S— groups are present, these —S— groups may be directly bonded to each other. As said substituent group, it is preferably selected from —O— and —S—. In addition, although the carbon atom number of the hydrocarbyl group is reduced by the substitution for the group —$CH_2$— or the group —CH=, for the sake of convenience, the carbon atom number of the hydrocarbyl group before the substitution is referred to as the carbon atom number of the hetero hydrocarbyl group. For example, as the hetero hydrocarbyl, taking the linear or branched heteroalkyl as an example, the $c_4$ linear alkyl for example

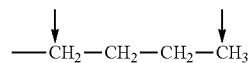

(wherein the groups indicated by the arrows are not inside the molecule structure but at the end of the main chain) is subjected to a direct substitution of one substituent group —O—, resulting in

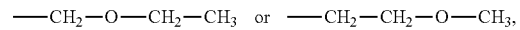

referred to as the $C_4$ linear heteroalkyl. Alternatively, the $c_4$ branched alkyl such as

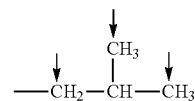

(the groups indicated by the arrows in the formula are not within the molecule structure but at the end of the main chains and side chains) is subjected to a direct substitution of one substituent group —N=, which will result in

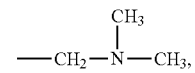

referred to as $c_4$ branched heteroalkyl.

In addition, the so-called "hetero hydrocarbyl" includes linear or branched heteroalkyl, linear or branched hetero alkenyl, linear or branched hetero alkynyl, linear or branched heterocyclyl, linear or branched hetero cycloalkenyl, linear or branched hetero cycloalkynyl, linear or branched heteroaryl or a combination group thereof, among others, preferably linear or branched heteroalkyl, linear or branched hetero alkenyl, linear or branched heterocyclyl, linear or branched hetero cycloalkenyl, linear or branched heteroaryl or a combination group thereof. According to the present invention, as the hetero hydrocarbyl, for example, $C_{3-50}$ hetero hydrocarbyl, $C_{3-40}$ hetero hydrocarbyl, $C_{3-30}$ hetero hydrocarbyl, $C_{3-20}$ hetero hydrocarbyl, $C_{3-10}$ hetero hydrocarbyl, $C_{3-8}$ hetero hydrocarbyl, $C_{3-6}$ hetero hydrocarbyl can be enumerated, among others preferably $C_{3-20}$ linear or branched heteroalkyl or $C_{3-6}$ linear or branched heteroalkyl.

In the context of the present specification, the expression "number+valence+group" or similar terms refers to a group obtained by removeing an amount represented by the number of hydrogen atoms from a basic structure (chain, ring or combination thereof and the like) to which the group corresponds, and preferably refers to a group obtained by removing an amount represented by the number of hydrogen atoms attached to the carbon atoms contained in the structure (preferably saturated carbon atoms and/or different carbon atoms). For example, "trivalent linear or branched alkyl" refers to a group obtained by removing three hydrogen atoms from the linear or branched alkane (namely the basic structure to which the linear or branched alkyl corresponds); and "divalent linear or branched heteroalkyl" then refers to a group obtained by removing two hydrogen atoms from the linear or branched hetero alkane (preferably removing the hydrogen atoms attached to the carbon atoms contained in the hetero alkane, or further, removing the hydrogen atoms attached to different carbon atoms). For example, divalent propyl can be *—$CH_2$—$CH_2$—$CH_2$—*,

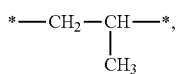

trivalent propyl can be

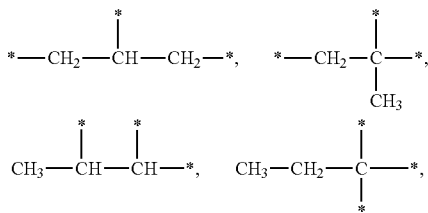

tetravalent propyl can be

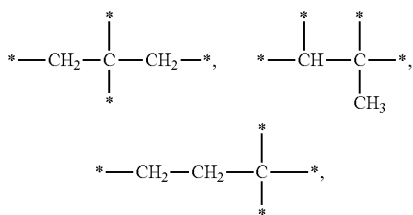

wherein * represents the attachment end that can be bonded to the other moiety in this group.

In the context of the present specification, a hydrocarbyl or hetero hydrocarbyl group substituted by a substituent group or the like refers to a hydrocarbyl or heterohydrocarbyl group obtained by substituting a substituent group for a hydrogen atom in the hydrocarbyl or heterohydrocarbyl group.

The substituent group is preferably selected from $C_{1-20}$ alkyl, $C_{1-20}$ alkoxyl, $C_{6-10}$ aryl, hydroxy, amino, mercapto and halogen atom.

In the context of the present specification, a hydrocarbyl or hetero hydrocarbyl group substituted by one or more (for example 1-5, 1-4, 1-3, 1-2 or 1) substituent groups or the like refers to a hydrocarbyl or hetero hydrocarbyl group obtained by substituting one or more substituent groups for a hydrogen atom in the hydrocarbyl or heterohydrocarbyl group. In the present invention, the substituent group is preferably selected from $C_{1-20}$ alkyl, $C_{1-20}$ alkoxyl, $C_{6-10}$ aryl, hydroxy, amino, mercapto and halogen atom.

In the context of the present specification, a hydrocarbyl or hetero hydrocarbyl group optionally substituted by one or more (for example 1-5, 1-4, 1-3, 1-2 or 1) substituent groups or the like refers to either a hydrocarbyl or hetero hydrocarbyl group obtained by substituting one or more substituent groups for a hydrogen atom in the hydrocarbyl or heterohydrocarbyl group, or a hydrocarbyl or hetero hydrocarbyl group that is not substituted by the substituent group. In the present invention, the substituent group is preferably selected from $C_{1-20}$ alkyl, $C_{1-20}$ alkoxyl, $C_{6-10}$ aryl, hydroxy, amino, mercapto and halogen atom.

In this specification, the term "single bond" is sometimes used in the definition of a group. The so-called "single bond" means that the group does not exist. For example, assuming the structural formula —$CH_2$-A-$CH_3$, where group A is defined to be selected from single bond and methyl. In view of this, if A is single bond, it means that the group A does not exist, and the structural formula is correspondingly simplified to —$CH_2$—$CH_3$.

In the context of the present specification, the alkyl group represents a group obtained by removing one hydrogen atom from the alkane without violating the valence, and preferably a group obtained by removing one hydrogen atom attached to one terminal carbon atom from the alkane. In the present invention, the alkyl can be $C_{1-300}$ linear or branched alkyl, $C_{1-30}$ linear or branched alkyl, $C_{1-20}$ linear or branched alkyl, $C_{1-10}$ linear or branched alkyl, $C_{1-6}$ linear or branched alkyl, $C_{1-4}$ linear or branched alkyl. It can be those enumerated as the hydrocarbyl hereinabove. As the specific examples of these alkyl groups, methyl, ethyl, propyl, isopropyl, butyl, sec-butyl, tert-butyl, pentyl, isopentyl, hexyl, heptyl, octyl, nonyl, decyl, undecyl, dodecyl, tridecyl, tetradecyl, pentadecyl, hexadecyl and isomers thereof, and the like can be enumerated, but not limited thereto.

In the context of the present specification, the alkylene group represents a group obtained by removing two hydrogen atoms from the alkane without violating the valence, and preferably a group obtained by removing each one hydrogen atom attached to two different carbon atoms, and more preferably a group obtained by removing each one hydrogen atom attached to two terminal carbon atoms from the alkane. In the present invention, the alkylene group can be $C_{1-20}$ linear or branched alkylene, $C_{1-10}$ linear or branched alkylene, $C_{1-6}$ linear or branched alkylene, $C_{1-4}$ linear or branched alkylene, $C_{1-3}$ linear or branched alkylene. As the specific example of these alkyl groups, the groups obtained by further removing one hydrogen atom from the groups of the specific examples of the above-mentioned alkyl group can be enumerated, but not limited thereto.

In the context of the present specification, the aryl group means a group obtained by removing one hydrogen atom from the aromatic hydrocarbon without violating the valence. The aryl group of the present invention can be $C_{6-20}$ aryl, $C_{6-16}$ aryl, $C_{6-10}$ aryl. It can be those enumerated as the hydrocarbyl hereinabove. As the specific examples of these aryl groups, phenyl, biphenyl, naphthyl, fluorenyl, phenanthryl, anthryl, and the like can be enumerated, but not limited thereto.

In the context of the present specification, the arylene group means a group obtained by removing two hydrogen atoms from the aromatic hydrocarbon without violating the valence. The arylene of the present invention can be $C_{6-20}$ arylene, $C_{6-16}$ arylene, $C_{6-10}$ arylene. As the specific example of these arylene groups, phenylene, biphenylene, naphthylidene, fluorenylidene, phenanthrylene, anthrylene, and the like, may be enumerated, but not limited thereto.

In the context of the present specification, the alkylaryl (arylalkyl) group means a group obtained by removing one hydrogen atom from the alkyl aromatic hydrocarbon without violating the valence. It can be a group obtained by removing one hydrogen atom from the aryl moiety of the alkyl aromatic hydrocarbon, therefore an alkyl aryl group can be formed (namely the attachment to the other moiety is via the alkyl group); or a group obtained by removing one hydrogen atom from the alkyl moiety of the alkyl aromatic hydrocarbon, therefore an aryl alkyl group can be formed (namely the attachment to the other moiety is via the aryl group). That is, the alkylaryl group of the present invention may be an alkyl aryl---* or an aryl alkyl---* (where * represents an attachment end in this group that can be bonded to the other group). Preferred is a group obtained by removing one hydrogen atom from the alkyl moiety of an aryl alkane. Among others, the alkyl moiety may be a straight chain alkyl group. In the present invention, the alkylaryl group may be a group obtained by substituting any of the above-mentioned aryl groups for any of the above-mentioned alkyl groups, or may be a group obtained by substituting any of the above-mentioned alkyl groups for any of the above-mentioned aryl groups. At this time, the carbon atom number of the alkyl group and the carbon atom number of the aryl group are each independently represented. For example, $C_{1-6}$ linear or branched alkyl $C_{6-10}$ aryl represents a group formed by the bonding of $C_{1-6}$ linear or branched alkyl and $C_{6-10}$ aryl, $C_{1-6}$ linear or branched alkyl phenyl represents a group formed by the bonding of $C_{1-6}$ linear or branched alkyl and phenyl. As the specific example of the alkylaryl group, benzyl, phenylethyl, phenylpropyl, dimethylphenyl, naphthylmethyl, naphthylethyl and the like can be enumerated, but not limited thereto.

However, in the present invention, when the number of carbon atoms of the aryl group is not indicated (or the number of carbon atoms of the aryl group is unknown), the number of carbon atoms preceding the group means the number of all carbon atoms of the arylalkyl group. For example, $C_{13-20}$ alkylaryl means the total carbon atom number of alkyl and aryl is 13-20. Similarly, $C_{13-20}$ arylalkylaryl represents the total carbon atom number of aryl+alkyl+aryl is 13-20 carbon atoms, in which case the arylalkyl group can be considered to be substituted by aryl, and the total carbon atom number is 13-20.

In the context of the present specification, the alkylenearyl (arylenealkyl) group means a group obtained by removing two hydrogen atoms from the alkyl aromatic hydrocarbon without violating the valence. Preferred is a group formed by removing each one hydrogen atom attached to two different carbon atoms, more preferably a group formed by removing each one hydrogen atom attached to two carbon atoms from the alkyl moiety of the aryl alkane. In the present invention, the alkylenearyl group can be a group obtained by further removing one hydrogen atom from the above-mentioned alkylaryl (arylalkyl) group. As the specific example of these alkylenearyl groups, the groups such as phenylenemethyl, phenyleneethyl, phenylenepropyl can be enumerated, but not limited thereto.

In the context of the present specification, the alkyloxy represents a group obtained by the bonding of the above-mentioned alkyl moiety and "—O—". In the present invention, the alkyloxy can be $C_{1-30}$ linear or branched alkoxyl, $C_{1-20}$ linear or branched alkoxyl, $C_{1-10}$ linear or branched alkoxyl, $C_{1-6}$ linear or branched alkoxyl, $C_{1-4}$ linear or branched alkoxyl. As the specific examples of these alkyloxy groups, methyloxy, ethyloxy, propyloxy, isopropyloxy, butyloxy, sec-butyloxy, tert-butyloxy, pentyloxy, isopentyloxy, hexyloxy, heptyloxy, octyloxy, nonyloxy, decyloxy, undecyloxy, dodecyloxy, tridecyloxy, tetradecyloxy, pentadecyloxy, hexadecyloxy and isomers thereof can be enumerated, but not limited thereto.

In the context of the present specification, the cycloalkyl group means a group obtained by removing one hydrogen atom from a cycloalkane without violating the valence. In the present invention, cycloalkyl can be $C_{3-50}$ cycloalkyl, $C_{3-40}$ cycloalkyl, $C_{3-30}$ cycloalkyl, $C_{3-20}$ cycloalkyl, $C_{3-10}$ cycloalkyl, $C_{3-8}$ cycloalkyl, $C_{3-6}$ cycloalkyl.

In the context of the present specification, the cycloalkenyl group represents a group having at least one carbon-carbon double bond, for example 1, 2, 3 and 4 carbon-carbon double bonds, preferably 1 or 2 double bonds, on the ring of the above-mentioned cycloalkyl group.

In the context of the present specification, the cycloalkynyl group represents a group having at least one carbon-carbon triple bond, for example 1, 2, 3 and 4 carbon-carbon triple bonds, preferably 1 or 2 carbon-carbon triple bonds, on the ring of the above-mentioned cycloalkyl group.

In the context of the present specification, the alkenyl group represents a group having at least one carbon-carbon double bond, for example 1, 2, 3, 4 and 5 carbon-carbon double bonds, preferably 1 or 2 carbon-carbon double bonds, in the above-mentioned alkyl group. The carbon atom number of the alkenyl group is at least 2.

In the context of the present specification, the alkynyl group represents a group having at least one carbon-carbon triple bond, for example 1, 2, 3, 4 and 5 carbon-carbon triple bonds, preferably 1 or 2 carbon-carbon triple bonds, in the above-mentioned alkyl group. The carbon atom number of the alkynyl group is at least 2.

The integral number of the present invention can be an integral number of 0 or more, it can be an integral number between 0-30, specifically, it can be 0, 1, 2, 3, 4, 5, 6, 7, 8, 9, 10, 11, 12, 13, 14, 15, 16, 17, 18, 19, 20; preferably 0, 1, 2, 3, 4, 5, 6, 7, 8, 9, 10; more preferably 0, 1, 2, 3, 4, 5.

[Phenol derivative] The present invention provides a phenol derivative, which has a structure as represented by the formula (I):

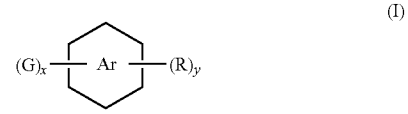

(I)

In the formula (I), x groups G are bonded to the ring group Ar, y groups R are bonded to the ring group Ar;

x groups G are, identical to or different from each other, each independently selected from —OH,

and —$OR_0$, wherein groups $R_0$ are each independently selected from $C_{1-50}$ hydrocarbyl optionally substituted by one or more substituent groups, $C_{6-20}$ aryl substituted by one or more substituent groups and $C_{3-50}$ hetero hydrocarbyl optionally substituted by one or more substituent groups; x is selected from an integral number of 1-10;

y groups R are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups, $C_{1-50}$ alkoxyl optionally substituted by one or more substituent groups and a group represented by the formula (II), wherein at least one group R is selected from a group represented by the formula (II);

  (II)

Groups L in y groups R are each independently selected from single bond, (m+1)-valent $C_{1-50}$ hydrocarbyl optionally substituted by one or more substituent groups and (m+1)-valent $C_{3-50}$ hetero hydrocarbyl optionally substituted by one or more substituent groups; y is selected from an integral number of 1-10 (preferably an integral number of 1-5);

m groups A in formula (II) are each independently selected from a group represented by the formula (III), a group represented by the formula (IV), a group represented by the formula (V), a group represented by the formula (VI), a group represented by the formula (VII) and a group represented by the formula (VIII); the numbers m in formula (II) are each independently selected from an integral number of 1-10;

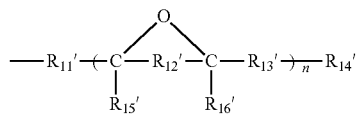  (III)

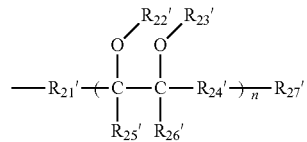  (IV)

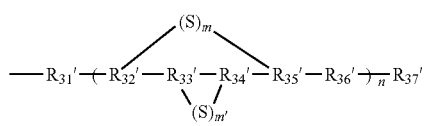  (V)

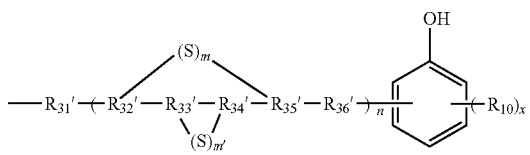  (VI)

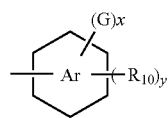  (VII)

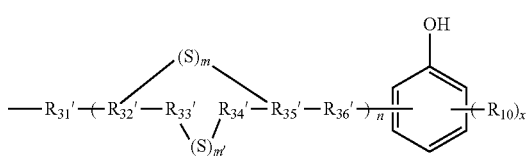  (VIII)

In the formula (III), $R_{11}'$ is selected from single bond and $C_{1-20}$ linear or branched alkylene (preferably selected from single bond and $C_{1-4}$ linear or branched alkylene); groups $R_{12}'$ in n repeating units are, identical to or different from each other, each independently selected from single bond and $C_{1-20}$ linear or branched alkylene (preferably each independently selected from single bond and $C_{1-4}$ linear or branched alkylene); groups $R_{13}'$ in n repeating units are, identical to or different from each other, each independently selected from single bond and $C_{1-20}$ linear or branched alkylene (preferably each independently selected from single bond and $C_{1-4}$ linear or branched alkylene); $R_{14}'$ is selected from hydrogen and $C_{1-20}$ linear or branched alkyl (preferably selected from hydrogen and $C_{1-4}$ linear or branched alkyl); groups $R_{15}'$ in n repeating units are, identical to or different from each other, each independently selected from hydrogen and $C_{1-20}$ linear or branched alkyl (preferably each independently selected from hydrogen and $C_{1-4}$ linear or branched alkyl); groups $R_{16}'$ in n repeating units are, identical to or different from each other, each independently selected from hydrogen and $C_{1-20}$ linear or branched alkyl (preferably each independently selected from hydrogen and $C_{1-4}$ linear or branched alkyl); n is an integral number of 1-10 (preferably an integral number of 1-3);

In the formula (IV), group $R_{21}'$ is selected from single bond and $C_{1-20}$ linear or branched hydrocarbylene (preferably selected from single bond and $C_{1-4}$ linear or branched alkylene); groups $R_{22}'$ and $R_{23}'$ in n repeating units are, identical to or different from each other, each independently selected from

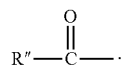

and hydrogen (preferably each independently

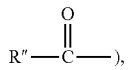

wherein R" is $C_{1-30}$ linear or branched alkyl (preferably selected from $C_{1-20}$ linear or branched alkyl); in each repeating unit, at least one group of groups $R_{22}'$ and $R_{23}'$ is

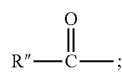

groups $R_{24}'$ in n repeating units are, identical to or different from each other, each independently selected from single bond and $C_{1-20}$ linear or branched hydrocarbylene (preferably each independently selected from single bond and $C_{1-4}$ linear or branched alkylene); groups $R_{25}'$ and $R_{26}'$ in n repeating units are, identical to or different from each other, each independently selected from hydrogen and $C_{1-20}$ linear or branched alkyl (preferably each independently selected from hydrogen and $C_{1-4}$ linear or branched alkyl); group $R_{27}'$ is selected from hydrogen and $C_{1-20}$ linear or branched hydrocarbyl (preferably selected from hydrogen and $C_{1-10}$ linear or branched alkyl); n is a positive integer (preferably a positive integral number of 1-30, more preferably a positive integral number of 1-5);

In the formula (V) and the formula (VI), group $R_{31}'$ is each independently selected from single bond and $C_{1-20}$ linear or branched alkylene (preferably selected from single bond and $C_{1-4}$ linear or branched alkylene); groups $R_{32}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{33}'$ in n repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{34}'$ in n repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{35}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{36}'$ in n repeating units are, identical to or different from each other, each independently selected from single bond and $C_{1-20}$ linear or branched alkylene (preferably each independently selected from single bond, $C_{1-4}$ linear or branched alkylene); group $R_{37}'$ is selected from hydrogen and $C_{1-20}$ linear or branched alkyl (preferably selected from hydrogen and $C_{1-4}$ linear or branched alkyl); n is an integral number of 1-10 (preferably an integral number of 1-3); the numbers m in n repeating units are, identical to or different from each other, each independently selected from an integral number of 0-10 (preferably an integral number of 0-5); the numbers m' in n repeating units are, identical to or different from each other, each independently selected from an integral number of 0-10 (preferably an integral number of 0-5); in each repeating unit of the formulae (V) and (VI), when m is greater than 0, the linking group formed by m sulfur atoms is bonded to groups $R_{32}'$ and $R_{35}'$; when m' is greater than 0, the linking group formed by m' sulfur atoms is bonded to groups $R_{33}'$ and $R_{34}'$; in each repeating unit of the formulae (V) and (VI), when group $R_{33}'$ is single bond, one end connected to group $R_{33}'$ of the linking group formed by m' sulfur atoms is bonded to group $R_{32}'$, when group $R_{34}'$ is single bond, one end connected to group $R_{34}'$ of the linking group formed by m' sulfur atoms is bonded to group $R_{35}'$; in the formula (VI), x groups $R_{10}$ are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups and $C_{1-50}$ alkoxyl optionally substituted by one or more substituent groups (preferably selected from hydrogen, $C_{1-50}$ linear or branched alkyl, $C_{1-50}$ linear or branched alkenyl, linear or branched $C_{3-50}$ heteroalkyl and $C_{1-50}$ linear or branched alkyloxy), x is selected from an integral number of 1-10 (preferably an integral number of 1-5);

In the formula (VII), x groups G are, identical to or different from each other, each independently selected from —OH,

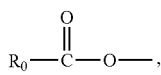

—$OR_0$, wherein groups $R_0$ are each independently selected from $C_{1-50}$ hydrocarbyl optionally substituted by one or more substituent groups, $C_{6-20}$ aryl substituted by one or more substituent groups and $C_{3-50}$ hetero hydrocarbyl optionally substituted by one or more substituent groups (preferably selected from $C_{1-50}$ linear or branched alkyl and linear or branched $C_{3-50}$ heteroalkyl); x is selected from an integral number of 1-10 (preferably an integral number of 1-5); y is selected from an integral number of 1-10 (preferably an integral number of 1-5); in the formula (VII), y groups $R_{10}$ are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups and $C_{1-50}$ alkoxyl optionally substituted by one or more substituent groups (preferably selected from hydrogen, $C_{1-50}$ linear or branched alkyl, $C_{1-50}$ linear or branched alkenyl, linear or branched $C_{3-50}$ heteroalkyl and $C_{1-50}$ linear or branched alkyloxy), x is selected from an integral number of 1-10 (preferably an integral number of 1-5), y is selected from an integral number of 1-10 (preferably an integral number of 1-5);

In the formula (VIII), group $R_{31}'$ is each independently selected from single bond and $C_{1-20}$ linear or branched alkylene (preferably selected from single bond and $C_{1-4}$ linear or branched alkylene); groups $R_{32}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{33}'$ in n repeating units are, identical to or different from each other, each independently selected from H and divalent $C_{1-20}$ linear or branched alkyl (preferably each independently selected from H and divalent $C_{1-4}$ linear or branched alkyl); groups $R_{34}'$ in n repeating units are, identical to or different from each other, each independently selected from H and divalent $C_{1-20}$ linear or branched alkyl (preferably each independently selected from H and divalent $C_{1-4}$ linear or branched alkyl); groups $R_{35}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{36}'$ in n repeating units are, identical to or different from each other, each independently selected from single bond and $C_{1-20}$ linear or branched alkylene (preferably each independently selected from single bond, $C_{1-4}$ linear or branched alkylene); the numbers m in n repeating units are, identical to or different from each other, each independently selected from an integral number of 0-10 (preferably an integral number of 0-5); the numbers m' in n repeating units are, identical to or different from each other, each independently selected from an integral number of 0-10 (preferably an integral number of 0-5), m+m'>0; in each repeating unit of the formula (VIII), when m is greater than 0, the linking group formed by m sulfur atoms is bonded to groups $R_{32}'$ and $R_{35}'$; when m' is greater than 0, the linking group formed by m' sulfur atoms is bonded to groups $R_{33}'$ and $R_{34}'$; in each repeating unit of the formula (VIII), when group $R_{33}'$ is H, one end connected to group $R_{33}'$ of the linking group formed by m' sulfur atoms is bonded to group $R_{32}'$; when group $R_{34}'$ is H, one end connected to group $R_{34}'$ of the linking group formed by m' sulfur atoms is bonded to group $R_{35}'$; in the formula (VIII), x groups $R_{10}$ are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups and $C_{1-50}$ alkoxyl optionally substituted by one or more substituent groups (preferably selected from hydrogen, $C_{1-50}$ linear or branched alkyl, $C_{1-50}$ linear or branched alkenyl, linear or branched $C_{3-50}$ heteroalkyl and $C_{1-50}$ linear or branched alkyloxy), x is selected from an integral number of 1-10 (preferably an integral number of 1-5); in each repeating unit of the formula (VIII), groups $R_{31}'$ and $R_{36}'$ can be each independently substituted by a group represented by the formula (VIII-1); in each repeating unit of the formula (VIII), groups $R_{32}'$, $R_{33}'$, $R_{34}'$ and $R_{35}'$ can be each independently substituted by a group represented by the formula (V),

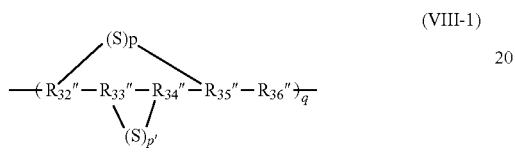

(VIII-1)

In the formula (VIII-1), groups $R_{32}''$ in q repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{33}''$ in q repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{34}''$ in q repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{35}''$ in q repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{36}''$ in q repeating units are, identical to or different from each other, each independently selected from single bond and $C_{1-20}$ linear or branched alkylene (preferably each independently selected from single bond, $C_{1-4}$ linear or branched alkylene); q is an integral number of 1-10 (preferably an integral number of 1-3); the numbers p in q repeating units are, identical to or different from each other, each independently selected from an integral number of 0-10 (preferably an integral number of 0-5); the numbers p' in q repeating units are, identical to or different from each other, each independently selected from an integral number of 0-10 (preferably an integral number of 0-5); in each repeating unit of the formula (VIII-1), when p is greater than 0, the linking group formed by p sulfur atoms is bonded to groups $R_{32}''$ and $R_{35}''$; when p' is greater than 0, the linking group formed by p' sulfur atoms is bonded to groups $R_{33}''$ and $R_{34}''$; in each repeating unit of the formula (VIII-1), when group $R_{33}''$ is single bond, one end connected to group $R_{33}''$ of the linking group formed by p' sulfur atoms is bonded to group $R_{32}''$, when group $R_{34}''$ is single bond, one end connected to group $R_{34}''$ of the linking group formed by p' sulfur atoms is bonded to group $R_{35}''$;

The ring group

in the formula (I) is each independently selected from (x+y)-valent $C_{3-20}$ cycloalkyl (preferably $C_{3-6}$ cycloalkyl, more preferably cyclopentyl, cyclohexyl) and (x+y)-valent $C_{6-20}$ aryl (preferably $C_{6-14}$ aryl, more preferably phenyl, biphenylyl, naphthyl, anthryl, phenanthryl);

The ring group

in the formula (VII) is each independently selected from (x+y+1)-valent $C_{3-20}$ cycloalkyl (preferably $C_{3-6}$ cycloalkyl, more preferably cyclopentyl, cyclohexyl), (x+y+1)-valent $C_{6-20}$ aryl (preferably $C_{6-14}$ aryl, more preferably phenyl, biphenylyl, naphthyl, anthryl, phenanthryl);

The above-mentioned "substituent group" is selected from $C_{1-20}$ alkyl, $C_{1-20}$ alkoxyl, $C_{6-10}$ aryl, hydroxy, amino, mercapto and halogen atom.

In an embodiment of the present invention, group $R_0$ in group G is selected from $C_{1-50}$ linear or branched alkyl and linear or branched $C_{3-50}$ heteroalkyl. In an embodiment of the present invention, group $R_0$ in group G is selected from $C_{1-30}$ linear or branched alkyl. In an embodiment of the present invention, group $R_0$ in group G is selected from $C_{1-10}$ linear or branched alkyl. In an embodiment of the present invention, group $R_0$ in group G is selected from $C_{1-4}$ linear or branched alkyl.

In an embodiment of the present invention, x in the formula (I) is an integral number of 1-5. In an embodiment of the present invention, groups R in the formula (I) each independently are preferably selected from hydrogen, $C_{1-50}$ linear or branched alkyl, $C_{1-50}$ linear or branched alkenyl, linear or branched $C_{3-50}$ heteroalkyl, $C_{1-50}$ linear or branched alkyloxy and a group represented by the formula (II), wherein at least one group R is selected from a group represented by the formula (II).

In an embodiment of the present invention, group L is preferably selected from single bond, (m+1)-valent $C_{1-50}$ linear or branched alkyl and (m+1)-valent linear or branched $C_{3-50}$ heteroalkyl. In an embodiment of the present invention, group L is preferably selected from single bond, (m+1)-valent $C_{1-20}$ linear or branched alkyl. In an embodiment of the present invention, group L is preferably selected from single bond, (m+1)-valent $C_{1-4}$ linear or branched alkyl.

In an embodiment of the present invention, m in formula (II) is preferably an integral number of 1-5.

In an embodiment of the present invention, the ring groups

in the formula (I) and the formula (VII) are each independently selected from $C_{3-6}$ cycloalkane group and $C_{6-14}$ aryl group, preferably each independently selected from cyclohexane group and benzene ring group.

In an embodiment of the present invention, in the formula (I), x is 1, y is 1, group G and group R are located at the meta-position in relation to one another. In other words, based on group G, group R is located at the meta-position.

In an embodiment of the present invention, in the formula (I), x is 1, y is 2, group G is located at the ortho-position of one group R and at the meta-position of another group R. In other words, based on group G, one group R is located at the ortho-position, and one group R is located at the meta-position. Preferably, two groups R are located at the para position (each located at the para-position in relation to one another).

In the present invention, in each repeating unit of the formula (V), the formula (VI) and the formula (VIII), the groups (S)m, (S)m', (S)p, (S)p', $R_{32}'$, $R_{33}'$, $R_{34}'$, $R_{35}'$, $R_{32}''$, $R_{33}''$, $R_{34}''$, and $R_{35}''$ conform to the Bonding Rule.

In an embodiment of the present invention, in each repeating unit represented by the formula (V) and the formula (VI), when m is greater than 0, the linking group formed by m sulfur atoms is bonded to groups $R_{32}'$ and $R_{35}'$; when m' is greater than 0, the linking group formed by m' sulfur atoms is bonded to groups $R_{33}'$ and $R_{34}'$. In an embodiment of the present invention, in each repeating unit represented by the formula (V) and the formula (VI), when group $R_{33}'$ is single bond, one end that is connected to group $R_{33}'$ of the linking group formed by m' sulfur atoms is bonded to group $R_{32}'$, when group $R_{34}'$ is single bond, one end that is connected to group $R_{34}'$ of the linking group formed by m' sulfur atoms is bonded to group $R_{35}'$.

In an embodiment of the present invention, in each repeating unit represented by the formula (V) and the formula (VI), when m is 0, no sulfur atom is bonded to groups $R_{32}'$ and $R_{35}'$; when m' is 0, no sulfur atom is bonded to groups $R_{33}'$ and $R_{34}'$. In an embodiment of the present invention, in each repeating unit represented by the formula (V) and the formula (VI), when group $R_{33}'$ is not single bond, the linking group formed by m' sulfur atoms is bonded to group $R_{33}'$, when group $R_{34}'$ is not single bond, the linking group formed by m' sulfur atoms is bonded to group $R_{34}'$.

In an embodiment of the present invention, in each repeating unit shown in the formula (V), the formula (VI) and the formula (VIII), m sulfur atoms being bonded to groups $R_{32}'$ and $R_{35}'$ means that the end sulfur atom of m sulfur atoms (or only one sulfur atom present) is bonded to groups $R_{32}'$ and $R_{35}'$ (when m is 1, only one sulfur atom is present, here this sulfur atom is bonded to groups $R_{32}'$ and $R_{35}'$); m' sulfur atoms being bonded to groups $R_{33}'$ and $R_{34}'$ means that the end sulfur atom of m' sulfur atoms (or only one sulfur atom present) is bonded to groups $R_{33}'$ and $R_{34}'$ (when m' is 1, only one sulfur atom is present, here this sulfur atom is bonded to groups $R_{33}'$ and $R_{34}'$).

In an embodiment of the present invention, in each repeating unit represented by the formula (V) and the formula (VI), when groups $R_{33}'$ and $R_{34}'$ are not single bond, m' is greater than 0, the linking group formed by m' sulfur atoms is bonded to groups $R_{33}'$ and $R_{34}'$, groups $R_{33}'$ and $R_{34}'$ are each independently selected from trivalent $C_{1-20}$ linear or branched alkyl (preferably each independently selected from trivalent $C_{1-4}$ linear or branched alkyl). In an embodiment of the present invention, in each repeating unit represented by the formula (V) and the formula (VI), when groups $R_{33}'$ and $R_{34}'$ are not single bond, and m' is 0, no sulfur atom is bonded to groups $R_{33}'$ and $R_{34}'$, groups $R_{33}'$ and $R_{34}'$ are each independently selected from divalent $C_{1-20}$ linear or branched alkyl (preferably each independently selected from divalent $C_{1-4}$ linear or branched alkyl).

In an embodiment of the present invention, in each repeating unit represented by the formula (V) and the formula (VI), when groups $R_{33}'$ and $R_{34}'$ are not single bond, and m is greater than 0, groups $R_{32}'$ and $R_{35}'$ are each independently selected from trivalent $C_{1-20}$ linear or branched alkyl (preferably each independently selected from trivalent $C_{1-4}$ linear or branched alkyl). In an embodiment of the present invention, in each repeating unit represented by the formula (V) and the formula (VI), when groups $R_{33}'$ and $R_{34}'$ are not single bond, and m is 0, groups $R_{32}'$ and $R_{35}'$ are each independently selected from divalent $C_{1-20}$ linear or branched alkyl (preferably each independently selected from divalent $C_{1-4}$ linear or branched alkyl).

In an embodiment of the present invention, in each repeating unit represented by the formula (V) and the formula (VI), when group $R_{33}'$ is single bond, $R_{34}'$ is not single bond, and m' is greater than 0, the linking group formed by m' sulfur atoms is bonded to groups $R_{32}'$ and $R_{34}'$, $R_4'$ is selected from trivalent $C_{1-20}$ linear or branched alkyl (preferably each independently selected from trivalent $C_{1-4}$ linear or branched alkyl). In an embodiment of the present invention, in each repeating unit represented by the formula (V) and the formula (VI), when group $R_{33}'$ is single bond, $R_{34}'$ is not single bond, and m' is 0, no sulfur atom is bonded to group $R_{34}'$, $R_{34}'$ is selected from divalent $C_{1-20}$ linear or branched alkyl (preferably each independently selected from divalent $C_{1-4}$ linear or branched alkyl).

In an embodiment of the present invention, in each repeating unit represented by the formula (V) and the formula (VI), when group $R_{33}'$ is single bond, $R_{34}'$ is not single bond, m is greater than 0, and m' is greater than 0, Rai is selected from tetravalent $C_{1-20}$ linear or branched alkyl (preferably selected from tetravalent $C_{1-4}$ linear or branched alkyl), $R_{35}'$ is selected from trivalent $C_{1-20}$ linear or branched alkyl (preferably selected from trivalent $C_{1-4}$ linear or branched alkyl). In an embodiment of the present invention, in each repeating unit represented by the formula (V) and the formula (VI), when group $R_{33}'$ is single bond, $R_{34}'$ is not single bond, m is 0, and m' is greater than 0, $R_{32}'$ is selected from trivalent $C_{1-20}$ linear or branched alkyl (preferably selected from trivalent $C_{1-4}$ linear or branched alkyl), $R_{35}'$ is selected from divalent $C_{1-20}$ linear or branched alkyl (preferably selected from divalent $C_{1-4}$ linear or branched alkyl).

In an embodiment of the present invention, in each repeating unit represented by the formula (V) and the formula (VI), when group $R_{33}'$ is not single bond, $R_{34}'$ is single bond, and m' is greater than 0, m' sulfur atoms are bonded to groups $R_{33}'$ and $R_{35}'$, $R_{33}'$ is selected from trivalent $C_{1-20}$ linear or branched alkyl (preferably each independently selected from trivalent $C_{1-4}$ linear or branched alkyl). In an embodiment of the present invention, in each repeating unit represented by the formula (V) and the formula (VI), when group $R_{33}'$ is not single bond, $R_{34}'$ is single bond, and m' is 0, no sulfur atom is bonded to group $R_{33}'$, $R_{33}'$ is selected from divalent $C_{1-20}$ linear or branched alkyl (preferably each independently selected from divalent $C_{1-4}$ linear or branched alkyl).

In an embodiment of the present invention, in each repeating unit represented by the formula (V) and the formula (VI), when group $R_{33}'$ is not single bond, $R_{34}'$ is single bond, m is greater than 0, and m' is greater than 0, $R_{32}'$ is selected from trivalent $C_{1-20}$ linear or branched alkyl (preferably selected from trivalent $C_{1-4}$ linear or branched alkyl), $R_{35}'$ is selected from tetravalent $C_{1-20}$ linear or branched alkyl (preferably selected from tetravalent $C_{1-4}$ linear or branched alkyl). In an embodiment of the present invention, in each repeating unit represented by the formula (V) and the formula (VI), when group $R_{33}'$ is not single bond, $R_{34}'$ is single bond, m is 0, and m' is greater than 0, $R_{32}'$ is selected from divalent $C_{1-20}$ linear or branched alkyl (preferably selected from divalent $C_{1-4}$ linear or branched alkyl), $R_{35}'$ is selected from trivalent $C_{1-20}$ linear or branched alkyl (preferably selected from trivalent $C_{1-4}$ linear or branched alkyl).

In an embodiment of the present invention, in each repeating unit represented by the formula (V) and the formula (VI), when groups $R_{33}'$ and $R_{34}'$ are both single bond, and m' is greater than 0, the linking group formed by m' sulfur atoms is bonded to groups $R_{32}'$ and $R_{35}'$, here when m is greater than 0, groups $R_{32}'$ and $R_{35}'$ are each independently selected from tetravalent $C_{1-20}$ linear or branched alkyl (preferably each independently selected from tetravalent $C_{1-4}$ linear or branched alkyl), here when m is 0, groups $R_{32}'$ and $R_{35}'$ are each independently selected from trivalent $C_{1-20}$ linear or branched alkyl (preferably each independently selected from trivalent $C_{1-4}$ linear or branched alkyl).

In an embodiment of the present invention, in each repeating unit represented by the formula (V) and the formula (VI), when groups $R_{33}'$ and $R_{34}'$ are both single bond, m' is 0, and m is greater than 0, groups $R_{32}'$ and $R_{35}'$ are each independently selected from trivalent $C_{1-20}$ linear or branched alkyl (preferably each independently selected from trivalent $C_{1-4}$ linear or branched alkyl). In an embodiment of the present invention, in each repeating unit represented by the formula (V) and the formula (VI), when groups $R_{33}'$ and $R_{34}'$ are both single bond, m' is 0, and m is 0, groups $R_{32}'$ and $R_{35}'$ are each independently selected from divalent $C_{1-20}$ linear or branched alkyl (preferably each independently selected from divalent $C_{1-4}$ linear or branched alkyl).

In an embodiment of the present invention, for example, the structures that can be formed each repeating unit represented by the formula (V) and the formula (VI) comprise:

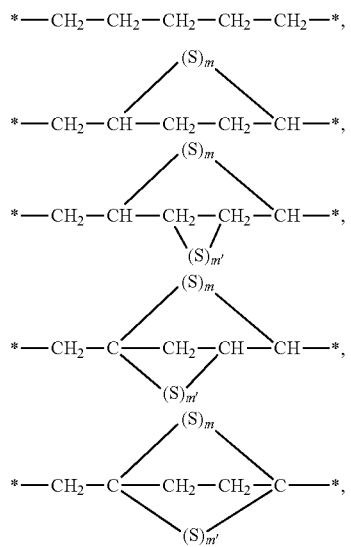

but are not limited thereto.

In an embodiment of the present invention, the phenol derivative of the present invention is selected from the following specific compounds or a mixture thereof in any proportion:

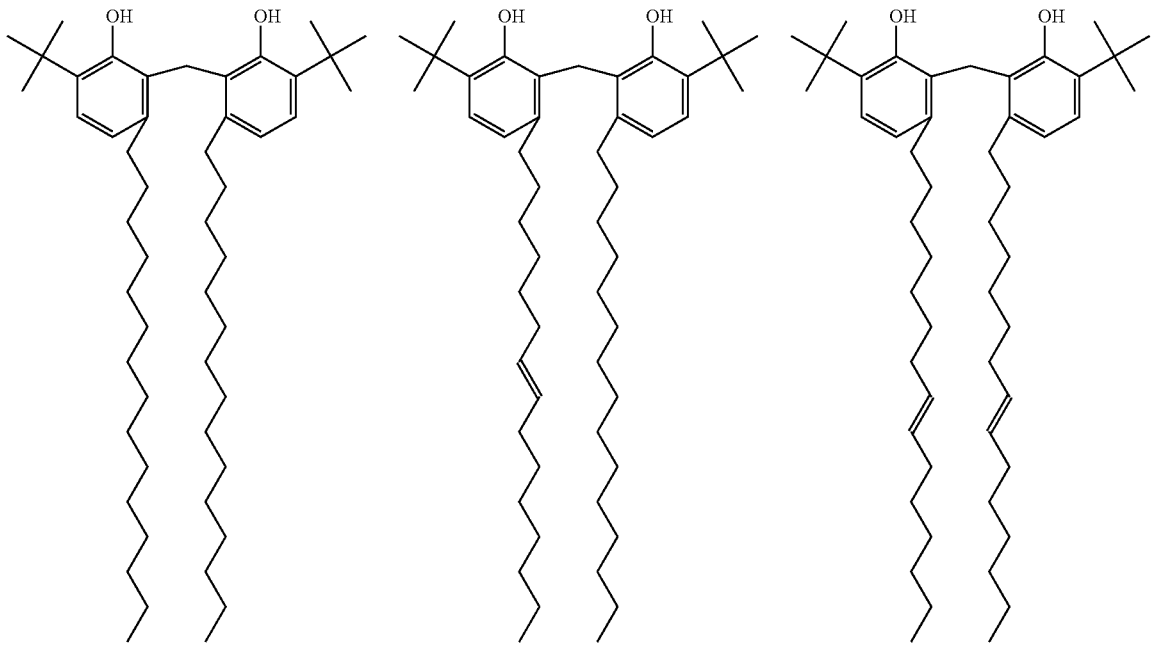

59
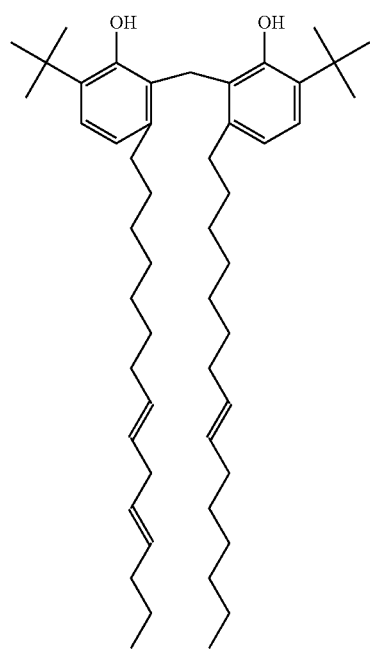
-continued
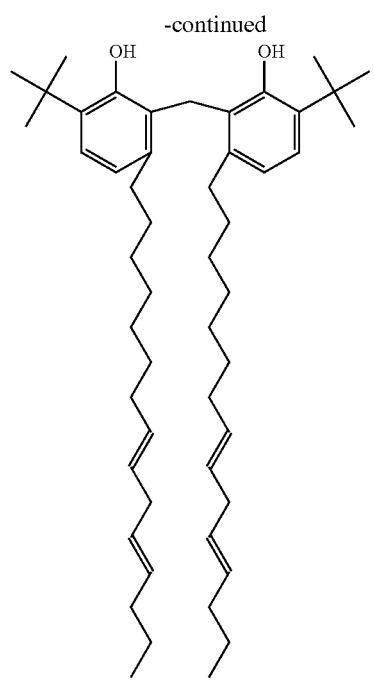
60
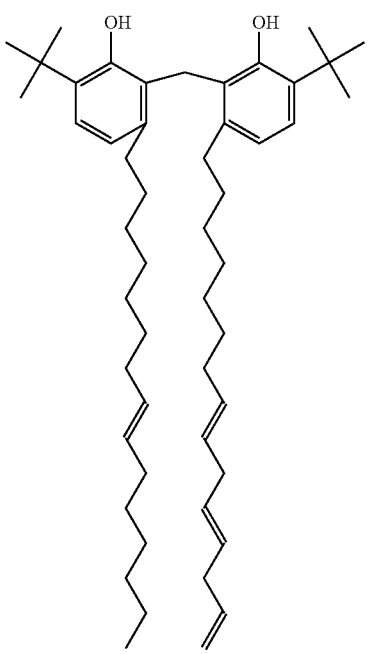
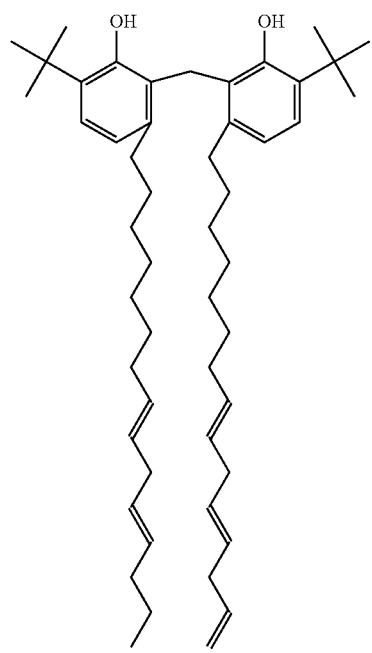
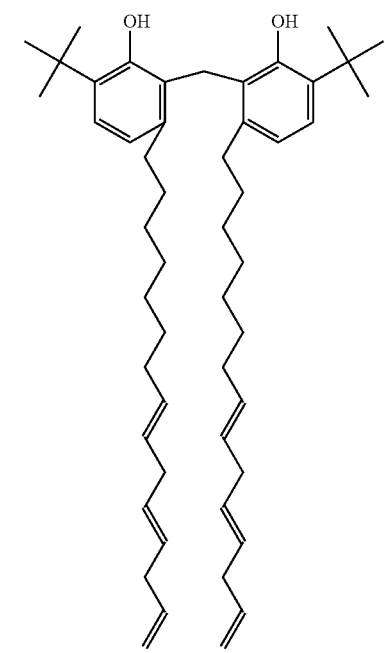

-continued
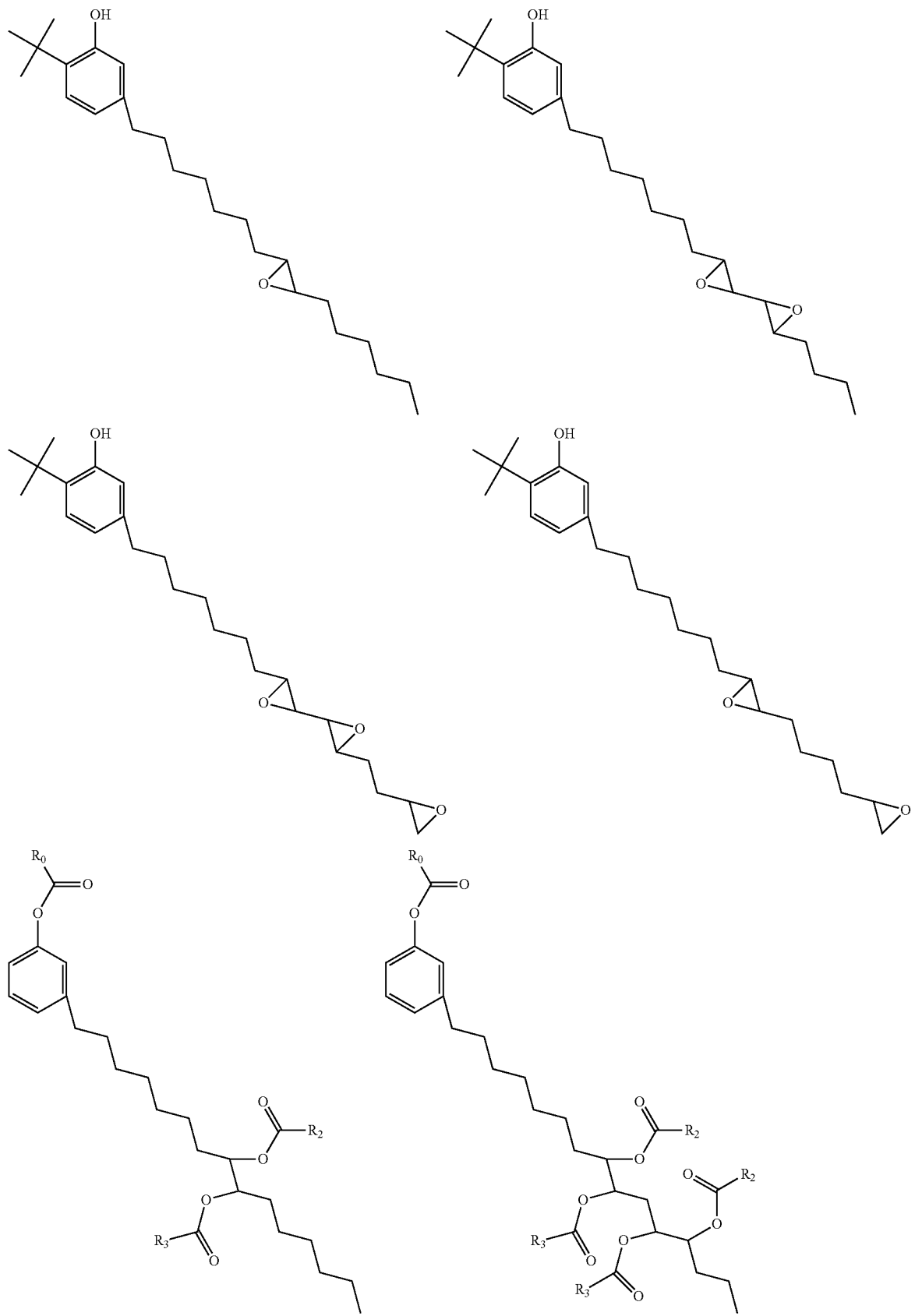

63
64
-continued
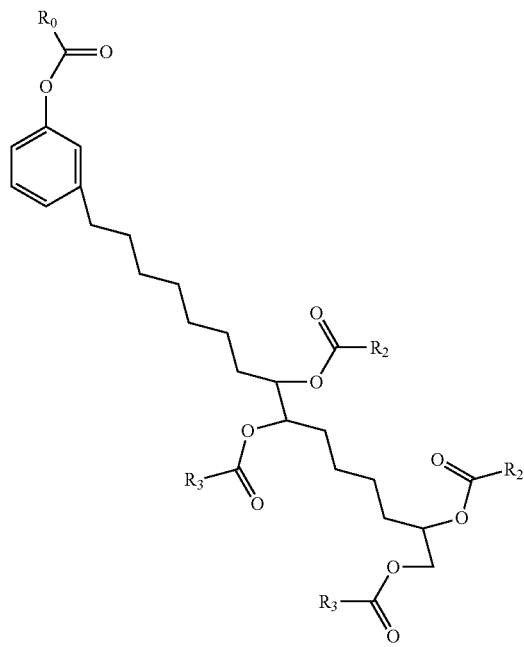
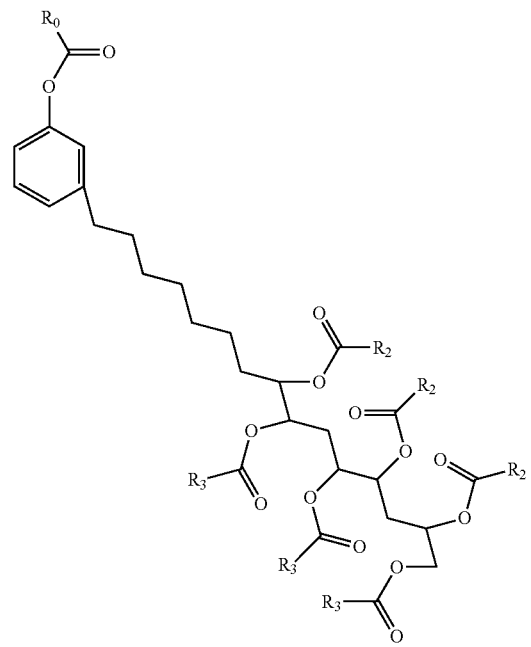
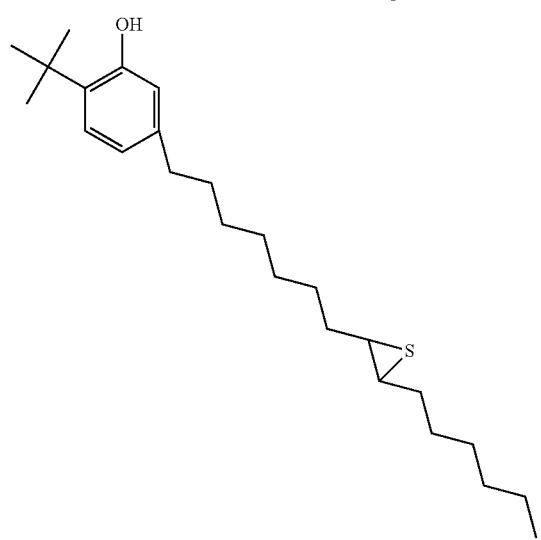
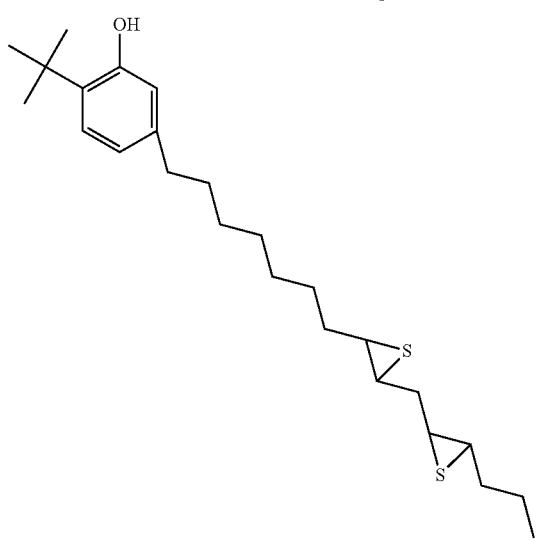
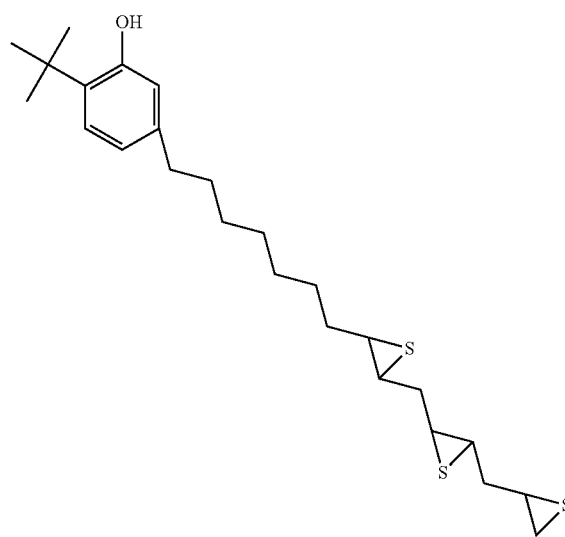
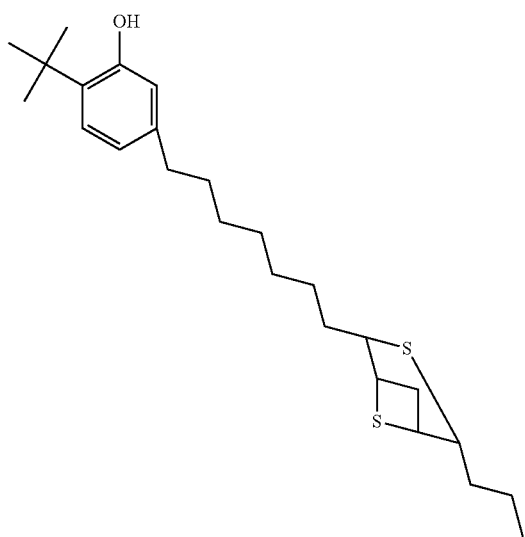

65
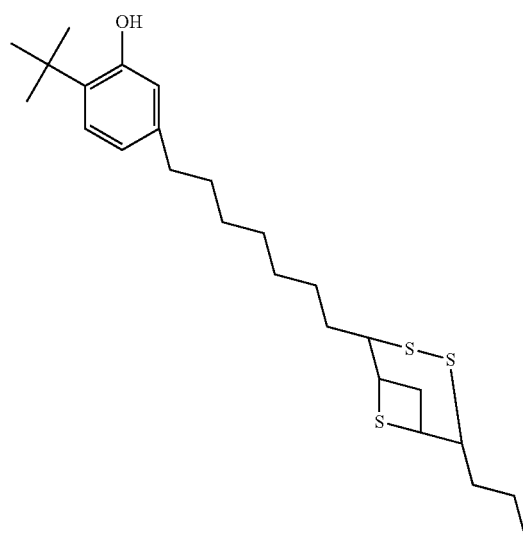
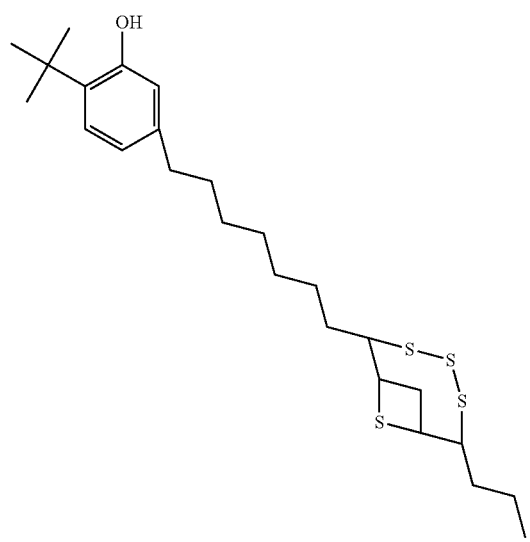
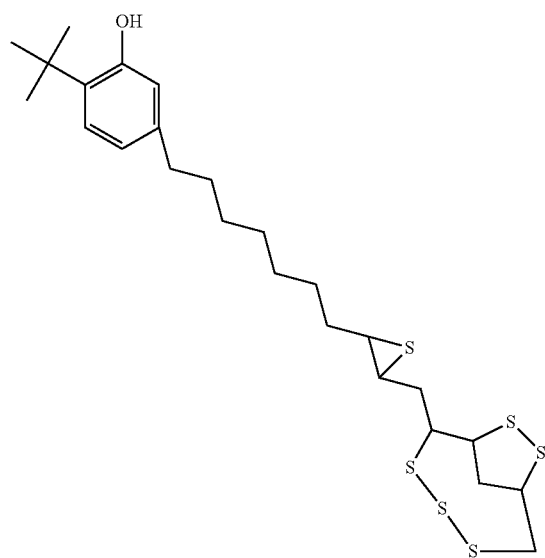
66
-continued
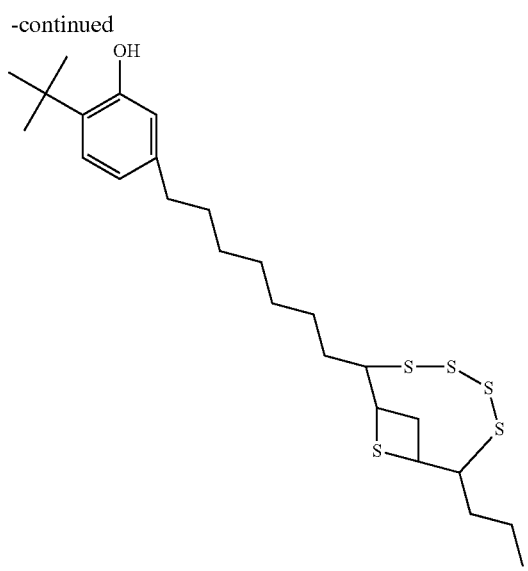
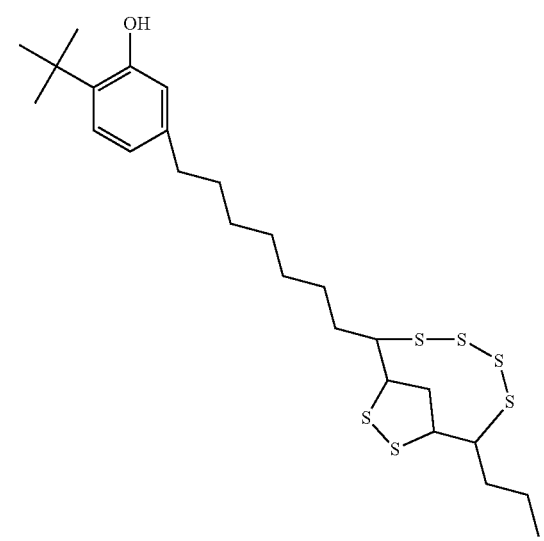
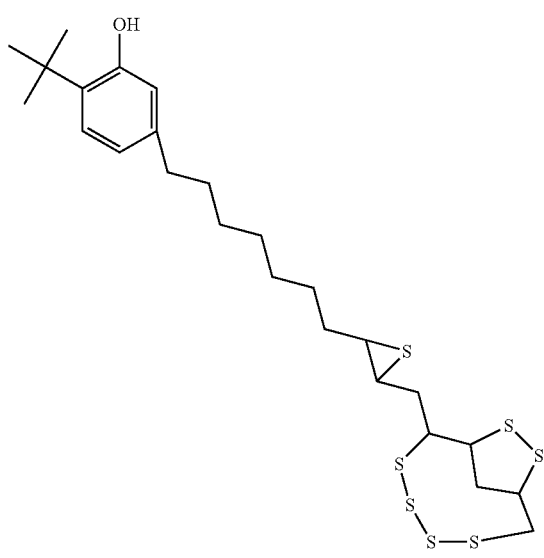

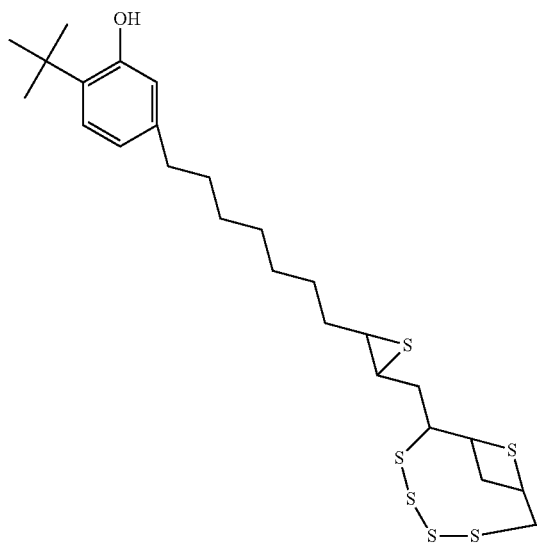
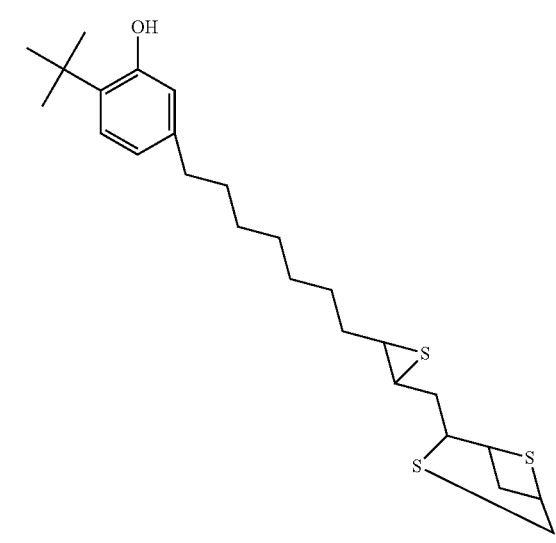
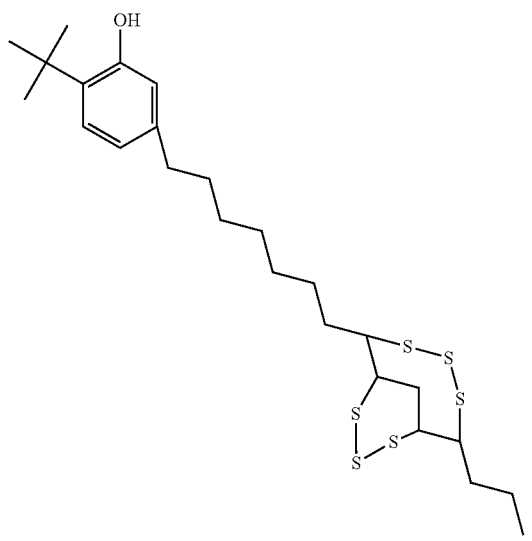
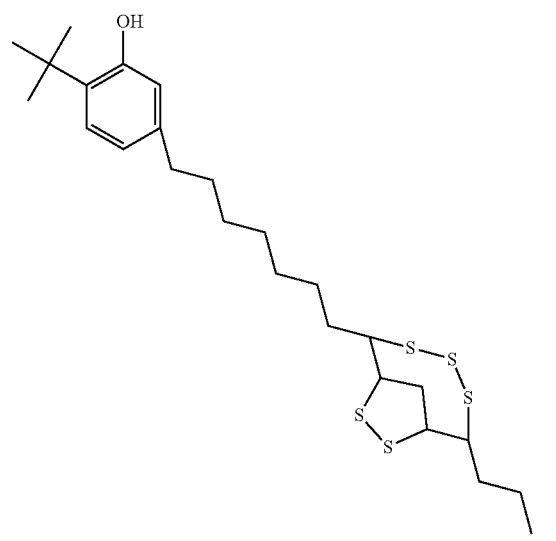
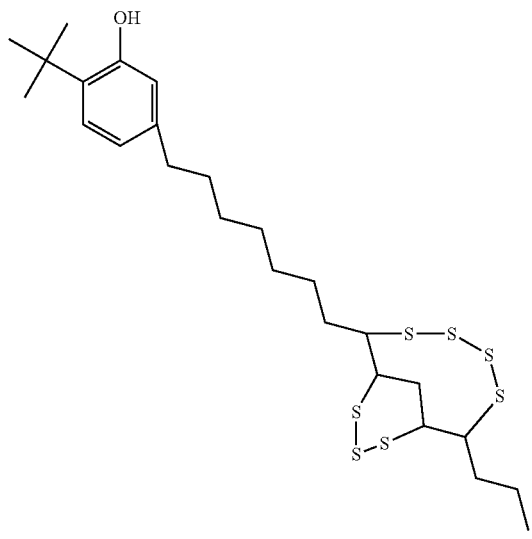
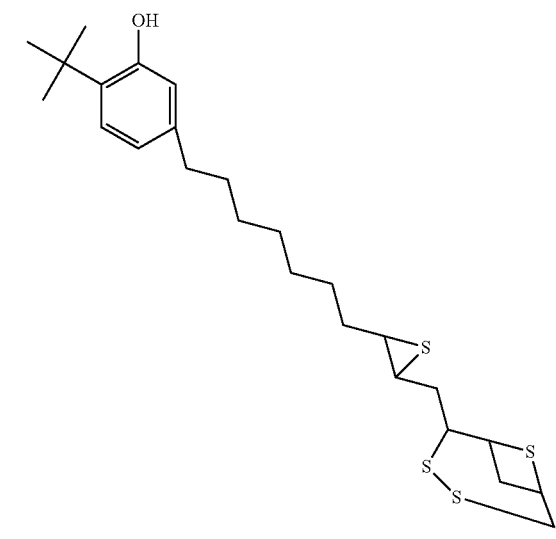

-continued
69
70
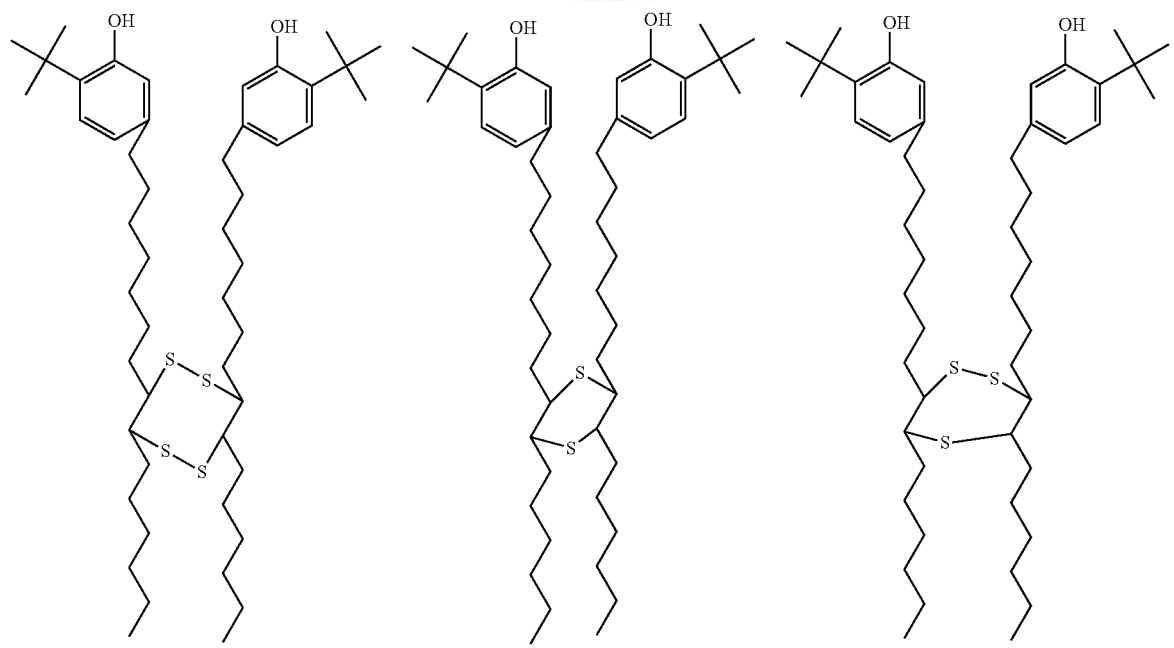
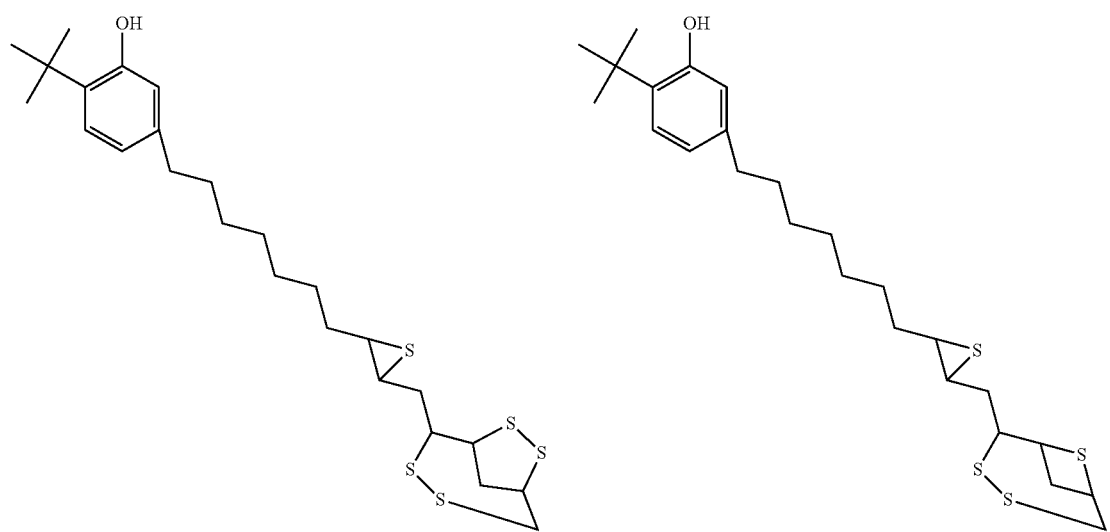

71
72
-continued
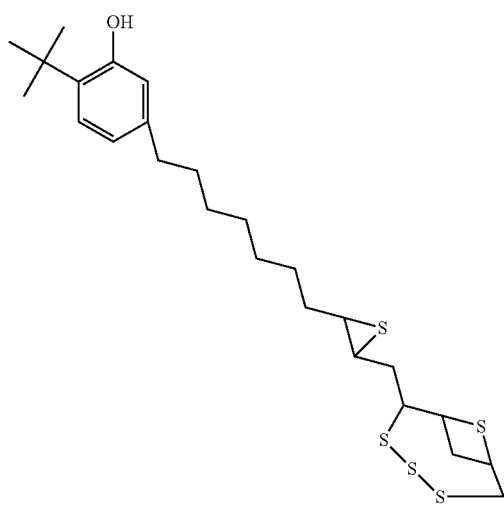
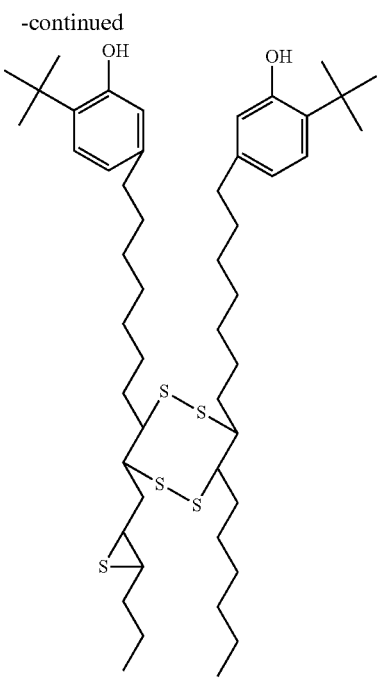
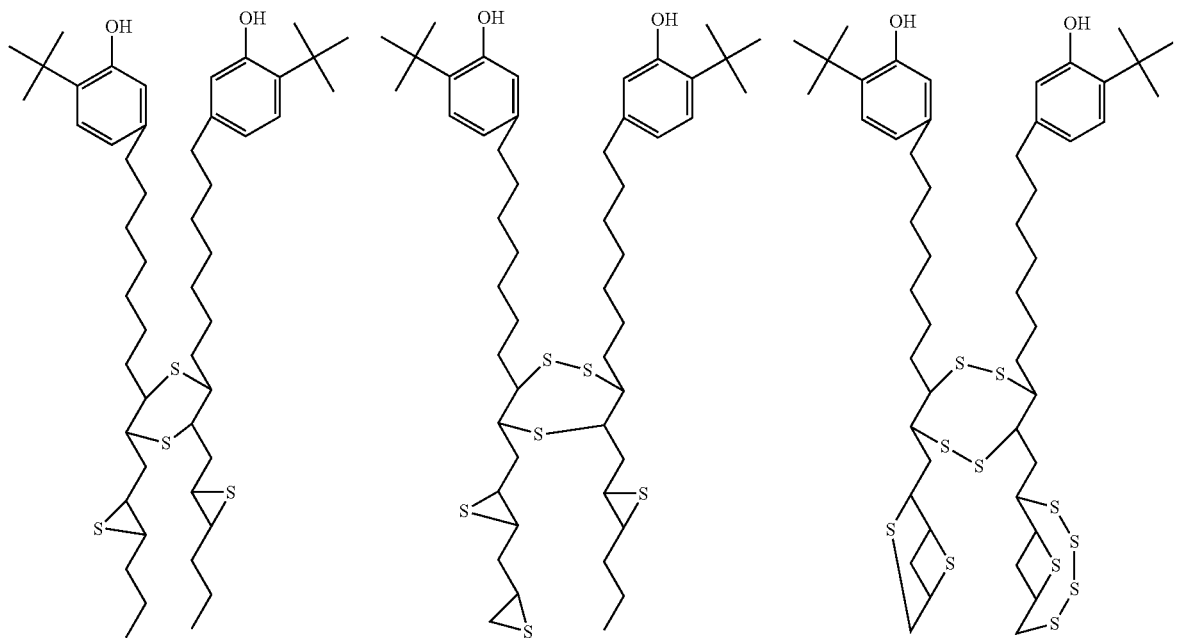

73 74
-continued
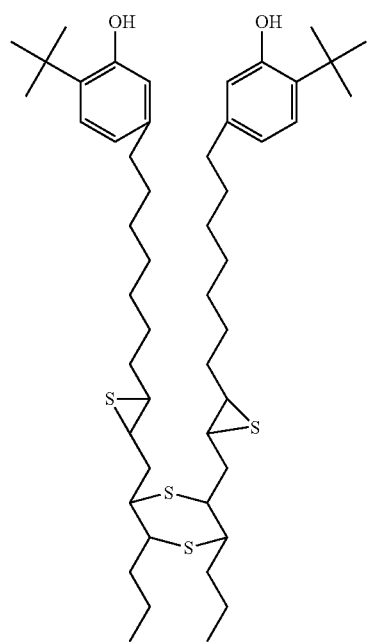
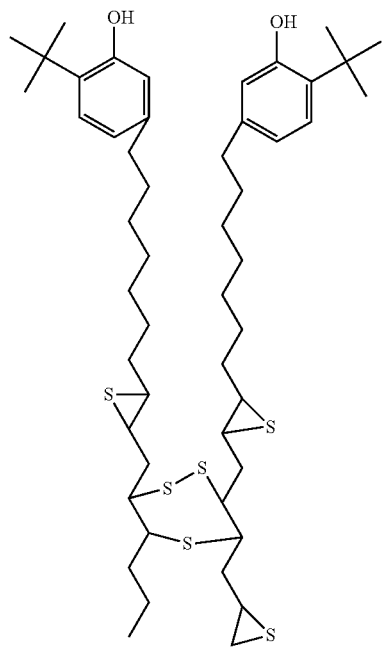
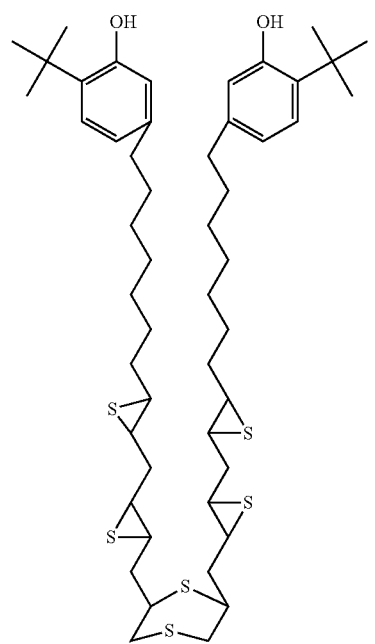
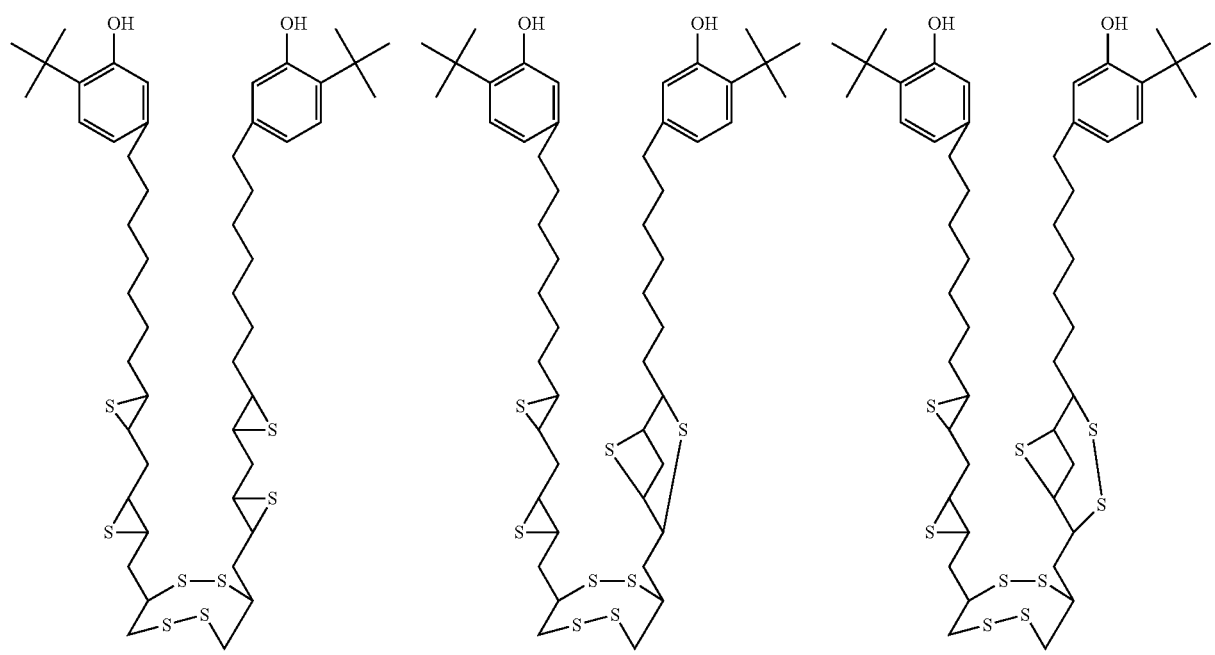

-continued
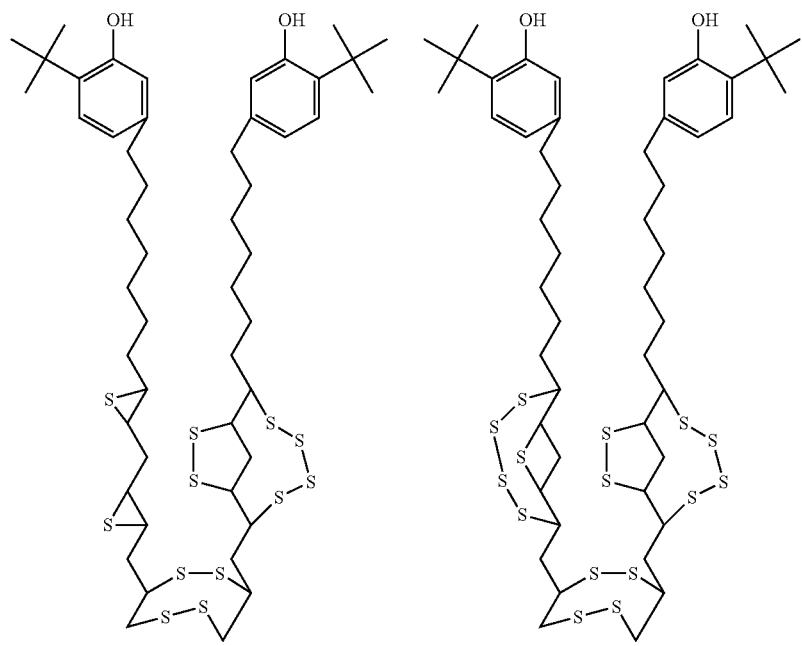
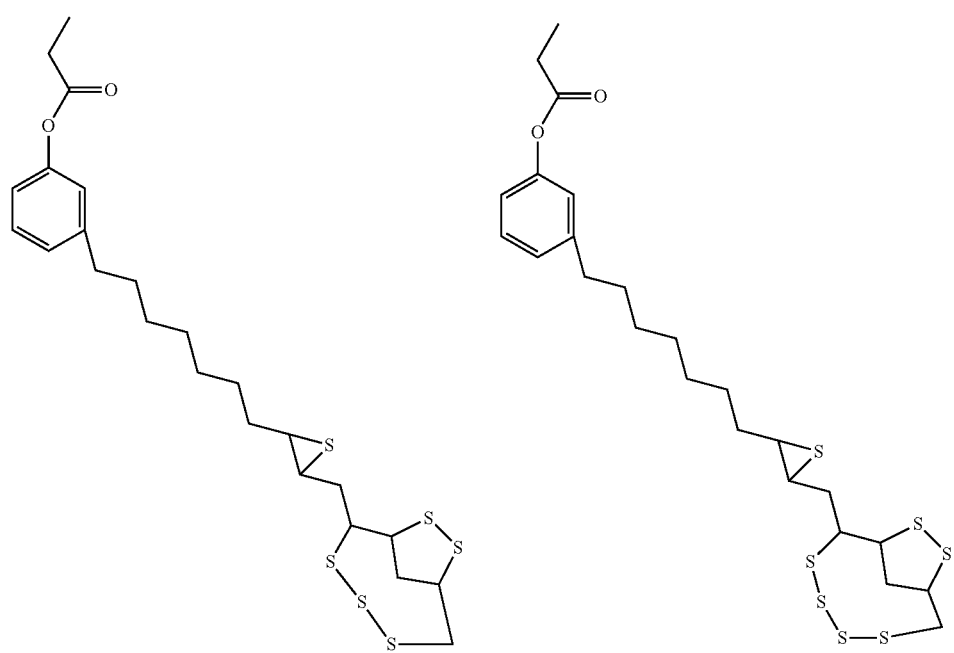

-continued
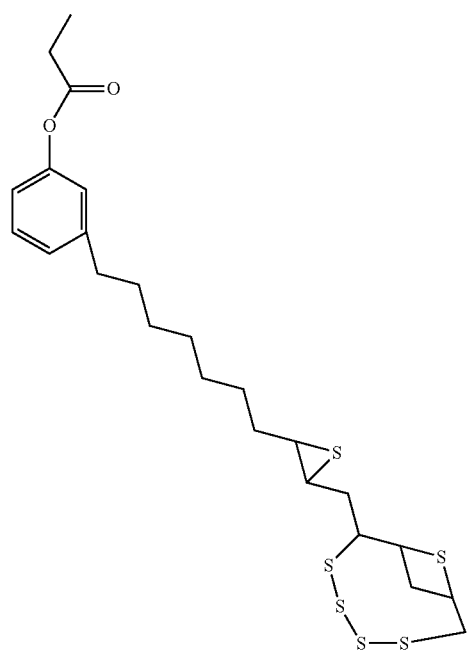
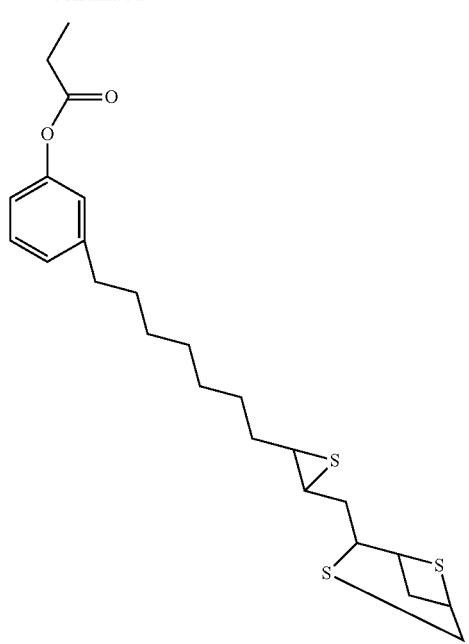
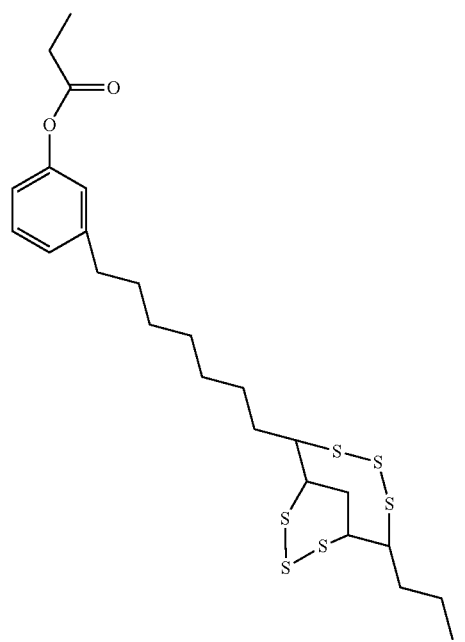
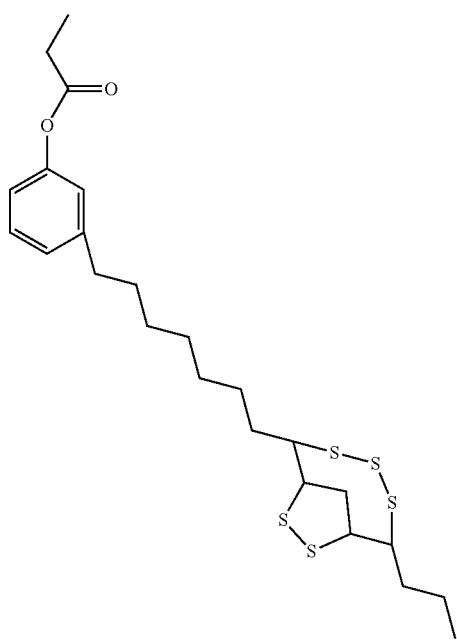

-continued
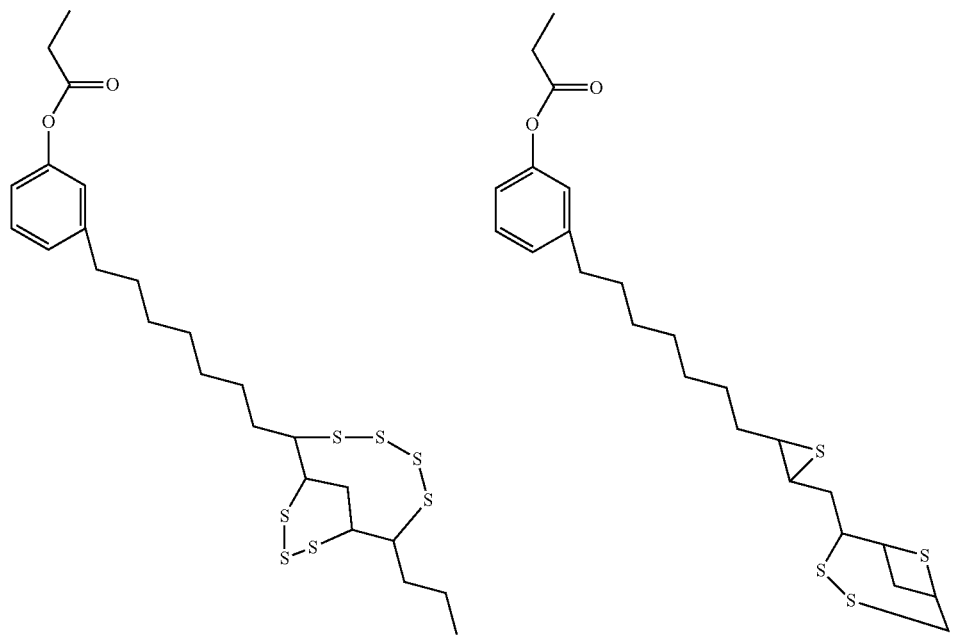
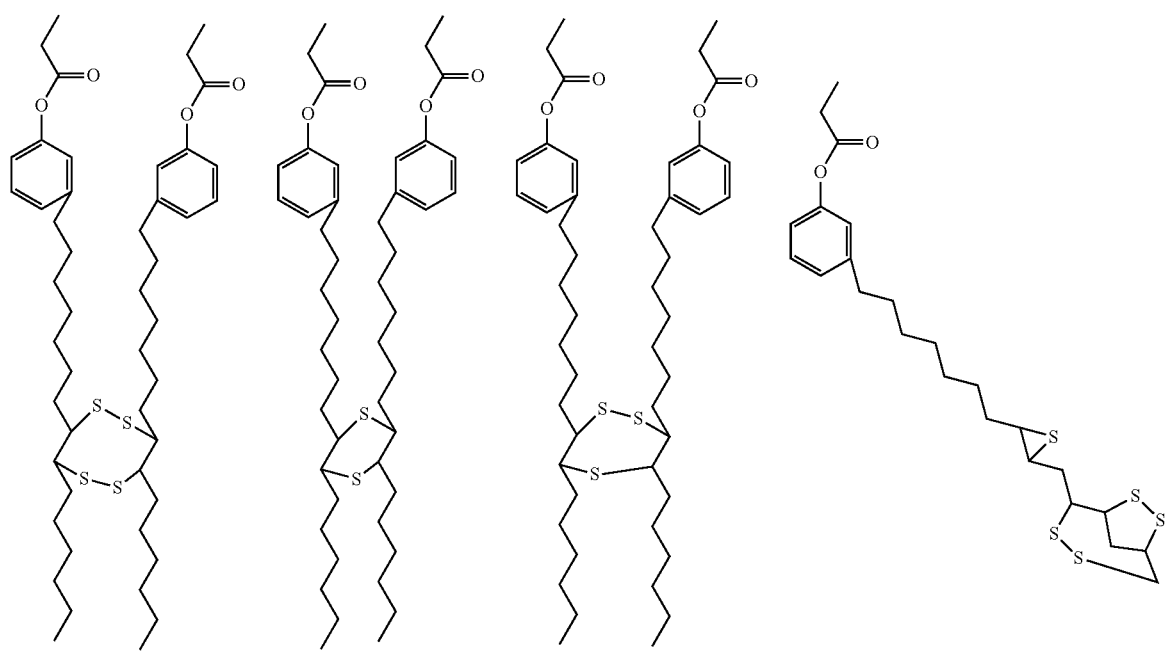

81 82
-continued
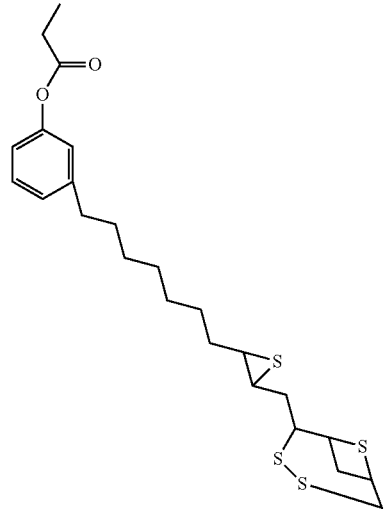
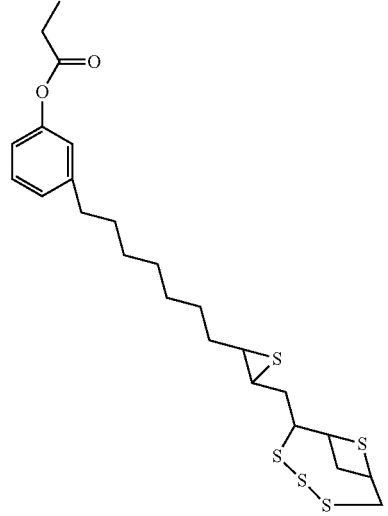
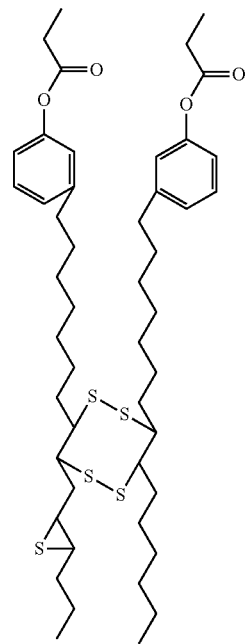
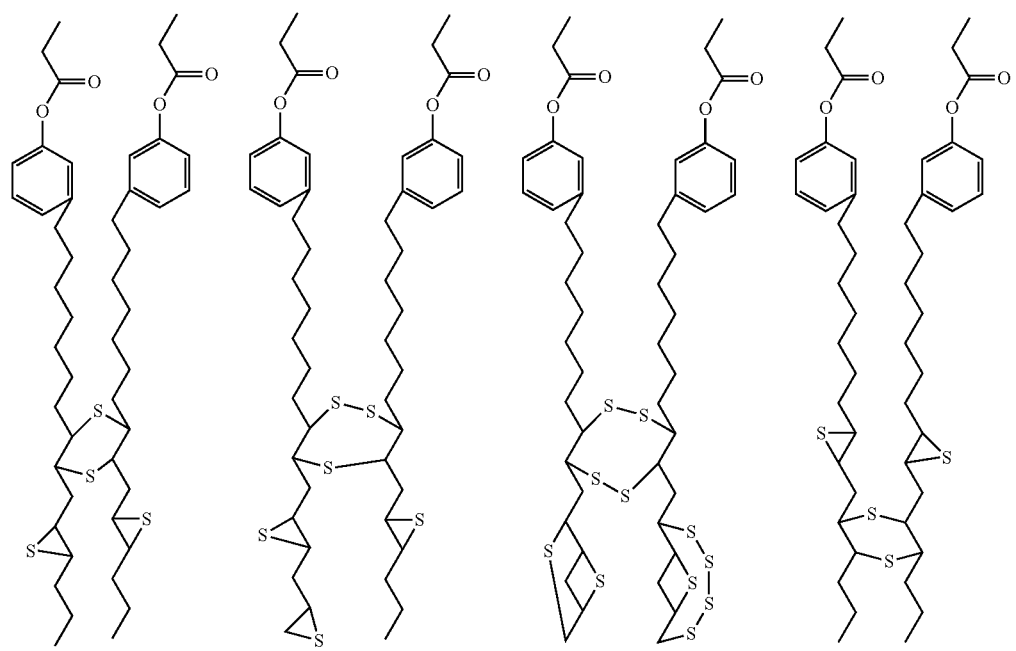

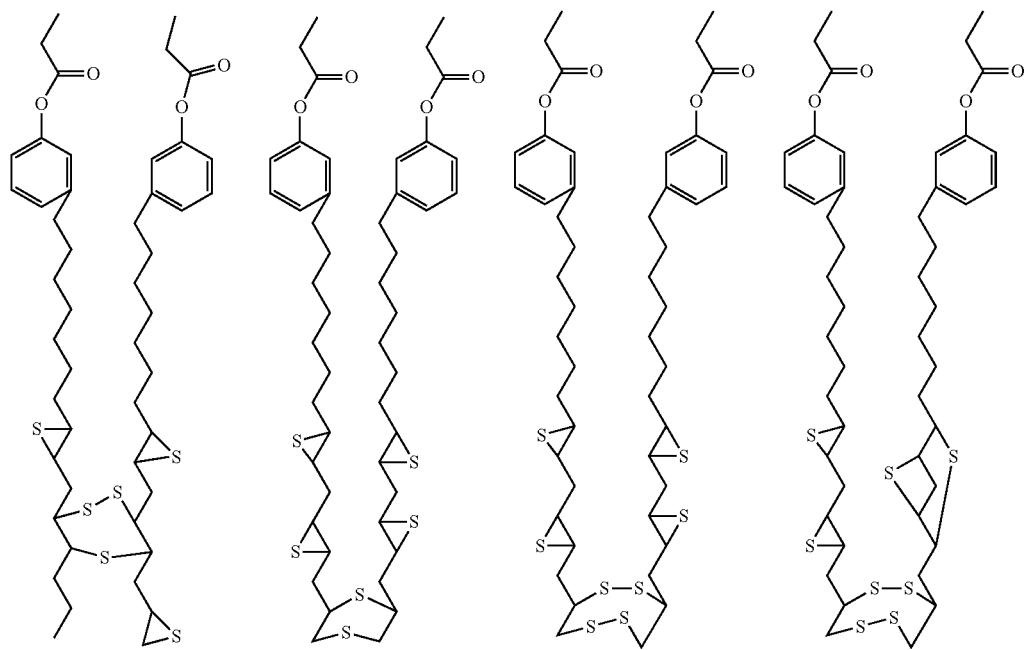
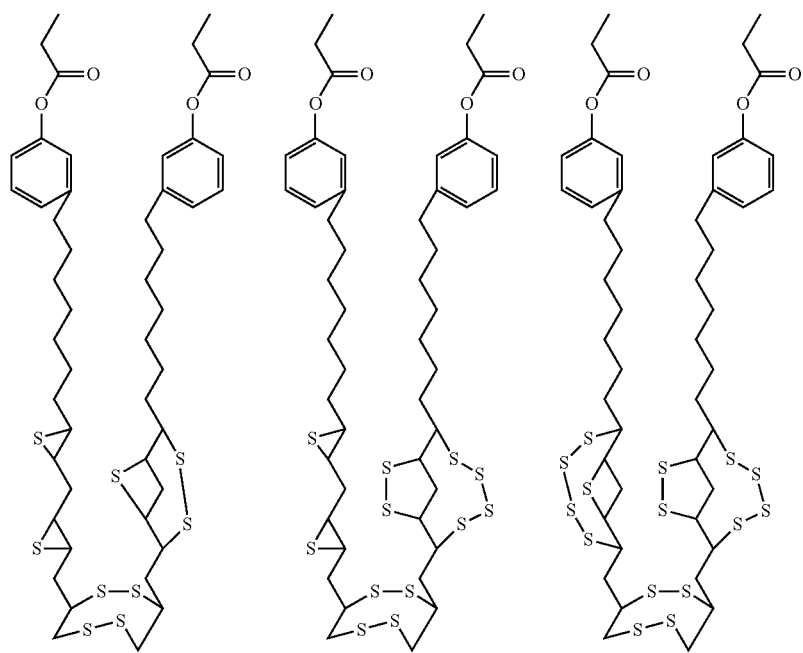 [SMILES: CCC(=O)Oc1cccc(CCCCCCCC2SSC(CC3CSSCC(CC4SC4CC4SC4CCCCCCCc4cccc(OC(=O)CC)c4)SS3)C3CC2S3)c1 ; CCC(=O)Oc1cccc(CCCCCCCC2SSSSC(CC3CSSCC(CC4SC4CC4SC4CCCCCCCc4cccc(OC(=O)CC)c4)SS3)C3CC2SS3)c1 ; CCC(=O)Oc1cccc(CCCCCCCC2SSSSC(CC3CSSCC(CC4SSSSC(CCCCCCCc5cccc(OC(=O)CC)c5)C5CC4S5)SS3)C3CC2SS3)c1]

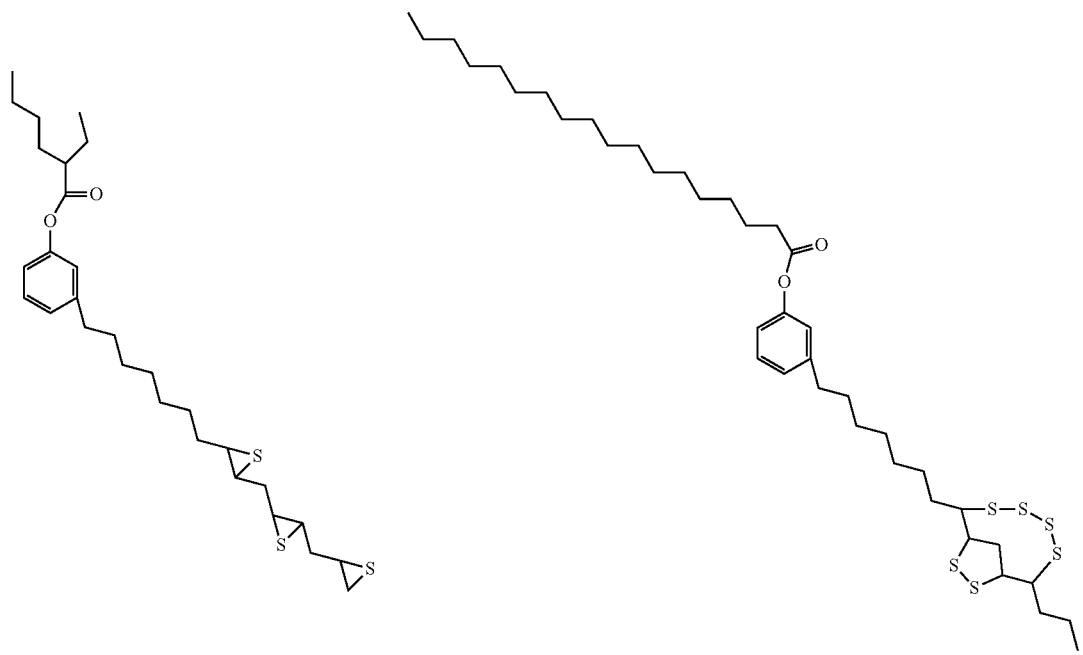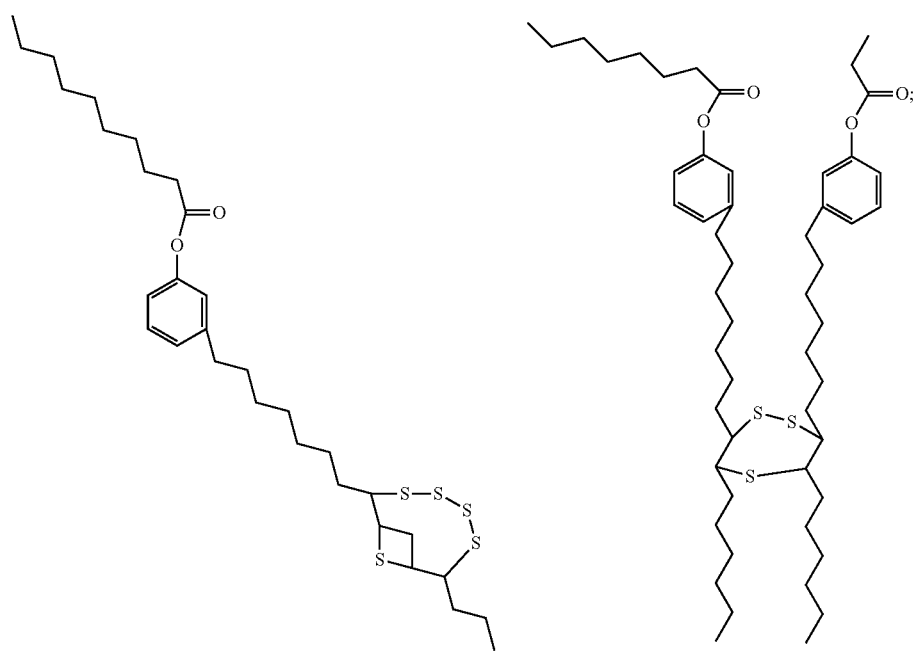

In an embodiment of the present invention, in the structure represented by the following formula:

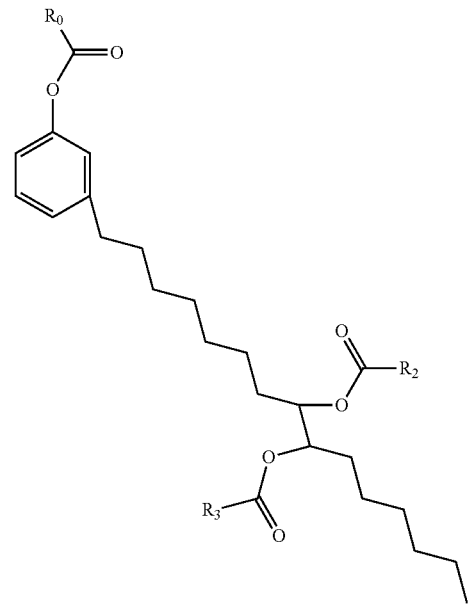

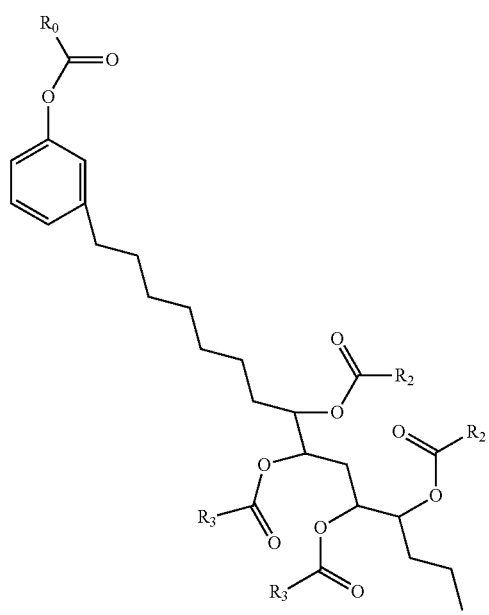

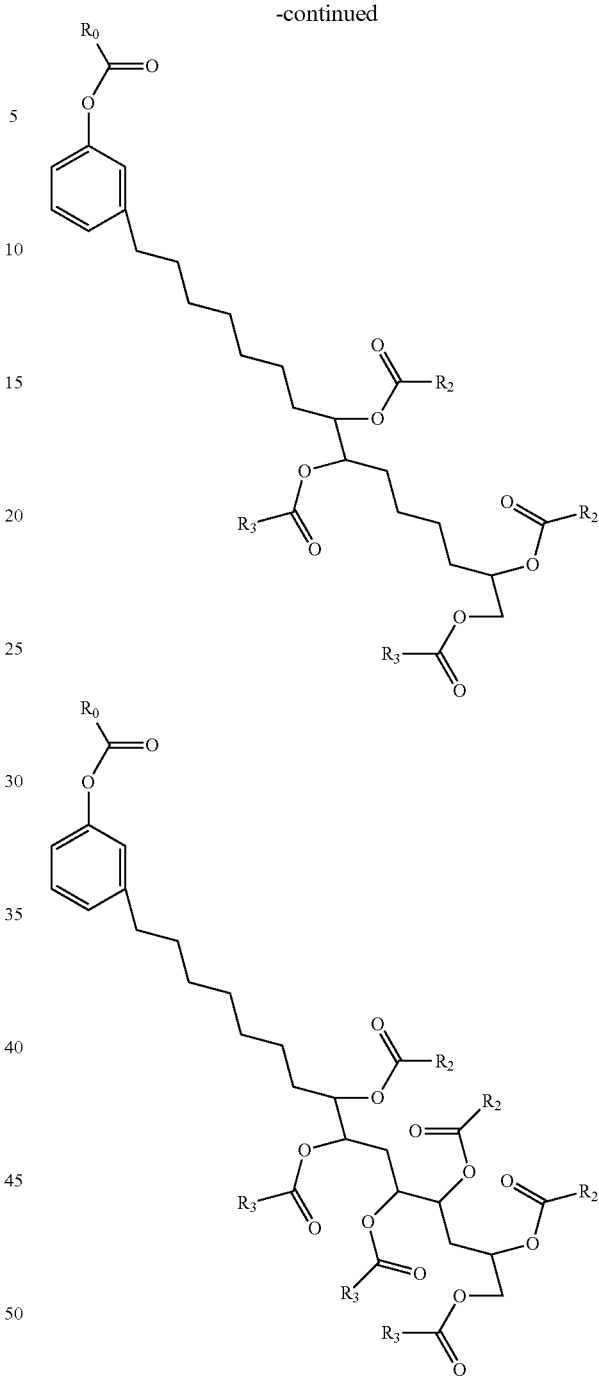

$R_0$, $R_2$ and $R_3$ are defined as above (preferably, groups $R_0$ are ethyl, groups $R_2$ are each independently selected from $C_2$-$C_{18}$ alkyl, groups $R_3$ are each independently selected from $C_2$-$C_{18}$ alkyl).

The phenol derivative of the present invention can be a single phenol derivative, or a mixture of multiple phenol derivatives conforming to the above-mentioned general formula (I) in any proportion. In this case, whether the single compound or the mixture of compounds are contained within the scope of the present invention.

In an embodiment of the present invention, the phenol derivative of the present invention has a structure as represented by the formula (I):

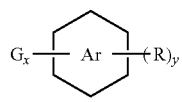 (I)

In the formula (I), x groups G are bonded to the ring group Ar, y groups R are bonded to the ring group Ar;

x groups G are, identical to or different from each other, each independently selected from —OH,

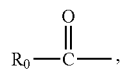

—OR$_0$, wherein group R$_0$ is selected from C$_{1-50}$ hydrocarbyl optionally substituted by one or more substituent groups and C$_{3-50}$ hetero hydrocarbyl optionally substituted by one or more substituent groups (preferably selected from C$_{1-50}$ linear or branched alkyl and linear or branched C$_{3-50}$ heteroalkyl); x is selected from an integral number of 1-10 (preferably an integral number of 1-5);

y groups R are, identical to or different from each other, each independently selected from hydrogen, C$_{1-50}$ hydrocarbyl optionally substituted by one or more substituent groups, C$_{3-50}$ hetero hydrocarbyl optionally substituted by one or more substituent groups and C$_{1-50}$ alkyloxy optionally substituted by one or more substituent groups (preferably selected from hydrogen, C$_{1-50}$ linear or branched alkyl, linear or branched C$_{3-50}$ heteroalkyl, C$_{1-50}$ linear or branched alkyloxy), a group represented by the formula (II), wherein at least one group R is selected from a group represented by the formula (II);

 (II)

Groups L in y groups R are each independently selected from single bond, (m+1)-valent C$_{1-50}$ hydrocarbyl optionally substituted by one or more substituent groups and (m+1)-valent C$_{3-50}$ hetero hydrocarbyl optionally substituted by one or more substituent groups (preferably selected from single bond, (m+1)-valent C$_{1-50}$ linear or branched alkyl and (m+1)-valent linear or branched C$_{3-50}$ heteroalkyl); y is selected from an integral number of 1-10 (preferably an integral number of 1-5); m groups A in formula (II) are each independently selected from a group represented by the formula (III), a group represented by the formula (IV), a group represented by the formula (V), a group represented by the formula (VI), a group represented by the formula (VII); the numbers m in formula (II) are each independently selected from an integral number of 1-10 (preferably an integral number of 1-5);

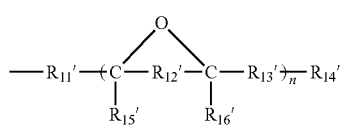 (III)

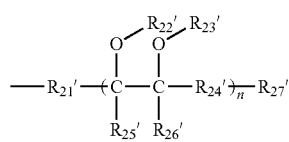 (IV)

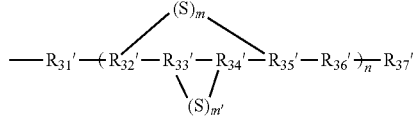 (V)

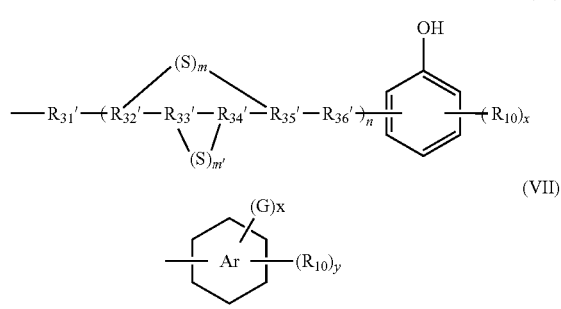

(VI)

(VII)

In the formula (III), R$_{11}$' is selected from single bond, C$_{1-20}$ linear or branched alkylene (preferably selected from single bond and C$_{1-4}$ linear or branched alkylene); groups R$_{12}$' in n repeating units are, identical to or different from each other, each independently selected from single bond, C$_{1-20}$ linear or branched alkylene (preferably each independently selected from single bond, C$_{1-4}$ linear or branched alkylene); groups R$_{13}$' in n repeating units are, identical to or different from each other, each independently selected from single bond, C$_{1-20}$ linear or branched alkylene (preferably each independently selected from single bond, C$_{1-4}$ linear or branched alkylene); the group R$_{14}$' is selected from hydrogen, C$_{1-20}$ linear or branched alkyl (preferably selected from hydrogen, C$_{1-4}$ linear or branched alkyl); groups R$_{15}$' in n repeating units are, identical to or different from each other, each independently selected from hydrogen, C$_{1-20}$ linear or branched alkyl (preferably each independently selected from hydrogen, C$_{1-4}$ linear or branched alkyl); groups R$_{16}$' in n repeating units are, identical to or different from each other, each independently selected from hydrogen, C$_{1-20}$ linear or branched alkyl (preferably each independently selected from hydrogen, C$_{1-4}$ linear or branched alkyl); n is an integral number of 1-10 (preferably an integral number of 1-3);

In the formula (IV), group R$_{21}$' is selected from single bond, C$_{1-20}$ linear or branched hydrocarbylene (preferably selected from single bond and C$_{1-4}$ linear or branched alkylene); groups R$_{22}$' and R$_{23}$' in n repeating units are, identical to or different from each other, each independently selected from

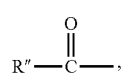

hydrogen (preferably each independently selected from

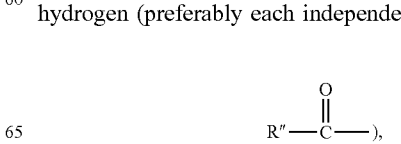), wherein R″ is selected from $C_{1-30}$ linear or branched alkyl (preferably selected from $C_{1-20}$ linear or branched alkyl); in each repeating unit, at least one group of groups $R_{22}'$ and $R_{23}'$ is selected from

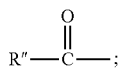

groups $R_{24}'$ in n repeating units are, identical to or different from each other, each independently selected from single bond, Ci-ao linear or branched hydrocarbylene (preferably each independently selected from single bond, $C_{1-4}$ linear or branched alkylene); groups $R_{25}'$ and $R_{26}'$ in n repeating units are, identical to or different from each other, each independently selected from hydrogen, $C_{1-20}$ linear or branched alkyl (preferably each independently selected from hydrogen, $C_{1-4}$ linear or branched alkyl); group $R_{27}'$ is selected from hydrogen, $C_{1-20}$ linear or branched hydrocarbyl (preferably selected from hydrogen, $C_{1-10}$ linear or branched alkyl); n is a positive integral number (preferably a positive integral number of 1-30, more preferably a positive integral number of 1-5);

In the formula (V) and the formula (VI), group $R_{31}'$ is each independently selected from single bond, $C_{1-20}$ linear or branched alkylene (preferably selected from single bond and $C_{1-4}$ linear or branched alkylene); groups $R_{32}'$ in n repeating units are, identical to or different from each other, each independently selected from divalent, trivalent or tetravalent $C_{1-20}$ linear or branched alkyl optionally substituted by the group of the formula (V) (preferably each independently selected from divalent, trivalent or tetravalent $C_{1-4}$ linear or branched alkyl optionally substituted by the group of the formula (V)); groups $R_{33}'$ in n repeating units are, identical to or different from each other, each independently selected from single bond, divalent or trivalent $C_{1-20}$ linear or branched alkyl (preferably each independently selected from single bond, divalent or trivalent $C_{1-4}$ linear or branched alkyl); groups $R_{34}'$ in n repeating units are, identical to or different from each other, each independently selected from single bond, divalent or trivalent $C_{1-20}$ linear or branched alkyl (preferably each independently selected from single bond, divalent or trivalent $C_{1-4}$ linear or branched alkyl); groups $R_{35}'$ in n repeating units are, identical to or different from each other, each independently selected from divalent, trivalent or tetravalent $C_{1-20}$ linear or branched alkyl optionally substituted by the group of the formula (V) (preferably each independently selected from divalent, trivalent or tetravalent $C_{1-4}$ linear or branched alkyl optionally substituted by the group of the formula (V)); groups $R_{36}'$ in n repeating units are, identical to or different from each other, each independently selected from single bond, $C_{1-20}$ linear or branched alkylene (preferably each independently selected from single bond, $C_{1-4}$ linear or branched alkylene); group $R_{37}'$ is selected from hydrogen, $C_{1-20}$ linear or branched alkyl (preferably selected from hydrogen, $C_{1-4}$ linear or branched alkyl); n is an integral number of 1-10 (preferably an integral number of 1-3); the numbers m in n repeating units are, identical to or different from each other, each independently selected from an integral number of 0-10 (preferably an integral number of 0-5); the numbers m' in n repeating units are, identical to or different from each other, each independently selected from an integral number of 0-10 (preferably an integral number of 0-5); in each repeating unit of the formulae (V) and (VI), when m is greater than 0, m sulfur atoms are bonded to the group $R_2'$ and $R_5'$; when m' is greater than 0, m' sulfur atoms are bonded to groups $R_3'$ and $R_4'$; in each repeating unit of the formulae (V) and (VI), when group $R_3'$ is single bond, m' sulfur atoms are bonded to the group $R_2'$, when group $R_4'$ is single bond, m' sulfur atoms are bonded to the group $R_5'$;

In the formula (VII), x groups G are, identical to or different from each other, each independently selected from —OH,

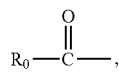

—$OR_0$, wherein group $R_0$ is selected from $C_{1-50}$ hydrocarbyl optionally substituted by one or more substituent groups and $C_{3-50}$ hetero hydrocarbyl optionally substituted by one or more substituent groups (preferably selected from $C_{1-50}$ linear or branched alkyl and linear or branched $C_{3-50}$ heteroalkyl); x is selected from an integral number of 1-10 (preferably an integral number of 1-5);

The ring groups

in the formula (I) and the formula (VII) are each independently selected from (x+y)-valent $C_{3-20}$ cycloalkyl (preferably $C_{3-6}$ cycloalkyl, more preferably cyclopentyl, cyclohexyl), (x+y)-valent $C_{6-20}$ aryl (preferably $C_{6-14}$ aryl, more preferably phenyl, biphenylyl, naphthyl, anthracyl, phenanthryl), (x+y)-valent $C_{13-20}$ arylalkylaryl (preferably $C_{13-18}$ arylalkylaryl, more preferably benzylphenyl, phenylethylphenyl, phenylmethylnaphthyl, phenylethylnaphthyl).

[Preparation Process of the Phenol Derivative]

The present invention provides a process of preparing a phenol derivative, which comprises a first step of subjecting the compound represented by the general formula (I') to at least one reaction of an epoxidation reaction, a sulfurization reaction and a coupling reaction, and a second step of subjecting to one or more reactions of an optional esterification reaction, an optional alkylation reaction and an optional hydrogenation reaction;

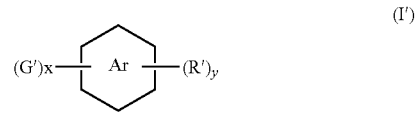

(I')

In the formula (I'), x groups G' are bonded to the ring group Ar, y groups R' are bonded to the ring group Ar;
x groups G' are, identical to or different from each other, each independently selected from —OH and H, wherein at least one group G' is-OH; x is selected from an integral number of 1-10 (preferably an integral number of 1-5);
y groups R' are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups, $C_{1-50}$ alkyloxy optionally substituted by one or more substituent groups and a group represented by the formula (II') (preferably selected from hydrogen, $C_{1-50}$ linear or branched alkyl, linear or branched $C_{3-50}$ heteroalkyl, $C_{1-50}$ linear or branched alkyloxy and a group represented by the formula (II')), wherein at least one group R' is selected from a group represented by the formula (II');

  (II')

Groups L in y groups R' are each independently selected from single bond, (m+1)-valent $C_{1-50}$ hydrocarbyl optionally substituted by one or more substituent groups and (m+1)-valent $C_{3-50}$ hetero hydrocarbyl optionally substituted by one or more substituent groups (preferably selected from single bond, (m+1)-valent $C_{1-50}$ linear or branched alkyl and (m+1)-valent linear or branched $C_{3-50}$ heteroalkyl); y is selected from an integral number of 1-10 (preferably an integral number of 1-5); m groups A' in the formula (II') are each independently selected from a group represented by the formula (III'); the numbers m in the formula (II') are each independently selected from an integral number of 1-10 (preferably an integral number of 1-5);

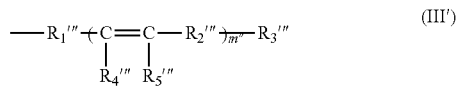  (III')

Wherein group $R_1'''$ is selected from single bond and $C_{1-20}$ linear or branched alkylene (preferably selected from single bond and $C_{1-4}$ linear or branched alkylene); groups $R_2'''$ in m" repeating units are, identical to or different from each other, each independently selected from single bond and $C_{1-20}$ linear or branched alkylene (preferably each independently selected from single bond and $C_{1-4}$ linear or branched alkylene); group $R_3'''$ is selected from hydrogen and $C_{1-20}$ linear or branched alkyl (preferably selected from hydrogen and $C_{1-4}$ linear or branched alkyl); groups $R_4'''$ in m" repeating units are, identical to or different from each other, each independently selected from hydrogen and $C_{1-20}$ linear or branched alkyl (preferably each independently selected from hydrogen and $C_{1-4}$ linear or branched alkyl); groups $R_5'''$ in m" repeating units are, identical to or different from each other, each independently selected from hydrogen and $C_{1-20}$ linear or branched alkyl (preferably each independently selected from hydrogen and $C_{1-4}$ linear or branched alkyl); m" is an integral number of 1-10 (preferably an integral number of 1-5, more preferably an integral number of 1-3);

The ring group

is selected from (x+y)-valent $C_{3-20}$ cycloalkyl (preferably $C_{3-6}$ cycloalkyl, more preferably cyclopentyl, cyclohexyl) and (x+y)-valent $C_{6-20}$ aryl (preferably $C_{6-14}$ aryl, more preferably phenyl, biphenylyl, naphthyl, anthryl, phenanthryl);

The above-mentioned "substituent group" is selected from $C_{1-20}$ alkyl, $C_{1-20}$ alkoxyl, $C_{6-10}$ aryl, hydroxy, amino, mercapto and halogen atom.

In an embodiment of the present invention, a hydrolyzing reaction is also included after the epoxidation reaction in the first step. In the process of preparing the phenol derivative according to any of the aforesaid aspects, the esterification reaction in the second step is performed after the hydrolyzing reaction step.

In an embodiment of the present invention, the preparation process of the phenol derivative can also comprise a third step of subjecting to at least one reaction selected from an epoxidation reaction, a sulfurization reaction and a coupling reaction and different from the reactions in the first step.

In an embodiment of the present invention, the phenol compound represented by the general formula (X) of the present invention is preferably derived from cardanol in the cashew nut shell liquid as the natural plant product, which has a structure of:

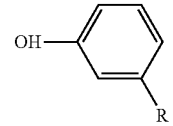

Wherein, R is $C_{15}H_{31+x}$, x is 0, −2, −4 or −6. In an embodiment of the present invention, the long chain of $C_{15}H_{31+x}$ represented by R is free of unsaturated double bond. In an embodiment of the present invention, the long chain of $C_{15}H_{31+x}$ represented by R contains 1 unsaturated double bond. In an embodiment of the present invention, the long chain of $C_{15}H_{31+x}$ represented by R contain 2 unsaturated double bonds. In an embodiment of the present invention, the long chain of $C_{15}H_{31+x}$ represented by R contain 3 unsaturated double bonds. In an embodiment of the present invention, the long chain of $C_{15}H_{31+x}$ represented by R is a carbon chain containing 15 carbon atoms and 0-3 olefinic bonds, wherein the olefinic bond(s) may appear at 8-position, 11-position and 14-position respectively.

In an embodiment of the present invention, in case that one or more reactions of an optional esterification reaction, an optional alkylation reaction and an optional hydrogenation reaction in the second step is performed, either the compound represented by the general formula (I') can be subjected to at least one reaction of an epoxidation reaction, a sulfurization reaction and a coupling reaction in the first step, followed by one or more reactions of an optional esterification reaction, an optional alkylation reaction and an optional hydrogenation reaction in the second step, or the compound represented by the general formula (I') can be subjected to one or more reactions of an optional esterification reaction, an optional alkylation reaction and an optional hydrogenation reaction in the second step, followed by at least one reaction of an epoxidation reaction, a sulfurization reaction and a coupling reaction in the first step.

Namely, in the process of preparing the phenol derivative of the present invention, the order between one or more steps of the optional esterification reaction step, the optional alkylation reaction step, and the optional hydrogenation reaction step (the first step) and at least one step selected from the coupling reaction step, the epoxidation reaction step, and the sulfurization reaction step (the second step) is not limited, and can be arbitrarily adjusted according to the requirement. Moreover, in the first step, if the multistep reaction is performed, the order among the optional esterification reaction step, the optional alkylation reaction step, and the optional hydrogenation reaction step is also not limited, and can be arbitrarily adjusted according to the requirement. Moreover, in the second step, if the multistep reaction is performed, the order among the coupling reaction step, the epoxidation reaction step, and the sulfurization reaction step is also not limited, and can be arbitrarily adjusted according to the requirement. It will be appreciated by those skilled in the art that, in the case that the side reaction is reduced as much as possible, the order of the above-mentioned reaction steps can be adjusted.

In an embodiment of the present invention, the process of preparing the phenol derivative of the present invention can also comprise a third step of subjecting to at least one reaction selected from an epoxidation reaction, a sulfurization reaction and a coupling reaction and different from the reactions in the first step. The third step can be performed after the first step and before the second step, and can also be performed after the first step and the second step.

According to the process of preparing the phenol derivative of the present invention, the epoxidation reaction is to react —C=C— in the compound represented by the formula (I') with an epoxidizing agent, or to react a product obtained from subjecting the compound represented by the formula (I') to one or more reactions of an optional esterification reaction, an optional alkylation reaction and an optional hydrogenation reaction in the second step (thereinafter also known as the product of the second step) with an epoxidizing agent. The epoxidation reaction causes an electrophilic addition reaction of an epoxidizing agent with a carbon-carbon double bond (olefinic bond) to generate an epoxy group. When there is one carbon-carbon double bond in the molecule, a single epoxy group is generated, and when there are two or more carbon-carbon double bonds in the molecule, a single epoxy group and/or two or more epoxy groups can be generated depending on the reaction conditions, the molar ratio of the reactants, and the like, in this case, the generated epoxide can be a mixture of epoxides having the single epoxy group located at different positions, or a mixture of epoxides having different numbers of epoxy groups in the molecule, or a mixture of the above two. Either all groups —C=C— in the compound represented by the formula (I') or the product obtained from any step can be reacted with an epoxidizing agent, or a part of groups —C=C— in the compound represented by the formula (I') or the product obtained from any step can be reacted with an epoxidizing agent.

According to the preparation process of the present invention, the used epoxidizing agent can be those epoxidizing agents useful for the epoxidation reaction well known in the art. The epoxidizing agent is preferably a peroxide, for example can be selected from one or more of hydrogen peroxide, peroxyformic acid, peroxyacetic acid, peroxysulfonic acid, m-chloro peroxybenzoic acid, tert-butyl hydroperoxide, tert-butyl peroxyacetate, methyl ethyl ketone peroxide, dibenzoyl peroxide and cyclohexanone peroxide.

According to the preparation process of the present invention, in the epoxidation reaction, based on the compound represented by the formula (I') or the product obtained from any step, the molar ratio of the compound represented by the formula (I') or the product of the second step to the epoxidizing agent, depending on the number of the epoxy group (s) to be generated, is preferably 1:1-10, more preferably 1:2-5. The conditions of the epoxidation reaction can be those epoxidation conditions well known in the art, for example the reaction temperature is 0° C.-100° C., preferably 10° C.-80° C. Usually, the longer the reaction time is, the higher the conversion is, and under the overall consideration of the reaction conversion and the reaction economy, the reaction time is generally 0.5-10 hours, preferably 3-5 hours.

According to the preparation process of the present invention, in the epoxidation reaction, a catalyst is optionally but preferably added. The catalyst useful for the epoxidation reaction well known in the art can be used as the catalyst, and the catalyst is preferably an inorganic acid, for example can be selected from one or more of sulfuric acid, hydrochloric acid, phosphoric acid, nitric acid, a heteropoly acid and a solid acid. The mass of the catalyst is not particularly limited, and is usually 0.01%-3%, preferably 0.2%-0.6% by the mass of the compound represented by the formula (I') or the product of the second step. According to the process of preparing the phenol derivative of the present invention, the sulfurization reaction is to react —C=C— in the compound represented by the formula (I') with a sulfurizing agent, or to react the product obtained by subjecting the compound represented by the formula (I') to one or more reactions of an optional esterification reaction, an optional alkylation reaction and an optional hydrogenation reaction in the second step (thereinafter also known as the product of the second step) with a sulfurizing agent. The epoxidation reaction is an electrophilic addition reaction of a sulfurizing agent and a carbon-carbon double bond (olefinic bond) to generate a sulfur ring group. When there is one carbon-carbon double bond in the molecule, a single sulfur ring group is generated, and when there are two or more carbon-carbon double bonds in the molecule, a single sulfur ring group and/or two or more sulfur ring groups can be generated depending on the reaction conditions, the molar ratio of the reactants, and the like; or alternatively the reaction can be performed between C=C double bonds of different molecules to connect two molecules through a sulfur linking group. In this case, the generated cyclic sulfide can be a mixture of cyclic sulfides having the single sulfur ring group located at different positions, or a mixture of cyclic sulfides having different numbers of sulfur ring groups in the molecule, or a mixture of the above two. Either all groups —C=C— in the compound represented by the formula (I') or the product of the second step can be reacted with a sulfurizing agent, or a part of groups —C=C— in the compound represented by the formula (I') or the product of the second step can be reacted with a sulfurizing agent.

According to the preparation process of the present invention, a sulfurizing agent well known in the art and useful in the thia cyclization reaction (cyclic sulfurization reaction) can be used as the sulfurizing agent. The sulfurizing agent is preferably an inorganic sulfurizing agent and/or an organic sulfurizing agent, the inorganic sulfurizing agent can be selected from one or more of sulphur, $Na_2S$, $K_2S$, ZnS, $H_2S$ and SCl; the organic sulfurizing agent can be selected from one or more of ditertbutyl polysulfide (DBPS), dimethyl disulphide (DMDS), dimethyl sulfide (DMS), ethyl mercaptan (EM), n-butyl mercaptan (NBM) and tertnonyl polysulfide (TNPS); the sulfurizing agent is more preferably one or more of sulphur, $Na_2S$ and thiol.

According to the preparation process of the present invention, in the sulfurization reaction, based on the compound represented by the formula (I') or the product obtained from any step, the reaction mole ratio of the compound represented by the formula (I') or the product of the second step to the sulfurizing agent depending on the number of the sulfur ring group(s) to be generated, is preferably 1:1-6, more preferably 1:2-4. The sulfurization reaction conditions can be those sulfurization conditions well known in the art, for example the reaction temperature is 100° C.-240° C., preferably 140° C.-190° C. Usually, the longer the reaction time is, the higher the conversion is, and under the overall consideration of the reaction conversion and the reaction economy, the reaction time is generally 0.5-10 hours, preferably 3-5 hours.

According to the preparation process of the present invention, in the sulfurization reaction, a catalyst is optionally but preferably added. The catalyst useful for the sulfurization reaction well known in the art can be used as the catalyst, the catalyst is preferably selected from $C_{1-6}$ organic amine and inorganic base, for example can be selected from one or more of methylamine, dimethylamine, ethylamine, diethylamine, propylamine, dipropyl amine, tripropyl amine, butylamine, amylamine, hexylamine, ammonia water, sodium hydroxide, potassium hydroxide, zinc hydroxide, sodium oxide, potassium oxide, zinc oxide, sodium carbonate, potassium carbonate and zinc carbonate. The mass of the catalyst is not particularly limited, and is usually 0.01%-10%, preferably 0.1%-5% by the mass of the compound represented by the formula (I') or the product of the second step.

According to the process of preparing the phenol derivative of the present invention, the coupling reaction is to react the compound represented by the formula (I') with a coupling agent, or to react the product obtained by subjecting the compound represented by the formula (I') to at least one reaction of an epoxidation reaction, and a sulfurization reaction in the first step and/or one or more reactions of an optional esterification reaction, an optional alkylation reaction and an optional hydrogenation reaction in the second step (thereinafter also known as the product obtained from any step) with a coupling agent.

According to the preparation process of the present invention, a coupling agent well known in the art and useful in the coupling reaction can be used as the coupling agent. The coupling agent is preferably $C_1$-$C_6$ aldehyde. $C_1$-$C_6$ aldehyde refers to an aldehyde having 1-6 carbon atoms, and it can be selected from formaldehyde, acetaldehyde, propaldehyde, butyraldehyde, valeraldehyde or hexaldehyde and the like. In the coupling reaction, based on the compound represented by the formula (I') or the product obtained from any step, the molar ratio of the compound represented by the formula (I') or the product obtained from any step to the coupling agent is preferably 1-10:1 (more preferably 2-5:1). The conditions of the coupling reaction can be those couple conditions well known in the art, for example reaction temperature is preferably 20° C.-120° C., more preferably 50° C.-100° C. In general, the longer the reaction time, the better it is, and usually it is preferably 0.5-10 hours, most preferably 3-5 hours.

According to the preparation process of the present invention, in the coupling reaction, a catalyst is optionally but preferably added. The catalyst is preferably an acidic catalyst or a basic catalyst. The acidic catalyst can be selected from one or more of sulfuric acid, hydrochloric acid, nitric acid and phosphoric acid (preferably sulfuric acid). The basic catalyst can be selected from hydroxides of alkali metals and/or alkaline earth metals, can be selected from one or more of sodium hydroxide, potassium hydroxide, magnesium hydroxide, calcium hydroxide and barium hydroxide (preferably sodium hydroxide). The addition amount of the catalyst is preferably 0.1%-10%, more preferably 0.8%-2% by the mass of the compound represented by the formula (I') or the product obtained from any step.

According to the process of preparing the phenol derivative of the present invention, the alkylation reaction is to react ortho- and para-position hydrogens of the hydroxy groups on the ring group present in the compound represented by the formula (I') with an alkylating agent, or to react ortho- and para-position hydrogens of the hydroxy groups on the ring group present in the product obtained from subjecting the compound represented by the formula (I') to at least one reaction of an epoxidation reaction, a sulfurization reaction and a coupling reaction in the first step and/or to one or more reactions of an optional esterification reaction and an optional hydrogenation reaction in the second step (thereinafter also known as the product obtained from any step) with an alkylating agent. According to the preparation process of the present invention, an alkylating agent well known in the art and useful in the alkylation reaction can be used as the alkylating agent. The alkylating agent is preferably selected from one or more of halohydrocarbon, fatty alcohol and alkene, more preferably haloalkane and/or alkene, for example can be selected from one or more of tert-butyl chloride, tert-butyl bromide, isobutylene and isopropylene. In the alkylation reaction, based on a compound represented by the formula (I') or the product obtained from any step, the molar ratio of the compound represented by the formula (I') or the product obtained from any step to the alkylating agent is preferably 1:1-5 (more preferably 1:1-2.5). The conditions of the alkylation reaction can be those alkylation conditions well known in the art, for example the reaction temperature is preferably 20° C.-100° C., more preferably 40° C.-80° C. Usually, the longer the reaction time is, the higher the conversion is, and under the overall consideration of the reaction conversion and the reaction economy, the reaction time is preferably 0.5 hours-10 hours, more preferably 3 hours-5 hours.

In the alkylation reaction, a catalyst is optionally but preferably added. The catalyst comprises one or more of metallic chloride, inorganic acid, organic acid and Lewis acid, is preferably selected from metallic chloride and inorganic acid, for example can be selected from one or more of zinc chloride, aluminum chloride, tin chloride, concentrated sulphuric acid, concentrated hydrochloric acid, concentrated nitric acid, boron trifluoride and heteropoly acid. The mass of the catalyst is preferably 0.1%-10%, more preferably 1%-6% by the mass of the compound represented by the formula (I') or the product obtained from any step.

According to the process of preparing the phenol derivative of the present invention, the hydrogenation reaction is to react the unsaturated bond (—C═C—) in the compound represented by the formula (I') with a hydrogenating agent, or to react the unsaturated bond (—C═C—) present in the product obtained from subjecting the compound represented by the formula (I') to at least one reaction of an epoxidation reaction, a sulfurization reaction and a coupling reaction in the first step and/or to one or more reactions of an optional esterification reaction and an optional alkylation reaction in the second step (thereinafter also known as the product obtained from any step) with a hydrogenating agent.

According to the preparation process of the present invention, a hydrogenating agent well known in the art and useful in the hydrogenation reaction can be used as the hydrogenating agent. The hydrogenating agent is preferably hydrogen gas. In the hydrogenation reaction, based on a compound represented by the formula (I') or the product obtained from any step, the molar ratio of the compound represented by the formula (I') or the product obtained from any step to the hydrogenating agent is preferably 1:1-10 (more preferably 1:2-5). The conditions of the hydrogenation reaction can be those hydrogenation conditions well known in the art, for example the reaction temperature is preferably 60° C.-260° C., more preferably 180° C.-220° C. According to the process of preparing the phenol derivative of the present invention, the esterification reaction is to react a hydroxy group on the ring group of a compound represented by the formula (I') with an esterifying agent, or to react the product obtained from subjecting the compound represented by the formula (I') to at least one reaction of an epoxidation reaction, a sulfurization reaction and a coupling reaction in the first step and/or to one or more reactions of an optional alkylation reaction and an optional hydrogenation reaction in the second step (thereinafter also known as the product obtained from any step) with an esterifying agent.

According to the preparation process of the present invention, an esterifying agent well known in the art and useful in the esterification reaction can be used as the esterifying agent. The esterifying agent is selected from

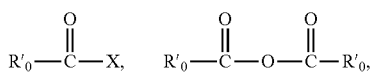

wherein groups $R_0'$ are, identical to or different from each other, each independently selected from $C_{1-50}$ linear or branched alkyl (preferably $C_{1-30}$ linear or branched alkyl), X is selected from F, Cl, Br, I, OH. In addition, the esterifying agent can comprise one or more of fatty acid, fatty acid anhydride and haloalkane, wherein the alkyl is $C_1$-$C_{30}$ linear or branched alkyl (more preferably $C_1$-$C_{20}$ linear or branched alkyl). The esterifying agent is preferably $C_1$-$C_{30}$ linear or branched organic carboxylic acid (more preferably $C_1$-$C_{20}$ linear or branched organic carboxylic acid). In the esterification reaction, based on the compound represented by the formula (I') or the product obtained from any step, the molar ratio of the compound represented by the formula (I') or the product obtained from any step to an esterifying agent is 1:1-10 (preferably 1:2-8). The conditions of the esterification reaction can be those esterification conditions well known in the art, for example the reaction temperature is 80° C.-260° C. (preferably 120° C.-210° C.). In general, the longer the reaction time is, the higher the conversion is, usually the reaction time is 0.5 h-10 h (preferably 3 h-5 h).

In the esterification reaction, a catalyst is optionally but preferably added. The catalyst is preferably an inorganic base or a weak acid salt of an inorganic base, for example can be selected from one or more of sodium hydroxide, potassium hydroxide, calcium hydroxide, sodium carbonate and potassium carbonate. The used amount of the catalyst is 0.1%-15% (preferably 5%-10%) by the mass of the compound represented by the formula (I') or the product obtained from any step. In the first esterification, a solvent is optionally but preferably added. Said solvent is preferably one or more of toluene, xylene, petroleum ether and cyclohexane, for example can be selected from toluene and/or xylene. The used amount of said solvent is 0.1%-15% (preferably 5%-10%) by the mass of the compound represented by the formula (I') or the product obtained from any step. The catalyst and the solvent can be removed by one or more of the methods comprising acid washing, water washing, distillating, filtering, drying and recrystallization without particular limitation.

According to the preparation process of the present invention, the reactants and the reaction conditions of at least one reaction selected from an epoxidation reaction, a sulfurization reaction and a coupling reaction in the third step, different from the first step, as mentioned above, are identical to those in the epoxidation reaction, the sulfurization reaction, and the coupling reaction, as mentioned above.

According to the preparation process of the present invention, a hydrolyzing reaction can be performed after the epoxidation reaction in the first step. By the hydrolyzing reaction, the epoxy group can be subjected to the ring-opening to produce an ortho-diol structure. The ring-opening reaction can be performed under the conditions of the ring-opening reaction well known in the art. The conventional conditions of the ring-opening reaction comprise: the molar ratio of the reaction feed water to the epoxy compound in the first step is 20-25:1, the reaction temperature is 150-200° C., the reaction pressure is 0.8-2.0 MPa. A catalyst can be optionally used in the ring-opening reaction, and the catalyst can be a conventional inorganic acid (one or more of sulfuric acid, hydrochloric acid, phosphoric acid, nitric acid, a heteropoly acid and a solid acid), and may also be a conventional inorganic base (alkali metal hydroxide and alkaline earth metal hydroxide).

According to the preparation process of the present invention, the hydrolyzing reaction step is followed by the esterification reaction in the second step, and thereby the ortho-diol generated in the hydrolyzing reaction is converted into an ester. The esterifying agent, the reaction conditions and the like of the esterification reaction can be identical to those of the above-mentioned esterification reaction of the present invention.

In the process of preparing the phenol derivative of the present invention, alternatively the epoxide prepared in the epoxidation reaction of the first step can be reacted with the second esterifying agent to perform the second esterification reaction. The second esterifying agent comprises one or more of fatty acid, fatty acid anhydride and haloalkane, wherein the alkyl is $C_1$-$C_{30}$ linear or branched alkyl (more preferably $C_1$-$C_{20}$ linear or branched alkyl). The second esterifying agent is preferably $C_1$-$C_{30}$ linear or branched organic carboxylic acid (more preferably $C_1$-$C_{20}$ linear or branched organic carboxylic acid). The reaction conditions of the second esterification reaction comprise: the molar ratio of the epoxide to the second esterifying agent is 1:1-10 (preferably 1:2-8); the reaction temperature is 80° C.-260° C. (preferably 120° C.-210° C.); in general, the longer reaction time is, the higher the conversion is, usually the reaction time is 5h-20h (preferably 8h-18h). In the second esterification reaction, a catalyst is optionally but preferably added. The catalyst is preferably inorganic acid, and for example can be selected from one or more of sulfuric acid, hydrochloric acid, nitric acid and phosphoric acid. The used amount of the catalyst is 0.1%-10% (preferably 0.2%-2%) by the mass of the epoxide. In the second esterification reaction, a solvent is optionally but preferably added. Said solvent is preferably one or more of toluene, xylene, petroleum ether and cyclohexane, for example can be selected from toluene and/or xylene. The used amount of said solvent is 0.1%-15% (preferably 5%-10%) by the mass of the epoxide.

In the process of preparing the phenol derivative of the present invention, the esterification reaction, the alkylation reaction, and the hydrogenation reaction in the second step are the optional reaction, namely, these reaction in said step can be discretionarily performed as required. The reaction conditions well known in the art can be used as the conditions for these reactions in said step.

In the preparation process of the present invention, in the above-mentioned steps of the reactions, a solvent can be optionally, but preferably used. Said solvent is preferably one or more of toluene, ethanol, acetone, chloroform and petroleum ether.

In the preparation process of the present invention, after the above-mentioned steps of the reactions, the reaction product may be subjected to a purification treatment by using the method well known in the art, the method of the purification treatment comprises one or more of water washing, distillation, filtration, drying, and recrystallization methods, without particular limitation.

In an embodiment of the present invention, the process of preparing the phenol derivative of the present invention comprises a step of subjecting a compound represented by the general formula (I') to an epoxidation reaction or a sulfurization reaction, and a step of subjecting to one or more reactions of an optional esterification reaction, an optional alkylation reaction, an optional hydrogenation reaction and an optional coupling reaction;

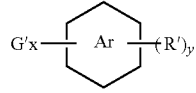
(I')

In the formula (I'), x groups G' are bonded to the ring group Ar, y groups R' are bonded to the ring group Ar;

x groups G' are, identical to or different from each other, each independently selected from —OH, H, wherein at least one group G' is-OH; x is selected from an integral number of 1-10 (preferably an integral number of 1-5);

y groups R' are, identical to or different from each other, each independently selected from hydrogen, $C_{1-50}$ hydrocarbyl optionally substituted by one or more substituent groups, $C_{3-50}$ hetero hydrocarbyl optionally substituted by one or more substituent groups and $C_{1-50}$ alkyloxy optionally substituted by one or more substituent groups (preferably selected from hydrogen, $C_{1-50}$ linear or branched alkyl, linear or branched $C_{3-50}$ heteroalkyl, $C_{1-50}$ linear or branched alkyloxy), the group represented by the formula (II'), wherein at least one group R' is selected from the group represented by the formula (II');

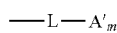
(II')

Groups L in y groups R' are each independently selected from single bond, (m+1)-valent $C_{1-50}$ hydrocarbyl optionally substituted by one or more substituent groups and (m+1)-valent $C_{3-50}$ hetero hydrocarbyl optionally substituted by one or more substituent groups (preferably selected from single bond, (m+1)-valent $C_{1-50}$ linear or branched alkyl and (m+1)-valent linear or branched $C_{3-50}$ heteroalkyl); y is selected from an integral number of 1-10 (preferably an integral number of 1-5); m groups A in the formula (II') are each independently selected from the group represented by the formula (III'); m in formula (II') is (each independently) selected from an integral number of 1-10 (preferably an integral number of 1-5);

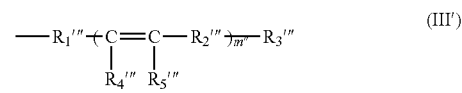
(III')

Wherein group $R_1'''$ is selected from single bond, $C_{1-20}$ linear or branched alkylene (preferably selected from single bond and $C_{1-4}$ linear or branched alkylene); groups $R_2'''$ in m" repeating units are, identical to or different from each other, each independently selected from single bond, $C_{1-20}$ linear or branched alkylene (preferably each independently selected from single bond, $C_{1-4}$ linear or branched alkylene); group $R_3'''$ is selected from hydrogen, $C_{1-20}$ linear or branched alkyl (preferably selected from hydrogen, $C_{1-4}$ linear or branched alkyl); groups $R_4'''$ in m" repeating units are, identical to or different from each other, each independently selected from hydrogen, $C_{1-20}$ linear or branched alkyl (preferably each independently selected from hydrogen, $C_{1-4}$ linear or branched alkyl); groups $R_5'''$ in m" repeating units are, identical to or different from each other, each independently selected from hydrogen, $C_{1-20}$ linear or branched alkyl (preferably each independently selected from hydrogen, $C_{1-4}$ linear or branched alkyl); m" is an integral number of 1-10 (preferably an integral number of 1-3);

The ring group

is selected from (x+y)-valent $C_{3-20}$ cycloalkyl (preferably $C_{3-6}$ cycloalkyl, more preferably cyclopentyl, cyclohexyl), (x+y)-valent $C_{6-20}$ aryl (preferably $C_{6-14}$ aryl, more preferably phenyl, biphenylyl, naphthyl, anthracyl, phenanthryl), (x+y)-valent $C_{13-20}$ arylalkylaryl (preferably $C_{13-18}$ arylalkylaryl, more preferably benzylphenyl, phenylethylphenyl, phenylmethylnaphthyl, phenylethylnaphthyl).

According to the present invention, in the preparation process of the phenol derivative, the reaction product can be a phenol derivative of a single structure, or a mixture containing phenol derivatives of different structures. These reaction products are all contemplated by the present invention, and the diversity in their occurrence forms does not affect the achievement of the effects of the present invention. Therefore, these reaction products are collectively referred to as the phenol derivative of the present invention without distinction in the context of the present specification. Especially, with respect to the cardanol, in the carbon chain as R of the cardanol being of 15 carbon atoms, the olefinic bond(s) may appear at 8-position, 11-position and 14-position respectively, and the proportions of saturated and unsaturated cardanols in the cardanol are respectively: about 41% of the cardanol having three olefinic bonds, about 22% of the cardanol having two olefinic bonds, about 34% of the cardanol having one olefinic bond, and the balance of the saturated cardanol. In view of this, according to the present invention, there is no absolute necessity to further purify the reaction products or to further separate a phenol derivative having a specific structure from these reaction products. Of course, sometimes such purification or separation is preferable for further improvement of the intended effect of the present invention, but is not essential to the present invention. Nevertheless, as the purification or separation method, for example, the purification or separation of the reaction product by a method such as washing, filtering, distillating, recrystallization, column chromatography, and preparative chromatography can be enumerated.

According to the present invention, in the preparation process of the phenol derivative, after said reaction step is completed, volatile substances such as solvents which may be present are removed from the reaction mixture obtained in the step by a known conventional separation method (such as evaporation), and then the reaction product from said step can be obtained.

In the following embodiments, the preferred phenol derivatives of the present invention and the corresponding preparation processes therefor are enumerated.

First Embodiment

According to the first embodiment of the present invention, the phenol derivative of the present invention has a structure as shown by formula (I-1):

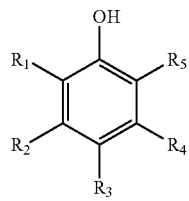

(I-1)

In the general formula (I-1), groups $R_1$, $R_2$, $R_3$, $R_4$, and $R_5$, identical to or different from each other, are each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups, $C_{1-50}$ alkoxyl optionally substituted by one or more substituent groups, a group represented by the general formula (III), provided that at least one group of groups $R_1$, $R_2$, $R_3$, $R_4$ and $R_5$ is a group represented by the general formula (III);

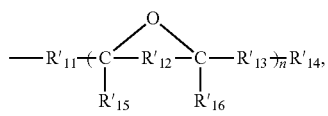

(III)

In the general formula (III), group $R_{11}'$ is selected from single bond and $C_{1-20}$ linear or branched alkylene (preferably selected from single bond and $C_{1-4}$ linear or branched alkylene); groups $R_{12}'$ in n repeating units are, identical to or different from each other, each independently selected from single bond and $C_{1-20}$ linear or branched alkylene (preferably each independently selected from single bond and $C_{1-4}$ linear or branched alkylene); groups $R_{13}'$ in n repeating units are, identical to or different from each other, each independently selected from single bond and $C_{1-20}$ linear or branched alkylene (preferably each independently selected from single bond and $C_{1-4}$ linear or branched alkylene); group $R_{14}'$ is selected from hydrogen and $C_{1-20}$ linear or branched alkyl (preferably selected from hydrogen and $C_{1-4}$ linear or branched alkyl); groups $R_{15}'$ in n repeating units are, identical to or different from each other, each independently selected from hydrogen and $C_{1-20}$ linear or branched alkyl (preferably each independently selected from hydrogen and $C_{1-4}$ linear or branched alkyl); groups $R_{16}'$ in n repeating units are, identical to or different from each other, each independently selected from hydrogen and $C_{1-20}$ linear or branched alkyl (preferably each independently selected from hydrogen and $C_{1-4}$ linear or branched alkyl); n is an integral number of 1-10 (preferably an integral number of 1-3).

In the general formula (I-1), preferably, groups $R_1$, $R_3$ and $R_5$ are, identical to or different from each other, each independently selected from hydrogen, $C_{1-4}$ linear or branched alkyl, at least one group of groups $R_1$, $R_3$, and $R_5$ is selected from $C_{1-4}$ linear or branched alkyl; groups $R_2$ and $R_4$ are, identical to or different from each other, each independently selected from hydrogen, $C_{1-30}$ linear or branched alkyl, and a group represented by the general formula (III), wherein at least one group is a group represented by the general formula (III).

In the general formula (I-1), further preferably, one group of groups $R_1$ and $R_5$ is selected from $C_{1-4}$ linear or branched alkyl, the other group is selected from hydrogen; group $R_3$ is selected from hydrogen, $C_{1-4}$ linear or branched alkyl; one group of groups $R_2$ and $R_4$ is selected from a group represented by the general formula (III), the other group is selected from hydrogen.

In the general formula (I-1), more preferably, group $R_1$ is selected from $C_{1-4}$ linear or branched alkyl, $R_5$ is selected from hydrogen; group $R_3$ is selected from hydrogen, $C_{1-4}$ linear or branched alkyl; group $R_2$ is selected from hydrogen, $R_4$ is selected from a group represented by the general formula (III).

Further preferably, the phenol derivative as represented by the formula (I-1) of the present invention is selected from the following specific compounds or a mixture thereof in any proportion:

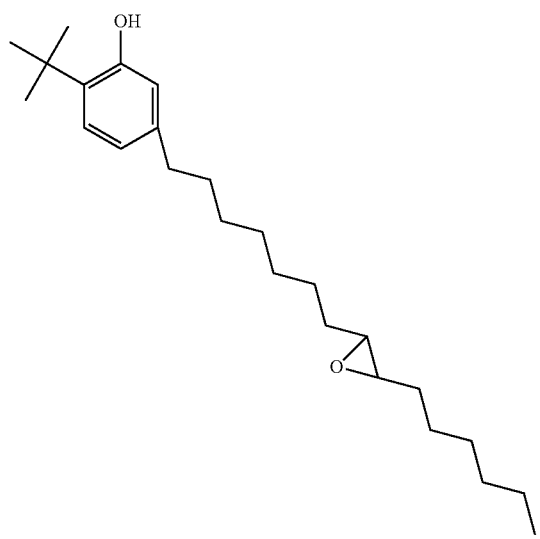

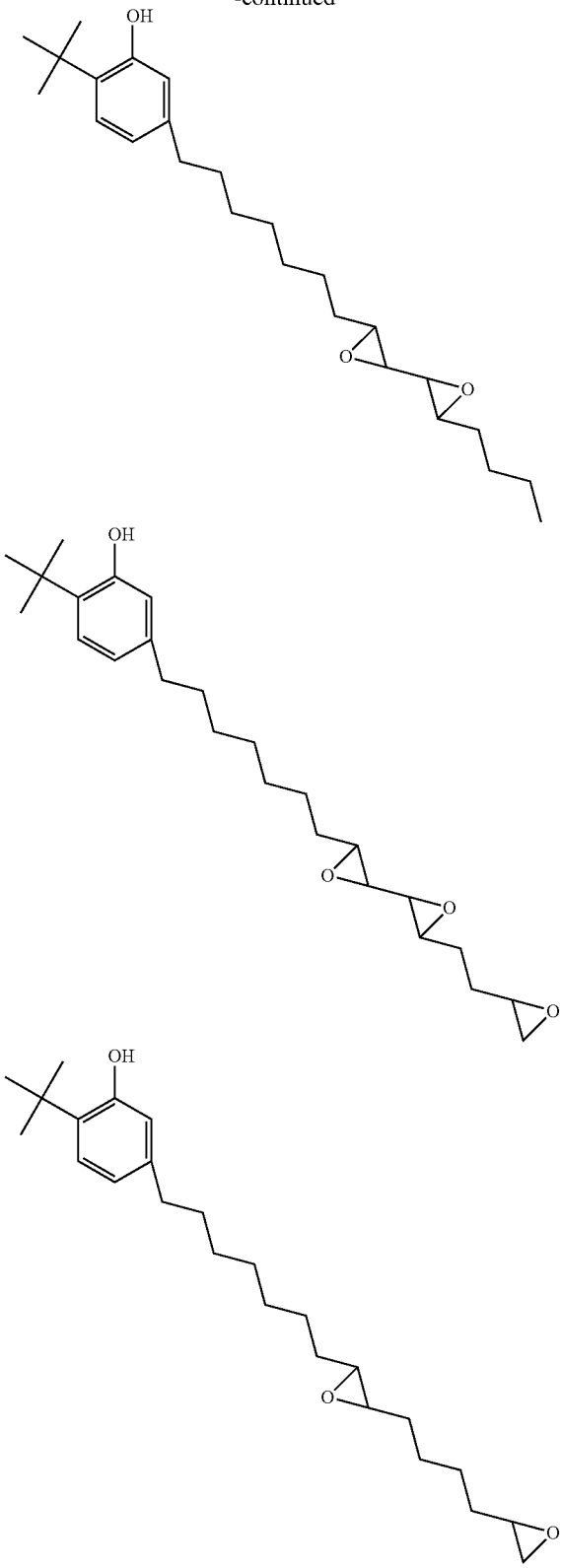

The process of preparing a phenol derivative represented by the formula (I-1) of the first embodiment of the present invention comprises a step of subjecting the phenol compound represented by the general formula (X) to the epoxidation reaction,

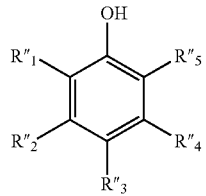

In the general formula (X), groups $R_1''$, $R_2''$, $R_3''$, $R_4''$ and $R_5''$ are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups, $C_{1-50}$ alkoxyl optionally substituted by one or more substituent groups and a group represented by the general formula (III'), wherein at least one group is selected from a group represented by the general formula (III');

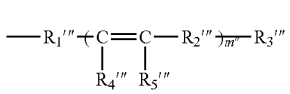

Wherein group $R_1'''$ is selected from single bond and $C_{1-20}$ linear or branched alkylene (preferably selected from single bond and $C_{1-4}$ linear or branched alkylene); groups $R_2'''$ in m repeating units are, identical to or different from each other, each independently selected from single bond and $C_{1-20}$ linear or branched alkylene (preferably each independently selected from single bond and $C_{1-4}$ linear or branched alkylene); group $R_3'''$ is selected from hydrogen and $C_{1-20}$ linear or branched alkyl (preferably selected from hydrogen and $C_{1-4}$ linear or branched alkyl); groups $R_4'''$ in m repeating units are, identical to or different from each other, each independently selected from hydrogen and $C_{1-20}$ linear or branched alkyl (preferably each independently selected from hydrogen and $C_{1-4}$ linear or branched alkyl); groups $R_5'''$ in m repeating units are, identical to or different from each other, each independently selected from hydrogen and $C_{1-20}$ linear or branched alkyl (preferably each independently selected from hydrogen and $C_{1-4}$ linear or branched alkyl); m'' is an integral number of 1-10 (preferably an integral number of 1-5, more preferably an integral number of 1-3).

In the process of preparing a phenol derivative represented by the formula (I-1) according to the first embodiment of the present invention, in the general formula (X), preferably, groups $R_1''$, $R_3''$ and $R_5''$ are, identical to or different from each other, each independently selected from hydrogen, $C_{1-4}$ linear or branched alkyl, at least one group of groups $R_1''$, $R_3''$, and $R_5''$ is selected from $C_{1-4}$ linear or branched alkyl; groups $R_2''$ and $R_4''$ are, identical to or different from each other, each independently selected from hydrogen, a group represented by the general formula (III') and $C_{1-30}$ linear or branched alkyl, wherein at least one group is a group represented by the formula (III').

In the process of preparing a phenol derivative represented by the formula (I-1) according to the first embodiment of the present invention, further preferably, in the general formula (X), one group of groups $R_1''$ and $R_5''$ is selected from $C_{1-4}$ linear or branched alkyl, the other group is selected from hydrogen; group $R_3''$ is selected from hydrogen, $C_{1-4}$ linear or branched alkyl; one group of groups $R_2''$ and $R_4''$ is selected from a group represented by the general formula (III'), the other group is selected from hydrogen.

In the process of preparing a phenol derivative represented by the formula (I-1) according to the first embodiment of the present invention, more preferably in the general formula (X), group $R_1''$ is selected from $C_{1-4}$ linear or branched alkyl, group $R_5''$ is selected from hydrogen; group $R_3''$ is selected from hydrogen, $C_{1-4}$ linear or branched alkyl; group $R_2''$ is selected from hydrogen, the group $R_4''$ is selected from a group represented by the general formula (III').

In the process of preparing a phenol derivative represented by the formula (I-1) according to the first embodiment of the present invention, the epoxidation reaction is to react the phenol compound represented by the general formula (X) with an epoxidizing agent. The epoxidizing agent is preferably a peroxide, for example can be selected from one or more of hydrogen peroxide, peroxyformic acid, peroxyacetic acid, peroxysulfonic acid, m-chloro peroxybenzoic acid, tert-butyl hydroperoxide, tert-butyl peroxyacetate, methyl ethyl ketone peroxide, dibenzoyl peroxide and cyclohexanone peroxide. The molar ratio of the phenol compound represented by the general formula (X) to the epoxidizing agent is preferably 1:1-10, more preferably 1:2-5. The epoxidation reaction temperature is 0° C.-100° C., preferably 10° C.-80° C.; usually, the longer the reaction time is, the higher the conversion is; and under the overall consideration of the reaction conversion and the reaction economy, the reaction time is generally 0.5-10 hours preferably 3-5 hours.

In the process of preparing a phenol derivative represented by the formula (I-1) according to the first embodiment of the present invention, in the epoxidation reaction a catalyst is optionally but preferably added. The catalyst is preferably an inorganic acid, for example can be selected from one or more of sulfuric acid, hydrochloric acid, phosphoric acid, nitric acid, a heteropoly acid and a solid acid. The mass of the catalyst is 0.01%-3%, preferably 0.2%-0.6% by mass of the phenol compound represented by the general formula (X).

In the process of preparing a phenol derivative represented by the formula (I-1) according to the first embodiment of the present invention, after the completion of the epoxidation reaction, the reaction product may be subjected to a purification treatment by using the method well known in the art, the method of the purification treatment comprises one or more of water washing, distillation, filtration, drying, and recrystallization methods, without particular limitation; after an inorganic acid catalyst has been added in the epoxidation reaction, the method of the purification treatment comprises one or more of alkali washing, water washing, distillation, filtration, drying, and recrystallization methods.

In the process of preparing a phenol derivative shown in the formula (I-1) according to the first embodiment of the present invention, additionally one or more reaction of an optional esterification reaction, an optional alkylation reaction, an optional hydrogenation reaction and a coupling reaction can be performed. Preferably, when at least one group of groups $R_1''$, $R_3''$ and $R_5''$ in the phenol compound represented by the general formula (X) is hydrogen, the phenol compound represented by the general formula (X) can be subjected to the epoxidation reaction, followed by an alkylation reaction (preferably tertbutylation reaction), and a product is collected. The reaction conditions for subjecting the phenol compound represented by the general formula (X) to the epoxidation reaction are the same as those described above. The alkylation reaction (preferably tert-butylation reaction) is to react a reaction product obtained from subjecting the phenol compound represented by the general formula (X) to the epoxidation reaction with an alkylating agent (tertbutylation agent). The alkylating agent is selected from halohydrocarbon, fatty alcohol and alkene, preferably selected from $C_{1-4}$ alkyl halide and $C_{2-4}$ alkene, for example can be selected from one or more of tert-butyl chloride, tert-butyl bromide, isopropylene and isobutylene (the tertbutylating agent is preferably one or more of tert-butyl chloride, tert-butyl bromide and isobutylene).

The phenol derivative represented by the formula (I-1) of the present invention is excellent in the antioxygenic property, can be used as antioxidant, and can be applied in lubricating oil, lubricating grease, the fuel oil, the plastic and the rubber.

Second Embodiment

According to the second embodiment of the present invention, the phenol derivative of the present invention has a structure as represented by the formula (I-2):

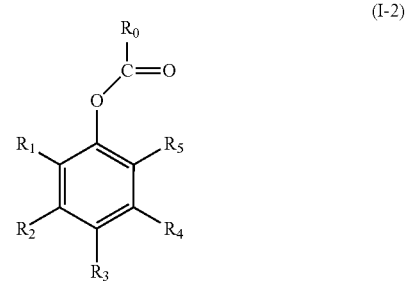

(I-2)

In the general formula (I-2), group $R_0$ is $C_{1-30}$ linear or branched alkyl (preferably selected from $C_{1-20}$ linear or branched alkyl); groups $R_1$, $R_2$, $R_3$, $R_4$ and $R_5$ are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups, $C_{1-50}$ alkoxyl optionally substituted by one or more substituent groups and a group represented by the general formula (IV), provided that at least one group of groups $R_1$, $R_2$, $R_3$, $R_4$ and $R_5$ is a group represented by the general formula (IV);

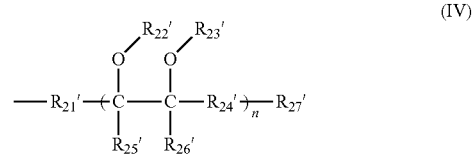

(IV)

In the general formula (IV), group $R_{21}'$ is selected from single bond and $C_{1-20}$ linear or branched alkylene (preferably selected from single bond and $C_{1-4}$ linear or branched alkylene); groups $R_{22}'$ and $R_{23}'$ in n repeating units are, identical to or different from each other, each independently selected from

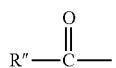

and hydrogen (preferably each independently

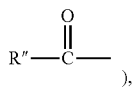

wherein R" is $C_{1-30}$ linear or branched alkyl (preferably selected from $C_{1-20}$ linear or branched alkyl); in each repeating unit, at least one group of groups $R_{22}'$ and $R_{23}'$ is

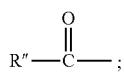

groups $R_{24}'$ in n repeating units are, identical to or different from each other, each independently selected from single bond and $C_{1-20}$ linear or branched hydrocarbylene (preferably each independently selected from single bond and $C_{1-4}$ linear or branched alkylene); groups Ras' and $R_{26}'$ in n repeating units are, identical to or different from each other, each independently selected from hydrogen and $C_{1-20}$ linear or branched alkyl (preferably each independently selected from hydrogen and $C_{1-4}$ linear or branched alkyl); group $R_{27}'$ is selected from hydrogen and $C_{1-20}$ linear or branched hydrocarbyl (preferably selected from hydrogen and $C_{1-10}$ linear or branched alkyl); n is a positive integral number (preferably a positive integral number of 1-30, more preferably a positive integral number of 1-5).

In the general formula (I-2), preferably, groups $R_1$, $R_3$, and $R_5$, identical to or different from each other, are each independently selected from hydrogen, $C_{1-4}$ linear or branched alkyl; groups $R_2$ and $R_4$ are, identical to or different from each other, each independently selected from hydrogen, Ci-30 linear or branched alkyl and a group represented by the general formula (IV), wherein at least one group is selected from a group represented by the general formula (IV).

In the general formula (I-2), further preferably, groups $R_1$, $R_3$, and $R_5$ are, identical to or different from each other, each independently selected from hydrogen, $C_{1-4}$ linear or branched alkyl; one group of groups $R_2$ and $R_4$ is selected from a group represented by the general formula (IV), the other group is selected from hydrogen.

In the general formula (I-2), further preferably, groups $R_1$, $R_3$ and $R_5$ are all selected from hydrogen; one group of groups $R_2$ and $R_4$ is selected from a group represented by the general formula (IV), the other group is selected from hydrogen.

Further preferably, the phenol derivative represented by the formula (I-2) of the second embodiment of the present invention can be selected from the following compounds or a mixture thereof in any proportion, wherein $R_0$ is ethyl, $R_2$ is independently selected from $C_2$-$C_{18}$ alkyl, $R_3$ is independently selected from $C_2$-$C_{18}$ alkyl.

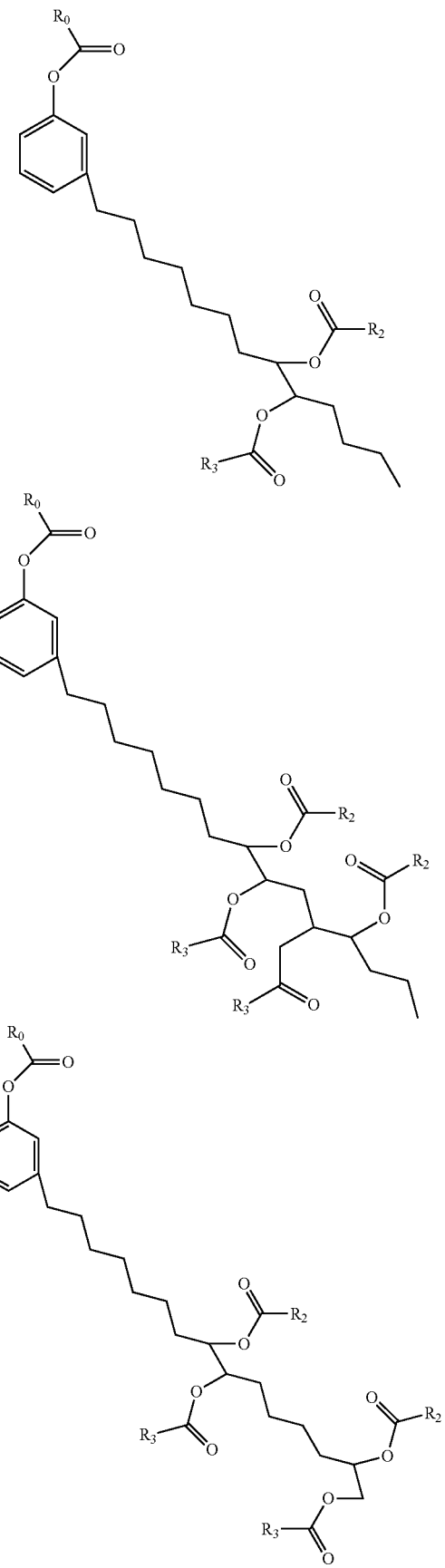

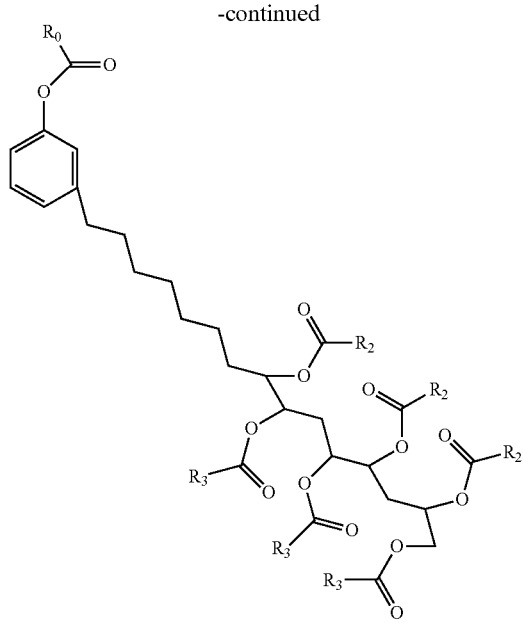

The process of preparing a phenol derivative represented by the formula (I-2) of the second embodiment of the present invention comprises a step of subjecting the phenol compound represented by the general formula (X) to a first esterification reaction, an epoxidation reaction, and a second esterification reaction,

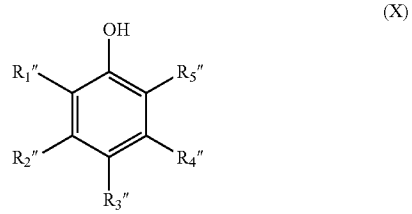

In the general formula (X), groups $R_1''$, $R_2''$, $R_3''$, $R_4''$ and $R_5''$ are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups, $C_{1-50}$ alkoxyl optionally substituted by one or more substituent groups and a group represented by the general formula (III'), wherein at least one group is selected from a group represented by the general formula (III');

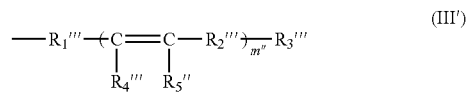

In the group of the general formula (III'), group $R_1'''$ is selected from single bond and $C_{1-20}$ linear or branched alkylene (preferably selected from single bond and $C_{1-4}$ linear or branched alkylene); groups $R_2'''$ in m repeating units are, identical to or different from each other, each independently selected from single bond and $C_{1-20}$ linear or branched alkylene (preferably each independently selected from single bond and $C_{1-4}$ linear or branched alkylene); group $R_3'''$ is selected from hydrogen and $C_{1-20}$ linear or branched alkyl (preferably selected from hydrogen and $C_{1-4}$ linear or branched alkyl); groups $R_4'''$ in m repeating units are, identical to or different from each other, each independently selected from hydrogen and $C_{1-20}$ linear or branched alkyl (preferably each independently selected from hydrogen and $C_{1-4}$ linear or branched alkyl); groups $R_5'''$ in m repeating units are, identical to or different from each other, each independently selected from hydrogen and $C_{1-20}$ linear or branched alkyl (preferably each independently selected from hydrogen and $C_{1-4}$ linear or branched alkyl); m'' is an integral number of 1-10 (preferably an integral number of 1-5, more preferably an integral number of 1-3).

In the process of preparing a phenol derivative represented by the formula (I-2) according to the second embodiment of the present invention, in the general formula (X), preferably, groups $R_1''$, $R_3''$ and $R_5''$ are, identical to or different from each other, each independently selected from hydrogen, $C_{1-4}$ linear or branched alkyl; groups $R_2''$ and $R_4''$ are, identical to or different from each other, each independently selected from hydrogen, $C_{1-30}$ linear or branched alkyl and a group represented by the general formula (III'), wherein at least one group is selected from a group represented by the general formula (III').

In the process of preparing a phenol derivative represented by the formula (I-2) according to the second embodiment of the present invention, in the general formula (X), further preferably, groups $R_1''$, $R_3''$ and $R_5''$ are, identical to or different from each other, each independently selected from hydrogen, $C_{1-4}$ linear or branched alkyl; one group of groups $R_2''$ and $R_4''$ is selected from a group represented by the general formula (III'), the other group is selected from hydrogen.

In the process of preparing a phenol derivative represented by the formula (I-2) according to the second embodiment of the present invention, in the general formula (X), further preferably, groups $R_1''$, $R_3''$ and $R_5''$ are all selected from hydrogen; one group of groups $R_2''$ and $R_4''$ is selected from a group represented by the general formula (III'), the other group is selected from hydrogen.

In the process of preparing a phenol derivative as shown in the formula (I-2) of the second embodiment of the present invention, the first esterification is to subject the phenol compound represented by the general formula (X) and the first esterifying agent to the esterification reaction to produce the phenolic ester compound represented by the general formula (Z).

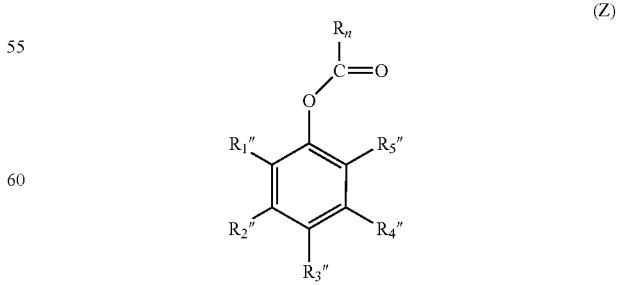

In the general formula (Z), the groups are defined as above. The first esterification can lead the phenolic hydroxyl group in the phenol compound represented by the general formula (X) through the esterification reaction.

According to the process of preparing a phenol derivative as shown in the formula (I-2) of the second embodiment of the present invention, the first esterifying agent comprises one or more of alkyl acid anhydride, haloalkane and alkyl acid, wherein the alkyl is preferably $C_{1-30}$ linear or branched alkyl. The first esterifying agent is preferably alkyl acid anhydride.

According to the process of preparing a phenol derivative as shown in the formula (I-2) of the second embodiment of the present invention, the reaction conditions of the first esterification comprise: the molar ratio of the phenol compound represented by the general formula (X) to the first esterifying agent is 1:1-10 (preferably 1:1-5); the reaction temperature is 20° C.-120° C. (preferably 40° C.-80° C.); in general, the longer the reaction time is, the higher the conversion is, usually the reaction time is 0.5h-10h (preferably 3h-5h). In the first esterification, a catalyst is optionally but preferably added. The catalyst is preferably an inorganic base or a weak acid salt of an inorganic base, for example can be selected from one or more of sodium hydroxide, potassium hydroxide, calcium hydroxide, sodium carbonate and potassium carbonate. The used amount of the catalyst is 0.1%-15% (preferably 5%-10%) by mass of the phenol compound represented by the general formula (X). In the first esterification, a solvent is optionally but preferably added. Said solvent is preferably one or more of toluene, xylene, petroleum ether and cyclohexane, for example can be selected from toluene and/or xylene. The used amount of said solvent is 0.1%-15% (preferably 5%-10%) by mass of the phenol compound represented by the general formula (X).

According to the process of preparing a phenol derivative as shown in the formula (I-2) of the second embodiment of the present invention, the epoxidation reaction is to react the phenolic ester compound represented by the general formula (Z) with an epoxidizing agent to produce the epoxide of the phenolic ester compound represented by the general formula (Z). The epoxidizing agent is preferably a peroxide, and for example can be selected from one or more of hydrogen peroxide, meta-chloroperbenzoic acid, teri-butyl hydroperoxide, di-tert-butyl peroxide, peracetic acid and benzoyl peroxide.

According to the process of preparing a phenol derivative as shown in the formula (I-2) of the second embodiment of the present invention, the molar ratio of the phenolic ester compound represented by the general formula (Z) to the epoxidizing agent is preferably 1:1-10, more preferably 1:2-5. The epoxidation reaction temperature is 20° C.-100° C., preferably 50° C.-80° C.; usually, the longer the reaction time is, the higher the conversion is, and under the overall consideration of the reaction conversion and the reaction economy, the reaction time is generally 0.5-10 hours, preferably 3-5 hours.

According to the process of preparing a phenol derivative as shown in the formula (I-2) of the second embodiment of the present invention, in the epoxidation reaction, a catalyst is optionally but preferably added. The catalyst is preferably an inorganic acid, and for example can be selected from one or more of sulfuric acid, hydrochloric acid, phosphoric acid, nitric acid, a heteropoly acid and a solid acid. The mass of the catalyst is 0.01%-3%, preferably 0.2%-0.6% by mass of the phenol compound represented by the general formula (X). In the epoxidation reaction, a solvent is optionally but preferably added. Said solvent is preferably one or more of toluene, xylene, petroleum ether and cyclohexane, for example can be selected from toluene and/or xylene. The used amount of said solvent is 0.1%-15% (preferably 5%-10%) by mass of the phenol compound represented by the general formula (X).

According to the process of preparing a phenol derivative as shown in the formula (I-2) of the second embodiment of the present invention, the second esterification reaction is to react the epoxide of the phenolic ester compound represented by the general formula (Z) with the second esterifying agent to produce the phenolic ester compound according to the present invention. The second esterifying agent comprises one or more of fatty acid, fatty acid anhydride and haloalkane, wherein the alkyl is $C_1$-$C_{30}$ linear or branched alkyl (more preferably $C_1$-$C_{20}$ linear or branched alkyl). The second esterifying agent is preferably $C_1$-$C_{30}$ linear or branched organic carboxylic acid (more preferably $C_1$-$C_{20}$ linear or branched organic carboxylic acid).

According to the process of preparing a phenol derivative as shown in the formula (I-2) of the second embodiment of the present invention, the reaction conditions of the second esterification reaction comprise: the molar ratio of the epoxide of the phenolic ester compound represented by the general formula (Z) to the second esterifying agent is 1:1-10 (preferably 1:2-8); the reaction temperature is 80° C.-260° C. (preferably 120° C.-210° C.); in general, the longer the reaction time is, the higher the conversion is, usually the reaction time is 5h-20h (preferably 8h-18h). In the second esterification reaction, a catalyst is optionally but preferably added. The catalyst is preferably inorganic acid, and for example can be selected from one or more of sulfuric acid, hydrochloric acid, nitric acid and phosphoric acid. The used amount of the catalyst is 0.1%-10% (preferably 0.2%-2%) by the mass of the epoxide of the phenolic ester compound represented by the general formula (Z). In the second esterification reaction, a solvent is optionally but preferably added. Said solvent is preferably one or more of toluene, xylene, petroleum ether and cyclohexane, for example can be selected from toluene and/or xylene. The used amount of said solvent is 0.1%-15% (preferably 5%-10%) by the mass of the epoxide of the phenolic ester compound represented by the general formula (Z).

According to the process of preparing a phenol derivative as shown in the formula (I-2) of the second embodiment of the present invention, additionally one or more reactions of an optional alkylation reaction, an optional hydrogenation reaction and a coupling reaction can be performed.

Third Embodiment

According to the third embodiment of the present invention, the phenol derivative of the present invention has a structure as represented by the general formula (I-3):

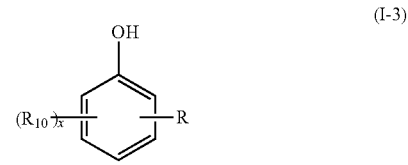

In the general formula (I-3), group R is selected from a group represented by the formula (V), a group represented by the formula (VI) and a group represented by the formula (VIII); x groups $R_{10}$ in the general formula (I-3) are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups and $C_{1-50}$ alkoxyl optionally substituted by one or more substituent groups (preferably selected from hydrogen, $C_{1-50}$ linear or branched alkyl, $C_{1-50}$ linear or branched alkenyl, linear or branched $C_{3-50}$ heteroalkyl and $C_{1-50}$ linear or branched alkyloxy) the numbers x in the general formula (I-3) are, identical to or different from each other, each independently 0, 1, 2, 3 or 4 (preferably 0, 1 or 2);

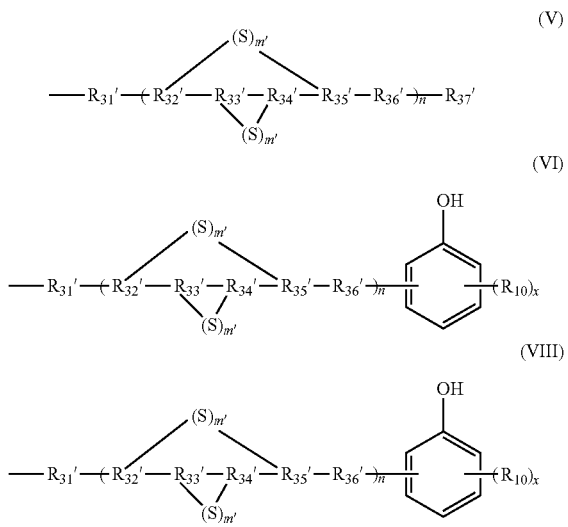

(V)

(VI)

(VIII)

In the formula (V) and the formula (VI), group $R_{31}'$ is each independently selected from single bond and $C_{1-20}$ linear or branched alkylene (preferably selected from single bond and $C_{1-4}$ linear or branched alkylene); groups $R_{32}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{33}'$ in n repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{34}'$ in n repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{35}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{36}'$ in n repeating units are, identical to or different from each other, each independently selected from single bond and $C_{1-20}$ linear or branched alkylene (preferably each independently selected from single bond, $C_{1-4}$ linear or branched alkylene); group $R_{37}'$ is selected from hydrogen and $C_{1-20}$ linear or branched alkyl (preferably selected from hydrogen and $C_{1-4}$ linear or branched alkyl); n is an integral number of 1-10 (preferably an integral number of 1-3); the numbers m in n repeating units are, identical to or different from each other, each independently selected from an integral number of 0-10 (preferably an integral number of 0-5); the numbers m' in n repeating units are, identical to or different from each other, each independently selected from an integral number of 0-10 (preferably an integral number of 0-5); in each repeating unit of the formulae (V) and (VI), when m is greater than 0, the linking group formed by m sulfur atoms is bonded to groups $R_{32}'$ and $R_{35}'$; when m' is greater than 0, the linking group formed by m' sulfur atoms is bonded to groups $R_{33}'$ and $R_{34}'$; in each repeating unit of the formulae (V) and (VI), when group $R_{33}'$ is single bond, one end connected to group $R_{33}'$ of the linking group formed by m' sulfur atoms is bonded to group $R_{32}'$, when group $R_{34}'$ is single bond, one end connected to group $R_{34}'$ of the linking group formed by m' sulfur atoms is bonded to group $R_{35}'$; in the formula (VI), x groups $R_{10}$ are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups and $C_{1-50}$ alkoxyl optionally substituted by one or more substituent groups (preferably selected from hydrogen, $C_{1-50}$ linear or branched alkyl, $C_{1-50}$ linear or branched alkenyl, linear or branched $C_{3-50}$ heteroalkyl and $C_{1-50}$ linear or branched alkyloxy), x is selected from an integral number of 1-10 (preferably an integral number of 1-5);

In the formula (VIII), group $R_{31}'$ is each independently selected from single bond and $C_{1-20}$ linear or branched alkylene (preferably selected from single bond and $C_{1-4}$ linear or branched alkylene); groups $R_{32}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{33}'$ in n repeating units are, identical to or different from each other, each independently selected from H and divalent $C_{1-20}$ linear or branched alkyl (preferably each independently selected from H and divalent $C_{1-4}$ linear or branched alkyl); groups $R_{34}'$ in n repeating units are, identical to or different from each other, each independently selected from H and divalent $C_{1-20}$ linear or branched alkyl (preferably each independently selected from H and divalent $C_{1-4}$ linear or branched alkyl); groups $R_{35}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{36}'$ in n repeating units are, identical to or different from each other, each independently selected from single bond and $C_{1-20}$ linear or branched alkylene (preferably each independently selected from single bond, $C_{1-4}$ linear or branched alkylene); the numbers m in n repeating units are, identical to or different from each other, each independently selected from an integral number of 0-10 (preferably an integral number of 0-5); the numbers m' in n repeating units are, identical to or different from each other, each independently selected from an integral number of 0-10 (preferably an integral number of 0-5), m+m'>0; in each repeating unit of the formula (VIII), when m is greater than 0, the linking group formed by m sulfur atoms is bonded to groups $R_{32}'$ and $R_{35}'$; when m' is greater than 0, the linking group formed by m' sulfur atoms is bonded to groups $R_{33}'$ and $R_{34}'$; in each repeating unit of the formula (VIII), when group $R_{33}'$ is H, one end connected to group $R_{33}'$ of the linking group formed by m' sulfur atoms is bonded to group $R_{32}'$; when group $R_{34}'$ is H, one end connected to group $R_{34}'$ of the linking group formed by m' sulfur atoms is bonded to group $R_{35}'$; in the formula (VIII), x groups $R_{10}$ are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups and $C_{1-50}$ alkoxyl optionally substituted by one or more substituent groups (preferably selected from hydrogen, $C_{1-50}$ linear or branched alkyl, $C_{1-50}$ linear or branched alkenyl, linear or branched $C_{3-50}$ heteroalkyl and $C_{1-50}$ linear or branched alkyloxy), x is selected from an integral number of 1-10 (preferably an integral number of 1-5); in each repeating unit of the formula (VIII), groups $R_{31}'$ and $R_{36}'$ can be each independently substituted by a group represented by the formula (VIII-1); in each repeating unit of the formula (VIII), groups $R_{32}'$, $R_{33}'$, $R_{34}'$ and $R_{35}'$ can be each independently substituted by a group represented by the formula (V),

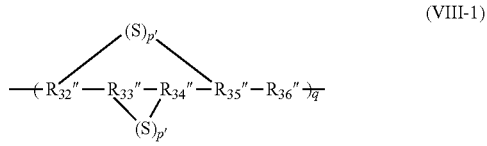

(VIII-1)

In the formula (VIII-1), groups $R_{32}''$ in q repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{33}''$ in q repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{34}''$ in q repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{35}''$ in q repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{36}''$ in q repeating units are, identical to or different from each other, each independently selected from single bond and $C_{1-20}$ linear or branched alkylene (preferably each independently selected from single bond, $C_{1-4}$ linear or branched alkylene); q is an integral number of 1-10 (preferably an integral number of 1-3); the numbers p in q repeating units are, identical to or different from each other, each independently selected from an integral number of 0-10 (preferably an integral number of 0-5); the numbers p' in q repeating units are, identical to or different from each other, each independently selected from an integral number of 0-10 (preferably an integral number of 0-5); in each repeating unit of the formula (VIII-1), when p is greater than 0, the linking group formed by p sulfur atoms is bonded to groups $R_{32}''$ and $R_{35}''$; when p' is greater than 0, the linking group formed by p' sulfur atoms is bonded to groups $R_{33}''$ and $R_{34}''$; in each repeating unit of the formula (VIII-1), when group $R_{33}''$ is single bond, one end connected to group $R_{33}''$ of the linking group formed by p' sulfur atoms is bonded to group $R_{32}''$, when group $R_{34}''$ is single bond, one end connected to group $R_{34}''$ of the linking group formed by p' sulfur atoms is bonded to group $R_{35}''$.

In the general formula (I-3), preferably, group R is located at the meta-position or the para-position of the phenolic hydroxyl group; x is 1 or 2, one or two groups $R_{10}$ are located at the ortho-position of the phenolic hydroxyl group, and each independently selected from $C_{1-4}$ linear or branched alkyl.

In the general formula (I-3), further preferably, group R is located at the meta-position of the phenolic hydroxyl group; x is 1 or 2, one or two groups $R_{10}$ are located at the ortho-position of the phenolic hydroxyl group, and each independently selected from $C_{1-4}$ linear or branched alkyl.

In the general formula (I-3), more preferably, group R is located at the meta-position of the phenolic hydroxyl group; x is 1, group $R_{10}$ is located at the ortho-position of the phenolic hydroxyl group and at the para-position of the group R, group $R_{10}$ is selected from $C_{1-4}$ linear or branched alkyl.

The phenol derivative according to the third embodiment of the present invention can be a single compound of the structure represented by the general formula (I-3), or a mixture containing compounds of two or more structures represented by the general formula (I-3); when the phenol derivative is a mixture of structures represented by the general formula (I-3), the values n for each group of each compound in the mixture can be identical or different, and the sums of the values n of each compound may be identical or different.

Further preferably, the phenol derivative according to the third embodiment of the present invention is selected from the following specific compounds or a mixture thereof in any proportion:

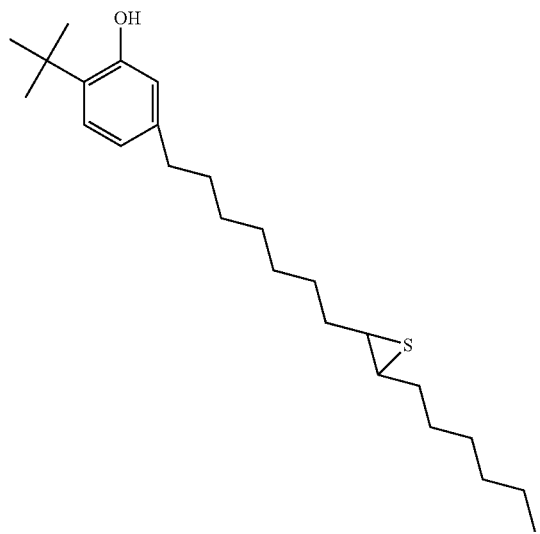

119
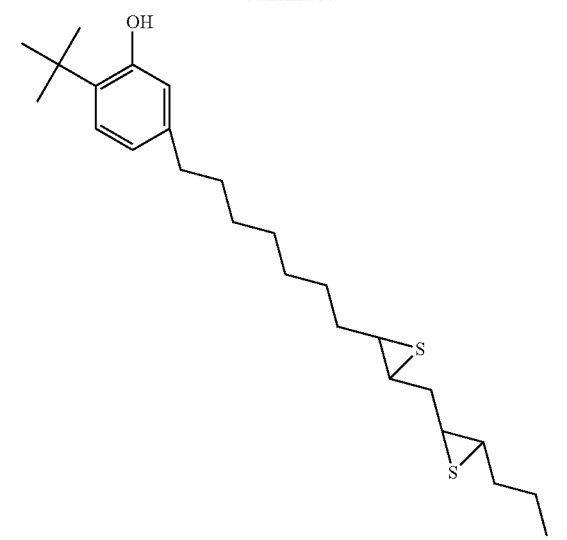
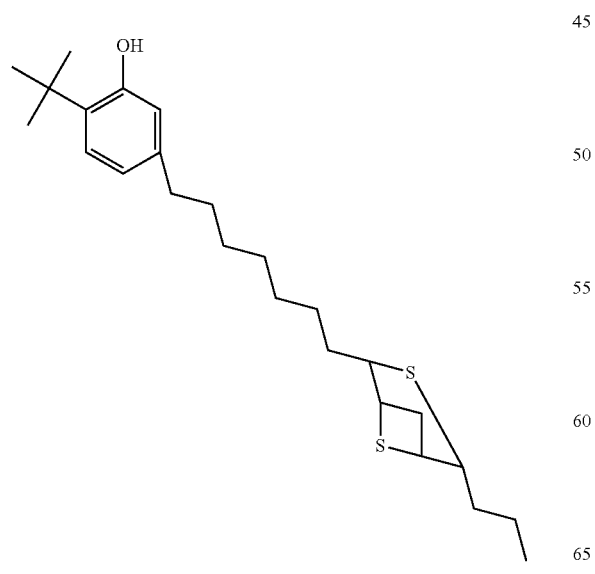
120
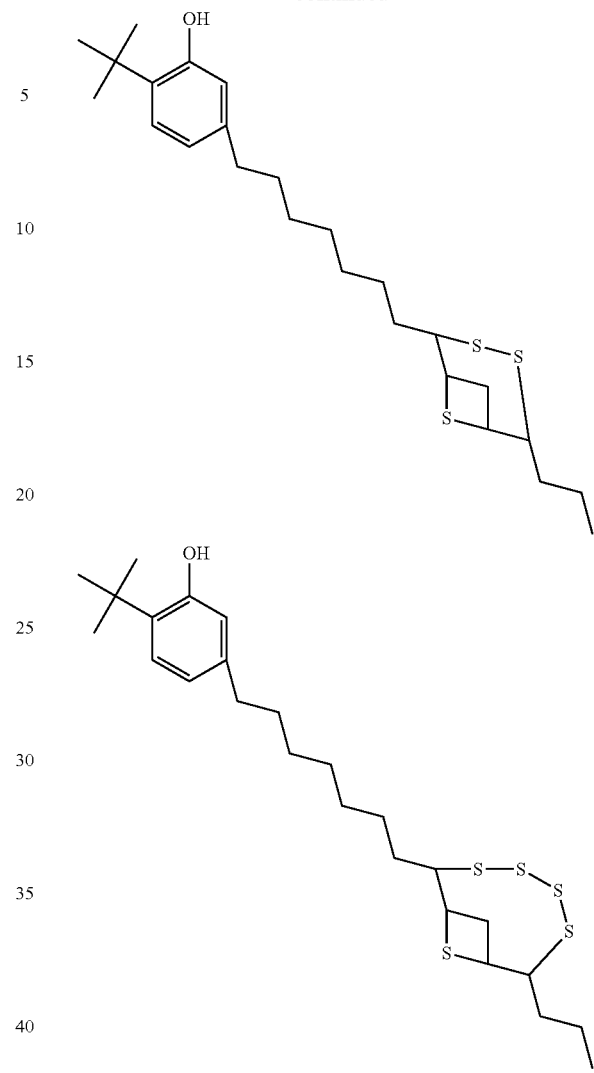
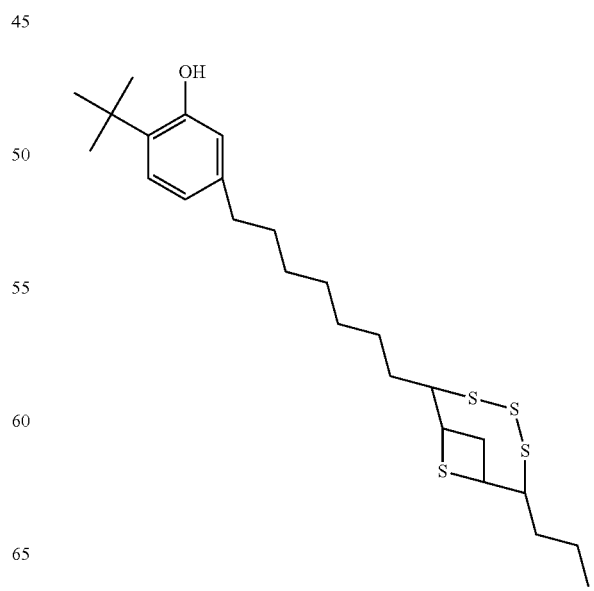

121
-continued
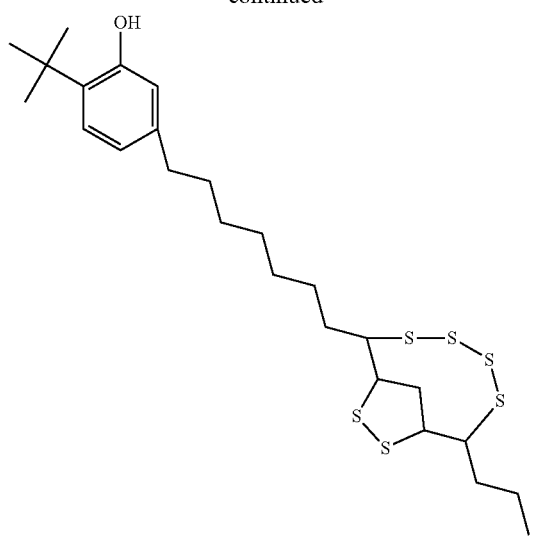
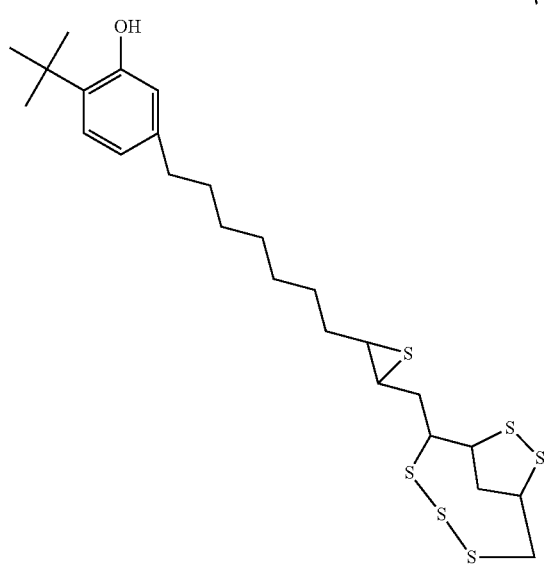
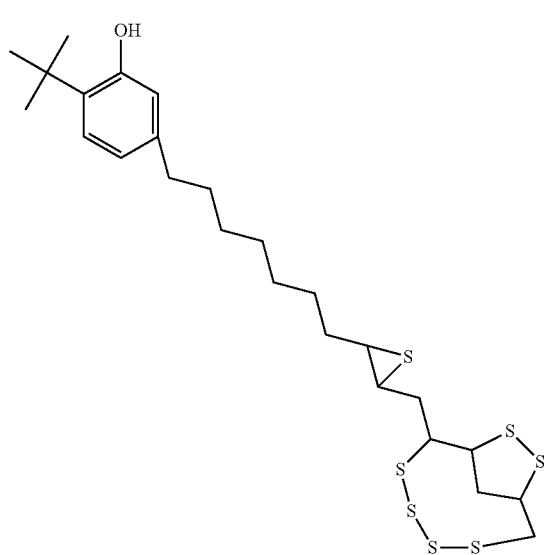
122
-continued
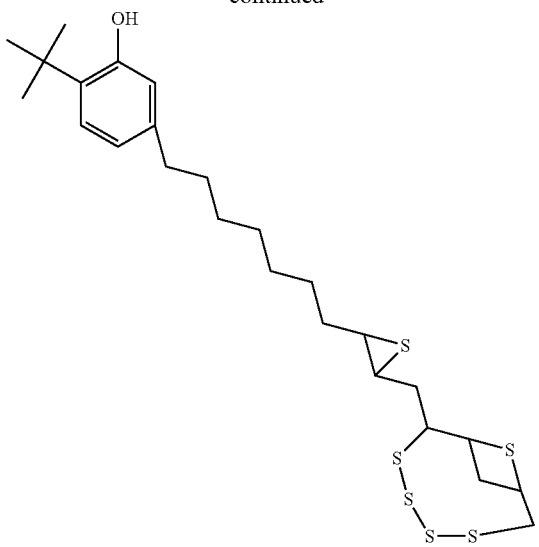
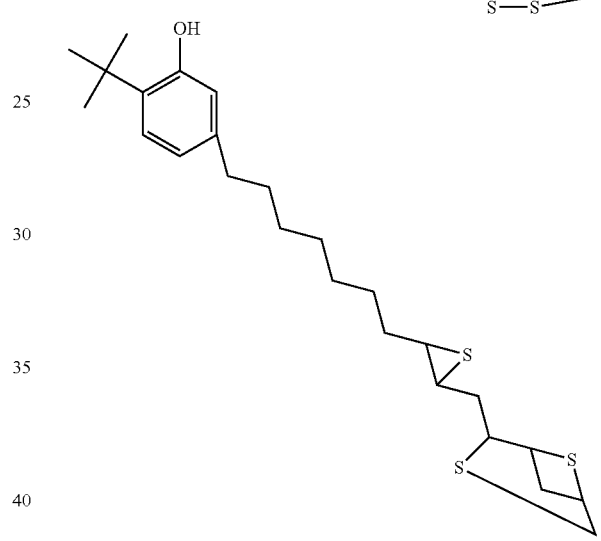
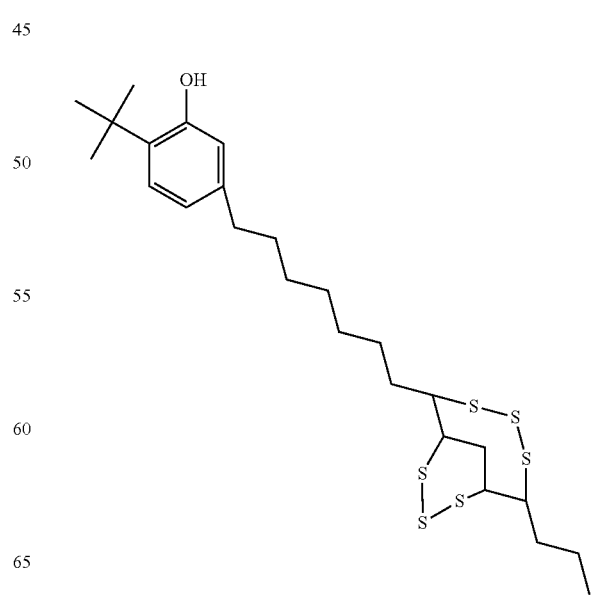

123
-continued
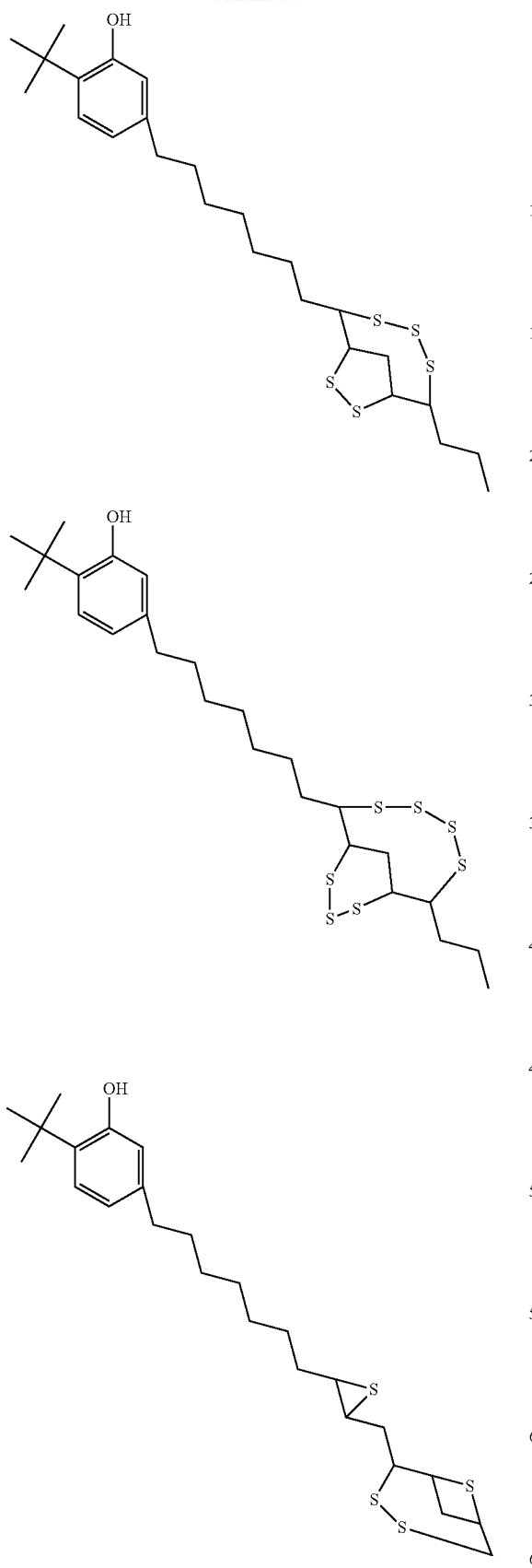
124
-continued
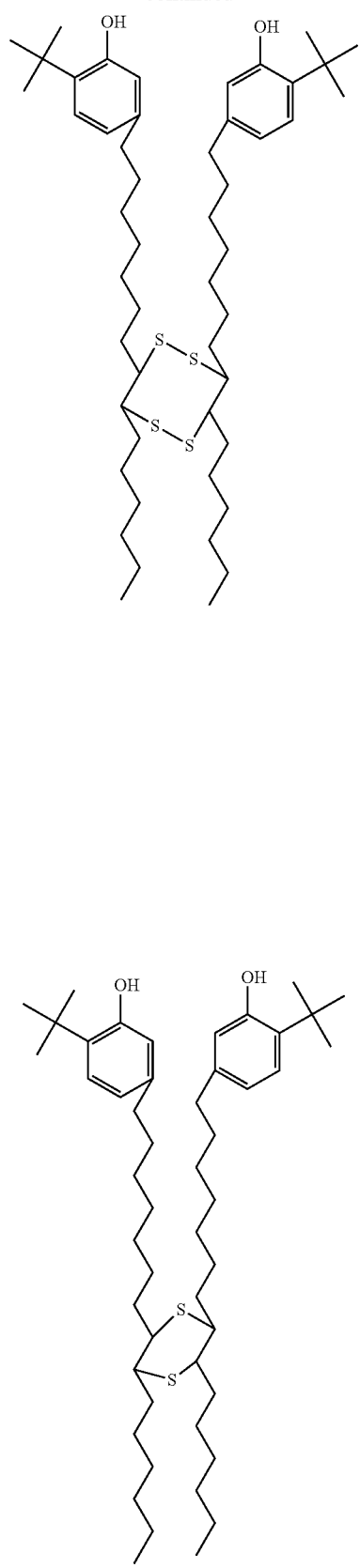

125
-continued
126
-continued
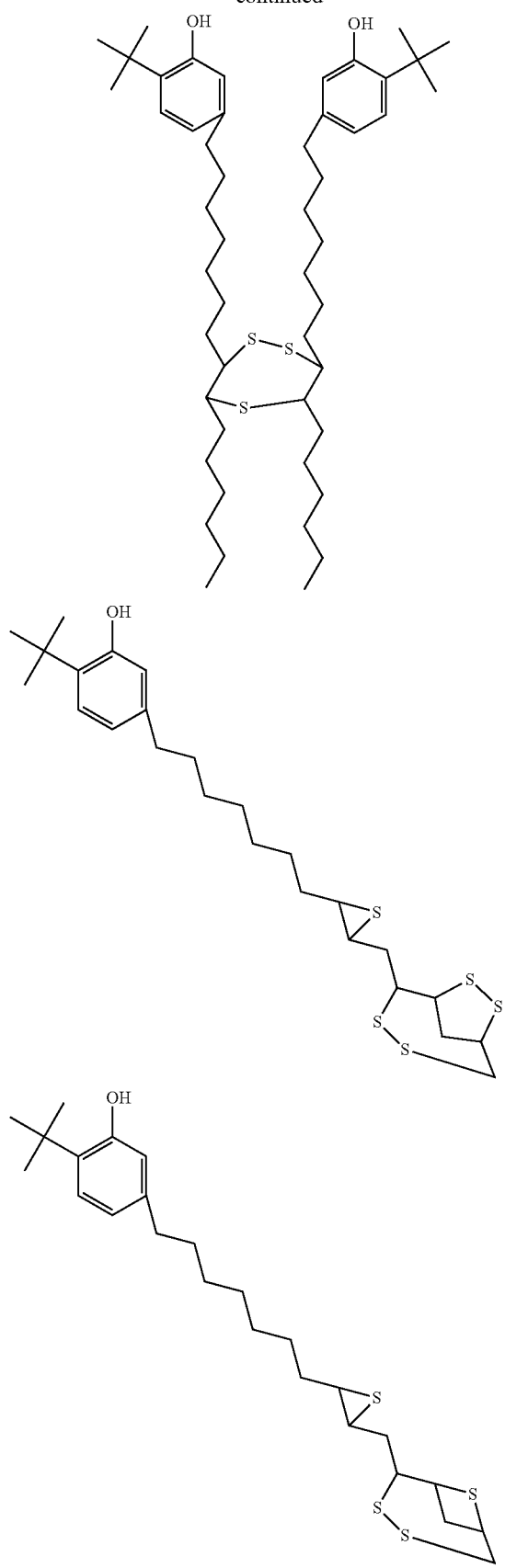
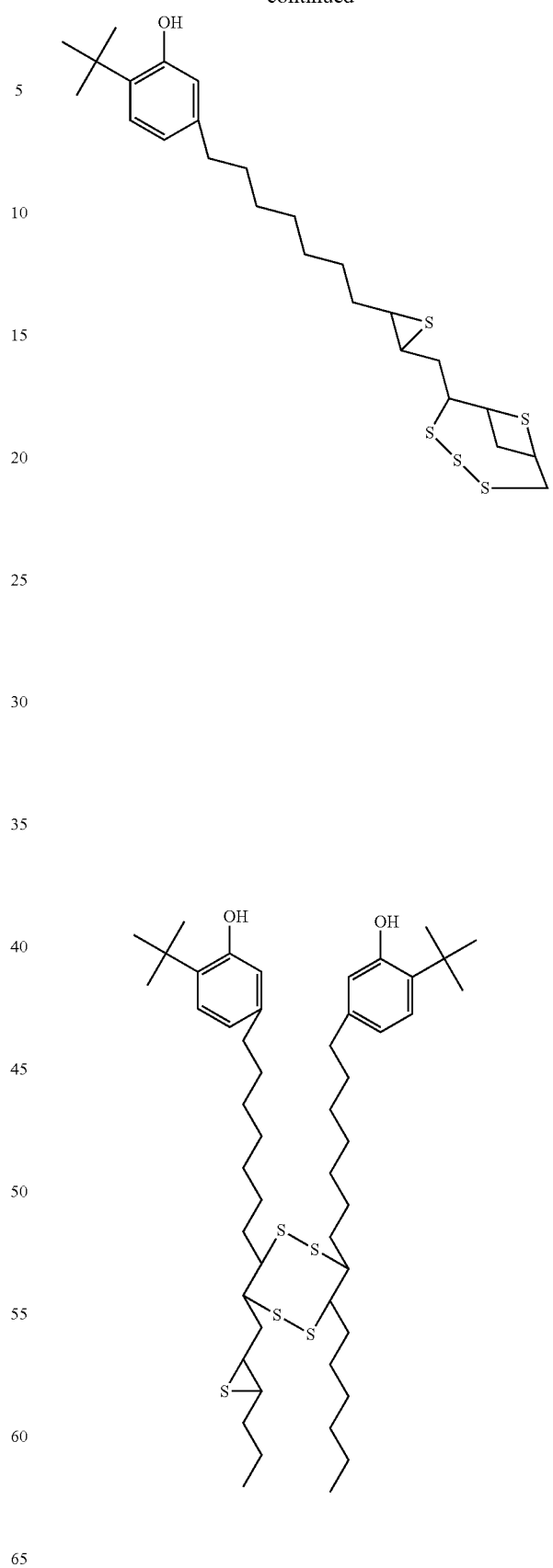

127
-continued
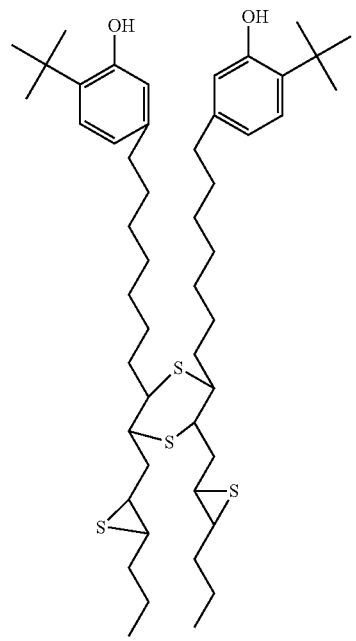
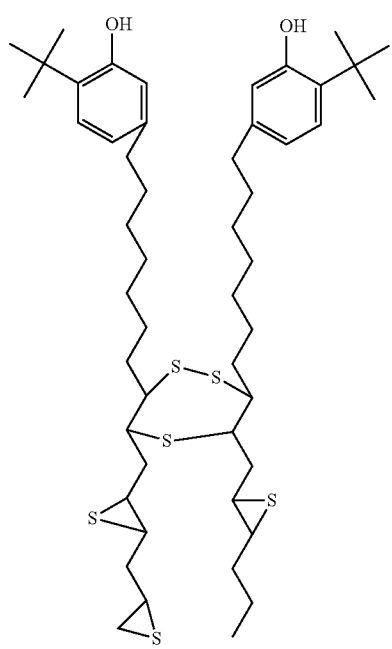
128
-continued
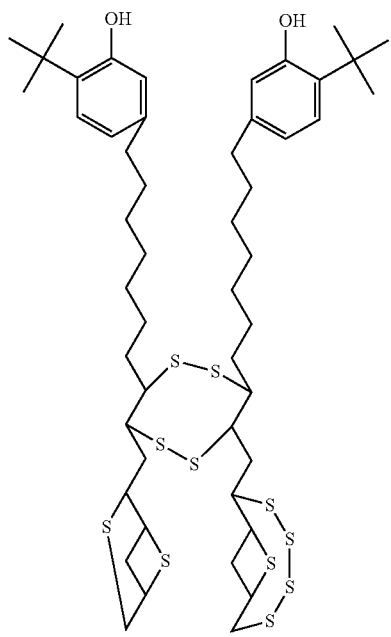 [SMILES: CC(C)(C)c1ccc(CCCCCCCC2SSC(CCCCCCCc3ccc(C(C)(C)C)c(O)c3)C(CC3SSSSCC4CC3S4)SSC2CC2SCC3CC2S3)cc1O]
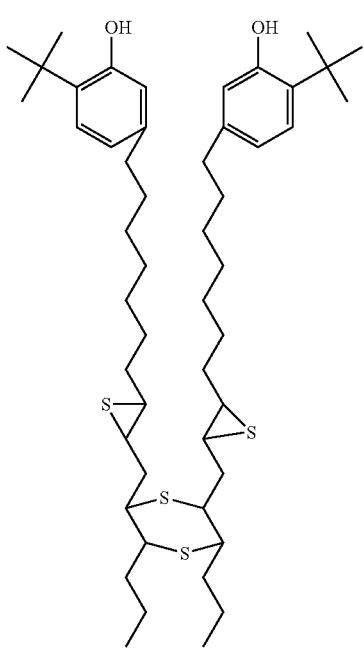

129
-continued
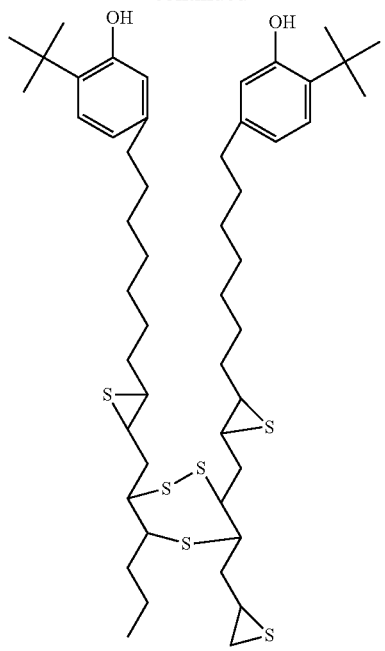
130
-continued
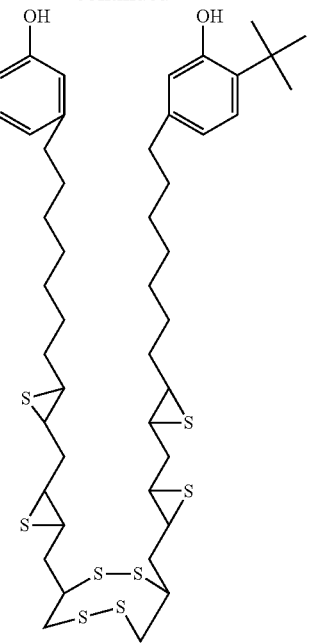
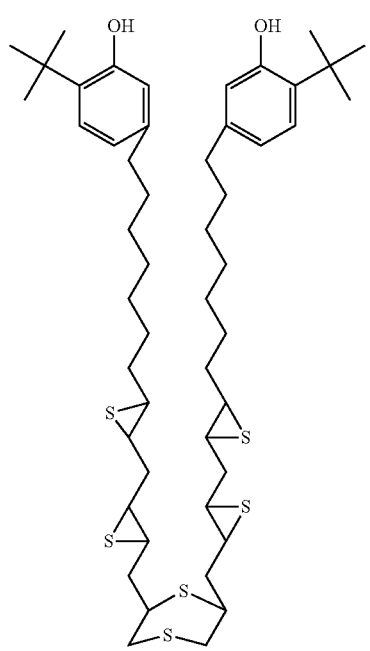
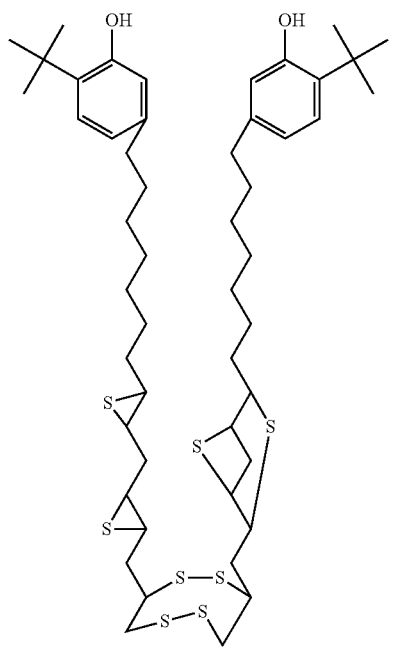

131
-continued

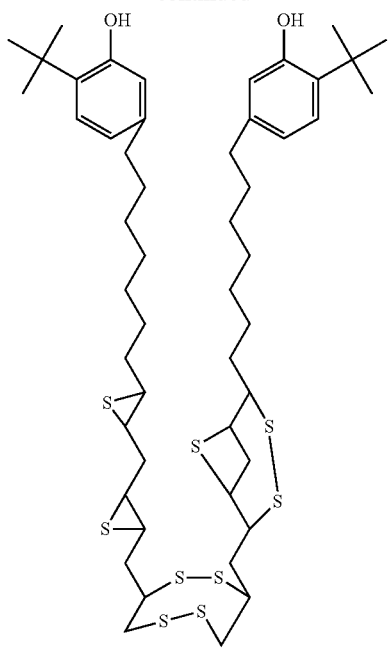

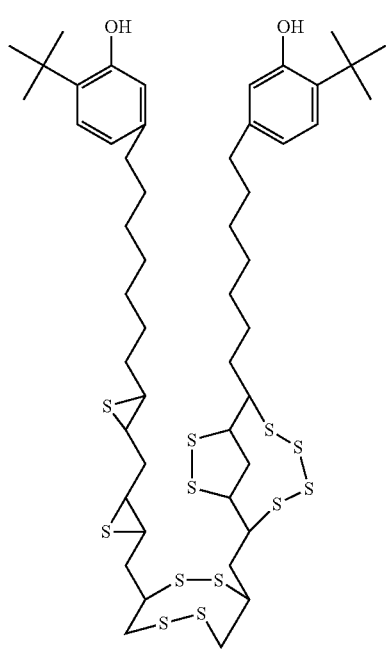

132
-continued

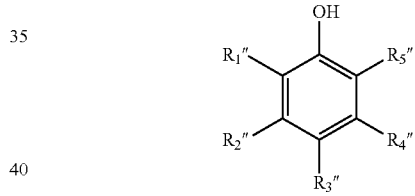

The process of preparing a phenol derivative of the third embodiment of the present invention comprises a step of subjecting the phenol compound represented by the general formula (X) to the sulfurization reaction, $$\text{(X)}$$

In the general formula (X), groups $R_1''$, $R_2''$, $R_3''$, $R_4''$ and $R_5''$ are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups, $C_{1-50}$ alkoxyl optionally substituted by one or more substituent groups and a group represented by the general formula (III'), wherein one group is selected from a group represented by the general formula (III');

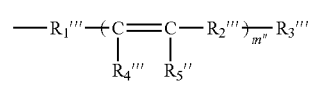

Wherein group $R_1'''$ is selected from single bond and $C_{1-20}$ linear or branched alkylene (preferably selected from single bond and $C_{1-4}$ linear or branched alkylene); groups $R_2'''$ in m repeating units are, identical to or different from each other, each independently selected from single bond and $C_{1-20}$ linear or branched alkylene (preferably each independently selected from single bond and $C_{1-4}$ linear or branched alkylene); group $R_3'''$ is selected from hydrogen and $C_{1-20}$ linear or branched alkyl (preferably selected from hydrogen and $C_{1-4}$ linear or branched alkyl); groups $R_4'''$ in m repeating units are, identical to or different from each other, each independently selected from hydrogen and $C_{1-20}$ linear or branched alkyl (preferably each independently selected from hydrogen and $C_{1-4}$ linear or branched alkyl); groups $R_5'''$ in m repeating units are, identical to or different from each other, each independently selected from hydrogen and $C_{1-20}$ linear or branched alkyl (preferably each independently selected from hydrogen and $C_{1-4}$ linear or branched alkyl); m" is an integral number of 1-10 (preferably an integral number of 1-5, more preferably an integral number of 1-3).

According to the process of preparing a phenol derivative of the third embodiment of the present invention, in the general formula (X), preferably, groups $R_1''$, $R_3''$ and $R_5''$ are, identical to or different from each other, each independently selected from hydrogen and $C_{1-4}$ linear or branched alkyl, at least one group of groups $R_1''$, $R_3''$, and $R_5''$ is selected from $C_{1-4}$ linear or branched alkyl; groups $R_2''$ and $R_4''$are, identical to or different from each other, each independently selected from hydrogen, $C_{1-30}$ linear or branched alkyl and a group represented by the general formula (III'), wherein one group is a group represented by the general formula (III').

According to the process of preparing a phenol derivative of the third embodiment of the present invention, in the general formula (X), further preferably, one group of groups $R_1''$ and $R_5''$ is selected from $C_{1-4}$ linear or branched alkyl, the other group is selected from hydrogen; the group $R_3''$ is selected from hydrogen, $C_{1-4}$ linear or branched alkyl; one group of groups $R_2''$ and $R_4''$ is a group represented by the general formula (III'), the other group is hydrogen.

According to the process of preparing a phenol derivative of the third embodiment of the present invention, in the general formula (X), more preferably, group $R_1''$ is selected from $C_{1-4}$ linear or branched alkyl, group $R_5''$ is selected from hydrogen; group $R_3''$ is selected from hydrogen, $C_{1-4}$ linear or branched alkyl; group $R_2''$ is selected from hydrogen, group $R_4''$ is selected from a group represented by the general formula (III').

According to the process of preparing a phenol derivative of the third embodiment of the present invention, the sulfurization reaction is to react the phenol compound represented by the general formula (X) with a sulfurizing agent. The sulfurization reaction is to perform the electrophilic addition between the sulfurizing agent and alkene, when the addition occurs in the alkene molecular chain, if there is one carbon-carbon double bond in the molecule, a single sulfur ring group is formed, and if there are more than one carbon-carbon double bond, a single sulfur ring group and a plurality of sulfur ring groups can be formed; when the addition occurs between the alkene molecular chain, the relatively complex sulfur ring structure may be formed. The sulfurizing agent is preferably an inorganic sulfurizing agent and/or an organic sulfurizing agent, the inorganic sulfurizing agent can be selected from one or more of sulphur, $Na_2S$, $K_2S$, ZnS, $H_2S$ and SCl; the organic sulfurizing agent can be selected from one or more of ditertbutyl polysulfide (DBPS), dimethyl disulphide (DMDS), dimethyl sulfide (DMS), ethyl mercaptan (EM), n-butyl mercaptan (NBM) and tert-nonyl polysulfide (TNPS); the sulfurizing agent is more preferably one or more of sulphur, $Na_2S$ and thiol. The molar ratio of the phenol compound represented by the general formula (X) to the sulfurizing agent is 1:1-6, more preferably 1:2-4. The sulfurization reaction temperature is 100° C.-240° C., preferably 140° C.-190° C.; usually, the longer the reaction time is, the higher the conversion is, and under the overall consideration of the reaction conversion and the reaction economy, the reaction time is generally 0.5-10 hours, preferably 3-5 hours.

According to the process of preparing a phenol derivative of the third embodiment of the present invention, in the sulfurization reaction, a catalyst is optionally but preferably added. The catalyst is preferably selected from $C_{1-6}$ organic amine and inorganic base, for example can be selected from one or more of methylamine, dimethylamine, ethylamine, diethylamine, propylamine, dipropyl amine, tripropyl amine, butylamine, amylamine, hexylamine, ammonia water, sodium hydroxide, potassium hydroxide, zinc hydroxide, sodium oxide, potassium oxide, zinc oxide, sodium carbonate, potassium carbonate and zinc carbonate. The mass of the catalyst is 0.01%-10%, preferably 0.1%-5% by the mass of the phenolic ester compound represented by the general formula (X). According to the process of preparing a phenol derivative of the third embodiment of the present invention, preferably, when at least one group in the groups $R_1''$, $R_3''$, and $R_5''$ in the phenol compound represented by the general formula (X) is hydrogen, either the phenol compound represented by the general formula (X) can be subjected to the sulfurization reaction, followed by the alkylation reaction and then the product is collected; or the phenol compound represented by the general formula (X) can be subjected to the sulfurization reaction, followed by the alkylation reaction and then the product is collected. The reaction conditions of the sulfurization reaction of the phenol compound represented by the general formula (X) or the reaction product obtained from subjecting the phenol compound represented by the general formula (X) and the alkylating agent to the alkylation reaction are identical to the reaction conditions of the above-mentioned sulfurization reaction(s). The alkylation reaction is to react the phenol compound represented by the general formula (X) or the reaction product obtained from subjecting the phenol compound represented by the general formula (X) and the sulfurizing agent to the sulfurization reaction with an alkylating agent. The alkylating agent is selected from one or more of halohydrocarbon, fatty alcohol and alkene, preferably haloalkane and/or alkene, for example can be selected from one or more of tert-butyl chloride, tert-butyl bromide, isobutylene and isopropylene. The molar ratio of the phenol compound represented by the general formula (X) or the reaction product obtained from subjecting the phenol compound represented by the general formula (X) and the sulfurizing agent to the sulfurization reaction to the alkylating agent is preferably 1:1-5, more preferably 1:1-2.5; the reaction temperature is preferably 20° C.-100° C., more preferably 40° C.-80° C.; usually, the longer the reaction time is, the higher the conversion is, and under the overall consideration of the reaction conversion and the reaction economy, the reaction time is preferably 0.5 hours-10 hours, more preferably 3 hours-5 hours. In the alkylation reaction, a catalyst is optionally but preferably added; the catalyst is preferably selected from one or more of inorganic acid, organic acid and Lewis acid, more preferably one or more of sulfuric acid, hydrochloric acid, nitric acid, metallic chloride, boron trifluoride and heteropoly acid, for example can be selected from one or more of sulfuric acid, hydrochloric acid, nitric acid, zinc chloride, aluminum chloride, iron bromide, boron trifluoride, sulfur trioxide and heteropoly acid. The mass of the catalyst is preferably 0.1%-10%, more preferably 1%-6% by mass of the phenol compound represented by the general formula (X).

Fourth Embodiment

According to the fourth embodiment of the present invention, the phenol derivative of the present invention has a structure as represented by the formula (I-4):

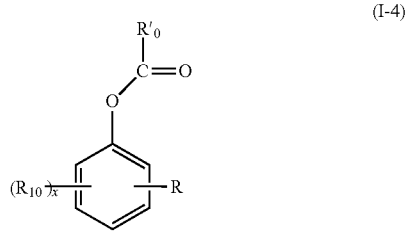
(I-4)

In the general formula (I-4), group $R_0'$ is $C_{1-30}$ linear or branched alkyl (preferably selected from $C_{1-20}$ linear or branched alkyl); group R is selected from a group represented by the formula (V), a group represented by the formula (VI) and a group represented by the formula (VIII); x groups $R_{10}$ in the general formula (I-4) are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups and $C_{1-50}$ alkoxyl optionally substituted by one or more substituent groups (preferably selected from hydrogen, $C_{1-50}$ linear or branched alkyl, $C_{1-50}$ linear or branched alkenyl, linear or branched $C_{3-50}$ heteroalkyl and $C_{1-50}$ linear or branched alkyloxy), the numbers x in the general formula (I-4) are, identical to or different from each other, each independently 0, 1, 2, 3 or 4 (preferably 0, 1 or 2);

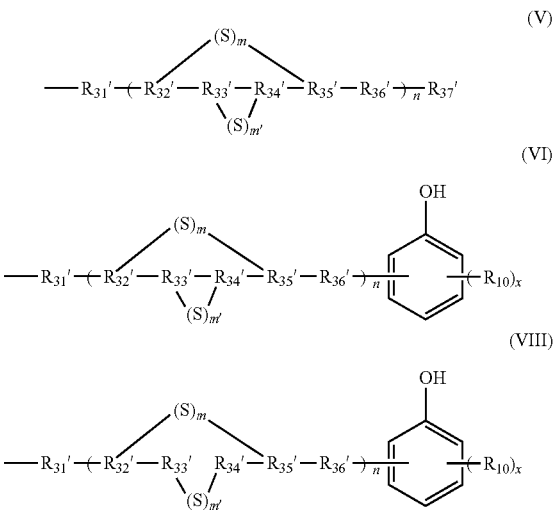

In the formula (V) and the formula (VI), group $R_{31}'$ is each independently selected from single bond and $C_{1-20}$ linear or branched alkylene (preferably selected from single bond and $C_{1-4}$ linear or branched alkylene); groups $R_{32}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{33}'$ in n repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{34}'$ in n repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{35}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{36}'$ in n repeating units are, identical to or different from each other, each independently selected from single bond and $C_{1-20}$ linear or branched alkylene (preferably each independently selected from single bond, $C_{1-4}$ linear or branched alkylene); group $R_{37}'$ is selected from hydrogen and $C_{1-20}$ linear or branched alkyl (preferably selected from hydrogen and $C_{1-4}$ linear or branched alkyl); n is an integral number of 1-10 (preferably an integral number of 1-3); the numbers m in n repeating units are, identical to or different from each other, each independently selected from an integral number of 0-10 (preferably an integral number of 0-5); the numbers m' in n repeating units are, identical to or different from each other, each independently selected from an integral number of 0-10 (preferably an integral number of 0-5); in each repeating unit of the formulae (V) and (VI), when m is greater than 0, the linking group formed by m sulfur atoms is bonded to groups $R_{32}'$ and $R_{35}'$; when m' is greater than 0, the linking group formed by m' sulfur atoms is bonded to groups $R_{33}'$ and $R_{34}'$; in each repeating unit of the formulae (V) and (VI), when group $R_{33}'$ is single bond, one end connected to group $R_{33}'$ of the linking group formed by m' sulfur atoms is bonded to group $R_{32}'$, when group $R_{34}'$ is single bond, one end connected to group $R_{34}'$ of the linking group formed by m' sulfur atoms is bonded to group $R_{35}'$; in the formula (VI), x groups $R_{10}$ are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups and $C_{1-50}$ alkoxyl optionally substituted by one or more substituent groups (preferably selected from hydrogen, $C_{1-50}$ linear or branched alkyl, $C_{1-50}$ linear or branched alkenyl, linear or branched $C_{3-50}$ heteroalkyl and $C_{1-50}$ linear or branched alkyloxy), x is selected from an integral number of 1-10 (preferably an integral number of 1-5);

In the formula (VIII), group $R_{31}'$ is each independently selected from single bond and $C_{1-20}$ linear or branched alkylene (preferably selected from single bond and $C_{1-4}$ linear or branched alkylene); groups $R_{32}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{33}'$ in n repeating units are, identical to or different from each other, each independently selected from H and divalent $C_{1-20}$ linear or branched alkyl (preferably each independently selected from H and divalent $C_{1-4}$ linear or branched alkyl); groups $R_{34}'$ in n repeating units are, identical to or different from each other, each independently selected from H and divalent $C_{1-20}$ linear or branched alkyl (preferably each independently selected from H and divalent $C_{1-4}$ linear or branched alkyl); groups $R_{35}'$ in n repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{36}'$ in n repeating units are, identical to or different from each other, each independently selected from single bond and $C_{1-20}$ linear or branched alkylene (preferably each independently selected from single bond, $C_{1-4}$ linear or branched alkylene); the numbers m in n repeating units are, identical to or different from each other, each independently selected from an integral number of 0-10 (preferably an integral number of 0-5); the numbers m' in n repeating units are, identical to or different from each other, each independently selected from an integral number of 0-10 (preferably an integral number of 0-5), m+m'>0; in each repeating unit of the formula (VIII), when m is greater than 0, the linking group formed by m sulfur atoms is bonded to groups $R_{32}'$ and $R_{35}'$; when m' is greater than 0, the linking group formed by m' sulfur atoms is bonded to groups $R_{33}'$ and $R_{34}'$; in each repeating unit of the formula (VIII), when group $R_{33}'$ is H, one end connected to group $R_{33}'$ of the linking group formed by m' sulfur atoms is bonded to group $R_{32}'$; when group $R_{34}'$ is H, one end connected to group $R_{34}'$ of the linking group formed by m' sulfur atoms is bonded to group $R_{35}'$; in the formula (VIII), x groups $R_{10}$ are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups and $C_{1-50}$ alkoxyl optionally substituted by one or more substituent groups (preferably selected from hydrogen, $C_{1-50}$ linear or branched alkyl, $C_{1-50}$ linear or branched alkenyl, linear or branched $C_{3-50}$ heteroalkyl and $C_{1-50}$ linear or branched alkyloxy), x is selected from an integral number of 1-10 (preferably an integral number of 1-5); in each repeating unit of the formula (VIII), groups $R_{31}'$ and $R_{36}'$ can be each independently substituted by a group represented by the formula (VIII-1); in each repeating unit of the formula (VIII), groups $R_{32}'$, $R_{33}'$, $R_{34}'$ and $R_{35}'$ can be each independently substituted by a group represented by the formula (V),

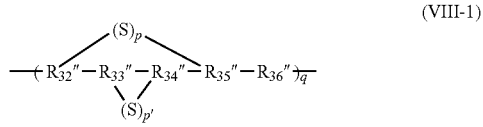

(VIII-1)

In the formula (VIII-1), groups $R_{32}''$ in q repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{33}''$ in q repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{34}''$ in q repeating units are, identical to or different from each other, each independently selected from single bond and divalent or trivalent $C_{1-20}$ linear or branched alkyl (preferably each independently selected from single bond, divalent or trivalent $C_{1-4}$ linear or branched alkyl); groups $R_{35}''$ in q repeating units are, identical to or different from each other, each independently selected from divalent, trivalent or tetravalent $C_{1-20}$ linear or branched alkyl (preferably each independently selected from divalent, trivalent or tetravalent $C_{1-4}$ linear or branched alkyl); groups $R_{36}''$ in q repeating units are, identical to or different from each other, each independently selected from single bond and $C_{1-20}$ linear or branched alkylene (preferably each independently selected from single bond, $C_{1-4}$ linear or branched alkylene); q is an integral number of 1-10 (preferably an integral number of 1-3); the numbers p in q repeating units are, identical to or different from each other, each independently selected from an integral number of 0-10 (preferably an integral number of 0-5); the numbers p' in q repeating units are, identical to or different from each other, each independently selected from an integral number of 0-10 (preferably an integral number of 0-5); in each repeating unit of the formula (VIII-1), when p is greater than 0, the linking group formed by p sulfur atoms is bonded to groups $R_{32}''$and $R_{35}''$; when p' is greater than 0, the linking group formed by p' sulfur atoms is bonded to groups $R_{33}''$and $R_{34}''$; in each repeating unit of the formula (VIII-1), when group $R_{33}''$ is single bond, one end connected to group $R_{33}''$ of the linking group formed by p' sulfur atoms is bonded to group $R_{32}''$, when group $R_{34}''$ is single bond, one end connected to group $R_{34}''$ of the linking group formed by p' sulfur atoms is bonded to group $R_{35}''$.

In the general formula (I-4), preferably, group R is located at the meta-position or the para-position of the phenolic hydroxyl group; x is 0, 1 or 2, one or two groups $R_{10}$ that are present are located at the ortho-position of the phenolic hydroxyl group, and each independently selected from $C_{1-4}$ linear or branched alkyl.

In the general formula (I-4), further preferably, group R is located at the meta-position of the phenolic hydroxyl group; x is 0, 1 or 2, one or two groups $R_{10}$ that are present are located at the ortho-position of the phenolic hydroxyl group, and each independently selected from $C_{1-4}$ linear or branched alkyl.

The phenol derivative of the present invention can be a single compound of the structure represented by the general formula (I-4), or a mixture of structures represented by the general formula (I-4); when the phenol derivative is a mixture of structures represented by the general formula (I-4), the values n for each group of each compound in the mixture can be identical or different, and the sums of the values n of each compound may be identical or different.

Further preferably, the phenol derivative of the present invention is selected from the following specific compounds or a mixture thereof in any proportion:

139
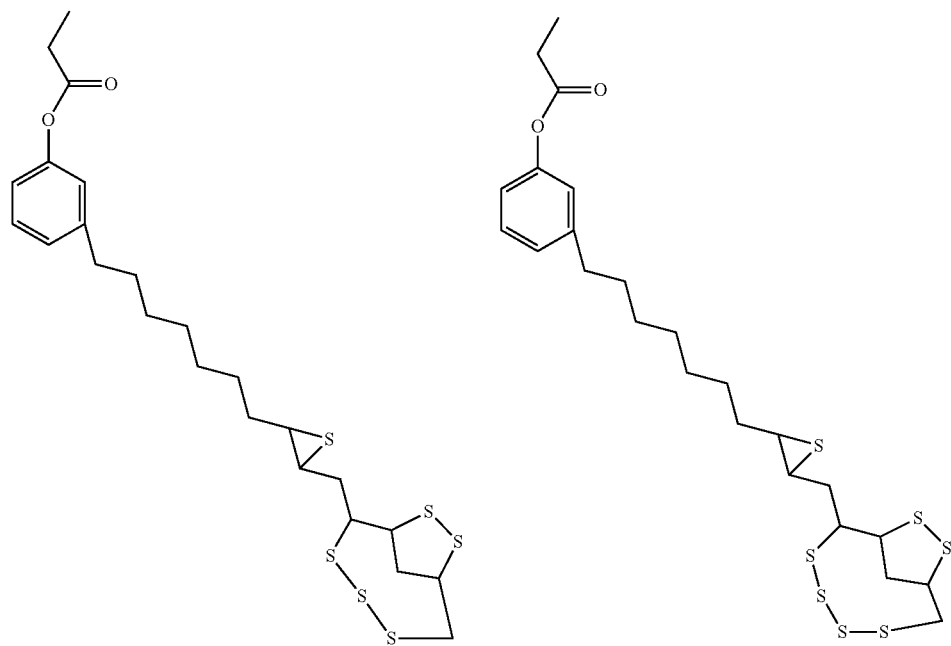 [SMILES: CCC(=O)Oc1cccc(CCCCCCCC2SC2CC2SSSCC3CC2SS3)c1 ; CCC(=O)Oc1cccc(CCCCCCCC2SC2CC2SSSSCC3CC2SS3)c1]
140
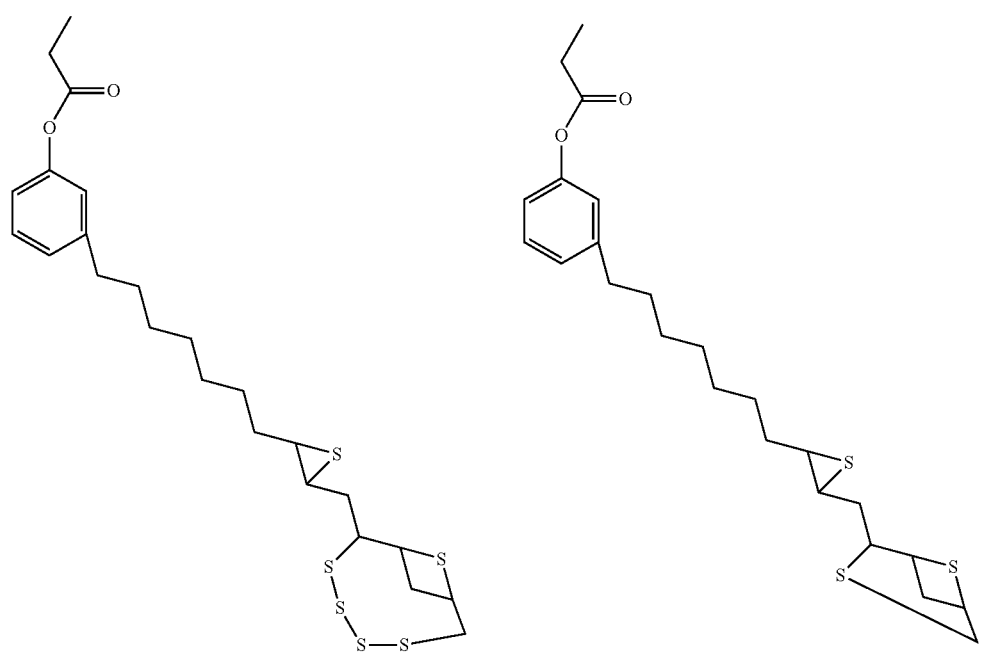 [SMILES: CCC(=O)Oc1cccc(CCCCCCCC2SC2CC2SSSSCC3CC2S3)c1 ; CCC(=O)Oc1cccc(CCCCCCCC2SC2CC2SCC3CC2S3)c1]

141
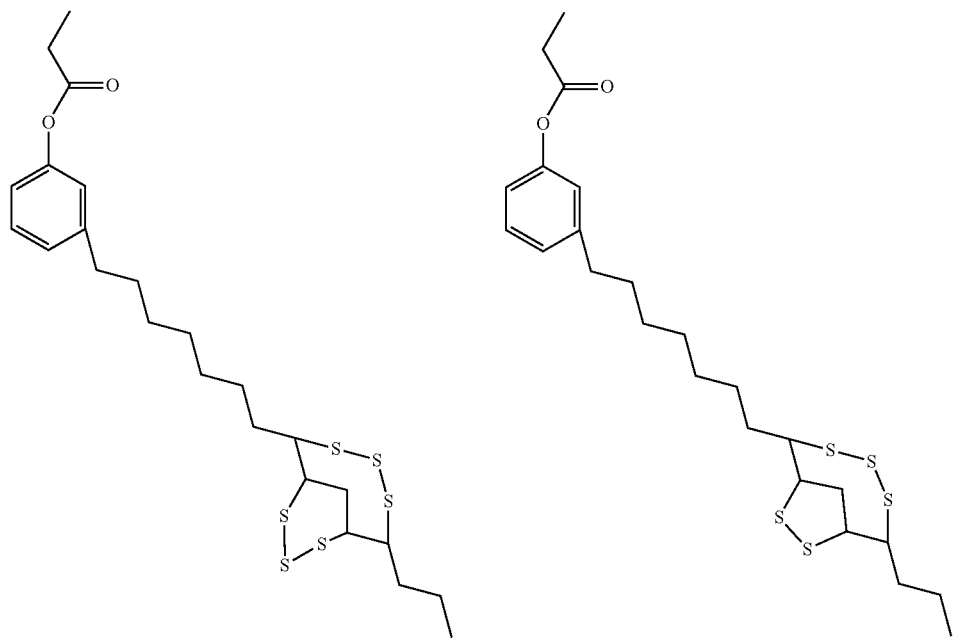
-continued
142
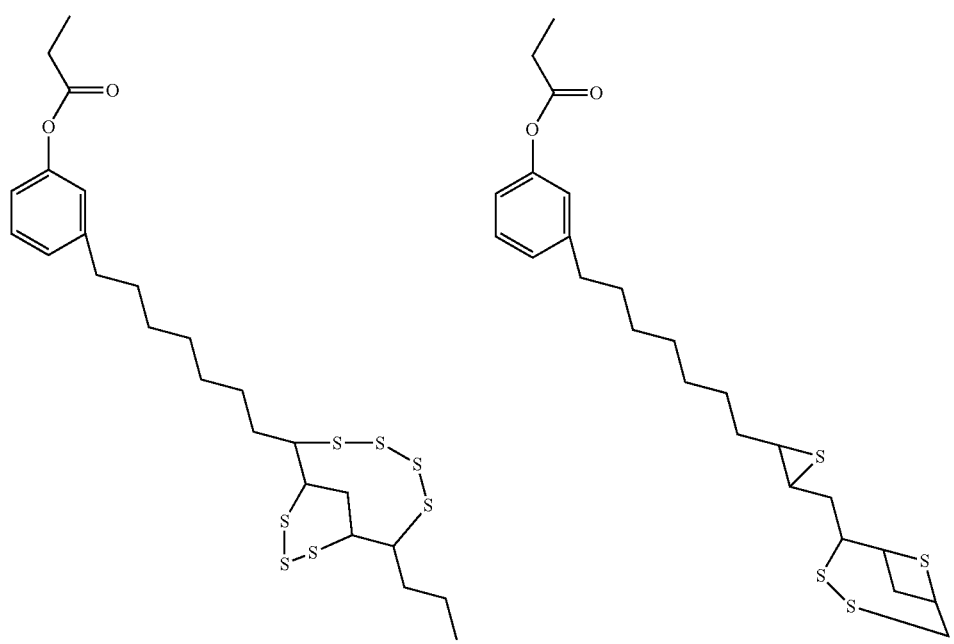

143 144
-continued
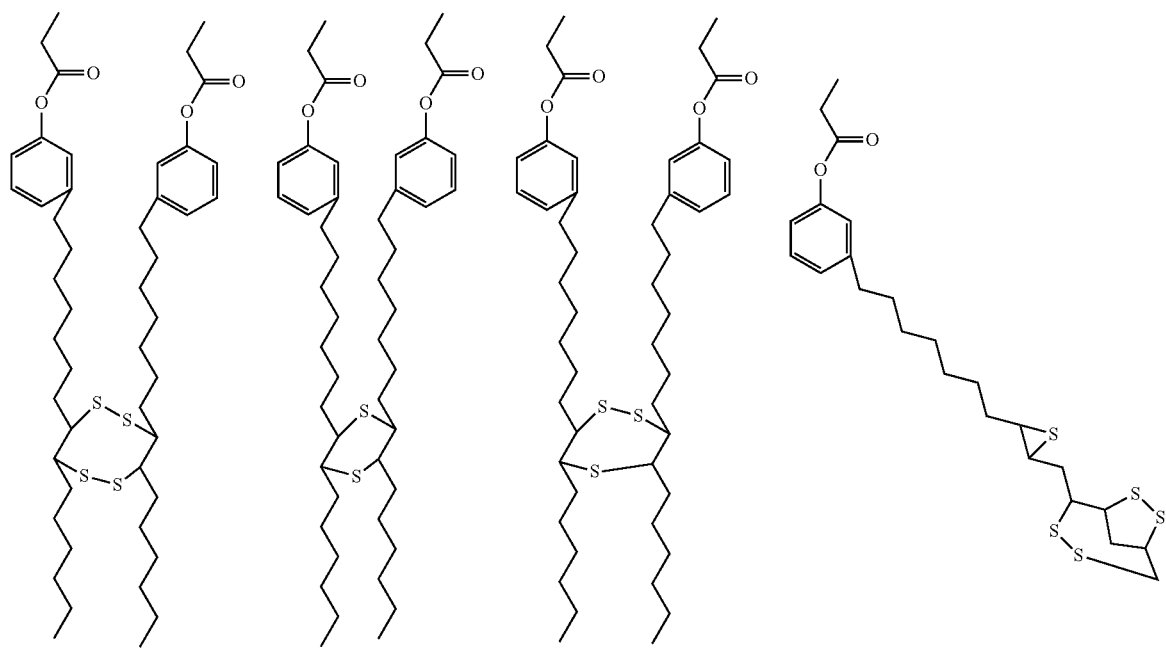
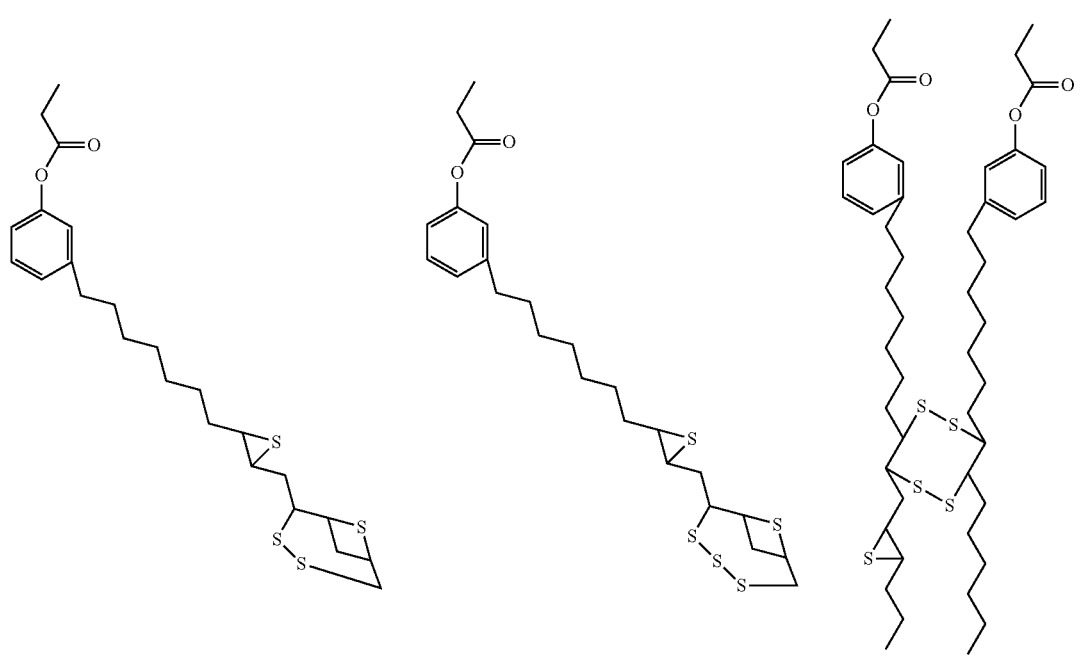

145
-continued
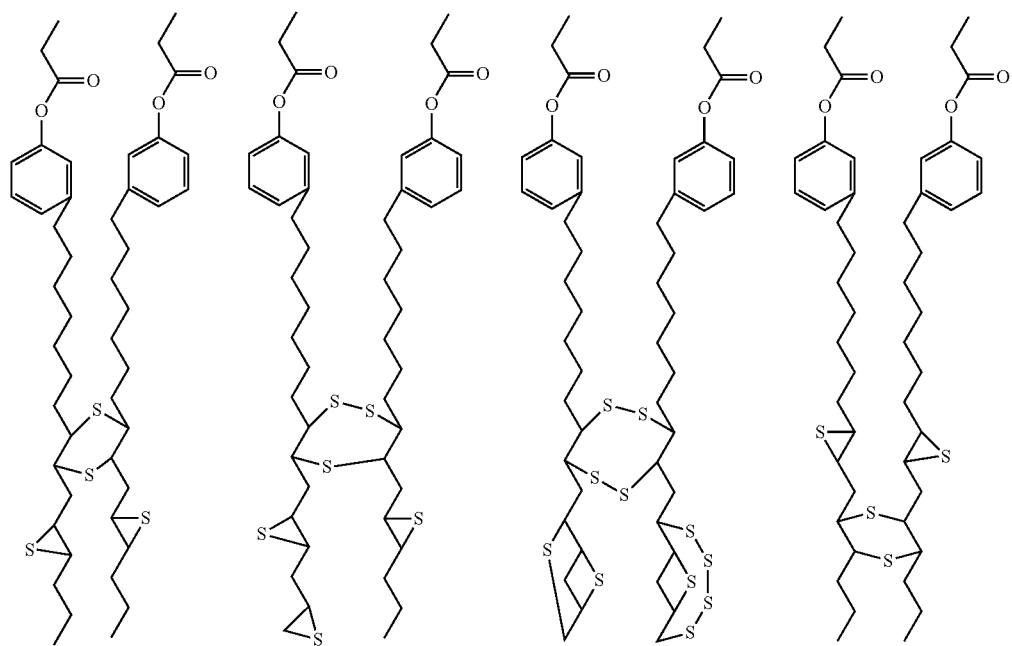
146
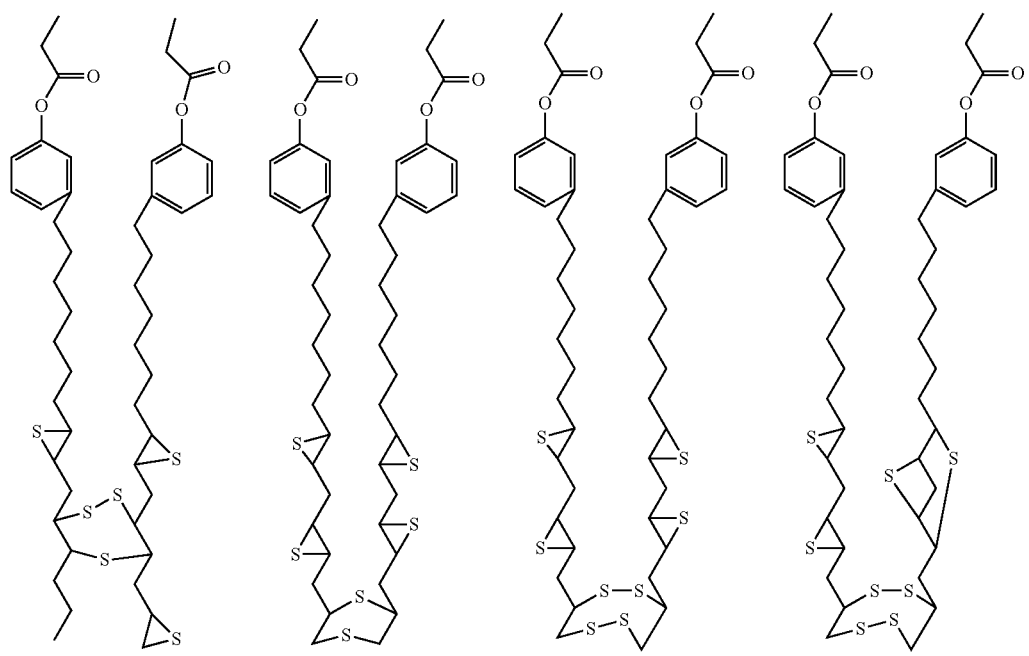

-continued
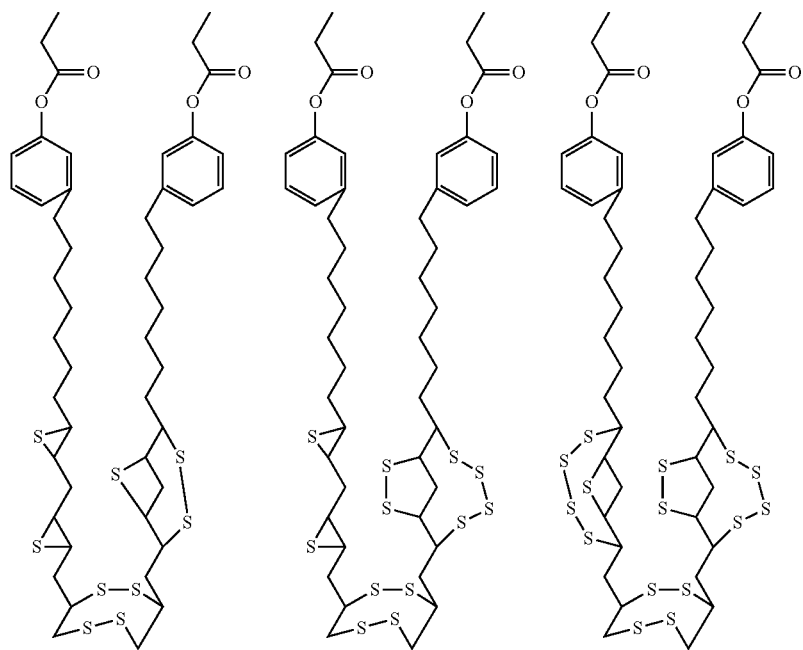 [SMILES: CCC(=O)Oc1cccc(CCCCCCCC2SSC(CC3CSSCC(CC4SC4CC4SC4CCCCCCCc4cccc(OC(=O)CC)c4)SS3)C3CC2S3)c1 ; CCC(=O)Oc1cccc(CCCCCCCC2SSSSC(CC3CSSCC(CC4SC4CC4SC4CCCCCCCc4cccc(OC(=O)CC)c4)SS3)C3CC2SS3)c1 ; CCC(=O)Oc1cccc(CCCCCCCC2SSSSC(CC3CSSCC(CC4SSSSC(CCCCCCCc5cccc(OC(=O)CC)c5)C5CC4S5)SS3)C3CC2SS3)c1]
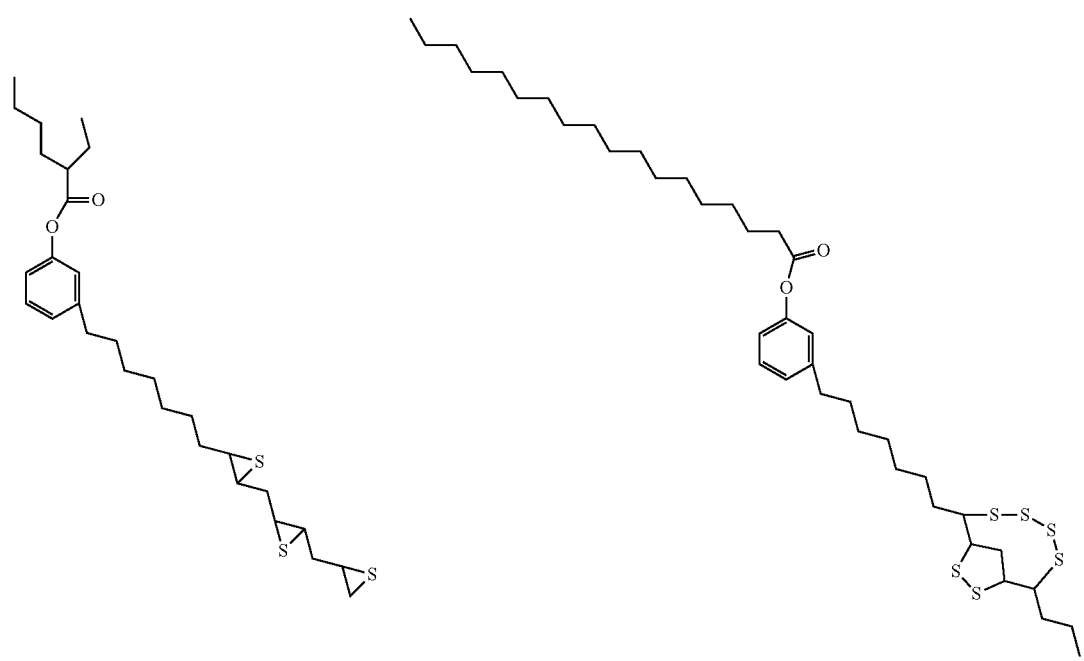

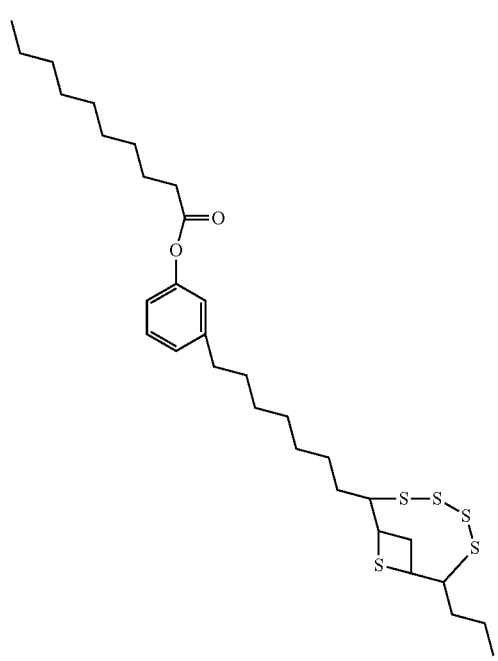
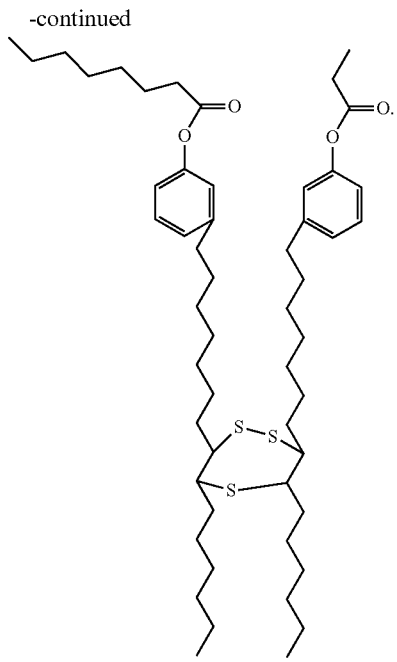

The process of preparing the phenol derivative of the present invention comprises a step of subjecting the phenol compound represented by the general formula (X) to the sulfurization reaction and the esterification reaction.

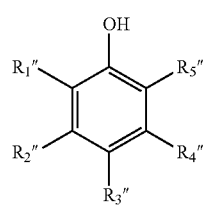

(X)

In the general formula (X), groups $R_1''$, $R_2''$, $R_3''$, $R_4''$ and $R_5''$ are, identical to or different from each other, each independently selected from hydrogen, $C_{1-50}$ hydrocarbyl optionally substituted by one or more substituent groups, $C_{6-20}$ aryl substituted by one or more substituent groups, $C_{3-50}$ hetero hydrocarbyl optionally substituted by one or more substituent groups, $C_{1-50}$ alkoxyl optionally substituted by one or more substituent groups and a group represented by the general formula (III'), wherein at least one group is selected from a group represented by the general formula (III');

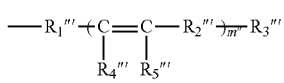

(III')

Wherein group $R_1'''$ is selected from single bond and $C_{1-20}$ linear or branched alkylene (preferably selected from single bond and $C_{1-4}$ linear or branched alkylene); groups $R_2'''$ in m repeating units are, identical to or different from each other, each independently selected from single bond and $C_{1-20}$ linear or branched alkylene (preferably each independently selected from single bond and $C_{1-4}$ linear or branched alkylene); group $R_3'''$ is selected from hydrogen and $C_{1-20}$ linear or branched alkyl (preferably selected from hydrogen and $C_{1-4}$ linear or branched alkyl); groups $R_4'''$ in m repeating units are, identical to or different from each other, each independently selected from hydrogen and $C_{1-20}$ linear or branched alkyl (preferably each independently selected from hydrogen and $C_{1-4}$ linear or branched alkyl); groups $R_5'''$ in m repeating units are, identical to or different from each other, each independently selected from hydrogen and $C_{1-20}$ linear or branched alkyl (preferably each independently selected from hydrogen and $C_{1-4}$ linear or branched alkyl); m" is an integral number of 1-10 (preferably an integral number of 1-5, more preferably an integral number of 1-3).

According to the process of preparing a phenol derivative of the fourth embodiment of the present invention, in the general formula (X), preferably, groups $R_1''$ and $R_5''$ are, identical to or different from each other, each independently selected from hydrogen, $C_{1-4}$ linear or branched alkyl; groups $R_2''$, $R_3''$ and $R_4''$ are, identical to or different from each other, each independently selected from hydrogen, $C_{1-30}$ linear or branched alkyl and a group represented by the general formula (III'), wherein at least one group is a group represented by the general formula (III').

According to the process of preparing a phenol derivative of the fourth embodiment of the present invention, in the general formula (X), more preferably, groups $R_1''$ and $R_5''$ are, identical to or different from each other, each independently selected from hydrogen, $C_{1-4}$ linear or branched alkyl; one of groups $R_2''$ and $R_4''$ is selected from a group represented by the general formula (III'), and the other one is selected from hydrogen, $C_{1-50}$ linear or branched hydrocarbyl (preferably $C_{1-30}$ linear or branched alkyl); $R_3''$ is selected from hydrogen, $C_{1-4}$ linear or branched alkyl.

According to the process of preparing a phenol derivative of the fourth embodiment of the present invention, the phenol compound represented by the general formula (X) can first subjected to a sulfurization reaction followed by an esterification reaction (the reactant of the esterification reaction is the product of the sulfurization reaction), or the phenol compound represented by the general formula (X) can first subjected to an esterification reaction followed by a sulfurization reaction (the reactant of the sulfurization reaction is the product of the esterification reaction).

According to the process of preparing a phenol derivative of the fourth embodiment of the present invention, the sulfurization reaction is to react the phenol compound represented by the general formula (X) or an esterification product thereof with a sulfurizing agent. The sulfurization reaction is to perform the electrophilic addition between the sulfurizing agent and alkene, when the addition occurs in the alkene molecular chain, if there is one carbon-carbon double bond in the molecule, the sulfur ring group is formed, and if there are more than one carbon-carbon double bond, the sulfur ring group and/or two or more sulfur ring groups can be formed; when the addition occurs between the alkene molecular chain, the relatively complex sulfur ring structure may be formed. The sulfurizing agent is preferably an inorganic sulfurizing agent and/or an organic sulfurizing agent, the inorganic sulfurizing agent can be selected from one or more of sulphur, $Na_2S$, $K_2S$, ZnS, $H_2S$ and SCl; the organic sulfurizing agent can be selected from one or more of ditertbutyl polysulfide (DBPS), dimethyl disulphide (DMDS), dimethyl sulfide (DMS), ethyl mercaptan (EM), n-butyl mercaptan (NBM) and tert-nonyl polysulfide (TNPS); the sulfurizing agent is more preferably one or more of sulphur, $Na_2S$ and thiol. The molar ratio of the phenol compound represented by the general formula (A) or an esterification product thereof to the sulfurizing agent is preferably 1:1-6, more preferably 1:2-4. The sulfurization reaction temperature is 100° C.-240° C., preferably 140° C.-190° C.; usually, the longer the reaction time is, the higher the conversion is, and under the overall consideration of the reaction conversion and the reaction economy, the reaction time is generally 0.5-10 hours, preferably 3-5 hours.

According to the process of preparing the phenol derivative of the present invention, in the sulfurization reaction, a catalyst is optionally but preferably added. The catalyst is preferably selected from $C_{1-6}$ organic amine and inorganic base, for example can be selected from one or more of methylamine, dimethylamine, ethylamine, diethylamine, propylamine, dipropyl amine, tripropyl amine, butylamine, amylamine, hexylamine, ammonia water, sodium hydroxide, potassium hydroxide, zinc hydroxide, sodium oxide, potassium oxide, zinc oxide, sodium carbonate, potassium carbonate and zinc carbonate The mass of the catalyst is 0.01%-10%, preferably 0.1%-5% by the mass of the phenolic ester compound represented by the general formula (A).

According to the process of preparing the phenol derivative of the present invention, the esterification reaction is to react the phenol compound represented by the general formula (X) or a sulfurization product thereof with an esterifying agent. The esterifying agent is preferably selected from

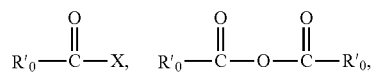

wherein groups $R_0'$ are, identical to or different from each other, each independently selected from $C_{1-50}$ linear or branched alkyl (preferably $C_{1-30}$ linear or branched alkyl), X is selected from F, Cl, Br, I, OH. The esterifying agent can also be selected from one or more of acetic anhydride, oleic anhydride, 2-ethyl caproic anhydride, acetic acid, oleic acid, 2-ethyl caproic acid, acetyl chloride, oleoyl chloride and 2-ethyl caproyl chloride. The molar ratio of the phenol compound represented by the general formula (X) or a sulfurization product thereof to the esterifying agent is preferably 1:1-10, more preferably 1:1-2. The esterification reaction temperature is 20° C.-120° C., preferably 40° C.-80° C.; usually, the longer the reaction time is, the higher the conversion is, and under the overall consideration of the reaction conversion and the reaction economy, the esterification reaction time is preferably 0.5 hours-10 hours, more preferably 3 hours-5 hours. In the esterification reaction, a catalyst is optionally but preferably added; the catalyst is preferably inorganic base, metal oxide, preferably alkalimetal hydroxide, alkali-metal carbonate, transition metal oxide, for example can be selected from one or more of potassium carbonate, sodium carbonate, zinc oxide, sodium hydroxide, potassium hydroxide; the addition amount of the catalyst is preferably 0.1%-15%, more preferably 5%-10% by the mass of the phenol compound represented by the general formula (A).

In the sulfurization reaction and the esterification reaction, a solvent can be added, and the solvent can be removed with the methods well known in the art after the completion of the reaction without particular limitation.

Fifth Embodiment

According to the fifth embodiment of the present invention, the phenol derivative of the present invention has a structure as represented by the formula (I-5):

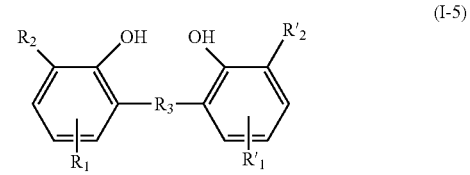

Wherein, $R_1$ and $R_1'$ can be identical or different and each independently selected from $C_nH_{(2n+m)}$, n is an integral number of 3-30 (preferably an integral number of 5-20, most preferably an integral number of 10-18, for example 10, 11, 12, 13, 14, 15, 16, 17, 18), m is 1, −1, −3 or −5 (preferably 1, −1 or −3); $R_2$ and $R_2'$ can be identical or different and each independently selected from $C_{1-20}$ linear or branched alkyl (preferably selected from $C_1$-$C_4$ linear or branched alkyl, most preferably tert-butyl); $R_3$ is selected from $C_1$-$C_6$ linear or branched alkylene (preferably selected from $C_1$-$C_4$ linear or branched alkylene, most preferably methylene).

According to the phenol derivative of the fifth embodiment of the present invention, wherein $R_1$ and $R_1'$ can be each independently located at the meta-position or the para-position of the hydroxy of the benzene ring in which said group(s) are located, preferably each independently located at the meta-position of the hydroxy of the benzene ring in which said group(s) are located.

The phenol derivative of the fifth embodiment of the present invention can be a compound of a single structure, or a mixture containing compounds of different structures.

Preferably, the specific phenol derivative of the fifth embodiment of the present invention comprises: 2,2'-methylene-bis(6-tert-butylcardanol), 2,2'-methylene-bis(3-pentadecyl-6-tert-butylphenol).

The process of preparing the phenol derivative of the fifth embodiment of the present invention comprises: reacting the phenol compound represented by the general formula (II-5) with $C_1$-$C_6$ aldehyde, and collecting the product;

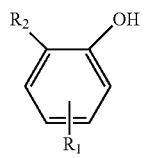
(II-5)

In the general formula (II-5), $R_1$ is $C_nH_{(2n+m)}$, n is an integral number of 3-30 (preferably an integral number of 5-20, most preferably an integral number of 10-18, for example 10, 11, 12, 13, 14, 15, 16, 17, 18), m is 1, −1, −3 or −5 (preferably 1, −1 or −3); $R_2$ is $C_{1-20}$ linear or branched alkyl (preferably $C_1$-$C_4$ linear or branched alkyl, most preferably tert-butyl); $R_1$ is located at meta-position or para-position of the hydroxy of the benzene ring in which said group is located, and preferably located at meta-position of the hydroxy of the benzene ring in which said group is located.

According to the process of preparing the phenol derivative of the fifth embodiment of the present invention, the molar ratio of the phenol compound represented by the general formula (II-5) to $C_1$-$C_6$ aldehyde is preferably 1-10:1, more preferably 2-5:1; the temperature for reacting the phenol compound represented by the general formula (II-5) with $C_1$-$C_6$ aldehyde is preferably 20° C.-120° C., more preferably 50° C.-100° C. In general, the longer the time for reacting the phenol compound represented by the general formula (II-5) with $C_1$-$C_6$ aldehyde, the better it is, and usually it is preferably 0.5-10 hours, most preferably 3-5 hours.

According to the process of preparing the phenol derivative of the fifth embodiment of the present invention, in the reaction of the phenol compound represented by the general formula (II-5) and $C_1$-$C_6$ aldehyde, a catalyst is optionally but preferably added; the catalyst is preferably an acidic catalyst or a basic catalyst. The acidic catalyst can be selected from one or more of sulfuric acid, hydrochloric acid, nitric acid and phosphoric acid (preferably sulfuric acid). The basic catalyst can be selected from hydroxides of alkali metals and/or alkaline earth metals, can be selected from one or more of sodium hydroxide, potassium hydroxide, magnesium hydroxide, calcium hydroxide and barium hydroxide (preferably sodium hydroxide). The addition amount of the catalyst is preferably 0.1%-10%, more preferably 0.8%-2% by the mass of the phenol compound represented by the general formula (II-5).

According to the process of preparing the phenol derivative of the fifth embodiment of the present invention, in the reaction of the phenol compound represented by the general formula (II-5) and $C_1$-$C_6$ aldehyde, a solvent is optionally but preferably added; said solvent is preferably one or more of toluene, ethanol, acetone, chloroform and petroleum ether; the addition amount of said solvent is preferably 10%-100%, more preferably 50%-80% by the total mass of the phenol compound represented by the general formula (II-5) and $C_1$-$C_6$ aldehyde.

According to the process of preparing the phenol derivative of the fifth embodiment of the present invention, the exemplary equation for the reaction of the phenol compound represented by the general formula (II-5) and $C_1$-$C_6$ aldehyde is shown as follows:

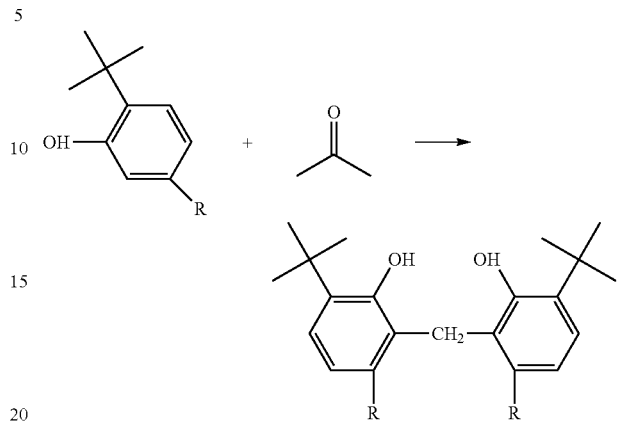

Wherein, R is $R_1$ in the above-mention general formula (II-5).

According to the process of preparing the phenol derivative of the fifth embodiment of the present invention, preferably, when the reaction product of the phenol compound represented by the general formula (II-5) and $C_1$-$C_6$ aldehyde contains an unsaturated bond, the reaction product can be subjected to the hydrotreatment in order to increase the saturation degree of the reaction product. The technological conditions of the hydrotreatment preferably comprise: hydrogen pressure: 1.0-6.0 MPa (preferably 3.0-4.0 MPa), temperature: 60° C.-260° C. (preferably 180° C.-220° C.), time: 0.5-10 hours (preferably 3-5 hours). Preferably, a hydrogenation catalyst is added during the hydrotreatment. The hydrogenation catalyst is preferably a transition metal, and for example can be selected from palladium carbon catalyst, and Raney's nickel. The addition amount of the hydrogenation catalyst is preferably 0.1%-10%, more preferably 0.5%-5% by the mass of the phenol compound represented by the general formula (II-5).

According to the process of preparing the phenol derivative of the fifth embodiment of the present invention, preferably, the phenol compound represented by the general formula (II-5) can be obtained by subjecting the phenol compound represented by the general formula (III-5) and an alkylating agent to the alkylation reaction:

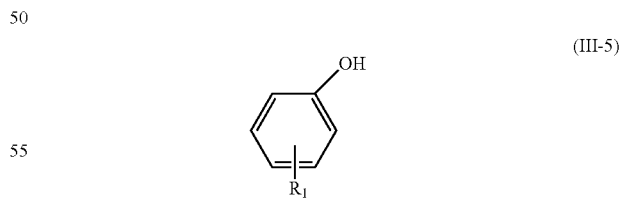
(III-5)

Wherein $R_1$ is $C_nH_{(2n+m)}$, n is an integral number of 3-30 (preferably an integral number of 5-20, most preferably an integral number of 10-18, for example 10, 11, 12, 13, 14, 15, 16, 17, 18), m is 1, −1, −3 or −5 (preferably 1, −1 or −3). In the phenol compound represented by the general formula (III-5), $R_1$ is located at meta-position or para-position of the hydroxy of the benzene ring in which said group is located, and preferably located at meta-position of the hydroxy of the benzene ring in which said group is located. The alkylating agent is preferably $R_2X$, wherein $R_2$ is $C_1$-$C_8$ linear or branched alkyl (preferably $C_1$-$C_4$ linear or branched alkyl, most preferably tert-butyl), X is F, Cl, Br, I (preferably Cl, Br). The molar ratio of the phenol compound represented by the general formula (III-5) to the alkylating agent is preferably 1:1-5, more preferably 1:1-2.5. The exemplary reaction equation for the alkylation reaction is shown as follows:

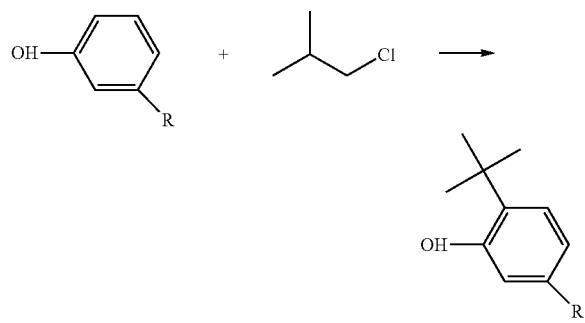

Wherein, R is $R_1$ in the above-mention general formula (II-5).

According to the process of preparing the phenol derivative of the fifth embodiment of the present invention, preferably, the alkylation reaction temperature is 20° C.-100° C., preferably 40° C.-70° C., the reaction time is 0.5-10 hours, is preferably 3-5 hours.

According to the process of preparing the phenol derivative of the fifth embodiment of the present invention, in the alkylation reaction, a catalyst is optionally but preferably added; the catalyst is preferably one or more of inorganic acid, organic acid and Lewis acid, for example can be selected from one or more of sulfuric acid, hydrochloric acid, nitric acid, metallic chloride, boron trifluoride and heteropoly acid, specifically, can be selected from one or more of zinc chloride, aluminum chloride and concentrated sulphuric acid. The addition amount of the catalyst is preferably 0.1%-10%, more preferably 1%-6% by the mass of the phenol compound represented by the general formula (III-5).

According to the process of preparing the phenol derivative of the fifth embodiment of the present invention, in the alkylation reaction, a solvent is optionally but preferably added; said solvent is preferably one or more of toluene, ethanol, acetone, chloroform and petroleum ether; the addition amount of said solvent is preferably 10%-120%, more preferably 50%-100% by the mass of the phenol compound represented by the general formula (III-5).

[Lubricating Oil/Lubricating Grease]

The present invention further provides a lubricating oil, which comprises a base oil and the above-mentioned phenol derivative of the present invention.

The present invention further provides a lubricating grease, which comprises a base oil and the above-mentioned phenol derivative of the present invention.

In the present invention, the base oil of the lubricating oil is not particularly limited, and mineral oil, synthetic oil, or a mixture of mineral oil and synthetic oil can be used. The viscosity index of the base oil is preferably 122 or more, more preferably 123 or more, and further preferably 125 or more.

As the mineral oil, the following can be enumerated: paraffin-based mineral oils, intermediate-based mineral oils, and naphthene-based mineral oils obtained by a conventional refining process such as solvent refining or hydrogenation refining; wax (gas-to-liquid wax) produced by the F-T process or the like, wax-isomerized oil produced by isomerizing wax such as mineral oil-based wax; and the like.

As the synthetic oil, the following can be enumerated: hydrocarbon-based synthetic oils, ether-based synthetic oils and the like. As the hydrocarbon-based synthetic oil, the following can be enumerated: alkylbenzene, alkylnaphthalene and the like. As the ether-based synthetic oil, the following can be enumerated: polyoxyalkyleneglycol, polyphenylether and the like.

Among them, from the viewpoint of improving fuel economy and low-temperature startability of the engine, preferred is at least one selected from mineral oils and synthetic oils in Groups 3-5 of API (American Petroleum Institute) base oil categories.

The base oil (A) may be a single system using one of the above-mentioned mineral oils and synthetic oils, or may be a mixed system such as a base oil obtained by mixing two or more mineral oils, a base oil obtained by mixing two or more synthetic oils, and a base oil obtained by mixing each one or two or more of mineral oils and synthetic oils.

In the present invention, the base oil of the lubricating grease is not particularly limited, and mineral oil-based or synthetic oil-based base oils usually for producing the lubricating grease can be enumerated. They may be used alone or in mixture.

As the mineral oil-base oil, the base oil can be obtained by refining through the appropriate combination of vacuum distillation, solvent deasphalting, solvent extraction, hydrocracking, solvent dewaxing, sulfuric acid washing, clay refining, hydrogenation refining and the like. Furthermore, as the synthetic oil-based base oil, poly-alpha-olefin (PAO)-based base oil, other hydrocarbon-based base oil, ester-based base oil, alkyldiphenylether-based base oil, polyalkylene glycol-based base oil (PAG), alkylbenzene-based base oil and the like can be enumerated.

The present invention also provides a base oil, which comprises the above-mentioned phenol derivative of the present invention. In an embodiment of the present invention, the base oil provided by the present invention contains 20 wt % or more of the above-mentioned phenol derivative of the present invention relative to the total weight of the base oil. In an embodiment of the present invention, the base oil provided by the present invention contains 30 wt % or more, 40 wt % or more, 50 wt % or more, 60 wt % or more, 70 wt % or more, 80 wt % or more, 90 wt % or more of the above-mentioned phenol derivative of the present invention relative to the total weight of the base oil. In an embodiment of the present invention, the base oil provided by the present invention per se is used as the base oil, namely, 100 wt % of the base oil is the phenol derivative of the present invention.

[Use]

The above-mentioned phenol derivative of the present invention can be used as the base oil of the lubricating oil. The phenol derivative of the present invention can be used as antioxidant, antiwear additive and lubricant, particularly suitably used as the antioxidant in lubricating oil, lubricating grease, plastic, and rubber, or can be used as the base oil of the lubricating oil and the lubricating grease and the antiwear additive of the lubricating oil and the lubricating grease.

EXAMPLES

Hereinafter, the present invention will be specifically explained through examples. However, the examples are merely to further illustrate one of the embodiments of the present invention, and the present invention is not limited to these examples.

The performance evaluation in examples and comparative examples was performed according to the following methods.

(1) High Temperature Antioxidation Performance Evaluation

The lubricating oil compositions prepared in examples or comparative examples were used as test sample, and the anti-oxidation performance of the test sample was evaluated by a pressure differential scanning calorimetry test (PDSC) to determine the oxidation induction period (in minutes) of the test sample. The PDSC testing device was the TA5000 DSC meter available from TA Company, the United States. The testing conditions comprised: 190° C., the oxygen pressure: 0.5 MPa, and the temperature rising rate: 10° C./min.

(2) Antiwear Performance Evaluation

The lubricating oil compositions prepared in examples and comparative examples were used as the test sample and subjected to the antiwear performance test. The testing device was an SRV vibration and friction testing machine. The test conditions were: 100N, 200N, 300N, frequency 50 Hz, amplitude 1 mm, 30° C., 1 h.

The lubricating oil compositions prepared in examples or comparative examples were used as test sample to perform a four-ball test. The method was SH/T 0189 lubricating oil antiwear performance measurement method (four-ball machine method). The test conditions comprised 1200 r/min, load: 392N, and time: 30 minutes.

(3) Anti-Corrosion Performance Evaluation

According to GB/T 5096 copper strip corrosion test method, the lubricating oil composition prepared in examples or comparative examples was used as the test sample to carry out the copper strip corrosion test, and the test condition was 100° C., 3h.

The raw materials used in the examples are all conventional commercially available products, some of which are listed as follows:

Cardanol, Shanghai Wujing Chemical Technology Co., Ltd., industrial product
Concentrated sulphuric acid, Sinopharm Chemical Reagent Co., Ltd., analytically pure
Hydrogen peroxide (30%), Sinopharm Chemical Reagent Co., Ltd., analytically pure
Formic acid, Sinopharm Chemical Reagent Co., Ltd., analytically pure
Sodium bicarbonate, Sinopharm Chemical Reagent Co., Ltd., analytically pure
Palladium carbon catalyst (metal palladium loaded on active carbon), Shaanxi Ruike New Material Co., Ltd., palladium content=5%.
Triethylamine, Sinopharm Chemical Reagent Co., Ltd., analytically pure
Toluene, Sinopharm Chemical Reagent Co., Ltd., analytically pure
Petroleum ether, Sinopharm Chemical Reagent Co., Ltd., analytically pure
Sulphur powder, Sinopharm Chemical Reagent Co., Ltd., analytically pure
T501: 2,6-ditert-butyl para-cresol
T511: 4,4-methylenebis(2,6-ditert-butyl para-phenol)
T512: isooctyl (3,5-ditert-butyl-4-hydroxyphenyl)propionate
T404: sulfurized cotton oil
T405: sulfurized olefin cotton oil The purity of the product was analyzed by gas chromatography, and the analysis conditions: the temperature of the vaporization chamber was 320° C., the column temperature was 280° C., and the programmed temperature rise was 10° C./min.

Example 1-1 Preparation of Epoxidized Cardanol 100 g cardanol, 8 g formic acid, 0.3 g sulfuric acid, 200 g hydrogen peroxide were added to a three-necked flask equipped with mechanical stirring, reflux condenser and temperature controller, stirred, and heated. The reaction temperature was maintained at 70° C. and the reaction was performed for 3 hours. After the completion of the reaction, the temperature was reduced to produce a red brown transparent liquid. The reaction product was filtered and caustic-washed with 5% KOH solution, and then water washed with distilled water to neutrality. The organic phase was distilled under reduced pressure at 100 Pa and 150° C. for 1 h to remove water and unreacted raw materials to produce 91.4 g orange red transparent liquid. The product conversion rate was 96.2%, and the purity of the epoxidized cardanol was greater than 98%.

Example 1-2 Preparation of Epoxidized Cardanol 100 g cardanol was added to a three-necked flask equipped with mechanical stirring, reflux condenser and temperature controller, and the stirring and heating was initiated. The reaction temperature was maintained at 12° C., 150 g metachlorobenzoyl hydroperoxide was slowly added, and the reaction was performed for 5 hours. After the completion of the reaction, the temperature was reduced to produce a red brown transparent liquid. The reaction product was filtered and caustic-washed with 5% KOH solution, and then water washed with distilled water to neutrality. The organic phase was distilled under reduced pressure at 100 Pa and 150° C. for 1 h to remove water and unreacted raw materials to produce 92.7 g orange red transparent liquid. The product conversion rate was 97.6%, and the purity of the epoxidized cardanol was greater than 98%.

Example 1-3 Preparation of 2-tert-butyl-4-epoxypentadecyl Phenol 35 g epoxidized cardanol prepared in Example 1-1 was dissolved in 100 ml acetone. After the completion of dissolving, the mixture was placed in a 250 ml three-necked reaction flask, and 0.9 g zinc chloride catalyst was added. The stirring and heating was initiated, and the reaction temperature was maintained at 60° C. 9.5 g tert-butyl chloride was slowly added dropwise into the reaction flask, after the completion of the dropwise addition, the reaction was continued for 3 hours. After the completion of the reaction, the temperature was reduced to produce a red brown transparent liquid. The reaction product was filtered and caustic-washed with 5% KOH solution, and then water washed with distilled water to neutrality. The collected liquid was distilled under reduced pressure at 1000 Pa and 120° C. for 1 h to remove solvent, water and unreacted raw materials to produce 36.3 g dark red brown thick liquid. The product conversion rate was 81.6%. The prepared product was subjected to the infrared spectrum analysis. The spectrum was shown in FIG. 1, and the analysis result was shown in Table 1-1.

TABLE 1-1

Infrared analysis result of the product of Example 1-3

| Characteristic absorption peak/cm$^{-1}$ | Absorption peak attribution |
|---|---|
| 3390.42 | Stretching vibration of C—OH |
| 2928.3, 2854.94 | Stretching vibration of C—H in CH$_3$ and CH$_2$ |
| 1705.87 | Stretching vibration of C=O |
| 1591.89, 1482.08, 1458.44 | Stretching vibration of benzene ring framework |
| 1070.44 | Stretching vibration of O—C |
| 917.34 | Stretching vibration of O—C—O |

Example 1-4 Preparation of 2-tert-butyl-4-epoxypentadecyl Phenol 35 g epoxidized cardanol prepared in Example 1-2 was dissolved in 100 ml acetone. After the completion of dissolving, the mixture was placed in a 250 ml three-necked reaction flask, and 0.4 g concentrated sulphuric acid catalyst was added. The stirring and heating was initiated, and the reaction temperature was maintained at 50° C. 12 g tert-butyl chloride was slowly added dropwise into the reaction flask, after the completion of the dropwise addition, the reaction was continued for 4 hours. After the completion of the reaction, the temperature was reduced to produce a red brown transparent liquid. The reaction product was filtered and caustic-washed with 5% sodium bicarbonate solution, and then water washed with distilled water to neutrality. The collected liquid was distilled under reduced pressure at 1000 Pa and 120° C. for 1 h to remove solvent, water and unreacted raw materials to produce 36.5 g dark red brown thick liquid. The product conversion rate was 82.1%.

Example 1-5 Preparation of 2-tert-butyl-4-epoxypentadecyl Phenol 35 g epoxidized cardanol prepared in Example 1-1 was dissolved in 100 ml acetone. After the completion of dissolving, the mixture was placed in a 250 ml three-necked reaction flask, and 2 g concentrated sulphuric acid catalyst was added. The stirring and heating was initiated, and the reaction temperature was maintained at 70° C. 14 g isobutylene was slowly introduced into the reaction flask, after the completion of the introduction, the reaction was continued for 5 hours. After the completion of the reaction, the temperature was reduced to produce a red brown transparent liquid. The reaction product was filtered and caustic-washed with 5% KOH solution, and then water washed with distilled water to neutrality. The collected liquid was distilled under reduced pressure at 1000 Pa and 120° C. for 1 h to remove solvent, water and unreacted raw materials to produce 36.8 g dark red brown thick liquid. The product conversion rate was 90.5%.

Comparative Example 1-1

0.5 mol (149 g) 2-octyldodecanol and 0.5 mol (143 g) methyl (3,5-ditert-butyl-4-hydroxyphenyl) propionate were placed in a 500 ml three-necked reaction flask, and 1.25 g LiOH catalyst was added. The mixture was stirred and heated. The pressure was reduced to 0.085 Mpa, and the reaction was performed at 160° C. for 4.2 hours. A light yellow liquid was obtained and warmed up to 260° C., and distilled under reduced pressure to remove unreacted raw materials to produce a yellow transparent liquid. The reaction conversion rate was 92.3%.

Example 1-6

2-tert-butyl-4-epoxypentadecyl phenol of Examples 1-3, 1-4 and 1-5, the product of Comparative Example 1-1, and the control antioxidant were dissolved in mineral oil S6 respectively to formulate 0.5% (mass fraction) solutions, and these solutions were respectively subjected to the antioxidation performance test. The testing device was the DSC meter, Type TA5000, available from TA Company, the United States. The testing conditions comprised: 190° C., the oxygen pressure: 0.5 MPa, and the temperature rising rate: 10° C./min. The measured oxidation induction period results were shown in Table 1-2.

TABLE 1-2

| Samples | Oxidation induction period/minutes |
|---|---|
| Solution in which the product of Example 1-3 was added | 26.4 |
| Solution in which the product of Example 1-4 was added | 26.1 |
| Solution in which the product of Example 1-5 was added | 28.3 |
| Solution in which the product of Comparative Example 1-1 was added | 18.6 |
| Solution in which T501 was added | 12.3 |
| Solution in which T511 was added | 23.7 |
| Solution in which T512 was added | 18.4 |

It could be seen from Table 1-2 that, compared with the compounds without the structure of the present invention, the phenol derivatives of the present invention could significantly increase the oxidation induction period, which was superior to the conventional phenolic antioxidants.

Example 2-1 Preparation of acetic acid meta pentadecenylphenol ester 100 g cardanol, 40.5 g acetic anhydride, and 7.5 g potassium carbonate were placed in a three-necked flask with reflex condenser and motor stirrer, the temperature was controlled at 70° C., and the reaction was performed for 4.5 hours. After the completion of the reaction, the temperature was reduced to 60° C., and the reaction mixture was taken out. 100 g 1% (mass fraction) KOH solution was added to perform the caustic-washing, followed by water washing with distilled water until the discharged water became neutral. Then the organic phase was distilled under reduced pressure at 100 Pa and 120° C. for 1 h, and cooled to produce 111.4 g light yellow clear liquid. The reaction conversion rate was 93.6%. The purity of acetic acid meta pentadecenylphenol ester in the product was greater than 95%.

Example 2-2 Preparation of the Epoxide of Acetic Acid Meta Pentadecenylphenol Ester 120 g acetic acid meta pentadecenylphenol ester obtained from Example 2-1, 8 g formic acid, 0.3 g sulfuric acid, and 160 g hydrogen peroxide were added to a three-necked flask with mechanical stirring, reflux condenser and temperature controller, and stirred and heated. The reaction temperature was maintained at 70° C. and the reaction was performed for 3 hours. After the completion of the reaction, the temperature was reduced to produce a red brown transparent liquid. The reaction product was filtered and caustic-washed with 5% (mass fraction), and then water washed with distilled water to neutrality. The organic phase was distilled under reduced pressure at 100 Pa and 150° C. for 1 h to remove water and unreacted raw materials to produce 139.7 g orange yellow transparent liquid, namely, the epoxide of acetic acid meta pentadecenylphenol ester. The product conversion rate was 98.1%, and the purity was greater than 98%.

Figure 2:
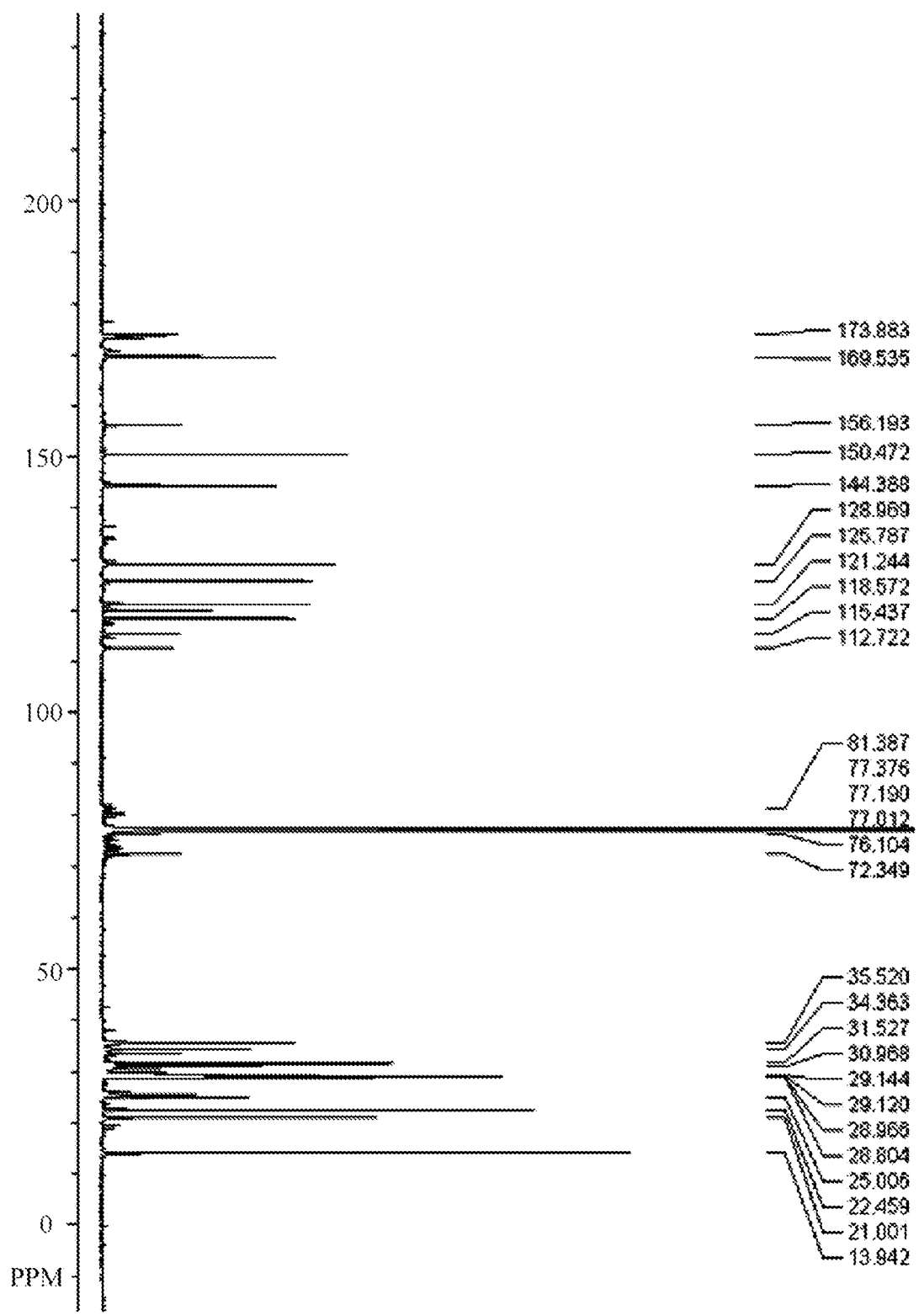
FIG. 2 is the nuclear magnetic resonance spectrum of the product of Example 2-3.

Example 2-3 Preparation of High Viscosity Biomass Base Oil 50 g of the epoxide of acetic acid meta pentadecenylphenol ester obtained from Example 2-2, 100 g octanoic acid, and 0.5 g sulfuric acid were added to a four-necked flask with mechanical stirring, reflux condenser, nitrogen gas tube and temperature controller, nitrogen gas was blew in, and the reaction mixture was stirred and heated. The reaction temperature was maintained at 180° C. and the reaction was performed for 15 hours. After the completion of the reaction, the temperature was reduced to produce a red brown transparent liquid. The reaction product was filtered and acidic-washed with 1% (mass fraction) hydrochloric acid solution, and then water washed with distilled water to neutrality. The organic phase was distilled under reduced pressure at 1000 Pa and 120° C. for 1 h to remove water, and the temperature was reduced to produce 70.1 g red brown thick liquid, namely, the phenolic ester compound of the present invention. The product conversion rate was 88.1%. The prepared product was subjected to the NMR spectroscopy analysis. The spectrum was shown in FIG. 2, and the analysis result was shown in Table 2-1.

TABLE 2-1

Result of NMR carbon spectroscopy analysis of the product of Example 2-3

| chemical shift | Carbon type |
| --- | --- |
| 72.149 | Tertiary carbon attached to oxygen in the alkyl chain |
| 112.722-128.969 | Tertiary carbon on the benzene ring |
| 169.553 | Carboxyl carbon of acetate ester |
| 173.883 | Carboxyl carbon of octanate ester |
| 144.383-156.193 | Quaternary carbon on the benzene ring |
| 13.942-35.52 | Carbon of the alkyl chain |

Example 2-4 Preparation of High Viscosity Biomass Base Oil 50 g of the epoxide of acetic acid meta pentadecenylphenol ester obtained from Example 2-2, 40 g valeric acid, and 0.25 g sulfuric acid were added to a four-necked flask with mechanical stirring, reflux condenser, nitrogen gas tube and temperature controller, nitrogen gas was blew in, and the reaction mixture was stirred and heated. The reaction temperature was maintained at 140° C. and the reaction was performed for 8 hours. After the completion of the reaction, the temperature was reduced to produce a red brown transparent liquid. The reaction product was filtered and acidic-washed with 1% (mass fraction) hydrochloric acid solution, and then water washed with distilled water to neutrality. The organic phase was distilled under reduced pressure at 1000 Pa and 120° C. for 1 h to remove water, and the temperature was reduced to produce 69.2 g red brown thick liquid, namely, the phenolic ester compound of the present invention. The product conversion rate was 91.3%.

Example 2-5 Preparation of High Viscosity Biomass Base Oil 50 g of the epoxide of acetic acid meta pentadecenylphenol ester obtained from Example 2-2, 186 g lauric acid, and 1 g sulfuric acid were added to a four-necked flask with mechanical stirring, reflux condenser, nitrogen gas tube and temperature controller, nitrogen gas was blew in, and the reaction mixture was stirred and heated. The reaction temperature was maintained at 210° C. and the reaction was performed for 18 hours. After the completion of the reaction, the temperature was reduced to produce a red brown transparent liquid. The reaction product was filtered and acidic-washed with 1% (mass fraction) hydrochloric acid solution, and then water washed with distilled water to neutrality. The organic phase was distilled under reduced pressure at 1000 Pa and 120° C. for 1 h to remove water, and the temperature was reduced to produce 88.04 g red brown thick liquid, namely, the phenolic ester compound of the present invention. The product conversion rate was 87.6%.

Example 2-6

The phenolic ester compounds obtained from the present invention, conventional commercially available mineral oil-type high viscosity base oils 150BS and 120BS, and soybean oil were subjected to the performance analysis and evaluation respectively, wherein the testing conditions of the PDSC antioxidation performance testing were as follows: the testing device was the TA5000 DSC meter available from TA Company, the United States, 190° C., the oxygen pressure: 0.5 MPa, and the temperature rising rate: 10° C./min; the standard method of the four-ball machine test was SH/T 0189, which had the following test conditions: 1200 r/min, load: 392N, and time: 30 minute. The results for the performance analysis and evaluation were shown in Table 2-2.

It could be seen from the comparison that compared with conventional mineral oil-type high viscosity base oil 150BS and 120BS,
the phenolic ester compounds of the present invention had obvious advantages in terms of viscosity-temperature performance (viscosity index), low-temperature performance (pour point), lubricating performance, and the like; and compared with soybean oil, which was also a biomass base oil, the phenolic ester compounds of the present invention had obvious advantages in terms of oxidation stability, low temperature performance (pour point), lubricating performance and the like, and therefore the phenolic ester compounds of the present invention were the lubricating oil base oil having excellent overall performance.

TABLE 2-2

| Sample | Kinematic viscosity @100° C./(mm$^2$/s) | Viscosity index | Pour point/° C. | PDSC oxidation induction period/min | Four-ball machine D39230/mm |
| --- | --- | --- | --- | --- | --- |
| Product of Example 2-3 | 46.5 | 122 | −20 | 23 | 0.51 |
| Product of Example 2-4 | 22.6 | 115 | −26 | 27 | 0.52 |

TABLE 2-2-continued

| Sample | Kinematic viscosity @100° C./(mm²/s) | Viscosity index | Pour point/° C. | PDSC oxidation induction period/min | Four-ball machine D39230/mm |
|---|---|---|---|---|---|
| Product of Example 2-5 | 70.8 | 130 | −15 | 19 | 0.48 |
| 150BS | 32.7 | 84 | −9 | 25 | 0.57 |
| 120BS | 21.3 | 90 | −9 | 21 | 0.61 |
| Soybean oil | 6 | 175 | −8 | 8 | 0.69 |

Example 3-1 Preparation of 6-tert-butyl Cardanol 30 g cardanol was dissolved in 100 ml acetone. After the completion of dissolving, the mixture was placed in a 250 ml three-necked reaction flask, and 0.9 g zinc chloride catalyst was added. The stirring and heating was initiated. The reaction temperature was maintained at 60° C. 9.5 g tert-butyl chloride was slowly added dropwise into the reaction flask, after the completion of the dropwise addition, the reaction was continued for 3 hours. After the completion of the reaction, the temperature was reduced to produce a red brown transparent liquid. The reaction product was filtered and caustic-washed with 5% KOH solution, and then water washed with distilled water to neutrality. The collected liquid was distilled under reduced pressure at 1000 Pa and 120° C. for 1 h to remove solvent, water and unreacted raw materials to produce 33.2 g red brown transparent thick liquid, namely 6-tert-butyl cardanol. The product conversion rate was 85.1%.

Example 3-2 Preparation of Sulfurized 6-tert-butyl Cardanol 70 g 6-tert-butyl cardanol prepared in Example 3-1 (about 0.2 mol) and 12.8 g sulphur powder (0.4 mol) were put in a 250 ml three-necked reaction flask, stirred, and heated. The reaction temperature was maintained at 180° C. and the reaction was continuously performed for 6 hours. After the completion of the reaction, the temperature was reduced. The reaction mixture was filtered to produce 76.3 g dark redbrown thick liquid, namely sulfurized 6-tert-butyl cardanol of the present invention. The product conversion rate was 92.1%.

Example 3-3 Preparation of Sulfurized 6-Tert-Butyl Cardanol 70 g 6-tert-butyl cardanol prepared in Example 3-1 (about 0.2 mol) and 19.2 g sulphur powder (0.6 mol) and 3.5 g ammonia water were put in a 250 ml three-necked reaction flask, stirred, and heated. The reaction temperature was maintained at 150° C. and the reaction was continuously performed for 5 hours. After the completion of the reaction, the temperature of the reaction mixture was reduced. The reaction mixture was filtered, acidic washed with 0.1% of hydrochloric acid and washed with deionized water to neutrality, then dewatered in vacuum to produce 79.3 g dark red brown thick liquid, namely sulfurized 6-tert-butyl cardanol of the present invention. The product conversion rate was 95.8%.

Example 3-4 Preparation of Sulfurized 6-tert-butyl Cardanol 70 g 6-tert-butyl cardanol prepared in Example 3-1 (about 0.2 mol) and 19.2 g sulphur powder (0.6 mol) and 0.35 g diethylamine were put in a 250 ml three-necked reaction flask, stirred, and heated. The reaction temperature was maintained at 160° C. and the reaction was continuously performed for 4 hours. After the completion of the reaction, the temperature of the reaction mixture was reduced. The reaction mixture was filtered, acidic washed with 0.1% of hydrochloric acid and washed with deionized water to neutrality, then dewatered in vacuum to produce 77.5 g dark red brown thick liquid, namely sulfurized 6-tert-butyl cardanol of the present invention. The product conversion rate was 93.6%.

Comparative Example 3-1

0.5 mol (149 g) 2-octyldodecanol and 0.5 mol (143 g) of methyl (3,5-ditert-butyl-4-hydroxyphenyl)propionate were placed in a 500 ml three-necked reaction flask, and 1.25 g LiOH catalyst was added. The mixture was stirred and heated. The pressure was reduced to 0.085 MPa, and the reaction was performed at 160° C. for 4.2 hours to produce a light yellow liquid, which was warmed up to 260° C., and distilled under reduced pressure to remove unreacted raw materials to produce a yellow transparent liquid. The reaction conversion rate was 92.3%.

Example 3-5

Sulfurized 6-tert-butyl cardanol of Examples 3-2, 3-3 and 3-4, the product of Comparative Example 3-1, and the control antioxidants T501, T511 and T512 were dissolved in mineral oil S6 respectively to formulate 0.5% (mass fraction) solutions, and these solutions were respectively subjected to the anti-oxidation performance test. The testing device was the DSC meter, Type TA5000, available from TA Company, the United States. The testing conditions comprised: 190° C., the oxygen pressure: 0.5 MPa, and the temperature rising rate: 10° C./min. The measured oxidation induction period results were shown in Table 3-1.

TABLE 3-1

| Sample | Oxidation induction period/minutes |
|---|---|
| Solution in which the product of Example 3-2 was added | 29.5 |
| Solution in which the product of Example 3-3 was added | 28.9 |
| Solution in which the product of Example 3-4 was added | 29.1 |
| Solution in which the product of Comparative Example 3-1 was added | 18.6 |
| Solution in which T501 was added | 12.3 |
| Solution in which T511 was added | 23.7 |
| Solution in which T512 was added | 18.4 |

It could be seen from Table 3-1 that, the phenol derivatives provided by the present invention could significantly increase the oxidation induction period, which was superior to the conventional phenolic antioxidants.

Example 3-6

Sulfurized 6-tert-butyl cardanol of Examples 3-2, 3-3 and 3-4 and sulfurized olefin cotton oil (T405) were dissolved in the mineral oil 150SN respectively to formulate into 1% (mass fraction) of solutions, which were subjected to the antiwear performance test. The testing device was an SRV vibration and friction testing machine. The test conditions were: 100N, 200N, 300N, frequency 50 Hz, amplitude 1 mm, 30° C., 1 h. The test results were shown in Table 3-2.

TABLE 3-2

| Evaluation item | Ex. 3-2 | Ex. 3-3 | Ex. 3-4 | T405 |
|---|---|---|---|---|
| 100N | | | | |
| Friction coefficient f | 0.118 | 0.119 | 0.118 | 0.119 |
| Scar diameter D/mm | 0.42 | 0.41 | 0.42 | 0.42 |
| 200N | | | | |
| Friction coefficient f | 0.108 | 0.110 | 0.109 | 0.133 |
| Scar diameter D/mm | 0.49 | 0.51 | 0.46 | 0.81 |
| 300N | | | | |
| Friction coefficient f | 0.118 | 0.116 | 0.118 | 0.119 |
| Scar diameter D/mm | 0.56 | 0.57 | 0.55 | 0.57 |
| OK Value | 1000N | 1050N | 1000N | 700N |

Example 4-1 Preparation of Cardanol Acetate 100 g cardanol, 40.5 g acetic anhydride, 7.5 g potassium carbonate were placed in a three-necked flask with reflex condenser and motor stirrer. The temperature was 70° C. and the reaction was performed for 4.5 hours. After the completion of the reaction, the temperature was reduced to 60° C., and the reaction mixture was taken out. 100 g 1% (concentration) KOH solution was added to perform the caustic-washing, followed by water washing with distilled water until the discharged water became neutral. Then the organic phase was distilled under reduced pressure at 100 Pa and 120° C. for 1 h, and cooled to produce 111.4 g light yellow clear liquid, namely, cardanol acetate, which had a structure of acetic acid meta pentadecenylphenol este. The reaction conversion rate was 93.6%. the purity of acetic acid meta pentadecenylphenol ester was greater than 95%.

Example 4-2 Preparation of Sulfurized Cardanol 62 g cardanol (about 0.2 mol) and 12.8 g sulphur powder (0.4 mol) were put in a 250 ml three-necked reaction flask, stirred, and heated. The reaction temperature was maintained at 190° C. and the reaction was performed for 3 hours. After the completion of the reaction, the temperature was reduced followed by the filtration to produce 66.8 g dark red brown thick liquid, namely the sulfurized cardanol. The product conversion rate was 89.3%.

Figure 3:
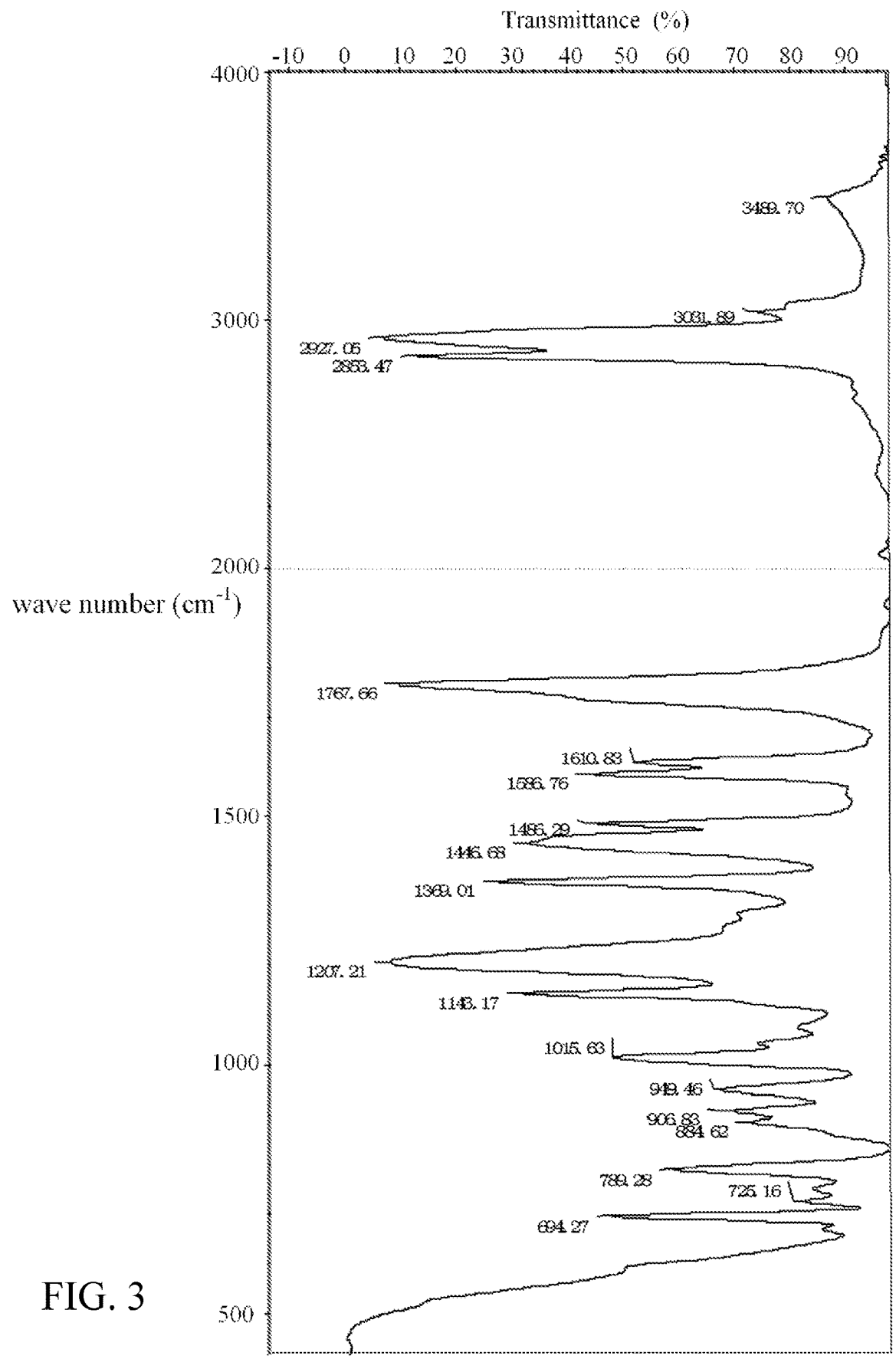
FIG. 3 is the infrared spectrum of the product of Example 4-3.

Example 4-3 Preparation of Sulfurized Cardanol Acetate 70 g cardanol acetate obtained from Example 4-1 (about 0.2 mol) and 12.8 g sulphur powder (0.4 mol) were put in a 250 ml three-necked reaction flask, stirred, and heated. The reaction temperature was maintained at 190° C. and the reaction was performed for 3 hours. After the completion of the reaction, the temperature was reduced. The reaction mixture was filtered to produce 71.3 g dark red brown thick liquid, namely sulfurized cardanol acetate. The product conversion rate was 86.1%. The obtained d product was subjected to the infrared spectrum analysis. The spectrum was shown in FIG. 3, and the analysis result was shown in Table 4-1.

TABLE 4-1

Infrared analysis result of the product of Example 4-3

| Characteristic absorption peak/cm$^{-1}$ | Absorption peak attribution |
|---|---|
| 3031.89 | Stretching vibration of =C—H on the benzene ring |
| 2927.05, 2833.47 | Stretching vibration of C—H in $CH_3$ and $CH_2$ |
| 1767.66 | Stretching vibration of C=O |
| 1610.83, 1586.76, 1488.29 | Stretching vibration of benzene ring framework |
| 1015.63 | Stretching vibration of O—C |
| 725.16 | In-plane swing of four or more successive —$CH_2$— groups |
| 694.27 | Stretching vibration of S—C |

Example 4-4 Preparation of Sulfurized Cardanol Acetate 70 g cardanol acetate obtained from Example 4-1 (about 0.2 mol) and 19.2 g sulphur powder (0.6 mol) and 3.5 g ammonia water were put in a 250 ml three-necked reaction flask, stirred, and heated. The reaction temperature was maintained at 150° C. and the reaction was continuously performed for 5 hours. After the completion of the reaction, the temperature of the reaction mixture was reduced. The reaction mixture was filtered, acidic washed with 0.1% of hydrochloric acid and washed with deionized water to neutrality, then dewatered in vacuum to produce 79.3 g dark red brown thick liquid, namely sulfurized cardanol acetate. The product conversion rate was 95.8%.

Example 4-5 Preparation of Sulfurized Cardanol Acetate 70 g cardanol acetate obtained from Example 4-1 (about 0.2 mol) and 19.2 g sulphur powder (0.6 mol) and 0.35 g diethylamine were put in a 250 ml three-necked reaction flask, stirred, and heated. The reaction temperature was maintained at 160° C. and the reaction was continuously performed for 4 hours. After the completion of the reaction, the temperature of the reaction mixture was reduced. The reaction mixture was filtered, acidic washed with 0.1% of hydrochloric acid and washed with deionized water to neutrality, then dewatered in vacuum to produce 77.5 g dark red brown thick liquid, namely sulfurized cardanol acetate. The product conversion rate was 93.6%.

Example 4-6 Preparation of Sulfurized Cardanol Acetate 120 g sulfurized cardanol obtained from Example 4-2, 45 g acetic anhydride, and 10.5 g potassium carbonate were placed in a three-necked flask with reflex condenser and motor stirrer, and the reaction was performed at 80° C. for 55 hours. After the completion of the reaction, the temperature was reduced to 60° C., and the reaction mixture was taken out. 100 g 1% (concentration) KOH solution was added to perform the caustic-washing, followed by water washing with distilled water until the discharged water became neutral. Then the organic phase was distilled under reduced pressure at 100 Pa and 120° C. for 1 h, and cooled to produce 127.3 g light yellow clear liquid, namely, sulfurized cardanol acetate. The reaction conversion rate was 91.2%.

Comparative Example 4-1

35 g erucic acid was poured into a flask. The flask was placed in a thermostatic water bath tank (temperature controlled at 25° C.). Sulfur monochloride, in a total amount of 6 g, was added dropwise through a separatory funnel. The low-temperature sulfurization was performed under a stirring rate of 650 rpm. Nitrogen gas as protection gas was introduced into the flask. The pressure was controlled at 0.05 MPa. The reaction was performed until no bubble would appear at the conduit inlet that was introduced into a sodium hydroxide solution (having a mass percentage concentration of 15%). The reaction was continued for another 15 minutes and then stopped. First, the product was sufficiently washed with 10% sodium hydroxide solution, then allowed to stand and separated into layers. The lower aqueous layer was discarded, then the organic layer was washed twice with distilled water, and finally distilled under reduced pressure to produce light yellow sulfurized erucic acid.

Example 4-7

The sulfurized cardanol acetates of Examples 4-3, 4-4, 4-5 and 4-6, T404, T405, and the product of Comparative Example 4-1 were dissolved in the mineral oil 150SN respectively to formulate the solutions having the mass fraction of 1%. These solutions were subjected to the antiwear performance test. The testing device was an SRV vibration and friction testing machine. The test conditions were: 100N, 200N, 300N, frequency 50 Hz, amplitude 1 mm, 30° C., 1 h. The test results were shown in Table 4-2.

TABLE 4-2

| Test conditions | Ex. 4-3 | Ex. 4-4 | Ex. 4-5 | Ex. 4-6 | T404 | T405 | Comp. Ex. 4-1 |
|---|---|---|---|---|---|---|---|
| 100N | | | | | | | |
| Friction coefficient f | 0.120 | 0.120 | 0.119 | 0.118 | 0.121 | 0.119 | 0.123 |
| D, mm | 0.42 | 0.41 | 0.40 | 0.40 | 0.43 | 0.42 | 0.45 |
| 200N | | | | | | | |
| Friction coefficient f | 0.108 | 0.107 | 0.109 | 0.107 | 0.130 | 0.133 | 0.126 |
| D, mm | 0.46 | 0.45 | 0.44 | 0.47 | 0.62 | 0.61 | 0.58 |
| 300N | | | | | | | |
| Friction coefficient f | 0.112 | 0.110 | 0.112 | 0.111 | 0.118 | 0.119 | 0.123 |
| D, mm | 0.57 | 0.56 | 0.55 | 0.56 | 0.61 | 0.57 | 0.63 |
| OK Value | 1000N | 1050N | 1100N | 1000N | 650N | 700N | 1000N |

It could be seen from Table 4-2 that the sulfurized phenolic ester derivative of the present invention had outstanding antiwear, anti-friction and extreme pressure performances compared with the compound having the structure of the present invention.

Example 4-8

Sulfurized cardanol acetates of Examples 4-3, 4-4, 4-5 and 4-6, T404, T405 and the product of Comparative Example 4-1, sulfurized erucic acid, were dissolved in mineral oil S6 respectively to formulate into solutions having the mass fraction of 0.5%. According to GB/T 7304 and GB/T 5096, the test for the total acid number and the test for the copper corrosion were performed. The test results were shown in Table 4-3.

TABLE 4-3

| Sample | total acid number/ (mgKOH/g) | Copper corrosion/ Grade |
|---|---|---|
| Solution in which the product of Example 4-3 was added | 0.06 | 1b |
| Solution in which the product of Example 4-4 was added | 0.05 | 1b |
| Solution in which the product of Example 4-5 was added | 0.06 | 1b |
| Solution in which the product of Example 4-6 was added | 0.06 | 1b |
| Solution in which T404 was added | 0.10 | 1b |
| Solution in which T405 was added | 0.10 | 2a |
| Solution in which the product of Comparative Example 4-1 was added | 0.12 | 2c |

It could be seen from Table 4-3 that the sulfurized phenolic ester derivative of the present invention had lower acidity and lower corrosion behavior to copper sheet, compared with the compound having the structure of the present invention.

Example 5-1 Preparation of Meta Pentadecyl Phenol 100 g cardanol and 1.5 g palladium carbon catalyst were placed in a 200 ml high-pressure reactor, the reactor was closed, and hydrogen gas was introduced to 3.5 MPa. The stirring and heating was initiated, and the reaction was performed at a temperature of 200° C. for 4.5 hours. After the completion of the reaction, the temperature was reduced to 60° C., and the viscous reaction mixture was taken out, and distilled under reduced pressure at 100 Pa and 160° C. for 1 h. After cooling, a milky white solid (84.7 g) was obtained. It was dissolved in petroleum ether, and then purified by crystallization to produce meta pentadecyl phenol with a purity of greater than 98%, and the reaction conversion rate was 83.6%.

Example 5-2 Preparation of 6-tert-butyl Cardanol 30 g cardanol was dissolved in 100 ml acetone. After the completion of dissolving, the mixture was placed in a 250 ml three-necked flask, and 0.9 g zinc chloride catalyst was added. The stirring and heating was initiated. The reaction temperature was maintained at 60° C. 9.5 g tert-butyl chloride was slowly added dropwise into the reaction flask, after the completion of the dropwise addition, the reaction was continued for 3 hours. After the completion of the reaction, the temperature was reduced to produce a red brown transparent liquid. The reaction product was filtered and caustic-washed with 5% KOH solution, and then water washed with distilled water to neutrality. The collected liquid was distilled under reduced pressure at 1000 Pa and 120° C. for 1 h to remove solvent, water and unreacted raw materials to produce 33.2 g red brown transparent thick liquid, namely 6-tert-butyl cardanol. The product conversion rate was 85.1%.

Example 5-3 Preparation of 3-pentadecyl-6-tert-butylphenol 30 g meta pentadecyl phenol of Example 5-1 was dissolved in 100 ml acetone. After the completion of dissolving, the mixture was placed in a 250 ml three-necked flask, and 1.5 g zinc chloride catalyst was added. The stirring and heating was initiated. The reaction temperature was maintained at 50° C. 9.5 g tert-butyl chloride was slowly added dropwise into the reaction flask, after the completion of the dropwise addition, the reaction was continued for 5 hours. After the completion of the reaction, the temperature was reduced to produce a red brown transparent liquid. The reaction product was filtered and caustic-washed with 5% KOH solution, and then water washed with distilled water to neutrality. The collected liquid was distilled under reduced pressure at 1000 Pa and 120° C. for 1 h to remove solvent, water and unreacted raw materials. The temperature was reduced to produce 31.2 g orange yellow solid, namely 3-pentadecyl-6-tert-butylphenol. The product conversion rate was 80.1%.

Example 5-4 Preparation of 2,2'-methylene-bis(6-tert-butylcardanol)

40 g 6-tert-butyl cardanol of Example 5-2, 120 ml aqueous ethanol solution with an ethanol content of 60% (mass fraction), and 0.6 g NaOH catalyst were added to a 250 ml three-necked flask, stirred, and heated. When the reaction temperature was increased to a constant temperature for refluxing, 1.2 g formaldehyde was slowly added dropwise into the reaction flask. After the completion of the dropwise addition, the reaction was continued for 3 hours. After the completion of the reaction, the temperature was reduced. The reaction mixture was transferred to a separatory funnel, the lower-layer aqueous phase was discharged, the upper-layer red brown transparent oily phase was washed with distilled water to neutrality. The organic phase was distilled under reduced pressure at 1000 Pa and 110° C. for 1 h to remove solvent, water and unreacted raw materials. 37.2 g orange yellow transparent liquid, namely 2,2'-methylene bis (6-tert-butylcardanol) was obtained. The product conversion rate was 85.4%.

Example 5-5 2,2'-methylene-bis(3-pentadecyl-6-tert-butylphenol)

200 g 3-pentadecyl-6-tert-butylphenol, 120 ml aqueous ethanol solution with an ethanol content of 70% (mass fraction), and 0.4 g NaOH catalyst were added to a 250 ml three-necked flask, stirred, and heated. When the reaction temperature was increased to a constant temperature for refluxing, 4.5 g formaldehyde was slowly added dropwise into the flask. After the completion of the dropwise addition, the reaction was continued for 5 hours. After the completion of the reaction, the temperature was reduced. The reaction mixture was filtered to produce 176.6 g deep yellow solid product, which was washed with distilled water and filtered by suction. The reaction product was washed to neutrality. The water-washed product was dissolved in petroleum ether, then purified by crystallization to produce a white solid product with a purity of greater than 98%, namely, 2,2'-methylene-bis(3-pentadecyl-6-tert-butylphenol). The reaction conversion rate was 81.2%. The prepared product was subjected to the infrared spectrum analysis. The infrared spectrum was shown in FIG. 4, and the analysis result was shown in Table 5-1.

TABLE 5-1

| Infrared analysis result of the product | |
|---|---|
| Characteristic absorption peak/cm$^{-1}$ | Absorption peak attribution |
| 3357.22 | Stretching vibration of C—OH |
| 2916.53, 2849.17 | Stretching vibration of C—H in CH$_3$ and CH$_2$ |
| 1618.51, 1586.2, 1477.8 | Stretching vibration of benzene ring framework |
| 1147.56 | Stretching vibration of O—C |
| 939.59 | Rocking vibration of-C(CH3) |
| 785.09 | Flexural vibration of C=CH |
| 722.91 | Rocking vibration of-C—(CH$_2$)n—CH3 |

Figure 4:
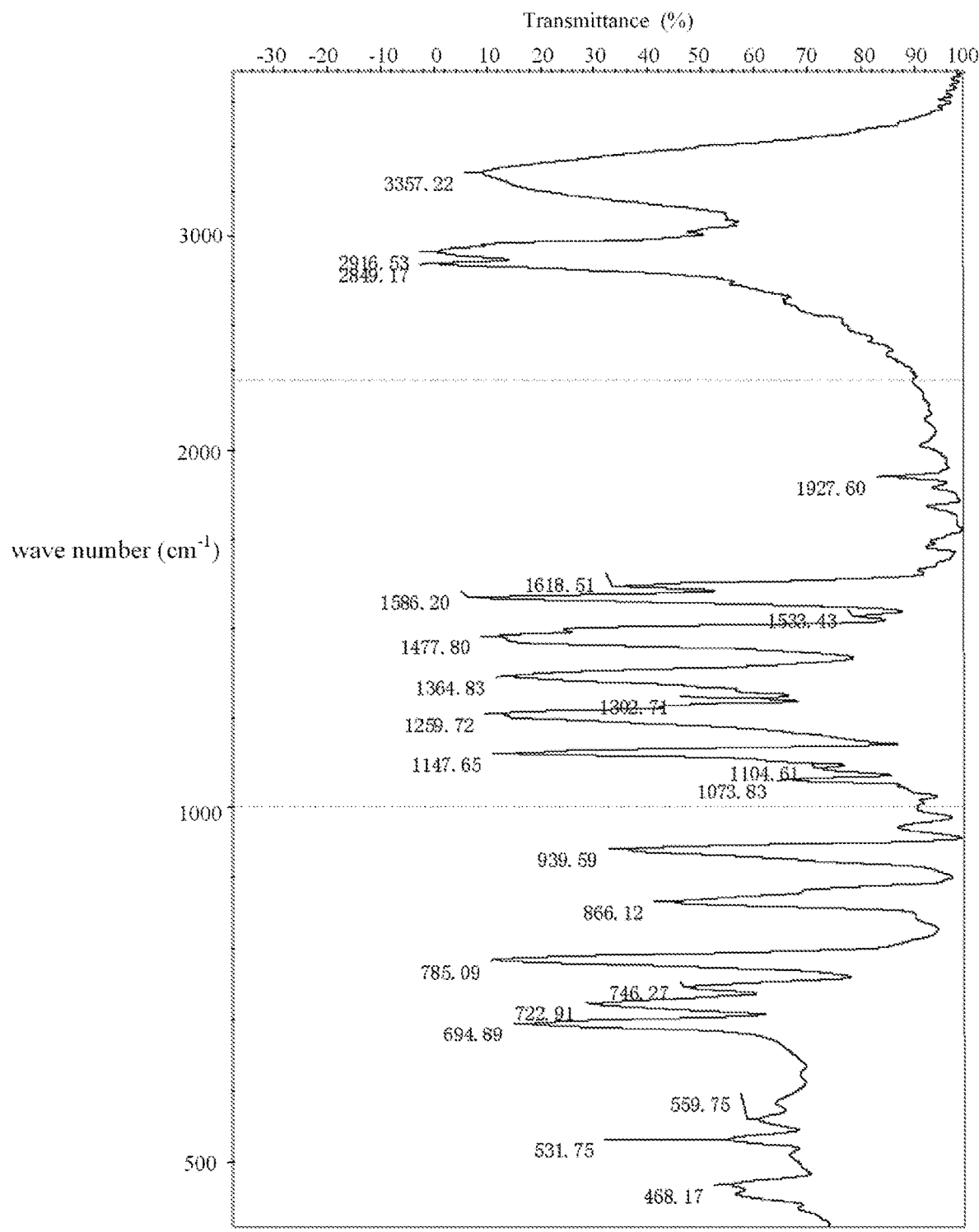
FIG. 4 is the infrared spectrum of the product of Example 5-5.

It could be seen from FIG. 4 and Table 5-1, the product of Example 5-5 was 2,2'-methylene-bis(3-pentadecyl-6-tert-butylphenol).

Comparative Example 5-1

0.2 mol (30.8 g) phenylthioethanol and 0.24 mol (70.08 g) methyl (3,5-ditert-butyl-4-hydroxyphenyl)propionate were added to a 250 ml three-necked flask, and 1 g LiOH catalyst was added. The mixture was stirred and heated. The pressure was reduced to 0.005 MPa, and the reaction was performed at 160° C. for 8 hours to produce a light brown viscous matter, which was warmed up to 260° C., and distilled under reduced pressure to remove unreacted raw materials to produce a red brown transparent thick liquid. The reaction conversion rate was 95%. The structure of the product was shown in the following formula.

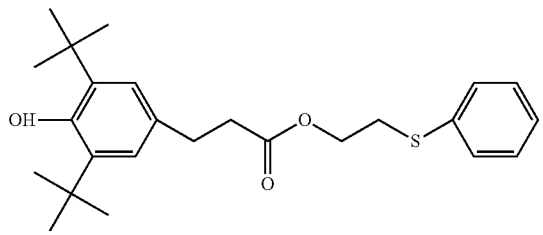 [SMILES: CC(C)(C)c1cc(CCC(=O)OCCSc2ccccc2)cc(C(C)(C)C)c1O]

Comparative Example 5-2

40 g 2,6-ditert-butyl phenol, 120 ml aqueous ethanol solution with an ethanol content of 60% (mass fraction), 0.5 g NaOH catalyst were added to a 250 ml three-necked flask, stirred, and heated. When the reaction temperature was increased to a constant temperature for refluxing, 2.2 g formaldehyde was slowly added dropwise into the reaction flask. After the completion of the dropwise addition, the reaction was continued for 2 hours. After the completion of the reaction, the temperature was reduced. The reaction mixture was transferred to a separatory funnel, the lower-layer aqueous phase was discharged, the upper-layer red brown transparent oily phase was washed with distilled water to neutrality. The organic phase was distilled under reduced pressure at 1000 Pa and 110° C. for 1 h to remove solvent, water and unreacted raw materials. An orange yellow transparent liquid, namely 4,4'-methylene-bis(2,6-ditert-butyl phenol) was obtained. The product conversion rate was 83.9%.

Example 5-6

The product of Example 5-4, the product of Example 5-5, the product of Comparative Example 5-1, T501, and T511, each in an addition amount of 5%, were dissolved in mineral oil S6 respectively to formulate mixed solutions of phenol derivatives and mineral oil S6, and these mixed solutions were respectively subjected to the PDSC anti-oxidation performance test. The testing device was the TA5000 DSC meter, available from TA Company, the United States. The testing conditions comprised: 190° C., the oxygen pressure: 0.5 MPa, and the temperature rising rate: 10° C./min. The test results were shown in Table 5-2.

TABLE 5-2

| Phenol derivative in the mixed solution | Oxidation induction period/min |
| --- | --- |
| Product of Example 5-4 | 52.7 |
| Product of Example 5-5 | 59.6 |
| Product of Comparative Example 5-1 | 18.4 |
| Product of Comparative Example 5-2 | 36.5 |
| T501 | 12.3 |
| T511 | 38.6 |

It could be seen from the above table that the phenol derivatives of the present invention had very excellent antioxidation performance and could be used as antioxidant.

Example 5-7

The product of Example 5-4, the product of Example 5-5, the product of Comparative Example 5-1, T501, and T511, each in an addition amount of 0.5%, were dissolved in synthetic oil PAO 6 respectively to formulate mixed solutions of phenol derivatives and synthetic oil PAO 6, and these mixed solutions were respectively subjected to the PDSC anti-oxidation performance test. The testing device was the TA5000 DSC meter, available from TA Company, the United States. The testing conditions comprised: 190° C., the oxygen pressure: 0.5 MPa, and the temperature rising rate: 10° C./min. The test results were shown in Table 5-3.

TABLE 5-3

| Phenol derivatives in the mixed solution | Oxidation induction period/min |
| --- | --- |
| Product of Example 5-4 | 94.9 |
| Product of Example 5-5 | 107.9 |
| Product of Comparative Example 5-1 | 26.5 |
| Product of Comparative Example 5-2 | 41.8 |
| T501 | 13.3 |
| T511 | 40.1 |

It could be seen from the above table that the phenol derivatives of the present invention had very prominent susceptibility in the synthetic oil and excellent antioxidation performance.

Although the embodiments of the present invention have been described in detail with reference to the examples, it should be noted that the scope of the present invention is not limited by the embodiments, but is defined by the appended claims. Those skilled in the art can appropriately modify the embodiments without departing from the technical spirit and scope of the present invention, and it is obvious that the modified embodiments are also included in the scope of the present invention.

INDUSTRIAL APPLICABILITY

The phenolic derivatives of the present invention have excellent antioxidation performance and can be used as antioxidants. The phenol derivatives of the present invention also have excellent lubricating performance and antiwear and antifriction performance, and can be used as excellent lubricating oil additives. In addition, the phenol derivatives of the present invention are excellent in viscosity-temperature properties and low-temperature properties, and can be used as high-viscosity base oils.

The invention claimed is:

1. A phenol derivative having a structure represented by formula (I-3):

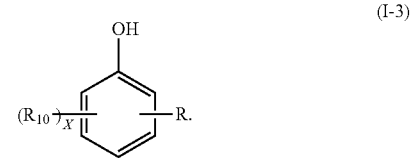

(I-3)

wherein:
group R is represented by formula (V),

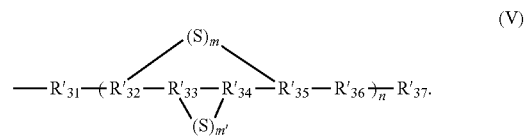

(V)

wherein, in formula (V),
  $R_{31}'$ is selected from single bond, $C_{1-20}$ linear alkylenes, and $C_{1-20}$ branched alkylenes;
  each $R_{32}'$ in the n repeating units is independently selected from divalent, trivalent and tetravalent $C_{1-4}$ linear, and divalent, trivalent and tetravalent branched alkyl;
  each $R_{33}'$ in the n repeating units is independently selected from single bond, divalent and trivalent $C_{1-4}$ linear alkyls, and single bond, divalent and trivalent $C_{1-4}$ branched alkyls;
  each $R_{34}'$ in the n repeating units is independently selected from single bond, divalent, and trivalent $C_{1-4}$ linear alkyls, and single bond, divalent, and trivalent $C_{1-4}$ branched alkyl;
  each $R_{35}'$ in the n repeating units is independently selected from divalent, trivalent and tetravalent $C_{1-4}$ linear alkyls, and divalent, trivalent and tetravalent $C_{1-4}$ branched alkyls;

each $R_{36}'$ in n repeating units is independently selected from single bond and $C_{1-20}$ linear alkylenes, and single bond and $C_{1-20}$ branched alkylenes;

each $R_{37}'$ is selected from hydrogen, $C_{1-20}$ linear alkyls, and branched alkyls, n is an integral number of 1-3;

each m in n repeating units is independently an integral number among 0, 1, 2, 3, 4, and 5;

each m' in n repeating units is independently an integral number among 0, 1, 2, 3, 4, and 5;

in each of the n repeating unit, when m is greater than 0, the linking group formed by m sulfur atoms is bonded to $R_{32}'$ and $R_{35}'$; when m' is greater than 0, the linking group formed by m' sulfur atoms is bonded to $R_{33}'$ and $R_{34}'$; when group $R_{33}'$ is a single bond, one end of the linking group formed by m' sulfur atoms is bonded to group $R_{32}'$; when group $R_{34}'$ is a single bond, one end the linking group formed by m' sulfur atoms is bonded to $R_{35}'$;

m+m'>0,

R is located at a meta-position or a para-position of the phenolic hydroxyl group; and x is 1 or 2, each $R_{10}$ is located at an ortho-position of the phenolic hydroxyl group and is independently selected from $C_{1-4}$ linear alkyls and $C_{1-4}$ branched alkyls.

2. A composition, which contains a phenol derivative according to claim 1.

3. A lubricating oil, which contains a base oil and a phenol derivative according to claim 1.

\* \* \* \* \*